United States Patent
Chalberg et al.

(10) Patent No.: US 10,000,741 B2
(45) Date of Patent: Jun. 19, 2018

(54) COMPOSITIONS AND METHODS FOR ENHANCED GENE EXPRESSION IN CONE CELLS

(71) Applicants: Avalanche Biotechnologies, Inc., Menlo Park, CA (US); University of Washington, Seattle, WA (US)

(72) Inventors: Thomas W. Chalberg, Redwood City, CA (US); Jay Neitz, Seattle, WA (US); Maureen Neitz, Seattle, WA (US)

(73) Assignees: Adverum Biotechnologies, Inc., Menlo Park, CA (US); University of Washington, Seattle, WA (US)

( * ) Notice: Subject to any disclaimer, the term of this patent is extended or adjusted under 35 U.S.C. 154(b) by 0 days. days.

(21) Appl. No.: 14/660,657

(22) Filed: Mar. 17, 2015

(65) Prior Publication Data
US 2015/0259395 A1    Sep. 17, 2015

Related U.S. Application Data

(60) Provisional application No. 62/127,185, filed on Mar. 2, 2015, provisional application No. 61/954,330, filed on Mar. 17, 2014.

(51) Int. Cl.
| | |
|---|---|
| *C07K 14/705* | (2006.01) |
| *C12N 15/86* | (2006.01) |
| *C12N 7/00* | (2006.01) |
| *A61K 35/761* | (2015.01) |
| *A61K 48/00* | (2006.01) |
| *A61K 38/00* | (2006.01) |

(52) U.S. Cl.
CPC ............. *C12N 7/00* (2013.01); *A61K 35/761* (2013.01); *C12N 15/86* (2013.01); *A61K 38/00* (2013.01); *A61K 48/00* (2013.01); *C12N 2750/14143* (2013.01); *C12N 2800/24* (2013.01); *C12N 2830/008* (2013.01); *C12N 2830/30* (2013.01); *C12N 2830/42* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 4,874,237 A | 10/1989 | Cringle | |
| 5,219,401 A | 6/1993 | Cathignol et al. | |
| 5,383,917 A | 1/1995 | Desai et al. | |
| 5,436,146 A | 7/1995 | Shenk et al. | |
| 5,527,533 A | 6/1996 | Tso et al. | |
| 5,641,749 A | 6/1997 | Yan et al. | |
| 5,712,380 A | 1/1998 | Kendall et al. | |
| 5,753,500 A | 5/1998 | Shenk et al. | |
| 5,792,845 A | 8/1998 | O'Reilly et al. | |
| 5,814,618 A | 9/1998 | Bujard et al. | |
| 5,861,484 A | 1/1999 | Kendall et al. | |
| 5,994,136 A | 11/1999 | Naldini et al. | |
| 6,013,516 A | 1/2000 | Verma et al. | |
| 6,040,183 A | 3/2000 | Ferrari et al. | |
| 6,054,485 A | 4/2000 | Schwartz et al. | |
| 6,093,570 A | 7/2000 | Ferrari et al. | |
| 6,132,732 A | 10/2000 | Young et al. | |
| 6,153,436 A | 11/2000 | Hermonat et al. | |
| 6,287,815 B1 | 9/2001 | Brown | |
| 6,329,181 B1 | 12/2001 | Xiao et al. | |
| 6,387,670 B1 | 5/2002 | Leblois-Prehaud et al. | |
| 6,458,157 B1 | 10/2002 | Suaning | |
| 6,482,634 B1 | 11/2002 | Wilson et al. | |
| 6,548,286 B1 | 4/2003 | Samulski et al. | |
| 6,723,551 B2 | 4/2004 | Kotin et al. | |
| 6,943,153 B1 | 9/2005 | Manning, Jr. et al. | |
| 7,070,959 B1 | 7/2006 | Papadopoulos et al. | |
| 7,071,159 B2 | 7/2006 | Kendall et al. | |
| 7,220,577 B2 | 5/2007 | Zolotukhin | |
| 7,585,676 B2 | 9/2009 | Mitrophanous et al. | |
| 7,635,474 B2 | 12/2009 | Daly et al. | |
| 7,666,405 B2 | 2/2010 | Amalfitano et al. | |
| 7,858,367 B2 | 12/2010 | Amalfitano et al. | |
| 7,972,278 B2 | 7/2011 | Graham et al. | |
| 8,075,137 B2 | 12/2011 | Klistorner et al. | |
| 8,118,752 B2 | 2/2012 | Helling et al. | |
| 8,137,274 B2 | 3/2012 | Weng et al. | |
| 8,163,543 B2 | 4/2012 | Urabe et al. | |
| 8,343,067 B2 | 1/2013 | Jones et al. | |
| 8,663,624 B2 | 3/2014 | Schaffer et al. | |
| 8,900,858 B2 | 12/2014 | Trono et al. | |
| 9,193,956 B2 | 11/2015 | Schaffer et al. | |
| 9,198,595 B2 * | 12/2015 | Neitz | A61B 5/0496 |
| 9,233,131 B2 | 1/2016 | Schaffer et al. | |

(Continued)

FOREIGN PATENT DOCUMENTS

| | | |
|---|---|---|
| EP | 0407122 | 1/1991 |
| EP | 2292781 | 3/2011 |

(Continued)

OTHER PUBLICATIONS

Mancuso, et al. (2008) "Colorblindness Cure: Gene Therapy Confers a New Sensation", Investigative Opthamology & Visual Science, 49:3252 (Meeting Abstract).*
Response to request under 27 CFR 1.105, dated Apr. 27, 2015, in U.S. Appl. No. 10/075,415, pp. 8-10 (3 pages long).*
Mancuso, et al. (2007) "Recombinant adeno-associated virus targets passenger gene expression to cones in primate retina", Journal of the Optical Society of America A, 24(5): 1411-16.*
Zhang, et al. (2011) "AAV-mediated Gene Therapy Restores Cone Function in a Rat With an M-cone Opsin Deficiency, A Model for Blue Cone Monochromacy", Investigative Opthamology & Visual Science, ARVO Annual Meeting Abstract, 52:1403.*
Search result 9, run by the STIC search facility, 2016, 2 pages.*
Li, et al. (2008) "Cone-specific expression using a human red opsin promoter in recombinant AAV" Vision Research, 28(3): 332-38.*

(Continued)

*Primary Examiner* — Robert M Kelly
(74) *Attorney, Agent, or Firm* — Cooley LLP

(57) ABSTRACT

The present disclosure provides polynucleotide cassettes, expression vectors and methods for the expression of a gene in cone cells.

26 Claims, 20 Drawing Sheets

(56) References Cited

U.S. PATENT DOCUMENTS

| | | | |
|---|---|---|---|
| 9,441,244 B2 | 9/2016 | Schaffer et al. | |
| 9,457,103 B2 | 10/2016 | Schaffer et al. | |
| 9,458,517 B2 | 10/2016 | Schaffer et al. | |
| 2002/0168342 A1 | 11/2002 | Wang et al. | |
| 2002/0194630 A1 | 12/2002 | Manning, Jr. et al. | |
| 2003/0087889 A1 | 5/2003 | Strong et al. | |
| 2004/0102765 A1 | 5/2004 | Koenig | |
| 2004/0234505 A1 | 11/2004 | Naylor et al. | |
| 2005/0053922 A1 | 3/2005 | Schaffer et al. | |
| 2005/0260203 A1 | 11/2005 | Wiegand et al. | |
| 2006/0128020 A1 | 6/2006 | Calos | |
| 2006/0166363 A1 | 7/2006 | Zolotukhin et al. | |
| 2006/0193830 A1 | 8/2006 | Hauswirth et al. | |
| 2006/0234347 A1 | 10/2006 | Harding et al. | |
| 2007/0188710 A1 | 8/2007 | Helling et al. | |
| 2007/0190028 A1 | 8/2007 | Qu et al. | |
| 2007/0190058 A1 | 8/2007 | Shams | |
| 2008/0152654 A1 | 6/2008 | Reich | |
| 2009/0112201 A1 | 4/2009 | Young | |
| 2009/0128776 A1 | 5/2009 | Keating et al. | |
| 2009/0191588 A1 | 7/2009 | Hermens et al. | |
| 2009/0191597 A1 | 7/2009 | Samulski et al. | |
| 2009/0202490 A1 | 8/2009 | Schaffer et al. | |
| 2009/0203071 A1 | 8/2009 | Chen | |
| 2009/0285826 A1 | 11/2009 | Bonnel et al. | |
| 2010/0008170 A1 | 1/2010 | Sato et al. | |
| 2010/0081707 A1 | 4/2010 | Ali et al. | |
| 2010/0091242 A1 | 4/2010 | Baglini et al. | |
| 2010/0272719 A1 | 10/2010 | Yu | |
| 2010/0297084 A1 | 11/2010 | Bennett et al. | |
| 2011/0001465 A1 | 1/2011 | Sung et al. | |
| 2011/0014655 A1 | 1/2011 | Otte et al. | |
| 2011/0052678 A1 | 3/2011 | Shantha et al. | |
| 2011/0116046 A1 | 5/2011 | Haeri et al. | |
| 2011/0136227 A1 | 6/2011 | Bakker et al. | |
| 2011/0270256 A1 | 11/2011 | Nelson et al. | |
| 2012/0100606 A1 | 4/2012 | Zolotukhin et al. | |
| 2012/0141422 A1 | 6/2012 | Barkats | |
| 2012/0164106 A1 | 6/2012 | Schaffer et al. | |
| 2012/0172419 A1 | 7/2012 | Neitz et al. | |
| 2012/0225930 A1 | 9/2012 | Acland et al. | |
| 2013/0023034 A1 | 1/2013 | Noordman et al. | |
| 2013/0031709 A1 | 2/2013 | Chen et al. | |
| 2013/0317091 A1 | 11/2013 | Ye et al. | |
| 2013/0323302 A1 | 12/2013 | Constable et al. | |
| 2014/0242031 A1 | 8/2014 | Schaffer et al. | |
| 2014/0275231 A1 | 9/2014 | Boye et al. | |
| 2014/0294771 A1 | 10/2014 | Schaffer et al. | |
| 2014/0341977 A1 | 11/2014 | Constable et al. | |
| 2014/0364338 A1 | 12/2014 | Schaffer et al. | |
| 2014/0371438 A1 | 12/2014 | Constable et al. | |
| 2015/0004101 A1 | 1/2015 | Constable et al. | |
| 2015/0079038 A1 | 3/2015 | Deverman et al. | |
| 2015/0111275 A1 | 4/2015 | Palanker et al. | |
| 2015/0118201 A1 | 4/2015 | Xiao et al. | |
| 2015/0132262 A1 | 5/2015 | Schaffer et al. | |
| 2015/0225702 A1 | 8/2015 | Schaffer et al. | |
| 2015/0232953 A1 | 8/2015 | Schaffer et al. | |
| 2015/0025939 A1 | 9/2015 | Chalberg et al. | |
| 2016/0015288 A1 | 1/2016 | Neitz et al. | |
| 2016/0184394 A1 | 6/2016 | Schaffer et al. | |
| 2016/0340393 A1 | 11/2016 | Schaffer et al. | |
| 2016/0375151 A1 | 12/2016 | Schaffer et al. | |
| 2016/0376323 A1 | 12/2016 | Schaffer et al. | |
| 2017/0183647 A1 | 6/2017 | Chavez et al. | |

FOREIGN PATENT DOCUMENTS

| | | |
|---|---|---|
| JP | H11100327 | 4/1999 |
| JP | 2002-539176 A | 11/2002 |
| JP | 2002363107 A | 12/2002 |
| WO | WO 92/08796 | 5/1992 |
| WO | WO 94/28143 | 12/1994 |
| WO | WO 95/22618 | 8/1995 |
| WO | WO 95/26409 | 10/1995 |
| WO | WO 98/13071 | 4/1998 |
| WO | WO 98/51323 | 11/1998 |
| WO | WO 1999/014354 | 3/1999 |
| WO | WO 99/16889 | 4/1999 |
| WO | WO 99/36511 | 7/1999 |
| WO | WO 99/45952 | 9/1999 |
| WO | WO 99/66959 | 12/1999 |
| WO | WO 00/01815 | 1/2000 |
| WO | WO 00/15822 | 3/2000 |
| WO | WO 02/12525 | 2/2002 |
| WO | WO 2002/082904 | 10/2002 |
| WO | WO 2003/080648 A2 | 10/2003 |
| WO | WO 2004/079332 | 9/2004 |
| WO | WO 2005/005610 | 1/2005 |
| WO | WO 2006/110689 A2 | 10/2006 |
| WO | WO 2007/084773 | 7/2007 |
| WO | WO 2007/148971 | 12/2007 |
| WO | WO 2008/142124 | 11/2008 |
| WO | WO 2008/150459 | 12/2008 |
| WO | WO 2009/073551 | 6/2009 |
| WO | WO 2009/104964 | 8/2009 |
| WO | WO 2009/105669 A2 | 8/2009 |
| WO | WO 2010/099960 | 9/2010 |
| WO | WO 2011/020710 | 2/2011 |
| WO | WO 2011/034947 | 3/2011 |
| WO | WO01034947 A2 * | 3/2011 |
| WO | WO 2011/088081 | 7/2011 |
| WO | WO 2011/112089 | 9/2011 |
| WO | WO 2011/122950 | 10/2011 |
| WO | WO 2011/126808 | 10/2011 |
| WO | WO 2011/137344 | 11/2011 |
| WO | WO 2012/068317 A2 | 5/2012 |
| WO | WO 2012/145601 | 10/2012 |
| WO | WO 2013/173129 | 11/2013 |
| WO | WO 2013/188316 | 12/2013 |
| WO | WO 2014/207190 | 12/2014 |
| WO | WO 2015/048534 A1 | 4/2015 |
| WO | WO 2015/134643 | 9/2015 |
| WO | WO 2015/142941 | 9/2015 |
| WO | WO 2016/141078 | 9/2016 |
| WO | WO 2017/112868 A1 | 6/2017 |

OTHER PUBLICATIONS

Yero, et al. (2005) "Immunization of mice with Neisseria meningitides serogroup B genomic expression libraries elicits functional antibodies and reduces the level of bacteremia in an infant rat infection model", Vaccine, 23(7): 932-39.*

Kozak (1986) "Point mutations define a sequence flanking the AUG initiator codon that modulates translation by eukaryotic ribosomes", Cell, 44(2): 283-92 (ABSTRACT ONLY).*

Comparison of L-opsin promoter to SEQ ID No. 80. Printed Feb. 2, 2017, by Examiner Kelly, 4 pages long.*

Acland, et al., "Long-term restoration of rod and cone vision by single dose rAAV mediated gene transfer to the retina in a canine model of childhood blindness." Mol Ther. 2005; 12(6): 1072-1082.

Adamis, et al., "Inhibition of vascular endothelial growth factor prevents retinal ischemia-associated iris neovascularization in a nonhuman primate." Arch Ophthalmol. 1996; 114(1): 66-71.

Adhi, et al., Optical coherence tomography—current and future applications. Curr Opin Ophthalmol. 2013; 24(3): 213-221.

Aiello, et al., "Suppression of retinal neovascularization in vivo by inhibition of vascular endothelial growth factor (VEGF) using soluble VEGF-receptor chimeric proteins." Proc Natl Acad Sci USA. 1995; 92(23):10457-10461.

Akimoto, et al., "Adenovirally expressed basic fibroblast growth factor rescues photoreceptor cells in RCS rats." Invest Ophthalmol Vis Sci. 1999; 40(2): 273-279.

Ali, et al., "Gene therapy for inherited retinal degeneration." Br J Ophthalmol. 1997; 81(9): 795-801.

Amado, et al., "Safety and efficacy of subretinal readministration of a viral vector in large animals to treat congenital blindness." Sci Transl Med. 2010; 2(21): 21ra16. doi: 10.1126/scitranslmed.3000659.

(56) References Cited

OTHER PUBLICATIONS

Anand, et al., "A deviant immune response to viral proteins and transgene product is generated on subretinal administration of adenovirus and adena-associated virus." Mol Ther. 2002; 5(2):125-132.
Arnold, et al., "Extracts from "clinical evidence": age related macular degeneration." BMJ. 2000; 321(7263):741-744.
Auricchio, et al., "Exchange of surface proteins impacts on viral vector cellular specificity and transduction characteristics: the retina as a model." Hum Mol Genet. 2001; 10(26): 3075-3081.
Auricchio, et al., "Inhibition of retinal neovascularization by intraocular viral-mediated delivery of anti-angiogenic agents." Mol Ther. 2002; 6(4): 490-494.
Bailey, et al., "Exercise increases soluble vascular endothelial growth factor receptor-1 (sFlt-1) in circulation of healthy volunteers." Med Sci Monit. 2006; 12(2): CR45-50.
Bainbridge, et al., "Effect of gene therapy on visual function in Leber's congenital amaurosis." N Engl J Med. 2008; 358(21): 2231-2239.
Bainbridge, et al., "Inhibition of retinal neovascularisation by gene transfer of soluble VEGF receptor sFlt-1." Gene Ther. 2002; 9(5): 320-326.
Barleon, et al., "Mapping of the sites for ligand binding and receptor dimerization at the extracellular domain of the vascular endothelial growth factor receptor FLT-1." J Biol Chem. 1997; 272(16):10382-10388.
Barleon, et al., "Soluble VEGFR-1 secreted by endothelial cells and monocytes is present in human serum and plasma from healthy donors." Angiogenesis. 2001; 4(2):143-154.
Belgore, et al., "Plasma levels of vascular endothelial growth factor (VEGF) and its receptor, Flt-1, in haematological cancers: a comparison with breast cancer." Am J Hematol. 2001; 66(1): 59-61.
Bennett, et al., "AAV2 gene therapy readministration in three adults with congenital blindness." Sci Transl Med. 2012; 4(120): 120ra15.
Bennett, et al., "Gene therapy for retinitis pigmentosa." Curr Opin Mol Ther. 2000; 2(4): 420-5.
Bennett, "Immune response following intraocular delivery of recombinant viral vectors." Gene Ther. 2003; 10(11): 977-982.
Bennicelli, et al., "Reversal of blindness in animal models of leber congenital amaurosis using optimized AAV2-mediated gene transfer." Mol Ther. 2008; 16(3): 458-465.
Berge, et al., "Pharmaceutical salts." J Pharm Sci. 1977; 66(1): 1-19.
Bhisitkul, "Vascular endothelial growth factor biology: clinical implications for ocular treatments." Br. J Ophthalmol. 2006; 90(12): 1542-1547.
Brinkmann, et al., "Origin of retinal pigment epithelium cell damage by pulsed laser irradiance in the nanosecond to microsecond time regimen." Laser Surg Med. 2000; 27: 451-464.
Brinkmann, et al., "Selective retina therapy (SRT): a review on methods, techniques, preclinical and first clinical results." Bull Soc Beige Ophtalmol. 2006; 302: 51-69.
Brown, et al., "Ranibizumab versus verteporfin photodynamic therapy for neovascular age-related macular degeneration: Two-year results of the ANCHOR study." Ophthalmology. 2009; 116(1): 57-65.
Campochiaro, et al., "Adenoviral vector-delivered pigment epithelium-derived factor for neovascular age-related macular degeneration: results of a phase I clinical trial." Hum Gene Ther. 2006; 17(2): 167-176.
Campochiaro, et al., "Monitoring ocular drug therapy by analysis of aqueous samples." Opthalmology. 2009; 116(11): 2158-2164.
Campochiaro, "Molecular targets for retinal vascular diseases." J Cell Physiol. 2007; 210(3): 575-581.
Cao, et al., "A subretinal matrigel rat choroidal neovascularization (CNV) model and inhibition of CNV and associated inflammation and fibrosis by VEGF trap." Invest Ophthalmol Vis Sci. 2010; 51(11): 6009-6017.
Cayouette, et al., "Adenovirus-mediated gene transfer of ciliary neurotrophic factor can prevent photoreceptor degeneration in the retinal degeneration (rd) mouse." Hum Gene Ther. 1997; 8(4): 423-430.
Chakrabarti, et al., "Normal T-cell turnover in sooty mangabeys harboring active simian immunodeficiency virus infection." J Virol. 2000; 74(3): 1209-1223.
Chalberg, et al., "φC31 integrase confers genomic integration and long-term transgene expression in rat retina." Invest Ophthalmol Vis Sci. 2005; 46(6): 2140-2146.
Chen, et al., "Use of nepafenac (Nevanac) in combination with intravitreal anti-VEGF agents in the treatment of recalcitrant exudative macular degeneration requiring monthly injections." Clin Ophthalmol. 2010; 4:1249-1252.
Choi, et al., "Production of recombinant adena-associated viral vectors." Curr Protoc Hum Genet. 2007; Chapter 12: Unit 12.9.doi: 10.1002/0471142905.hg1209s53.
Chung, et al., "Angiogenesis in myocardial infarction. An acute or chronic process?" Eur Heart J. 2002; 23(20): 1604-1608.
Cideciyan, et al., "Human RPE65 gene therapy for Leber congenital amaurosis: persistence of early visual improvements and safety at 1 year." Hum Gene Ther. 2009; 20(9): 999-1004.
Clark, et al., "Expression of clusterin/sulfated glycoprotein-2 under conditions of heat stress in rat Sertoli cells and a mouse Sertoli cell line." J Androl. 1997; 18(3): 257-63.
Clinical trial, A Phase I/II Controlled Dose-escalating Trial to Establish the Baseline Safety and Efficacy of a Single SubretinalInjection of rAAV.sFit-1 Into Eyes of Patients With Exudative Age-related Macular Degeneration (AMD). NCT01494805. Dec. 16, 2011.
Clinical trial. Safety and Tolerability Study of AAV2-sFLT-1 in Patients With Neovascular Age-Related Macular Degeneration (AMD). NCT01024998. Last updated: Jan. 28, 2014.
Csermely, et al., "The 90-kDa molecular chaperone family: structure, function, and clinical applications." A comprehensive review. Pharmacol Ther. 1998; 79(2):129-68.
Curtis, et al., "Risks of mortality, myocardial infarction, bleeding, and stroke associated with therapies for age-related macular degeneration." Arch Ophthalmol. 2010; 128(10): 1273-1279.
Dalkara, et al., "In vivo-directed evolution of a new adeno-associated virus for therapeutic outer retinal gene delivery from the vitreous." Sci Transl Med. 2013; 5(189): 189ra76.
Davidson, et al., "A model system for in vivo gene transfer into the central nervous system using an adenoviral vector." Nat Genet. 1993; 3(3): 219-223.
Davis, et al., "Direct gene transfer into skeletal muscle in vivo: factors affecting efficiency of transfer and stability of expression." Hum Gene Ther. 1993; 4(2): 151-159.
Dawson, et al., "Pigment epithelium-derived factor: a potent inhibitor of angiogenesis." Science. 1999; 285(5425):245-248.
De Vries, et al., "The fms-like tyrosine kinase, a receptor for vascular endothelial growth factor." Science. 1992; 255(5047): 989-991.
Dejneka, et al., "Gene therapy and retinitis pigmentosa: advances and future challenges." Bioessays 2001; 23(7): 662-8.
Dejneka, et al., "Gene therapy and animal models for retinal disease." Dev Ophthalmol. 2003; 37: 188-98.
Deonarain, M.P., "Ligand-targeted receptor-mediated vectors for gene delivery", Expert Opinion on Therapeutic Patents. 1998; 8: 53-69.
Diab, et al., "Angiogenic factors for the prediction of pre-eclampsia in women with abnormal midtrimester uterine artery Doppler velocimetry." Int J Gynaecol Obstet. 2008; 102(2):146-151.
Dudus, et al., "Persistent trans gene product in retina, optic nerve and brain after intraocular injection of rAAV." Vision Res. 1999; 39(15): 2545-2553.
Easton, et al., "The Hsp110 and Grp170 stress proteins: newly recognized relatives of the Hsp70s." Cell Stress Chaperones. 2000; 5(4): 276-90.
Edelstein et al., "Gene therapy clinical trials worldwide 1989-2004—an overview", Journal Gene Med. (2004); 6: 597-602.
European Patent Application No. 13791695.3, Extended European Search Report dated Dec. 21, 2015, 10 pages.

(56) References Cited

OTHER PUBLICATIONS

Excoffon, et al., "Directed evolution of adeno-associated virus to an infectious respiratory virus." Proc Natl Acad Sci U S A. 2009; 106(10): 3865-70.
Ferrara, "Vascular endothelial growth factor: basic science and clinical progress." Endocr Rev. 2004; 25(4): 581-611.
Fong, et al., "The use and development ofretroviral vectors to deliver cytokine genes for cancer therapy." Crit Rev Ther Drug Carrier Syst. 2000; 17(1): 1-60.
Fotsis, et al., "The endogenous oestrogen metabolite 2-methoxyoestradiol inhibits angiogenesis and suppresses tumour growth." Nature. 1994; 368(6468): 237-239.
Framme, et al., "Selective targeting of the retinal pigment epithelium in rabbit eyes with a scanning laser beam." Investigative Ophthalmology & Visual Science. 2007; 48(4): 1782-92.
Funk, et al., "Neovascular age-related macular degeneration: intraocular cytokines and growth factors and the influence of therapy with ranibizumab." Ophthalmology. 2009; 116(12): 2393-2399.
Galan, et al., "Association of age-related macular degeneration with polymorphisms in vascular endothelial growth factor and its receptor." Ophthalmology. 2010; 117(9): 1769-1774.
Geller, et al., "An HSV-1 vector expressing tyrosine hydroxylase causes production and release ofL-dopa from cultured rat striatal cells." J Neurochem. 1995; 64(2):487-496.
Geller, et al., "Infection of cultured central nervous system neurons with a defective herpes simplex virus 1 vector results in stable expression of Escherichia coli beta-galactosidase." Proc Natl Acad Sci USA. 1990; 87(3): 1149-1153.
Geller, et al., "Long-term increases in neurotransmitter release from neuronal cells expressing a constitutively active adenylate cyclase from a herpes simplex virus type 1 vector." Proc Natl Acad Sci USA. 1993; 90(16): 7603-7607.
Gerdes, et al., "Cell cycle analysis of a cell proliferation-associated human nuclear antigen defined by the monoclonal antibody Ki-67." J Immunol. 1984; 133(4):1710-1715.
Goldman, et al., "Paracrine expression of a native soluble vascular endothelial growth factor receptor inhibits tumor growth, metastasis, and mortality rate." Proc Natl Acad Sci USA. 1998; 95(15): 8795-8800.
Goverdhana, et al., Regulatable gene expression systems for gene therapy applications: progress and future challenges. Molecular Therapy : The Journal of the American Society of Gene Therapy. 2005; 12(2): 189-211.
Gragoudas, et al., "Pegaptanib for neovascular age-related macular degeneration." N Engl J Med. 2004; 351(27): 2805-2816.
Graubert, et al., "Vascular repair after menstruation involves regulation of vascular endothelial growth factor-receptor phosphorylation by sFLT-1." Am J Pathol. 2001; 158(4): 1399-1410.
Gray and Zolotukhin, "Design and Construction of Functional AAV Vectors." Methods in Molecular Biology. 2011; 807: 25-46.
Hasumi, et al., "Soluble FLT-1 expression suppresses carcinomatous ascites in nude mice bearing ovarian cancer." Cancer Res. 2002; 62(7): 2019-2023.
Hauswirth, et al., "Treatment of leber congenital amaurosis due to RPE65 mutations by ocular subretinal injection of adena-associated virus gene vector: short-term results of a phase I trial." Hum Gene Ther. 2008; 19(10): 979-990.
He, et al., "Alternative splicing of vascular endothelial growth factor (VEGF)-R1 (FLT-1) pre-mRNA is important for the regulation of VEGF activity." Mol Endocrinol. 1999; 13(4): 537-545.
Hoffman, et al., "Cell-mediated immune response and stability of intraocular transgene expression after adenovirus-mediated delivery." Invest Ophthalmol Vis Sci. 1997; 38(11): 2224-2233.
Honda, et al., "Experimental subretinal neovascularization is inhibited by adenovirus-mediated soluble VEGF/flt-1 receptor gene transfection: a role of VEGF and possible treatment for SRN in age-related macular degeneration." Gene Ther. 2000; 7(11): 978-985.
Hu, et al., "Design of retroviral vectors and helper cells for gene therapy." Pharmacol Rev. 2000; 52(4): 493-511.
Huang, et al., "Innate immune recognition of viruses and viral vectors." Hum Gene Ther. 2009; 20(4): 293-301.
Ibrahim, et al., "Heat shock and arsenite induce expression of the nonclassical class I histocompatibility HLA-G gene in tumor cell lines." Cell Stress Chaperones. 2000; 5(3): 207-18.
International Search Report and Written Opinion for International Application No. PCT/US2013/040011, dated Dec. 17, 2013, 57 pages.
International Preliminary Report on Patentability for International Application No. PCT/US2013/040011, dated Nov. 18, 2014, 2013, 48 pages.
International Search Report and Written Opinion for International Application No. PCT/US2013/045043, dated Nov. 12, 2013, 11 pages.
International Preliminary Report on Patentability for International Application No. PCT/US2013/045043, dated Nov. 12, 2013, 11 pages.
International Search Report and Written Opinion for International Application No. PCT/US2015/021087, dated Aug. 12, 2015, 12 pages.
Jacobson, et al., "Gene therapy for leber congenital amaurosis caused by RPE65 mutations: safety and efficacy in 15 children and adults followed up to 3 years." Arch Ophthalmol. 2012;130(1): 9-24.
Jacobson, et al., "Safety in nonhuman primates of ocular AAV2-RPE65, a candidate treatment for blindness in Leber congenital amaurosis." Hum Gene Ther. 2006; 17(8): 845-858.
Jacobson, et al., "Safety of recombinant adena-associated virus type 2-RPE65 vector delivered by ocular subretinal injection", Mol Ther. (2006); 13(6):1074-1084.
Johnson-Saliba and Jans, "Gene Therapy: Optimising DNA Delivery to the Nucleus", Curr. Drug. Targets 2001; 2(4): 371-399.
Kaplitt, et al., "Long-term gene expression and phenotypic correction using adenoassociated virus vectors in the mammalian brain." Nat Genet. 1994; 8(2):148-154.
Kendall, et al., "Identification of a natural soluble form of the vascular endothelial growth factor receptor, FLT-1, and its heterodimerization with KDR." Biochem Biophys Res Commun. 1996; 226(2): 324-328.
Kendall, et al., "Inhibition of vascular endothelial cell growth factor activity by an endogenously encoded soluble receptor." Proc Natl Acad Sci USA. 1993; 90(22):10705-10709.
Khaliq, et al., "Increased expression of placenta growth factor in proliferative diabetic retinopathy." Lab Invest. 1998; 78(1): 109-116.
Khani, et al., "AAV-mediated expression targeting of rod and cone photoreceptors with a human rhodopsin kinase promoter." Investigative Ophthalmology & Visual Science. 2007; 48(9): 3954-61.
Kiang, et al., "Cytoprotection and regulation of heat shock proteins induced by heat shock in human breast cancer T47-D cells: role of [Ca2+]i and protein kinases." FASEB J. 1998; 12(14): 1571-9.
Klein, et al., "Fifteen-year cumulative incidence of age-related macular degeneration: the Beaver Dam Eye Study." Ophthalmology. 2007; 114(2): 253-262.
Klein, et al., "The relation of cardiovascular disease and its risk factors to the 5-year incidence of age-related maculopathy: the Beaver Dam Eye Study." Ophthalmology. 1997; 104(11): 1804-1812.
Kliffen, et al., "Increased expression of angiogenic growth factors in age-related maculopathy." Br J Ophthalmol. 1997; 81(2): 154-162.
Klimczak, et al., "A novel adeno-associated viral variant for efficient and selective intravitreal transduction of rat Müller cells." PLoS One. 2009; 4(10): e7467.
Komaromy, et al., "Targeting gene expression to cones with human cone opsin promoters in recombinant AAV." Gene Ther. 2008; 15(14): 1049-55.
Kong, et al., "Regional suppression of tumor growth by in vivo transfer of a cDNA encoding a secreted form of the extracellular domain of the flt-1 vascular endothelial growth factor receptor." Hum Gene Ther. 1998; 9(6): 823-833.

(56) References Cited

OTHER PUBLICATIONS

Krysiak, et al., "Soluble vascular endothelial growth factor receptor-1 (sFLT-1) mediates downregulation of FLT-1 and prevents activated neutrophils from women with preeclampsia from additional migration by VEGF." Circ Res. 2005; 97(12): 1253-1261.
Krzystolik, et al., "Prevention of experimental choroidal neovascularization with intravitreal anti-vascular endothelial growth factor antibody fragment." Arch Ophthalmol. 2002; 120(3):338-346.
Kvanta, et al., "Subfoveal fibrovascular membranes in age-related macular degeneration express vascular endothelial growth factor." Invest Ophthalmol Vis Sci. 1996; 37(9): 1929-1934.
Kwak, et al., "VEGF is major stimulator in model of choroidal neovascularization." Invest Ophthalmol Vis Sci. 2000; 41(10): 3158-3164.
Lai, et al., "Generation of transgenic mice with mild and severe retinal neovascularisation." Br J Ophthalmol. 2005; 89(7): 911-916.
Lai, et al., "Inhibition of angiogenesis by adenovirus-mediated sFlt-1 expression in a rat model of corneal neovascularization." Hum Gene Ther. 2001; 12(10): 1299-1310.
Lai, et al., "Long-term Evaluation of AAV-Mediated sFlt-1 Gene Therapy for Ocular Neovascularization in Mice and Monkeys." Mol Ther. 2005; 12(4): 659-668.
Lai, et al., "Potential long-term inhibition of ocular neovascularisation by recombinant adena-associated virus-mediated secretion gene therapy." Gene Ther. 2002; 9(12): 804-813.
Lai, et al., "Preclinical safety evaluation of subretinal AAV2.sFlt-1 in non-human primates." Gene Ther. 2012; 19(10): 999-1009.
Lai, et al., "rAAV.sFlt-1 Gene Therapy Achieves Lasting Reversal of Retinal Neovascularization in the Absence of a Strong Immune Response to the Viral Vector." Invest Ophthalmol Vis Sci. 2009; 50(9): 4279-4287.
Lai, et al., "Recombinant adena-associated virus type 2-mediated gene delivery into the Rpe65-/- knockout mouse eye results in limited rescue." Genet Vaccines Ther. 2004; 2:3, 15 pages.
Lalwani, et al., "A variable-dosing regimen with intravitreal ranibizumab for neovascular age-related macular degeneration: year 2 of the PrONTO Study." Am J Ophthalmol. 2009; 148(1): 43-58.
Lavinksy, D. et al., "Modulation of transgene expression in retinal gene therapy by selective laser treatment." Investigative Ophthalmology & Visual Science. 2013; 54(3): 1873-1880.
Le Gal La Salle, et al., "An adenovirus vector for gene transfer into neurons and glia in the brain." Science. 1993; 259(5097): 988-990.
Le Meur, et al., "Postsurgical assessment and long-term safety of recombinant adeno-associated virus-mediated gene transfer into the retinas of dogs and primates." Arch Ophthalmol. 2005; 123(4): 500-506.
Le Meur, et al., "Restoration of vision in RPE65-deficient Briard dogs using an AAV serotype 4 vector that specifically targets the retinal pigmented epithelium." Gene Ther. 2007; 14(4): 292-303.
Lebherz, et al., "Novel AAV serotypes for improved ocular gene transfer." J Gene Med. 2008; 10(4): 375-382.
Levine, et al., "Circulating angiogenic factors and the risk of preeclampsia." N Engl J Med. 2004; 350(7): 672-683.
Li, et al., "Cone-specific expression using a human red opsin promoter in recombinant AAV." Vision Res. 2008; 48(3): 332-8.
Li, et al., "Gene therapy following subretinal AAV5 vector delivery is not affected by a previous intravitreal AAV5 vector administration in the partner eye." Mol Vis. 2009; 15: 267-275.
Li, et al., "Intraocular route of AAV2 vector administration defines humoral immune response and therapeutic potential." Mol Vis. 2008; 14: 1760-1769.
Lieber, et al., "Integrating adenovirus-adena-associated virus hybrid vectors devoid of all viral genes." J Virol. 1999; 73(11): 9314-9324.
Liu, et al., "Gene therapy for ocular diseases." Br J Ophthalmol. 2011; 95(5): 604-612.
Liu, et al., "Soluble Fms-like tyrosine kinase-1 expression inhibits the growth of multiple myeloma in nude mice." Acta Biochim Biophys Sin (Shanghai). 2007; 39(7): 499-506.

Lopez, et al., "Transdifferentiated retinal pigment epithelial cells are immunoreactive for vascular endothelial growth factor in surgically excised age-related macular degeneration-related choroidal neovascular membranes." Invest Ophthalmol Vis Sci. 1996; 37(5): 855-868.
Lukason, et al., "Inhibition of choroidal neovascularization in a nonhuman primate model by intravitreal administration of an AAV2 vector expressing a novel anti-VEGF molecule." Mol Ther. 2011; 19(2): 260-265.
Lundstrom, "Alphavirus vectors: applications for DNA vaccine production and gene expression." Intervirology. 2000; 43(4-6): 247-257.
Luo and Saltzman, "Synthetic DNA delivery systems", Nature Biotechnol. 2000; 18(1): 33-37.
Luthert, et al., "Photoreceptor rescue." Eye (Lond). 1998; 12(Pt 3b): 591-596.
Maclachlan, et al., "Preclinical safety evaluation of AAV2-sFLTOI—a gene therapy for age-related macular degeneration." Mol Ther. 2010; 19(2): 326-34.
Maclachlan, et al., "Preclinical safety evaluation of AAV2-sFLT01—a gene therapy for age-related macular degeneration." Mol Ther. 2011; 19(2): 326-334.
Mae, et al., "Gene transfer of the vascular endothelial growth factor receptor flt-1 suppresses pulmonary metastasis associated with lung growth." Am J Respir Cell Mol Biol. 2005; 33(6): 629-635.
Maguire, et al., "Age-dependent effects of RPE65 gene therapy for Leber's congenital amaurosis: a phase 1 dose-escalation trial." Lancet. 2009; 374(9701): 1597-1605.
Maguire, et al., "Safety and efficacy of gene transfer for Leber's congenital amaurosis." N Engl J Med. 2008; 358(21): 2240-8.
Maguire, et al., "Safety and efficacy of gene transfer for Leber's congenital amaurosis." N Engl J Med. 2008; 358(21): 2240-2248.
Mahasreshti, et al., "Adenovirus-mediated soluble FLT-1 gene therapy for ovarian carcinoma." Clin Cancer Res. 2001; 7(7): 2057-2066.
Mahasreshti, et al., "Intravenous delivery of adenovirus-mediated soluble FLT-1 results in liver toxicity." Clin Cancer Res. 2003; 9(7): 2701-2710.
Malamos, et al., "Correlation of high-definition optical coherence tomography and fluorescein angiography imaging in neovascular macular degeneration." Invest. Ophthalmol Vis Sci. 2009; 50(10): 4926-4933.
Manno, et al., "Successful transduction of liver in hemophilia by AAV-Factor IX and limitations imposed by the host immune response." Nat Med. 2006; 12(3): 342-347.
Martin et al., "Gene delivery to the eye using adeno-associated viral vectors", Methods. 2002; 28: 267-275.
Maynard, et al., "Excess placental soluble fms-like tyrosine kinase 1 (sFlt1) may contribute to endothelial dysfunction, hypertension, and proteinuria in preeclampsia." J Clin Invest. 2003; 111(5): 649-658.
Merigan, et al., "Tracking Transfection of Macaque Retinal Ganglion Cells With AAV2 Viral Vectors; in vivo Imaging Reveals Differences Between Two Promoters." Investigative Ophthalmology & Visual Science. 2008; vol. 49: 4514.
Michel, et al., "Stress-induced transcription of the clusterin/apoJ gene." Biochem J. 1997; 328 ( Pt 1): 45-50.
Miller, et al., "Human effector and memory CD8+ T cell responses to smallpox and yellow fever vaccines." Immunity. 2008; 28(5): 710-722.
Mitchell, et al., "Cost effectiveness of treatments for wet age-related macular degeneration." PharmacoEconomics 2011; 29(2): 107-31.
Mitchell, et al., "Ranibizumab (Lucentis) in neovascular age-related macular degeneration: evidence from clinical trials." Br J Ophthalmol. 2010; 94(1): 2-13.
Miyamoto, et al., "Prevention of leukostasis and vascular leakage in streptozotocininduced diabetic retinopathy via intercellular adhesion molecule-1 inhibition." Proc Natl Acad Sci USA. 1999; 96(19): 10836-10841.
Miyoshi, et al., "Development of a self-inactivating lentivirus vector." J Virol. 1998; 72(10): 8150-8157.

(56) References Cited

OTHER PUBLICATIONS

Narfstrom, et al., "Assessment of structure and function over a 3-year period after gene transfer in RPE65−/− dogs." Doc Ophthalmol. 2005; 111(1): 39-48.

Narfstrom, et al., "Functional and structural recovery of the retina after gene therapy in the RPE65 null mutation dog." Invest Ophthalmol Vis Sci. 2003; 44(4):1663-1672.

Narfstrom, et al., "In vivo gene therapy in young and adult RPE65−/− dogs produces long-term visual improvement." J Hered. 2003; 94(1): 31-37.

Nathans, et al., "Molecular genetics of human blue cone monochromacy." Science. 1989; 245(4920): 831-8.

Nemerow, "A new link between virus cell entry and inflammation: adenovirus interaction with integrins induces specific pro inflammatory responses." Mol Ther. 2009; 17(9): 1490-1491.

Neufeld, et al., "Vascular endothelial growth factor (VEGF) and its receptors." FASEB J. 1999; 13(1): 9-22.

Niederkorn, et al., "See no evil, hear no evil, do no evil: the lessons of immune privilege." Nat Immunol. 2006; 7(4): 354-359.

Ohno-Matsui, et al., "Novel mechanism for age-related macular degeneration: an equilibrium shift between the angiogenesis factors VEGF and PEDF." J Cell Physiol. 2001; 189(3): 323-333.

Oikawa, et al., "Three novel synthetic retinoids, Re 80, Am 580 and Am 80, all exhibit anti-angiogenic activity in vivo." Eur J Pharmacol. 1993; 249(1): 113-116.

Palu et al., "In pursuit of new developments for gene therapy of human diseases", J. of Biotechnology. 1999; 68: 1-13.

Park, et al., "The fourth immunoglobulin-like loop in the extracellular domain of FLT-1, a VEGF receptor, includes a major heparin-binding site." Biochem Biophys Res. Commun. 1999; 264(3): 730-734.

Paulus, et al., "Selective retinal therapy with microsecond exposures using a continuous line scanning laser." Retina. 2011; 31(2): 380-8.

Pechan, et al., "Novel anti-VEGF chimeric molecules delivered by AAV vectors for inhibition of retinal neovascularization", Gene Ther. (2009); 16(1): 10-16.

Perri, et al., "Replicon vectors derived from Sindbis virus and Semliki forest virus that establish persistent replication in host cells." J Virol. 2000; 74(20): 9802-9807.

Pfeifer and Verma, "Gene Therapy: Promises and Problems", Annu. Rev. Genomics. Hum. Genet. 2001; 2: 177-211.

Pieramici, et al., "Age-related macular degeneration and risk factors for the development of choroidal neovascularization in the fellow eye." Curr Opin Ophthalmol. 1998; 9(3): 38-46.

Pitcher, et al., "Development and homeostasis of T cell memory in rhesus macaque." J Immunol. 2002; 168(1): 29-43.

Pollock, et al, "Delivery of a stringent dimerizer-regulated gene expression system in a single retroviral vector." Proceedings of the National Academy of Sciences of the United States of America. 2000; 97(24): 13221-6.

Provost, et al., "Biodistribution of rAAV vectors following intraocular administration: evidence for the presence and persistence of vector DNA in the optic nerve and in the brain." Mol Ther. 2005; 11(2): 275-83.

Pshenichkin, et al., "Heat shock enhances CMV-IE promoter-driven metabotropic glutamate receptor expression and toxicity in transfected cells." Neuropharmacology. 2011; 60: 1292-1300.

Quantin, et al., "Adenovirus as an expression vector in muscle cells in vivo." Proc Natl Acad Sci USA. 1992; 89(7): 2581-2584.

Regeneron press release, Bayer and Regeneron Report Positive Top-Line Results of Two Phase 3 Studies with VEGF Trap-Eye in Wet Age-related Macular Degeneration. Nov. 22, 2010. http://newsroom.regeneron.com/releasedetail.cfm?ReleaseiD=532099 (last accessed Nov. 24, 2010).

Regillo, et al., "Randomized, double-masked, sham-controlled trial of ranibizumab for neovascular age-related macular degeneration: PIER Study year 1." Am J Ophthalmol. 2008; 145(2): 239-248.

Rein, et al., "Forecasting age-related macular degeneration through the year 2050: the potential impact of new treatments." Arch Ophthalmol. 2009; 127(4): 533-540.

Roberts, et al., "Pathogenesis and genetics of pre-eclampsia." Lancet. 2001; 357(9249): 53-56.

Robinson, et al., "The splice variants of vascular endothelial growth factor (VEGF) and their receptors." J Cell Sci. 2001; 114(Pt 5): 853-865.

Rolling, et al., "Long-term real-time monitoring of adena-associated virus-mediated gene expression in the rat retina." Clin Experiment Ophthalmol. 2000; 28(5): 382-386.

Romano, et al., "Latest developments in gene transfer technology: achievements, perspectives, and controversies over therapeutic applications." Stem Cells. 2000; 18(1): 19-39.

Rosenfeld, et al., "In vivo transfer of the human cystic fibrosis transmembrane conductance regulator gene to the airway epithelium." Cell. 1992; 68(1): 143-155.

Rosenfeld, et al., "Ranibizumab for neovascular age-related macular degeneration." N Engl J Med. 2006; 355(14): 1419-1431.

Saishin, et al., "VEGF-TRAP(R1R2) suppresses choroidal neovascularization and VEGF-induced breakdown of the blood-retinal barrier." J Cell Physiol. 2003; 195(2): 241-248.

Salam, et al., "Treatment of proliferative diabetic retinopathy with anti-VEGF agents." Acta Ophthalmol. 2011; 89(5): 405-411.

Schmidt-Erfurth, "Clinical safety of ranibizumab in age-related macular degeneration." Expert Opin Drug Saf. 2010;9(1):149-165.

Schmidt-Erfurth, et al., "Efficacy and safety of monthly versus quarterly ranibizumab treatment in neovascular age-related macular degeneration: the EXCITE study." Ophthalmology. 2011; 118(5): 831-839.

Schuele, et al., "RPE damage thresholds and mechanisms for laser exposure in the microsecond-to-millisecond time regimen." Invest Ophthalmol Vis Sci. 2005; 46: 714-719.

Schwartz, et al., "Embryonic stem cell trials for macular degeneration: a preliminary report." Lancet. 2012; 379(9817): 713-720.

Seddon, et al., "Validation of a prediction algorithm for progression to advanced macular degeneration subtypes." JAMA Ophthalmol. 2013; 131(4): 448-455.

Shah et al., "Outcomes and risk factors associated with endophthalmitis after intravitreal injection of anti-vascular endothelial growth factor agents." Jefferson Digital Commons. 2011; pp. 1-14.

Sheridan, C., "Gene therapy finds its niche." Nat Biotechnol. 2011; 29(2): 121-8.

Shiose, et al., "Gene transfer of a soluble receptor of VEGF inhibits the growth of experimental eyelid malignant melanoma" Invest Ophthalmol Vis Sci. 2000; 41(9): 2395-2403.

Shoji and Nakashima, "Current Status of Delivery Systems to Improve Target Efficacy of Oligonu-cleotides", Current Pharmaceutical Design. (2004); 10(7): 785-796.

Silva, et al., "Age-related macular degeneration and risk factors for the development of choroidal neovascularisation in the fellow eye: a 3-year follow-up study." Ophthalmologica. 2011; 226(3): 110-118.

Simonelli, et al., "Gene therapy for Leber's congenital amaurosis is safe and effective through 1.5 years after vector administration." Mol Ther. 2010; 18(3): 643-650.

Sramek, C. et al., "Non-damaging retinal phototherapy: Dynamic range of heat shock protein expression." Investigative Ophthalmology & Visual Science. 2011; 52(3):1780-1787.

Stefansson, et al., "Metabolic physiology in age related macular degeneration." Prog Retin Eye Res. 2011; 30(1): 72-80.

Stellmach, et al., "Prevention of ischemia-induced retinopathy by the natural ocular antiangiogenic agent pigment epithelium-derived factor." Proc Natl Acad Sci USA. 2001; 98(5): 2593-2597.

Stieger, et al., "In vivo gene regulation using tetracycline-regulatable systems." Advanced Drug Delivery Reviews. 2009; 61(7-8): 527-41.

Stout, et al., "Surgical approaches to gene and stem cell therapy for retinal disease." Hum Gene Ther. 2011; 22(5): 531-535.

Stratford-Perricaudet, et al., "Widespread long-term gene transfer to mouse skeletal muscles and heart." J Clin Invest. 1992; 90(2): 626-630.

(56) References Cited

OTHER PUBLICATIONS

Streilein, et al., "Immunobiology and privilege of neuronal retina and pigment epithelium transplants." Vision Res. 2002; 42(4): 487-495.
Szewczenko-Pawlikowski, et al., "Heat shock-regulated expression of calreticulin in retinal pigment epithelium." Mol Cell Biochem. 1997; 177(1-2): 145-52.
Takayama, et al., "Suppression of tumor angiogenesis and growth by gene transfer of a soluble form of vascular endothelial growth factor receptor into a remote organ." Cancer Res. 2000; 60(8): 2169-2177.
Tolentino, et al., "Vascular endothelial growth factor is sufficient to produce iris neovascularization and neovascular glaucoma in a nonhuman primate." Arch Ophthalmol. 1996; 114(8): 964-670.
Urabe, et al., "Insect cells as a factory to produce adena-associated virus type 2 vectors." Hum Gene Ther. 2002; 13(16): 1935-1943.
US National Health Institute: "Safety and Efficacy Study of rAAV.sFlt-1 in Patients With Exudative Age-Related Macular Degeneration", NCT01494805, Clinical Trials, Updated Dec. 16, 2011; XP002751808, Retrieved from the Internet: URL:https:jjclinicaltrials.govjarchivejNCT01494805/2011_12_16 [retrieved on-Dec. 4, 2015].
US National Institute of Health: "Safety and Tolerability Study of AAV2-sFLT01 in Patients With Neovascular Age-Related Macular Degeneration (AMD)", NCT01024998, Clinical Trials, Updated Aug. 13, 2012; XP002751809, Retrieved from the Internet: URL:https:jjclinicaltrials.govjarchive/NCT01024998/2012_04_13 [retrieved on-Dec. 4, 2012].
Verma and Somia, "Gene therapy—promises, problems and prospects", Nature 1997; 389: 239-242.
Viard, et al., "Clusterin gene expression mediates resistance to apoptotic cell death induced by heat shock and oxidative stress." J Invest Dermatol. 1999; 112(3): 290-6.
Vigna, et al., "Lentiviral vectors: excellent tools for experimental gene transfer and promising candidates for gene therapy." J Gene Med. 2000; 2(5): 308-316.
Wada, et al., "Expression of vascular endothelial growth factor and its receptor (KDR/flk-1) mRNA in experimental choroidal neovascularization." Curr Eye Res. 1999; 18(3): 203-213.
Wang, et al., "A locus control region adjacent to the human red and green visual pigment genes." Neuron. 1992; 9(3): 429-40.
Wang, et al., "Spatiotemporal control of gene expression by a light-switchable transgene system." Nature Methods. 2012;9(3): 266-9.
Wells, et al., "Levels of vascular endothelial growth factor are elevated in the vitreous of patients with subretinal neovascularisation." Br J Ophthalmol. 1996; 80(4): 363-366.
Wenkel, et al., "Analysis of immune deviation elicited by antigens injected into the subretinal space." Invest Ophthalmol Vis Sci. 1998; 39(10): 1823-1834.
Wenkel, et al., "Evidence that retinal pigment epithelium functions as an immune-privileged tissue." Invest Ophthalmol Vis Sci. 2000; 41(11): 3467-73.
Wiesmann, et al., "Crystal structure at 1.7 A resolution of VEGF in complex with domain 2 of the Flt-1 receptor." Cell. 1997; 91(5):695-704.
Wolf, et al., "Preeclampsia and future cardiovascular disease: potential role of altered angiogenesis and insulin resistance." J Clin Endocrinol Metab. 2004; 89(12): 6239-6243.
Wong, et al., "Intravitreal VEGF and bFGF produce florid retinal neovascularization and hemorrhage in the rabbit." Curr Eye Res. 2001; 22(2): 140-147.
Wu, et al., "Self-complementary recombinant adeno-associated viral vectors: packaging capacity and the role of rep proteins in vector purity." Hum Gene Ther. 2007; 18(2): 171-82.
Wulff, et al., "Luteal angiogenesis: prevention and intervention by treatment with vascular endothelial growth factor trap(A40)." J Clin Endocrinol Metab. 2001; 86(7): 3377-3386.
Wykoff, et al., "Perioperative management of patients with reproted povidone-iodine or penicillin/cephalosporin allergies." Presented at the Annual Meeting for the Association for Research in Vision and Opthalmology. Fort Lauderdale, Fl. May 5, 2011; Abstract No. 6416/D880.
Xiao, et al., "Production of high-titer recombinant adena-associated virus vectors in the absence of helper adenovirus." J. Virol. 1998; 72(3): 2224-2232.
Yang, et al., "Cellular and humoral immune responses to viral antigens create barriers to lung-directed gene therapy with recombinant adenoviruses." J Virol. 1995; 69(4): 2004-2015.
Ye, et al., "sFlt-1 gene therapy of follicular thyroid carcinoma." Endocrinology. 2004; 145(2): 817-822.
Yin, et al., "Intravitreal injection of AAV2 transduces macaque inner retina." Invest Ophthalmol Vis Sci. 2011; 52(5): 2775-83.
Zhang, et al., "Suppression of tumor growth by oncolytic adenovirus-mediated delivery of an antiangiogenic gene, soluble Flt-1." Mol Ther. 2005; 11(4): 553-562.
Zheng, et al., "Genomic integration and gene expression by a modified adenoviral vector." Nat Biotechnol. 2000; 18(2): 176-180.
Aflibercept FDA Entry and Label, 2015. 28 pages. downloaded from http://www.accessdata.fda.gov/scripts/cder/drugsatfda/index.cfm?fuseaction=Search.Labei_ApprovaiHistory#apphist.
Alexander, John J., et al. "Restoration of cone vision in a mouse model of achromatopsia." Nature Medicine (2007); 13.6: 685-687.
Bainbridge, J. W., and Ali, R. R. "The eyes have it! Ocular gene therapy trials for LCA look promising." Gene Ther (2008); 15: 1191-1192.
Büning, Hildegard, et al. "Recent developments in adeno-associated virus vector technology." The Journal of Gene Medicine (2008); 10.7: 717-733.
Cai, Xue, et al. "Gene delivery to mitotic and postmitotic photoreceptors via compacted DNA nanoparticles results in improved phenotype in a mouse model of retinitis pigmentosa." The FASEB Journal (2010); 24.4: 1178-1191.
Campochiaro, "Gene Transfer for Neovascular Age-Related Macular Degeneration." Human Gene Therapy (2011); 22(5): 523-529.
Chiu, M. I., and Nathans, J. "Blue cones and cone bipolar cells share transcriptional specificity as determined by expression of human blue visual pigment-derived transgenes." The Journal of Neuroscience (1994); 14.6: 3426-3436.
Cideciyan, Artur V., et al. "Human gene therapy for RPE65 isomerase deficiency activates the retinoid cycle of vision but with slow rod kinetics." Proceedings of the National Academy of Sciences (2008); 105.39: 15112-15117.
Devalois, R.L. And Devalois, K.K. "A multi-stage color model." Vision Research (1993); 33.8: 1053-1065.
Glushakova, Lyudmyla G., et al. "Human blue-opsin promoter preferentially targets reporter gene expression to rat s-cone photoreceptors." Investigative Ophthalmology & Visual Science (2006); 47.8: 3505-3513.
Gunther, Karen L., et al. "A novel mutation in the short-wavelength-sensitive cone pigment gene associated with a tritan color vision defect." Visual Neuroscience (2006); 23.3-4: 403-409.
International Preliminary Report on Patentability for International Application No. PCT/US2015/021087, dated Sep. 20, 2016, 8 pages.
International Search Report and Written Opinion for International Application No. PCT/US2016/020482, dated Aug. 8, 2016, 12 pages.
International Search Report and Written Opinion for International Application No. PCT/US2010/048964, dated Jun. 17, 2011, 23 pages.
International Preliminary Report on Patentability for International Application No. PCT/US2010/048964, dated Mar. 20, 2012, 14 pages.
Jacobs, Gerald H. "A perspective on color vision in platyrrhine monkeys." Vision Research (1998); 38.21: 3307-3313.
Jacobs, Gerald H., et al. "Emergence of novel color vision in mice engineered to express a human cone photopigment." Science (2007); 315.5819: 1723-1725.

(56) References Cited

OTHER PUBLICATIONS

Ueyama, Hisao, et al. "Analysis of introns and promoters of L/M visual pigment genes in relation to deutan color-vision deficiency with an array of normal gene orders." Journal of Human Genetics (2009); 54.9: 525-530.
Komáromy, András M., et al. "Gene therapy rescues cone function in congenital achromatopsia." Human Molecular Genetics (2010): ddq136., 13 pages.
Kuchenbecker, James A., et al. "Topography of the long-to middle-wavelength sensitive cone ratio in the human retina assessed with a wide-field color multifocal electroretinogram." Visual Neuroscience (2008); 25.03: 301-306.
Lai, Timothy YY, et al. "The clinical applications of multifocal electroretinography: a systematic review." Survey of Ophthalmology (2007); 52.1: 61-96.
Lindenberg, Thomas, et al. "Cyclic summation versus m-sequence technique in the multifocal ERG." Graefe's Archive for Clinical and Experimental Ophthalmology (2003); 241.6: 505-510.
Makous, Walter. "Comment on "emergence of novel color vision in mice engineered to express a human cone photopigment"." Science (2007); 318.5848: 196b-196b.
Mancuso, K., et al. "Progress in Developing a Gene Therapy Approach for Treating Color Blindness." Investigative Ophthalmology & Visual Science 46.13 (2005): 4565-4565 & 2005 Annual Meeting of the Association for Research in Vision and Ophthalmology, FL. Lauderdale, FL, 46(Supp 5): 4565 (2005).
Mancuso, Katherine, et al. "Gene therapy for red-green colour blindness in adult primates." Nature (2009); 461.7265: 784-787.
Mancuso, Katherine, et al. "An adaptation of the Cambridge Colour Test for use with animals." Visual Neuroscience (2006); 23.3-4: 695-701.
Mauck, Matthew C., et al. "Longitudinal evaluation of expression of virally delivered transgenes in gerbil cone photoreceptors." Visual Neuroscience (2008); 25.3: 273.
Mauck, M. C., et al. "Longitudinal in vivo Characterization of Expression of Viral Delivered Genes for L-opsin and Green Fluorescent Protein in Cone Photoreceptors of Gerbils." Investigative Ophthalmology & Visual Science (2006); 47.13: 4071-4071.
Nathans, Jeremy, et al. "Molecular genetics of inherited variation in human color vision." Science (1986); 232.4747: 203-210.
Nathans, J., et al. "Molecular genetics of human color vision: the genes encoding blue, green, and red pigments." Science (1986); 232(4747): 193-202.
Neitz, Maureen, et al. "Spectral tuning of pigments underlying red-green color vision." Science (1991); 252.5008: 971-974.
Pang, Ji-jing, et al. "Gene therapy restores vision-dependent behavior as well as retinal structure and function in a mouse model of RPE65 Leber congenital amaurosis." Molecular Therapy (2006); 13.3: 565-572.
Papadakis et al. "Promoters and Control Elements: Designing Expression Cassettes for Gene Therapy." Current Gene Therapy (2004); 4(1): 89-113.
Reffin, J. P., S. Astell, and J. D. Mollon. "Trials of a computer-controlled colour vision test that preserves the advantages of pseudoisochromatic plates." Colour Vision Deficiencies X. Springer Netherlands (1991); pp. 69-76.
Regan, Benedict C., et al. "Luminance noise and the rapid determination of discrimination ellipses in colour deficiency." Vision Research (1994); 34.10: 1279-1299.
Rome, C., et al., "Spatial and temporal control of expression of therapeutic genes using heat shock protein promoters." Methods (2005); 35.2: 188-198.
Shaaban, Salam A., et al. "Transgenic mice expressing a functional human photopigment." Investigative Ophthalmology & Visual Science (1998); 39.6: 1036-1043.
Shapley, Robert. "Specificity of cone connections in the retina and color vision. Focus on "specificity of cone inputs to macaque retinal ganglion cells"." Journal of Neurophysiology (2006); 95.2: 587-588.
Sutter, Erich E. "The fast m-transform: a fast computation of cross-correlations with binary m-sequences." SIAM Journal on Computing (1991); 20.4: 686-694.
Swanson, William H., et al. "Temporal modulation sensitivity and pulse-detection thresholds for chromatic and luminance perturbations." JOSA A (1987); 4.10: 1992-2005.
Wiesel, Torsten N., and Hubel, David H. "Single-cell responses in striate cortex of kittens deprived of vision in one eye." J Neurophysiol (1963); 26.6: 1003-1017.
Ye, Guo-jie, et al. "Development and Evaluation of Cone-Specific Promoters in Non-human Primates for Gene Therapy of Congenital Cone Diseases Including Achromatopsia." Investigative Ophthalmology & Visual Science (2014); 55.13: 837-837.
Search Report (English translation) in Chinese Application No. 2013800375773, dated Nov. 24, 2016, 2 pages.
U.S. Appl. No. 14/444,347, filed Jul. 28, 2014, Schaffer et al.
U.S. Appl. No. 14/444,375, filed Jul. 28, 2014, Schaffer et al.
U.S. Appl. No. 14/606,543, filed Jan. 27, 2015, Schaffer et al.
U.S. Appl. No. 14/938,154, filed Nov. 11, 2015, Schaffer et al.
U.S. Appl. No. 15/229,699, filed Aug. 5, 2016, Schaffer et al.
U.S. Appl. No. 15/244,884, filed Aug. 23, 2016, Schaffer et al.
U.S. Appl. No. 15/244,892, filed Aug. 23, 2016, Schaffer et al.
Albert, Henrik, et al. "Site-specific integration of DNA into wild-type and mutant lox sites placed in the plant genome." The Plant Journal (1995); 7.4: 649-659.
Belteki, Gusztav, et al. "Site-specific cassette exchange and germline transmission with mouse ES cells expressing φC31 integrase." Nature Biotechnology (2003); 21.3: 321-324.
Bethke, Bruce, and Sauer, Brian. "Segmental genomic replacement by Cre-mediated recombination: genotoxic stress activation of the p53 promoter in single-copy transformants." Nucleic Acids Research (1997); 25.14: 2828-2834.
Bi, Yanzhen, et al. "Pseudo attP sites in favor of transgene integration and expression in cultured porcine cells identified by streptomyces phage phiC31 integrase." BMC Molecular Biology (2013); 14: 20, 12 pages.
Calcedo, Roberto, et al. "Worldwide epidemiology of neutralizing antibodies to adeno-associated viruses." Journal of Infectious Diseases (2009); 199.3: 381-390.
Calos, Michele P. "The φC31 Integrase System for Gene Therapy." Current Gene Therapy (2006); 6.6: 633-645.
Chalberg, Thomas W., et al. "Integration specificity of phage φC31 integrase in the human genome." Journal of Molecular Biology (2006); 357.1: 28-48.
Chalberg, Thomas W., et al. "φC31 integrase confers genomic integration and long-term transgene expression in rat retina." Investigative Ophthalmology & Visual Science (2005); 46.6: 2140-2146.
Dalkara, Deniz, et al. "In vivo—directed evolution of a new adeno-associated virus for therapeufic outer refinal gene delivery from the vitreous." Science Translational Medicine (2013); 5.189: 189ra76-189ra76.
Dull, et al., "A third-generation lentivirus vector with a conditional packaging system." Journal of Virology (1998),72(11):8463-8671.
GenBank [online], Accession No. U47119.2, "Cloning vector pCI, mammalian expression vector." May 10, 2004-uploaded, [retrieved on Apr. 12, 2017], https://wm.ncbi.nlm.nih.gov/nuccore/U47119, 2 pages.
Groth, Amy C., et al. "A phage integrase directs efficient site-specific integration in human cells." Proc Natl Acad Sci U S A. (2000); 97.11: 5995-6000.
Heinis, Christian, and Johnsson, Kai. "Using peptide loop insertion mutagenesis for the evolution of proteins." Methods Mol Biol. (2010); 634: 217-232.
Hoess, R.H. et al. "The role of the loxP spacer region in P1 site-specific recombination." Nucleic Acids Research (1986); 14.5: 2287-2300.
International Search Report and Written Opinion for International Application No. PCT/US2016/068312, dated May 3, 2017, 22 pages.
Kvaratskhelia, Mamuka, et al. "Molecular mechanisms of retroviral integration site selection." Nucleic Acids Research (2014); 42.16: 10209-10225.

(56) References Cited

OTHER PUBLICATIONS

Langer, Stephen J., et al. "A genetic screen identifies novel non-compatible loxP sites." Nucleic Acids Research (2002); 30.14: 3067-3077.
Lee, Gwang, and Saito, Izumu. "Role of nucleotide sequences of loxP spacer region in Cre-mediated recombination." Gene (1998); 216.1: 55-65.
Liu, Xiaomei, Han Ping, and Chun Zhang. "Rapid establishment of a HEK 293 cell line expressing FVIII-BDD using AAV site-specific integration plasmids." BMC Research Notes (2014); 7: 626, 6 pages.
Lu, et al., "Complete correction of hemophilia A with adeno-associated viral vectors containing a full-size expression cassette." Hum Gene Ther. (2008); 19(6):648-654. doi: 10.1089/hum.2007.0182.
Maheshri, Narendra, et al. "Directed evolution of adeno-associated virus yields enhanced gene delivery vectors." Nature Biotechnology (2006); 24.2: 198-204.
Mancuso et al., "Gene therapy treatment of color blindness in adult primates." Journal of Vision (2007); 7(15): 15a. (Abstract).
McLeod, Maureen, et al. "Identification of the crossover site during FLP-mediated recombination in the *Saccharomyces cerevisiae* plasmid 2 microns circle." Molecular and Cellular Biology (1986); 6.10: 3357-3367.
Müller, Oliver J., et al. "Random peptide libraries displayed on adeno-associated virus to select for targeted gene therapy vectors." Nature Biotechnology (2003); 21.9: 1040-1046.
Naldini, L., et al., "Efficient transfer, integration, and sustained long-term expression of the transgene in adult rat brains injected with a lentiviral vector." Proc. Natl. Acad. Sci. USA (1996), 93(21): 11382-11388.
Naldini, L., et al., "In vivo gene delivery and stable transduction of nondividing cells by a lentiviral vector." Science (1996), 272(5259): 263-267.
Naldini, L., et al., "Lentiviruses as gene transfer agents for delivery to non-dividing cells." Curr Opin Biotechnol. (1998), 5: 457-463.
Rapti, Kleopatra, et al. "Neutralizing antibodies against AAV serotypes 1, 2, 6, and 9 in sera of commonly used animal models." Molecular Therapy (2012); 20.1: 73-83.
Recchia, Alessandra, et al. "Site-specific integration of functional transgenes into the human genome by adeno/AAV hybrid vectors." Molecular Therapy (2004); 10.4: 660-670.
Samulski, Richard Jude, et al. "Helper-Free Stocks of Recombinant Adeno-Associated Viruses: Normal Integration Does Not Require Viral Gene Expression." Journal of Virology (1989); 63.9: 3822-3828.
Sauer, Brian. "Site-specific recombination: developments and applications." Current Opinion in Biotechnology (1994); 5.5: 521-527.
Schlake, Thomas, and Bode, Juergen. "Use of mutated FLP recognition target (FRT) sites for the exchange of expression cassettes at defined chromosomal loci." Biochemistry (1994); 33.43: 12746-12751.
Schmidt, Michael, et al. "Adeno-associated virus type 2 Rep78 induces apoptosis through caspase activation independently of p53." Journal of Virology (2000); 74.20: 9441-9450.
Senecoff, Julie F., et al. "DNA recognition by the FLP recombinase of the yeast µ plasmid: a mutational analysis of the FLP binding site." Journal of Molecular Biology (1988); 201.2: 405-421.
Stieger, et al., "AAV-mediated gene therapy for retinal disorders in large animal models." ILAR J. (2009); 50(2): 206-224.
Thyagarajan, Bhaskar, et al. "Site-specific genomic integration in mammalian cells mediated by phage φC31 integrase." Molecular and Cellular Biology (2001); 21.12: 3926-3934.
Xu, Zhengyao, et al. "Accuracy and efficiency define Bxb1 integrase as the best of fifteen candidate serine recombinases for the integration of DNA into the human genome." BMC Biotechnology (2013); 13: 87, 17 pages.
Zufferey, et al., "Multiply attenuated lentiviral vector achieves efficient gene delivery in vivo." Nat Biotechnol. (1997), 15(9): 871-875.
Mao, Yanxiong, et al. "Persistent Suppression of Ocular Neovascularization with Intravitreal Administration of AAVrh.10 Coding for Bevacizumab." Human Gene Therapy (2011); 22(12): 1525-1535.
European Patent Application No. 15765668.7, Partial Supplemental European Search Report dated Nov. 10, 2017, 8 pages.

\* cited by examiner

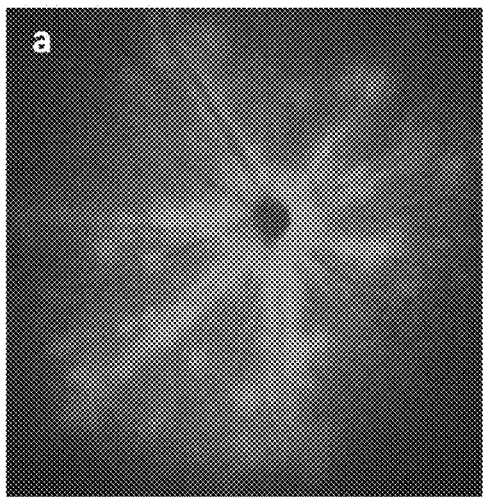
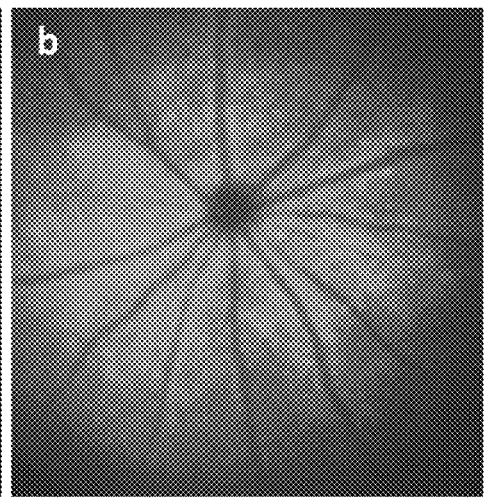
FIG. 7A  FIG. 7B
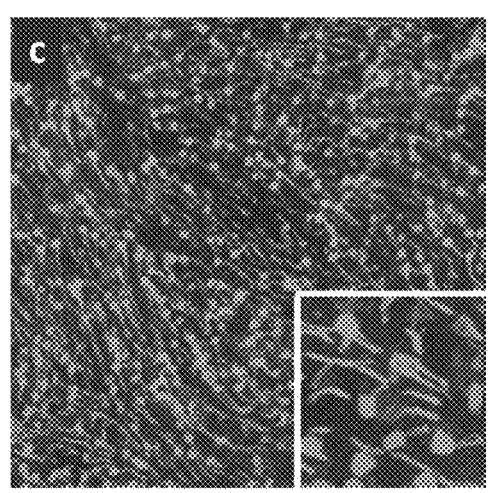
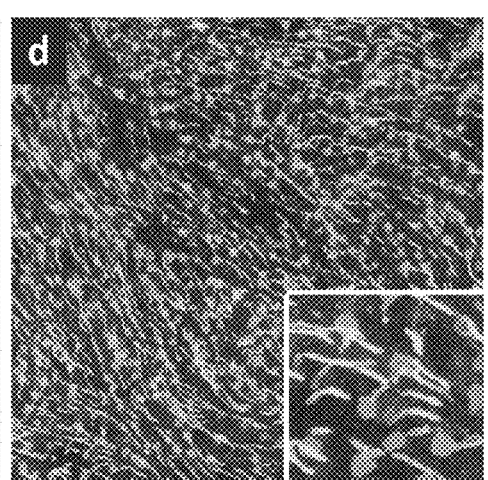
FIG. 7C  FIG. 7D
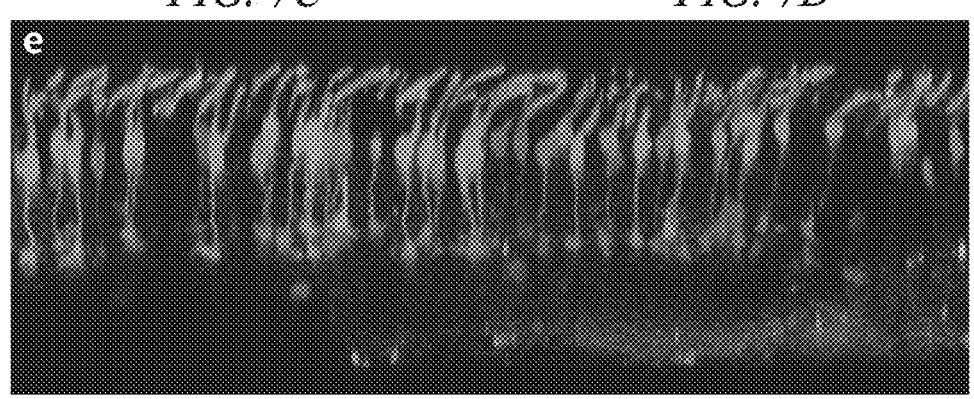
FIG. 7E

SEQUENCE LISTING

```
<160> NUMBER OF SEQ ID NOS: 103

<210> SEQ ID NO 1
<211> LENGTH: 494
<212> TYPE: DNA
<213> ORGANISM: Homo sapiens

<400> SEQUENCE: 1
```

-continued

```
ggatccggtt ccaggcctcg gccctaaata gtctccctgg gctttcaaga gaaccacatg    60 agaaggagg attcgggctc tgagcagttt caccacccac cccccagtct gcaaatcctg    120
acccgtgggt ccacctgccc caaaggcgga cgcaggacag tagaagggaa cagagaacac    180
ataaacacag agagggccac agcggctccc acagtcaccg ccaccttcct ggcggggatg    240
ggtggggcgt ctgagtttgg ttcccagcaa atccctctga gccgcccttg cgggctcgcc    300
tcaggagcag gggagcaaga ggtgggagga ggaggtctaa gtcccaggcc caattaagag    360
atcaggtagt gtagggtttg ggagctttta aggtgaagag gcccgggctg atcccacagg    420
ccagtataaa gcgccgtgac cctcaggtga tgcgccaggg ccggctgccg tcggggacag    480
ggctttccat agcc                                                      494

<210> SEQ ID NO 2
<211> LENGTH: 494
<212> TYPE: DNA
<213> ORGANISM: Homo sapiens

<400> SEQUENCE: 2
ttatttagta gaaacggggt ttcaccatgt tagtcaggct ggtcgggaac tcctgacctc    60
aggagatcta cccgccttgg cctcccaaag tgctgggatt acaggcgtgt gccactgtgc    120
ccagccactt ttttttagac agagtcttgg tctgttgccc aggctagagt tcagtggcgc    180
catctcagct cactgcaacc tccgcctccc agattcaagc gattctcctg cctcgacctc    240
ccagtagctg ggattacagg tttccagcaa atccctctga gccgccccg ggggctcgcc    300 tcaggagcaa ggaagcaagg ggtgggagga ggaggtctaa gtcccaggcc caattaagag    360
atcagatggt gtaggatttg ggagctttta aggtgaagag gcccgggctg atcccactgg    420
ccggtataaa gcaccgtgac cctcaggtga cgcaccaggg ccggctgccg tcggggacag    480
ggctttccat agcc                                                      494

<210> SEQ ID NO 3
<211> LENGTH: 568
<212> TYPE: DNA
<213> ORGANISM: Homo sapiens

<400> SEQUENCE: 3
ctaggcattg tcaagttgcc taagtcctgt tccatcaagg ctgtttactg atgtgcttcc    60
agggcactcc ccactcccag ccctttcctg cagcccaggg ctggttccta gcctctcagc    120
agacttaaga tgggcacctt ccacaaaggg gcagatgagt tgaggaaaac ttaactgata    180
cagttgtgcc agaagccaaa ataagaggcg tgcccttttct atagcccat taaaagaaca    240 aaaaagtgga agcatcttca gtgaatatgg gtcagcacct cccagacctc agggagtcca    300
cttctgttca tcccagcacc cagcattgca tatccagatt atttgagccc aatctcttat    360
cctctgaaga acacaatcgg ctttggggcc acaaaaggtt taggtagtgg tttagggatt    420
tctaatccca aactttgtcc ttgggaggtt taggattagt attgatcatt cacagagccc    480
aagtgttttt agaggagggg ttttgtgggg tgggaggatc acctataaga ggactcagag    540
gggggtgtgg ggcatccatg agaaaaat                                       568

<210> SEQ ID NO 4
<211> LENGTH: 1555
<212> TYPE: DNA
<213> ORGANISM: Homo sapiens
```

<400> SEQUENCE: 4

```
ccagggtgag attatgaggc tgagctgaga atatcaagac tgtaccgagt agggggcctt      60
ggcaagtgtg gagagcccgg cagctggggc agagggcgga gtacggtgtg cgtttacgga     120
cctcttcaaa cgaggtagga aggtcagaag tcaaaaaggg aacaaatgat gtttaaccac     180
acaaaaatga aaatccaatg gttggatatc cattccaaat acacaaaggc aacggataag     240
tgatccgggc caggcacaga aggccatgca cccgtaggat tgcactcaga gctcccaaat     300
gcataggaat agaagggtgg gtgcaggagg ctgagggtg gggaaagggc atgggtgttt      360
catgaggaca gagcttccgt ttcatgcaat gaaaagagtt tggagacgga tggtggtgac     420
tggactatac acttacacac ggtagcgatg gtacactttg tattatgtat attttaccac     480
gatcttttta aagtgtcaaa ggcaaatggc caaatggttc cttgtcctat agctgtagca     540
gccatcggct gttagtgaca agcccctga gtcaagatga cagcagcccc cataactcct      600
aatcggctct cccgcgtgga gtcatttagg agtagtcgca ttagagacaa gtccaacatc     660
taatcttcca ccctggccag ggcccagct ggcagcgagg gtgggagact ccgggcagag      720
cagagggcgc tgacattggg gcccggcctg gcttgggtcc ctctggcctt tccccagggg     780 ccctcttttcc ttggggcttt cttgggccgc cactgctccc gctcctctcc ccccatccca    840 cccccctcacc ccctcgttct tcatatcctt ctctagtgct ccctccactt tcatccaccc    900
ttctgcaaga gtgtgggacc acaaatgagt tttcacctgg cctggggaca cacgtgcccc    960
cacaggtgct gagtgacttt ctaggacagt aatctgcttt aggctaaaat gggacttgat   1020
cttctgttag ccctaatcat caattagcag agccggtgaa ggtgcagaac ctaccgcctt   1080
tccaggcctc ctcccacctc tgccacctcc actctccttc ctgggatgtg ggggctggca   1140
cacgtgtggc ccagggcatt ggtgggattg cactgagctg ggtcattagc gtaatcctgg   1200
acaagggcag acagggcgag cggagggcca gctccgggc tcaggcaagg ctgggggctt    1260
cccccagaca ccccactcct cctctgctgg acccccactt cataggcac ttcgtgttct     1320 caaagggctt ccaaatagca tggtggcctt ggatgcccag ggaagcctca gagttgctta   1380
tctccctcta gacagaaggg gaatctcggt caagagggag aggtcgccct gttcaaggcc   1440
acccagccag ctcatggcgg taatgggaca aggctggcca gccatcccac cctcagaagg   1500
gacccggtgg ggcaggtgat ctcagaggag gctcacttct gggtctcaca ttctt        1555
```

<210> SEQ ID NO 5
<211> LENGTH: 189
<212> TYPE: DNA
<213> ORGANISM: Artificial Sequence
<220> FEATURE:
<223> OTHER INFORMATION: Modified SV40 intron

<400> SEQUENCE: 5

```
gatccggtac tcgaggaact gaaaaaccag aaagttaact ggtaagttta gtcttttgt      60 cttttatttc aggtcccgga tccggtggtg gtgcaaatca aagaactgct cctcagtgga    120
tgttgccttt acttctaggc ctgtacggaa gtgttacttc tgctctaaaa gctgcggaat    180
tgtacccgc                                                             189
```

<210> SEQ ID NO 6
<211> LENGTH: 1114
<212> TYPE: DNA
<213> ORGANISM: Homo sapiens

<400> SEQUENCE: 6

```
atgagaaaaa tgtcggagga agagttttat ctgttcaaaa atatctcttc agtggggccg      60
tgggatgggc ctcagtacca cattgccct gtctgggcct tctacctcca ggcagctttc     120
atgggcactg tcttccttat agggttccca ctcaatgcca tggtgctggt ggccacactg     180
cgctacaaaa agttgcggca gcccctcaac tacattctgg tcaacgtgtc cttcggaggc     240
ttcctcctct gcatcttctc tgtcttccct gtcttcgtcg ccagctgtaa cggatacttc     300
gtcttcggtc gccatgtttg tgctttggag ggcttcctgg gcactgtagc aggtctggtt     360
acaggatggt cactggcctt cctggccttt gagcgctaca ttgtcatctg taagcccttc     420
ggcaacttcc gcttcagctc caagcatgca ctgacggtgg tcctggctac ctggaccatt     480
ggtattggcg tctccatccc accttctt ggctggagcc ggttcatccc tgagggcctg     540
cagtgttcct gtggccctga ctggtacacc gtgggcacca ataccgcag cgagtcctat     600
acgtggttcc tcttcatctt ctgcttcatt gtgcctctct ccctcatctg cttctcctac     660
actcagctgc tgagggccct gaaagctgtt gcagctcagc agcaggagtc agctacgacc     720
cagaaggctg aacgggaggt gagccgcatg gtggttgtga tggtaggatc cttctgtgtc     780
tgctacgtgc cctacgcggc cttcgccatg tacatggtca acaaccgtaa ccatgggctg     840
gacttacggc ttgtcaccat tccttcattc ttctccaaga gtgcttgcat ctacaatccc     900
atcatctact gcttcatgaa taagcagttc caagcttgca tcatgaagat ggtgtgtggg     960
aaggccatga cagatgaatc cgacacatgc agctcccaga aaacagaagt ttctactgtc    1020
tcgtctaccc aagttggccc caactgagga cccaatattg gcctgtttgc aacagctaga    1080
attaaatttt acttttaaaa aaaaaaaaaa aaaa                                1114
```

<210> SEQ ID NO 7
<211> LENGTH: 348
<212> TYPE: PRT
<213> ORGANISM: Homo sapiens

<400> SEQUENCE: 7

```
Met Arg Lys Met Ser Glu Glu Phe Tyr Leu Phe Lys Asn Ile Ser
1               5                  10                  15

Ser Val Gly Pro Trp Asp Gly Pro Gln Tyr His Ile Ala Pro Val Trp
            20                  25                  30

Ala Phe Tyr Leu Gln Ala Ala Phe Met Gly Thr Val Phe Leu Ile Gly
        35                  40                  45

Phe Pro Leu Asn Ala Met Val Leu Val Ala Thr Leu Arg Tyr Lys Lys
    50                  55                  60

Leu Arg Gln Pro Leu Asn Tyr Ile Leu Val Asn Val Ser Phe Gly Gly
65                  70                  75                  80

Phe Leu Leu Cys Ile Phe Ser Val Phe Pro Val Phe Val Ala Ser Cys
                85                  90                  95

Asn Gly Tyr Phe Val Phe Gly Arg His Val Cys Ala Leu Glu Gly Phe
            100                 105                 110

Leu Gly Thr Val Ala Gly Leu Val Thr Gly Trp Ser Leu Ala Phe Leu
        115                 120                 125

Ala Phe Glu Arg Tyr Ile Val Ile Cys Lys Pro Phe Gly Asn Phe Arg
    130                 135                 140

Phe Ser Ser Lys His Ala Leu Thr Val Val Leu Ala Thr Trp Thr Ile
145                 150                 155                 160

Gly Ile Gly Val Ser Ile Pro Pro Phe Phe Gly Trp Ser Arg Phe Ile
                165                 170                 175
```

```
Pro Glu Gly Leu Gln Cys Ser Cys Gly Pro Asp Trp Tyr Thr Val Gly
            180                 185                 190
Thr Lys Tyr Arg Ser Glu Ser Tyr Thr Trp Phe Leu Phe Ile Phe Cys
        195                 200                 205
Phe Ile Val Pro Leu Ser Leu Ile Cys Phe Ser Tyr Thr Gln Leu Leu
    210                 215                 220
Arg Ala Leu Lys Ala Val Ala Ala Gln Gln Gln Glu Ser Ala Thr Thr
225                 230                 235                 240
Gln Lys Ala Glu Arg Glu Val Ser Arg Met Val Val Met Val Gly
                245                 250                 255
Ser Phe Cys Val Cys Tyr Val Pro Tyr Ala Ala Phe Ala Met Tyr Met
                260                 265                 270
Val Asn Asn Arg Asn His Gly Leu Asp Leu Arg Leu Val Thr Ile Pro
            275                 280                 285
Ser Phe Phe Ser Lys Ser Ala Cys Ile Tyr Asn Pro Ile Ile Tyr Cys
        290                 295                 300
Phe Met Asn Lys Gln Phe Gln Ala Cys Ile Met Lys Met Val Cys Gly
305                 310                 315                 320
Lys Ala Met Thr Asp Glu Ser Asp Thr Cys Ser Ser Gln Lys Thr Glu
                325                 330                 335
Val Ser Thr Val Ser Ser Thr Gln Val Gly Pro Asn
            340                 345
```

<210> SEQ ID NO 8
<211> LENGTH: 1998
<212> TYPE: DNA
<213> ORGANISM: Homo sapiens

<400> SEQUENCE: 8

```
cccactggcc ggtataaagc accgtgaccc tcaggtgacg caccagggcc ggctgccgtc    60
ggggacaggg cttttccatag ccatggccca gcagtggagc ctccaaaggc tcgcaggccg   120
ccatccgcag acagctatg aggacagcac ccagtccagc atcttcacct acaccaacag    180
caactccacc agaggcccct tcgaaggccc gaattaccac atcgctccca gatgggtgta    240
ccacctcacc agtgtctgga tgatctttgt ggtcattgca tccgtcttca caaatgggct    300
tgtgctggcg gccaccatga gttcaagaa gctgcgccac ccgctgaact ggatcctggt    360
gaacctggcg gtcgctgacc tggcagagac cgtcatcgcc agcactatca gcgttgtgaa    420
ccaggtctat ggctacttcg tgctgggcca cccatatgtgt gtcctggagg ctacaccgt    480
ctccctgtgt gggatcacag gtctctggtc tctggccatc atttcctggg agagatggat    540
ggtggtctgc aagcccttg gcaatgtgag atttgatgcc aagctggcca tcgtgggcat    600
tgccttctcc tggatctggg ctgctgtgtg gacagccccg cccatctttg gttggagcag    660
gtactggccc cacggcctga agacttcatg cggcccagac gtgttcagcg gcagctcgta    720
ccccggggtg cagtcttaca tgattgtcct catggtcacc tgctgcatca ccccactcag    780
catcatcgtg ctctgctacc tccaagtgtg gctggccatc gagcggtgg caaagcagca    840
gaaagagtct gaatccaccc agaaggcaga gaaggaagtg acgcgcatgg tggtggtgat    900
ggtcctggca ttctgcttct gctggggacc atacgccttc ttcgcatgct ttgctgctgc    960
caaccctggc tacccttcc acccttttgat ggctgccctg ccggccttct ttgccaaaag   1020
tgccactatc tacaacccg ttatctatgt ctttatgaac cggcagtttc gaaactgcat   1080
cttgcagctt ttcgggaaga aggttgacga tggctctgaa ctctccagcg cctccaaaac   1140
```

```
ggaggtctca tctgtgtcct cggtatcgcc tgcatgaggt ctgcctccta cccatcccgc   1200
ccaccggggc tttggccacc tctcctttcc cctccttct ccatccctgt aaaataaatg    1260
taatttatct ttgccaaaac caacaaagtc acagaggctt tcactgcagt gtgggaccac   1320
ctgagcctct gcgtgtgcag gcactgggtc tcgagagggt gcaaggggga taaagaggag   1380
agagcgcttc atagacttta agttttcccg agcctcatgt ctaccgatgg cgtgaaagga   1440
tcctggcaaa acagaagtgt gaggcaggtg ggcgtctata tccatttcac caggctggtg   1500
gttacataat cggcaagcaa gagctgtgga ggggcttgct ggatgccctc agcacccagg   1560
aggagggagg gagctagcaa gctaaggcag gtggccctcc tggcccctta aggtccatct   1620
gctggaggcc cagagtcctt ggagtacagt ctacacctgg aggggaccca ttcctgccag   1680
tctgtggcag ggatggcgcg ccacctctgc caggccagga ccccaagccc gatcagcatc   1740
agcatggtgc aggtgcacag gcgtgagctg atcagtgacg aggggcaggc acacaaggtg   1800
gagacaaaga ccaagaggac ggttgccagt gagaggcgcg gactcaggaa cttgaacaac   1860
atctgcgggg gacggctttg gaggtgctcc gctgcctcca gttgggtgac ttgctgtagc   1920
atctccagct tggatattcg gctcttgaag gtctccgtga tctcctgcag gagacgaaaa   1980
tgcacgcacc agaagtca                                                 1998
```

<210> SEQ ID NO 9
<211> LENGTH: 364
<212> TYPE: PRT
<213> ORGANISM: Homo sapiens

<400> SEQUENCE: 9

```
Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Ile Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Val Val
            100                 105                 110

Asn Gln Val Tyr Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Met Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ala Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
```

```
                210               215                 220
Val Thr Cys Cys Ile Thr Pro Leu Ser Ile Val Leu Cys Tyr Leu
225             230             235                 240

Gln Val Trp Leu Ala Ile Arg Ala Val Ala Lys Gln Gln Lys Glu Ser
            245                 250             255

Glu Ser Thr Gln Lys Ala Glu Lys Glu Val Thr Arg Met Val Val Val
            260                 265             270

Met Val Leu Ala Phe Cys Phe Cys Trp Gly Pro Tyr Ala Phe Phe Ala
            275             280                 285

Cys Phe Ala Ala Ala Asn Pro Gly Tyr Pro Phe His Pro Leu Met Ala
            290             295                 300

Ala Leu Pro Ala Phe Phe Ala Lys Ser Ala Thr Ile Tyr Asn Pro Val
305             310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
            355                 360

<210> SEQ ID NO 10
<211> LENGTH: 1234
<212> TYPE: DNA
<213> ORGANISM: Homo sapiens

<400> SEQUENCE: 10
cggctgccgt cggggacagg gctttccata gccatggccc agcagtggag cctccaaagg      60
ctcgcaggcc gccatccgca ggacagctat gaggacagca cccagtccag catcttcacc     120
tacaccaaca gcaactccac cagaggcccc ttcgaaggcc cgaattacca catcgctccc     180
agatgggtgt accacctcac cagtgtctgg atgatctttg tggtcactgc atccgtcttc     240
acaaatgggc ttgtgctggc ggccaccatg aagttcaaga agctgcgcca cccgctgaac     300
tggatcctgg tgaacctggc ggtcgctgac ctagcagaga ccgtcatcgc cagcactatc     360
agcattgtga accaggtctc tggctacttc gtgctgggcc acccctatgtg tgtcctggag     420 ggctacaccg tctccctgtg tgggatcaca ggtctctggt ctctggccat catttcctgg     480
gagaggtggc tggtggtgtg caagcccttt ggcaatgtga gatttgatgc caagctggcc     540
atcgtgggca ttgccttctc ctggatctgg tctgctgtgt ggacagcccc gcccatcttt     600
ggttggagca ggtactggcc ccacggcctg aagacttcat gcggcccaga cgtgttcagc     660
ggcagctcgt acccccgggt gcagtcttac atgattgtcc tcatggtcac ctgctgcatc     720
atcccactcg ctatcatcat gctctgctac ctccaagtgt ggctggccat ccgagcggtg     780
gcaaagcagc agaaagagtc tgaatccacc cagaaggcag agaaggaagt gacgcgcatg     840
gtggtggtga tgatctttgc gtactgcgtc tgctggggac cctacacctt cttcgcatgc     900
tttgctgctg ccaaccctgg ttacgccttc cacccttttga tggctgccct gccggcctac     960
tttgccaaaa gtgccactat ctacaacccc gttatctatg tctttatgaa ccggcagttt    1020
cgaaactgca tcttgcagct tttcgggaag aaggttgacg atggctctga actctccagc    1080
gcctccaaaa cggaggtctc atctgtgtcc tcggtatcgc ctgcatgagg tctgcctcct    1140
acccatcccg cccaccgggg ctttggccac ctctcccttc cccctccttc tccatccctg    1200
taaaataaat gtaatttatc tttgccaaaa ccaa                                1234
```

<210> SEQ ID NO 11
<211> LENGTH: 364
<212> TYPE: PRT
<213> ORGANISM: Homo sapiens

<400> SEQUENCE: 11

```
Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Thr Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Ile Val
            100                 105                 110

Asn Gln Val Ser Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Leu Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ser Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
    195                 200                 205

Ser Gly Ser Ser Tyr Pro Gly Val Gln Ser Tyr Met Ile Val Leu Met
210                 215                 220

Val Thr Cys Cys Ile Ile Pro Leu Ala Ile Ile Met Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270

Met Ile Phe Ala Tyr Cys Val Cys Trp Gly Pro Tyr Thr Phe Phe Ala
    275                 280                 285

Cys Phe Ala Ala Ala Asn Pro Gly Tyr Ala Phe His Pro Leu Met Ala
290                 295                 300

Ala Leu Pro Ala Tyr Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
    355                 360
```

<210> SEQ ID NO 12

<211> LENGTH: 7326
<212> TYPE: DNA
<213> ORGANISM: Homo sapiens

<400> SEQUENCE: 12

| | | | | | |
|---|---|---|---|---|---|
| aggacacagc | gtccggagcc | agaggcgctc | ttaacggcgt | ttatgtcctt | tgctgtctga | 60 |
| ggggcctcag | ctctgaccaa | tctggtcttc | gtgtggtcat | tagcatgggc | ttcgtgagac | 120 |
| agatacagct | tttgctctgg | aagaactgga | ccctgcggaa | aaggcaaaag | attcgctttg | 180 |
| tggtggaact | cgtgtggcct | ttatctttat | ttctggtctt | gatctggtta | aggaatgcca | 240 |
| acccgctcta | cagccatcat | gaatgccatt | tccccaacaa | ggcgatgccc | tcagcaggaa | 300 |
| tgctgccgtg | gctccagggg | atcttctgca | atgtgaacaa | tccctgtttt | caaagcccca | 360 |
| ccccaggaga | atctcctgga | attgtgtcaa | actataacaa | ctccatcttg | gcaagggtat | 420 |
| atcgagattt | tcaagaactc | ctcatgaatg | caccagagag | ccagcacctt | ggccgtattt | 480 |
| ggacagagct | acacatcttg | tcccaattca | tggacaccct | ccggactcac | ccggagagaa | 540 |
| ttgcaggaag | aggaatacga | ataagggata | tcttgaaaga | tgaagaaaca | ctgacactat | 600 |
| ttctcattaa | aaacatcggc | ctgtctgact | cagtggtcta | ccttctgatc | aactctcaag | 660 |
| tccgtccaga | gcagttcgct | catggagtcc | cggacctggc | gctgaaggac | atcgcctgca | 720 |
| gcgaggccct | cctggagcgc | ttcatcatct | tcagccagag | acgcggggca | aagacggtgc | 780 |
| gctatgccct | gtgctccctc | tcccagggca | ccctacagtg | gatagaagac | actctgtatg | 840 |
| ccaacgtgga | cttcttcaag | ctcttccgtg | tgcttcccac | actcctagac | agccgttctc | 900 |
| aaggtatcaa | tctgagatct | tggggaggaa | tattatctga | tatgtcacca | gaattcaag | 960 |
| agtttatcca | tcggccgagt | atgcaggact | tgctgtgggt | gaccaggccc | ctcatgcaga | 1020 |
| atggtggtcc | agagaccttt | acaaagctga | tgggcatcct | gtctgacctc | ctgtgtggct | 1080 |
| accccgaggg | aagtggctct | cgggtgctct | ccttcaactg | gtatgaagac | aataactata | 1140 |
| aggcctttct | ggggattgac | tccacaagga | aggatcctat | ctattcttat | gacagaagaa | 1200 |
| caacatcctt | ttgtaatgca | ttgatccaga | gcctggagtc | aaatccttta | ccaaaatcg | 1260 |
| cttggagggc | ggcaaagcct | ttgctgatgg | gaaaaatcct | gtacactcct | gattcacctg | 1320 |
| cagcacgaag | gatactgaag | aatgccaact | caacttttga | agaactggaa | cacgttagga | 1380 |
| agttggtcaa | agcctgggaa | gaagtagggc | cccagatctg | gtacttcttt | gacaacagca | 1440 |
| cacagatgaa | catgatcaga | gataccctgg | ggaacccaac | agtaaaagac | ttttttgaata | 1500 |
| ggcagcttgg | tgaagaaggt | attactgctg | aagccatcct | aaacttcctc | tacaagggcc | 1560 |
| ctcgggaaag | ccaggctgac | gacatggcca | acttcgactg | gagggacata | tttaacatca | 1620 |
| ctgatcgcac | cctccgcctg | gtcaatcaat | acctggagtg | cttggtcctg | gataagtttg | 1680 |
| aaagctacaa | tgatgaaact | cagctcaccc | aacgtgccct | ctctctactg | gaggaaaaca | 1740 |
| tgttctgggc | cggagtggta | ttccctgaca | tgtatccctg | gaccagctct | ctaccacccc | 1800 |
| acgtgaagta | taagatccga | atggacatag | acgtggtgga | gaaaccaat | aagattaaag | 1860 |
| acaggtattg | ggattctggt | cccagagctg | atcccgtgga | agatttccgg | tacatctggg | 1920 |
| gcgggttgc | ctatctgcag | gacatggttg | aacaggggat | cacaaggagc | caggtgcagg | 1980 |
| cggaggctcc | agttggaatc | tacctccagc | agatgcccta | cccctgcttc | gtggacgatt | 2040 |
| ctttcatgat | catcctgaac | cgctgttttc | ctatcttcat | ggtgctggca | tggatctact | 2100 |
| ctgtctccat | gactgtgaag | agcatcgtct | tggagaagga | gttgcgactg | aaggagacct | 2160 |
| tgaaaaatca | gggtgtctcc | aatgcagtga | tttggtgtac | ctggttcctg | gacagcttct | 2220 |

```
ccatcatgtc gatgagcatc ttcctcctga cgatattcat catgcatgga agaatcctac    2280
attacagcga cccattcatc ctcttcctgt tcttgttggc tttctccact gccaccatca    2340
tgctgtgctt tctgctcagc accttcttct ccaaggccag tctggcagca gcctgtagtg    2400
gtgtcatcta tttcaccctc tacctgccac acatcctgtg cttcgcctgg caggaccgca    2460
tgaccgctga gctgaagaag gctgtgagct tactgtctcc ggtggcattt ggatttggca    2520
ctgagtacct ggttcgcttt gaagagcaag gcctggggct gcagtggagc aacatcggga    2580
acagtcccac ggaaggggac gaattcagct tcctgctgtc catgcagatg atgctccttg    2640
atgctgctgt ctatggctta ctcgcttggt accttgatca ggtgtttcca ggagactatg    2700 gaacccact tccttggtac tttcttctac aagagtcgta ttggcttggc ggtgaagggt     2760
gttcaaccag agaagaaaga gccctggaaa agaccgagcc cctaacagag gaaacggagg    2820
atccagagca cccagaagga atacacgact ccttctttga acgtgagcat ccagggtggg    2880
ttcctggggt atgcgtgaag aatctggtaa agattttga gccctgtggc cggccagctg      2940
tggaccgtct gaacatcacc ttctacgaga accagatcac cgcattcctg ggccacaatg    3000
gagctgggaa aaccaccacc ttgtccatcc tgacgggtct gttgccacca acctctggga    3060
ctgtgctcgt tgggggaagg gacattgaaa ccagcctgga tgcagtccgg cagagccttg    3120
gcatgtgtcc acagcacaac atcctgttcc accacctcac ggtggctgag cacatgctgt    3180
tctatgccca gctgaaagga agtcccagg aggaggccca gctggagatg aagccatgt      3240 tggaggacac aggcctccac cacaagcgga atgaagaggc tcaggaccta tcaggtggca    3300
tgcagagaaa gctgtcggtt gccattgcct tgtgggaga tgccaaggtg gtgattctgg     3360
acgaacccac ctctggggtg gacccttact cgagacgctc aatctgggat ctgctcctga    3420
agtatcgctc aggcagaacc atcatcatgt ccactcacca catggacgag gccgacctcc    3480
ttggggaccg cattgccatc attgcccagg aaggctcta ctgctcaggc accccactct    3540
tcctgaagaa ctgctttggc acaggcttgt acttaacctt ggtgcgcaag atgaaaaaca    3600
tccagagcca aaggaaaggc agtgagggga cctgcagctg ctcgtctaag ggtttctcca    3660
ccacgtgtcc agcccacgtc gatgacctaa ctccagaaca agtcctggat ggggatgtaa    3720
atgagctgat ggatgtagtt ctccaccatg ttccagaggc aaagctggtg gagtgcattg    3780
gtcaagaact tatcttcctt cttccaaata agaacttcaa gcacagagca tatgccagcc    3840
ttttcagaga gctggaggag acgctggctg accttggtct cagcagtttt ggaatttctg    3900
acactcccct ggaagagatt tttctgaagg tcacggagga ttctgattca ggacctctgt    3960
ttgcgggtgg cgctcagcag aaaagagaaa acgtcaaccc ccgacacccc tgcttgggtc    4020
ccagagagaa ggctggacag acaccccagg actccaatgt ctgctcccca ggggcgccgg    4080
ctgctcaccc agagggccag cctcccccag agccagagtg cccaggcccg cagctcaaca    4140
cggggacaca gctggtcctc cagcatgtgc aggcgctgct ggtcaagaga ttccaacaca    4200
ccatccgcag ccacaaggac ttcctggcgc agatcgtgct cccggctacc tttgtgtttt    4260
tggctctgat gctttctatt gttatccctc cttttggcga ataccccgct ttgacccttc    4320 accccctggat atatgggcag cagtacacct tcttcagcat ggatgaacca ggcagtgagc    4380
agttcacggt acttgcagac gtcctcctga ataagccagg cttttggcaac cgctgcctga    4440 aggaagggtg gcttccggag tacccctgtg caactcaac accctggaag actccttctg     4500
tgtccccaaa catcacccag ctgttccaga agcagaaatg gacacaggtc aacccttcac    4560
```

```
catcctgcag gtgcagcacc agggagaagc tcaccatgct gccagagtgc cccgagggtg    4620
ccggggggcct cccgccccccc cagagaacac agcgcagcac ggaaattcta caagacctga   4680
cggacaggaa catctccgac ttcttggtaa aaacgtatcc tgctcttata agaagcagct    4740
taaagagcaa attctgggtc aatgaacaga ggtatggagg aatttccatt ggaggaaagc    4800
tcccagtcgt ccccatcacg ggggaagcac ttgttgggtt tttaagcgac cttggccgga    4860
tcatgaatgt gagcgggggc cctatcacta gagaggcctc taaagaaata cctgatttcc    4920
ttaaacatct agaaactgaa gacaacatta aggtgtggtt taataacaaa ggctggcatg    4980
ccctggtcag ctttctcaat gtggcccaca acgccatctt acgggccagc ctgcctaagg    5040
acaggagccc cgaggagtat ggaatcaccg tcattagcca accctgaac ctgaccaagg     5100
agcagctctc agagattaca gtgctgacca cttcagtgga tgctgtggtt gccatctgcg    5160
tgattttctc catgtccttc gtcccagcca gctttgtcct ttatttgatc caggagcggg    5220
tgaacaaatc caagcacctc cagtttatca gtggagtgag ccccaccacc tactgggtga    5280
ccaacttcct ctgggacatc atgaattatt ccgtgagtgc tgggctggtg gtgggcatct    5340
tcatcgggtt tcagaagaaa gcctacactt ctccagaaaa ccttcctgcc cttgtggcac    5400
tgctcctgct gtatgatgg gcggtcattc ccatgatgta cccagcatcc ttcctgtttg     5460
atgtccccag cacagcctat gtggctttat cttgtgctaa tctgttcatc ggcatcaaca    5520
gcagtgctat taccttcatc ttggaattat ttgagaataa ccggacgctg ctcaggttca    5580
acgccgtgct gaggaagctg ctcattgtct tcccccactt ctgcctgggc cggggcctca    5640
ttgaccttgc actgagccag gctgtgacag atgtctatgc ccggtttggt gaggagcact    5700
ctgcaaatcc gttccactgg gacctgattg gaagaacct gtttgccatg tggtggaag     5760
gggtggtgta cttcctcctg accctgctgg tccagcgcca cttcttcctc tcccaatgga    5820
ttgccgagcc cactaaggag cccattgttg atgaagatga tgatgtggct gaagaaagac    5880
aaagaattat tactggtgga aataaaactg acatcttaag gctacatgaa ctaaccaaga    5940
tttatccagg cacctccagc ccagcagtgg acaggctgtg tgtcggagtt cgccctggag    6000
agtgctttgg cctcctggga gtgaatggtg ccggcaaaac aaccacattc aagatgctca    6060
ctggggacac cacagtgacc tcaggggatg ccaccgtagc aggcaagagt attttaacca    6120
atatttctga gtccatcaa atatgggct actgtcctca gtttgatgca attgatgagc     6180
tgctcacagg acgagaacat cttaccttt atgcccggct tcgaggtgta ccagcagaag    6240
aaatcgaaaa ggttgcaaac tggagtatta agagcctggg cctgactgtc tacgccgact    6300
gcctggctgg cacgtacagt gggggcaaca agcggaaact ctccacagcc atcgcactca    6360
ttggctgccc accgctggtg ctgctggatg agcccaccac agggatggac ccccaggcac    6420
gccgcatgct gtggaacgtc atcgtgagca tcatcagaga agggagggct gtggtcctca    6480
catcccacag catggaagaa tgtgaggcac tgtgtaccc gctggccatc atggtaaagg    6540
gcgccttttcg atgtatgggc accattcagc atctcaagtc caaatttgga gatggctata    6600
tcgtcacaat gaagatcaaa tccccgaagg acgacctgct tcctgacctg aaccctgtgg    6660
agcagttctt ccaggggaac ttcccaggca gtgtgcagag ggagaggcac tacaacatgc    6720
tccagttcca ggtctcctcc tcctccctgg cgaggatctt ccagctcctc ctctcccaca    6780
aggacagcct gctcatcgag gagtactcag tcacacagac cacactggac caggtgtttg    6840
taaattttgc taaacagcag actgaaagtc atgcctccc tctgcaccct cgagctgctg     6900
gagccagtcg acaagcccag gactgatctt tcacaccgct cgttcctgca gccagaaagg    6960
```

-continued

```
aactctgggc agctggaggc gcaggagcct gtgcccatat ggtcatccaa atggactggc    7020
cagcgtaaat gaccccactg cagcagaaaa caaacacacg aggagcatgc agcgaattca    7080
gaaagaggtc tttcagaagg aaaccgaaac tgacttgctc acctggaaca cctgatggtg    7140
aaaccaaaca aatacaaaat ccttctccag accccagaac tagaaacccc gggccatccc    7200
actagcagct ttggcctcca tattgctctc atttcaagca gatctgcttt tctgcatgtt    7260
tgtctgtgtg tctgcgttgt gtgtgatttt catggaaaaa taaatgcaa atgcactcat     7320 cacaaa                                                                7326
```

<210> SEQ ID NO 13
<211> LENGTH: 2273
<212> TYPE: PRT
<213> ORGANISM: Homo sapiens

<400> SEQUENCE: 13

```
Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
65                  70                  75                  80

Cys Phe Gln Ser Pro Thr Pro Gly Glu Ser Pro Gly Ile Val Ser Asn
                85                  90                  95

Tyr Asn Asn Ser Ile Leu Ala Arg Val Tyr Arg Asp Phe Gln Glu Leu
            100                 105                 110

Leu Met Asn Ala Pro Glu Ser Gln His Leu Gly Arg Ile Trp Thr Glu
        115                 120                 125

Leu His Ile Leu Ser Gln Phe Met Asp Thr Leu Arg Thr His Pro Glu
    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                165                 170                 175

Val Val Tyr Leu Leu Ile Asn Ser Gln Val Arg Pro Glu Gln Phe Ala
            180                 185                 190

His Gly Val Pro Asp Leu Ala Leu Lys Asp Ile Ala Cys Ser Glu Ala
        195                 200                 205

Leu Leu Glu Arg Phe Ile Ile Phe Ser Gln Arg Arg Gly Ala Lys Thr
    210                 215                 220

Val Arg Tyr Ala Leu Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                245                 250                 255

Leu Pro Thr Leu Leu Asp Ser Arg Ser Gln Gly Ile Asn Leu Arg Ser
            260                 265                 270

Trp Gly Gly Ile Leu Ser Asp Met Ser Pro Arg Ile Gln Glu Phe Ile
        275                 280                 285

His Arg Pro Ser Met Gln Asp Leu Leu Trp Val Thr Arg Pro Leu Met
    290                 295                 300
```

```
Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Ser Arg Val Leu Ser
            325                 330                 335

Phe Asn Trp Tyr Glu Asp Asn Asn Tyr Lys Ala Phe Leu Gly Ile Asp
            340                 345                 350

Ser Thr Arg Lys Asp Pro Ile Tyr Ser Tyr Asp Arg Arg Thr Thr Ser
            355                 360                 365

Phe Cys Asn Ala Leu Ile Gln Ser Leu Glu Ser Asn Pro Leu Thr Lys
370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
            405                 410                 415

Thr Phe Glu Glu Leu Glu His Val Arg Lys Leu Val Lys Ala Trp Glu
            420                 425                 430

Glu Val Gly Pro Gln Ile Trp Tyr Phe Phe Asp Asn Ser Thr Gln Met
            435                 440                 445

Asn Met Ile Arg Asp Thr Leu Gly Asn Pro Thr Val Lys Asp Phe Leu
450                 455                 460

Asn Arg Gln Leu Gly Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
            485                 490                 495

Phe Asp Trp Arg Asp Ile Phe Asn Ile Thr Asp Arg Thr Leu Arg Leu
            500                 505                 510

Val Asn Gln Tyr Leu Glu Cys Leu Val Leu Asp Lys Phe Glu Ser Tyr
            515                 520                 525

Asn Asp Glu Thr Gln Leu Thr Gln Arg Ala Leu Ser Leu Leu Glu Glu
            530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
            565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
            595                 600                 605

Ala Tyr Leu Gln Asp Met Val Glu Gln Gly Ile Thr Arg Ser Gln Val
            610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
            645                 650                 655

Ile Phe Met Val Leu Ala Trp Ile Tyr Ser Val Ser Met Thr Val Lys
            660                 665                 670

Ser Ile Val Leu Glu Lys Glu Leu Arg Leu Lys Glu Thr Leu Lys Asn
            675                 680                 685

Gln Gly Val Ser Asn Ala Val Ile Trp Cys Thr Trp Phe Leu Asp Ser
            690                 695                 700

Phe Ser Ile Met Ser Met Ser Ile Phe Leu Leu Thr Ile Phe Ile Met
705                 710                 715                 720
```

```
His Gly Arg Ile Leu His Tyr Ser Asp Pro Phe Ile Leu Phe Leu Phe
            725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
            755                 760                 765

Tyr Phe Thr Leu Tyr Leu Pro His Ile Leu Cys Phe Ala Trp Gln Asp
            770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
            805                 810                 815

Leu Gly Leu Gln Trp Ser Asn Ile Gly Asn Ser Pro Thr Glu Gly Asp
            820                 825                 830

Glu Phe Ser Phe Leu Leu Ser Met Gln Met Met Leu Leu Asp Ala Ala
            835                 840                 845

Val Tyr Gly Leu Leu Ala Trp Tyr Leu Asp Gln Val Phe Pro Gly Asp
            850                 855                 860

Tyr Gly Thr Pro Leu Pro Trp Tyr Phe Leu Leu Gln Glu Ser Tyr Trp
865                 870                 875                 880

Leu Gly Gly Glu Gly Cys Ser Thr Arg Glu Glu Arg Ala Leu Glu Lys
            885                 890                 895

Thr Glu Pro Leu Thr Glu Glu Thr Glu Asp Pro Glu His Pro Glu Gly
            900                 905                 910

Ile His Asp Ser Phe Phe Glu Arg Glu His Pro Gly Trp Val Pro Gly
            915                 920                 925

Val Cys Val Lys Asn Leu Val Lys Ile Phe Glu Pro Cys Gly Arg Pro
            930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
            965                 970                 975

Thr Gly Leu Leu Pro Pro Thr Ser Gly Thr Val Leu Val Gly Gly Arg
            980                 985                 990

Asp Ile Glu Thr Ser Leu Asp Ala Val Arg Gln Ser Leu Gly Met Cys
            995                 1000                1005

Pro Gln His Asn Ile Leu Phe His His Leu Thr Val Ala Glu His
            1010                1015                1020

Met Leu Phe Tyr Ala Gln Leu Lys Gly Lys Ser Gln Glu Glu Ala
            1025                1030                1035

Gln Leu Glu Met Glu Ala Met Leu Glu Asp Thr Gly Leu His His
            1040                1045                1050

Lys Arg Asn Glu Glu Ala Gln Asp Leu Ser Gly Gly Met Gln Arg
            1055                1060                1065

Lys Leu Ser Val Ala Ile Ala Phe Val Gly Asp Ala Lys Val Val
            1070                1075                1080

Ile Leu Asp Glu Pro Thr Ser Gly Val Asp Pro Tyr Ser Arg Arg
            1085                1090                1095

Ser Ile Trp Asp Leu Leu Leu Lys Tyr Arg Ser Gly Arg Thr Ile
            1100                1105                1110

Ile Met Ser Thr His His Met Asp Glu Ala Asp Leu Leu Gly Asp
            1115                1120                1125

Arg Ile Ala Ile Ile Ala Gln Gly Arg Leu Tyr Cys Ser Gly Thr
```

-continued

```
            1130                1135                1140

Pro Leu Phe Leu Lys Asn Cys Phe Gly Thr Gly Leu Tyr Leu Thr
    1145                1150                1155

Leu Val Arg Lys Met Lys Asn Ile Gln Ser Gln Arg Lys Gly Ser
    1160                1165                1170

Glu Gly Thr Cys Ser Cys Ser Ser Lys Gly Phe Ser Thr Thr Cys
    1175                1180                1185

Pro Ala His Val Asp Asp Leu Thr Pro Glu Gln Val Leu Asp Gly
    1190                1195                1200

Asp Val Asn Glu Leu Met Asp Val Val Leu His His Val Pro Glu
    1205                1210                1215

Ala Lys Leu Val Glu Cys Ile Gly Gln Glu Leu Ile Phe Leu Leu
    1220                1225                1230

Pro Asn Lys Asn Phe Lys His Arg Ala Tyr Ala Ser Leu Phe Arg
    1235                1240                1245

Glu Leu Glu Glu Thr Leu Ala Asp Leu Gly Leu Ser Ser Phe Gly
    1250                1255                1260

Ile Ser Asp Thr Pro Leu Glu Glu Ile Phe Leu Lys Val Thr Glu
    1265                1270                1275

Asp Ser Asp Ser Gly Pro Leu Phe Ala Gly Gly Ala Gln Gln Lys
    1280                1285                1290

Arg Glu Asn Val Asn Pro Arg His Pro Cys Leu Gly Pro Arg Glu
    1295                1300                1305

Lys Ala Gly Gln Thr Pro Gln Asp Ser Asn Val Cys Ser Pro Gly
    1310                1315                1320

Ala Pro Ala Ala His Pro Glu Gly Gln Pro Pro Glu Pro Glu
    1325                1330                1335

Cys Pro Gly Pro Gln Leu Asn Thr Gly Thr Gln Leu Val Leu Gln
    1340                1345                1350

His Val Gln Ala Leu Leu Val Lys Arg Phe Gln His Thr Ile Arg
    1355                1360                1365

Ser His Lys Asp Phe Leu Ala Gln Ile Val Leu Pro Ala Thr Phe
    1370                1375                1380

Val Phe Leu Ala Leu Met Leu Ser Ile Val Ile Pro Pro Phe Gly
    1385                1390                1395

Glu Tyr Pro Ala Leu Thr Leu His Pro Trp Ile Tyr Gly Gln Gln
    1400                1405                1410

Tyr Thr Phe Phe Ser Met Asp Glu Pro Gly Ser Glu Gln Phe Thr
    1415                1420                1425

Val Leu Ala Asp Val Leu Leu Asn Lys Pro Gly Phe Gly Asn Arg
    1430                1435                1440

Cys Leu Lys Glu Gly Trp Leu Pro Glu Tyr Pro Cys Gly Asn Ser
    1445                1450                1455

Thr Pro Trp Lys Thr Pro Ser Val Ser Pro Asn Ile Thr Gln Leu
    1460                1465                1470

Phe Gln Lys Gln Lys Trp Thr Gln Val Asn Pro Ser Pro Ser Cys
    1475                1480                1485

Arg Cys Ser Thr Arg Glu Lys Leu Thr Met Leu Pro Glu Cys Pro
    1490                1495                1500

Glu Gly Ala Gly Gly Leu Pro Pro Pro Gln Arg Thr Gln Arg Ser
    1505                1510                1515

Thr Glu Ile Leu Gln Asp Leu Thr Asp Arg Asn Ile Ser Asp Phe
    1520                1525                1530
```

```
Leu Val Lys Thr Tyr Pro Ala Leu Ile Arg Ser Ser Leu Lys Ser
1535                1540                1545

Lys Phe Trp Val Asn Glu Gln Arg Tyr Gly Gly Ile Ser Ile Gly
1550                1555                1560

Gly Lys Leu Pro Val Val Pro Ile Thr Gly Glu Ala Leu Val Gly
1565                1570                1575

Phe Leu Ser Asp Leu Gly Arg Ile Met Asn Val Ser Gly Gly Pro
1580                1585                1590

Ile Thr Arg Glu Ala Ser Lys Glu Ile Pro Asp Phe Leu Lys His
1595                1600                1605

Leu Glu Thr Glu Asp Asn Ile Lys Val Trp Phe Asn Asn Lys Gly
1610                1615                1620

Trp His Ala Leu Val Ser Phe Leu Asn Val Ala His Asn Ala Ile
1625                1630                1635

Leu Arg Ala Ser Leu Pro Lys Asp Arg Ser Pro Glu Glu Tyr Gly
1640                1645                1650

Ile Thr Val Ile Ser Gln Pro Leu Asn Leu Thr Lys Glu Gln Leu
1655                1660                1665

Ser Glu Ile Thr Val Leu Thr Thr Ser Val Asp Ala Val Val Ala
1670                1675                1680

Ile Cys Val Ile Phe Ser Met Ser Phe Val Pro Ala Ser Phe Val
1685                1690                1695

Leu Tyr Leu Ile Gln Glu Arg Val Asn Lys Ser Lys His Leu Gln
1700                1705                1710

Phe Ile Ser Gly Val Ser Pro Thr Thr Tyr Trp Val Thr Asn Phe
1715                1720                1725

Leu Trp Asp Ile Met Asn Tyr Ser Val Ser Ala Gly Leu Val Val
1730                1735                1740

Gly Ile Phe Ile Gly Phe Gln Lys Lys Ala Tyr Thr Ser Pro Glu
1745                1750                1755

Asn Leu Pro Ala Leu Val Ala Leu Leu Leu Leu Tyr Gly Trp Ala
1760                1765                1770

Val Ile Pro Met Met Tyr Pro Ala Ser Phe Leu Phe Asp Val Pro
1775                1780                1785

Ser Thr Ala Tyr Val Ala Leu Ser Cys Ala Asn Leu Phe Ile Gly
1790                1795                1800

Ile Asn Ser Ser Ala Ile Thr Phe Ile Leu Glu Leu Phe Glu Asn
1805                1810                1815

Asn Arg Thr Leu Leu Arg Phe Asn Ala Val Leu Arg Lys Leu Leu
1820                1825                1830

Ile Val Phe Pro His Phe Cys Leu Gly Arg Gly Leu Ile Asp Leu
1835                1840                1845

Ala Leu Ser Gln Ala Val Thr Asp Val Tyr Ala Arg Phe Gly Glu
1850                1855                1860

Glu His Ser Ala Asn Pro Phe His Trp Asp Leu Ile Gly Lys Asn
1865                1870                1875

Leu Phe Ala Met Val Val Glu Gly Val Val Tyr Phe Leu Leu Thr
1880                1885                1890

Leu Leu Val Gln Arg His Phe Phe Leu Ser Gln Trp Ile Ala Glu
1895                1900                1905

Pro Thr Lys Glu Pro Ile Val Asp Glu Asp Asp Val Ala Glu
1910                1915                1920
```

Glu Arg Gln Arg Ile Ile Thr Gly Gly Asn Lys Thr Asp Ile Leu
1925                1930                1935

Arg Leu His Glu Leu Thr Lys Ile Tyr Pro Gly Thr Ser Ser Pro
1940                1945                1950

Ala Val Asp Arg Leu Cys Val Gly Val Arg Pro Gly Glu Cys Phe
1955                1960                1965

Gly Leu Leu Gly Val Asn Gly Ala Gly Lys Thr Thr Thr Phe Lys
1970                1975                1980

Met Leu Thr Gly Asp Thr Thr Val Thr Ser Gly Asp Ala Thr Val
1985                1990                1995

Ala Gly Lys Ser Ile Leu Thr Asn Ile Ser Glu Val His Gln Asn
2000                2005                2010

Met Gly Tyr Cys Pro Gln Phe Asp Ala Ile Asp Glu Leu Leu Thr
2015                2020                2025

Gly Arg Glu His Leu Tyr Leu Tyr Ala Arg Leu Arg Gly Val Pro
2030                2035                2040

Ala Glu Glu Ile Glu Lys Val Ala Asn Trp Ser Ile Lys Ser Leu
2045                2050                2055

Gly Leu Thr Val Tyr Ala Asp Cys Leu Ala Gly Thr Tyr Ser Gly
2060                2065                2070

Gly Asn Lys Arg Lys Leu Ser Thr Ala Ile Ala Leu Ile Gly Cys
2075                2080                2085

Pro Pro Leu Val Leu Leu Asp Glu Pro Thr Thr Gly Met Asp Pro
2090                2095                2100

Gln Ala Arg Arg Met Leu Trp Asn Val Ile Val Ser Ile Ile Arg
2105                2110                2115

Glu Gly Arg Ala Val Val Leu Thr Ser His Ser Met Glu Glu Cys
2120                2125                2130

Glu Ala Leu Cys Thr Arg Leu Ala Ile Met Val Lys Gly Ala Phe
2135                2140                2145

Arg Cys Met Gly Thr Ile Gln His Leu Lys Ser Lys Phe Gly Asp
2150                2155                2160

Gly Tyr Ile Val Thr Met Lys Ile Lys Ser Pro Lys Asp Asp Leu
2165                2170                2175

Leu Pro Asp Leu Asn Pro Val Glu Gln Phe Phe Gln Gly Asn Phe
2180                2185                2190

Pro Gly Ser Val Gln Arg Glu Arg His Tyr Asn Met Leu Gln Phe
2195                2200                2205

Gln Val Ser Ser Ser Ser Leu Ala Arg Ile Phe Gln Leu Leu Leu
2210                2215                2220

Ser His Lys Asp Ser Leu Leu Ile Glu Glu Tyr Ser Val Thr Gln
2225                2230                2235

Thr Thr Leu Asp Gln Val Phe Val Asn Phe Ala Lys Gln Gln Thr
2240                2245                2250

Glu Ser His Asp Leu Pro Leu His Pro Arg Ala Ala Gly Ala Ser
2255                2260                2265

Arg Gln Ala Gln Asp
2270

<210> SEQ ID NO 14
<211> LENGTH: 2608
<212> TYPE: DNA
<213> ORGANISM: Homo sapiens

<400> SEQUENCE: 14

```
tccttcttca ttctgcagtt ggtgccagaa ctctggatcc tgaactggaa gaaaatgtct    60
atccaggttg agcatcctgc tggtggttac aagaaactgt ttgaaactgt ggaggaactg   120
tcctcgccgc tcacagctca tgtaacaggc aggatccccc tctggctcac cggcagtctc   180
cttcgatgtg ggccaggact cttttgaagtt ggatctgagc catttttacca cctgtttgat   240 gggcaagccc tcctgcacaa gtttgacttt aaagaaggac atgtcacata ccacagaagg   300
ttcatccgca ctgatgctta cgtacgggca atgactgaga aaaggatcgt cataacagaa   360
tttggcacct gtgctttccc agatccctgc aagaatatat tttccaggtt ttttttcttac   420 tttcgaggag tagaggttac tgacaatgcc cttgttaatg tctacccagt ggggggaagat   480 tactacgctt gcacagagac caactttatt acaaagatta atccagagac cttggagaca   540
attaagcagg ttgatctttg caactatgtc tctgtcaatg gggccactgc tcaccccccac   600 attgaaaatg atggaaccgt ttacaatatt ggtaattgct ttggaaaaaa ttttttcaatt   660 gcctacaaca ttgtaaagat cccaccactg caagcagaca aggaagatcc aataagcaag   720
tcagagatcg ttgtacaatt cccctgcagt gaccgattca agccatctta cgttcatagt   780
tttggtctga ctcccaacta tatcgttttt gtggagacac cagtcaaaat taacctgttc   840
aagttccttt cttcatggag tctttgggga gccaactaca tggattgttt tgagtccaat   900
gaaaccatgg gggtttggct tcatattgct gacaaaaaaa ggaaaaagta cctcaataat   960
aaatacagaa cttctccttt caacctcttc catcacatca acacctatga agacaatggg  1020
tttctgattg tggatctctg ctgctggaaa ggatttgagt ttgttttataa ttacttatat  1080 ttagccaatt tacgtgagaa ctgggaagag gtgaaaaaaa atgccagaaa ggctccccaa  1140
cctgaagtta ggagatatgt acttcctttg aatattgaca aggctgacac aggcaagaat  1200
ttagtcacgc tccccaatac aactgccact gcaattctgt gcagtgacga gactatctgg  1260
ctggagcctg aagttctctt ttcagggcct cgtcaagcat ttgagtttcc tcaaatcaat  1320
taccagaagt attgtgggaa accttacaca tatgcgtatg acttggctt gaatcacttt  1380 gttccagata ggctctgtaa gctgaatgtc aaaactaaag aaacttgggt ttggcaagag  1440
cctgattcat acccatcaga acccatcttt gtttctcacc cagatgcctt ggaagaagat  1500
gatggtgtag ttctgagtgt ggtggtgagc ccaggagcag gacaaaagcc tgcttatctc  1560
ctgattctga atgccaagga cttaagtgaa gttgcccggg ctgaagtgga gattaacatc  1620
cctgtcacct ttcatggact gttcaaaaaa tcttgagcat actccagcaa gatatgtttt  1680
tggtagcaaa actgagaaaa tcagcttcag gtctgcaatc aaattctgtt caattttagc  1740
ctgctatatg tcatggtttt aacttgcaga tgcgcacaat tttgcaatgt tttacagaaa  1800
gcactgagtt gagcaagcaa ttcctttatt taaaaaaaaa agtacgtatt tagataatca  1860
tacttcctct gtgagacagg ccataactga aaaactctta aatatttagc aatcaaatag  1920
gaaatgaatg tggacttact aaatggcttt taattcctat tataagagca tattttaggt  1980
acctatctgc tccaattata tttttaacat ttaaaaacca aagtcctcta cacttgattt  2040
atattatatg tggctttgct gagtcaagga agtatcatgc ataaggcttt aattactaaa  2100
tgtcaaacca aacttttttct caaaccaggg actatcatct aagattaatt acagtaatta  2160
ttttgcgtat acgtaactgc tcaaagatta tgaatcttat gaatgttaac ctttccgttt  2220
attacaagca agtactatta tttctgattt tataataaga aaatctgtgt ttaatcaact  2280
gaggcctctc aaccaaataa catctcagag attaagttat atattaaaag cttatgtaac  2340
```

-continued

```
ataaaagcaa gtacatatag tagtgactat atttaaaaaa acagcataaa atgcttaaaa    2400
atgtaatatt tactaaaatc agattatggg ataatgttgc aggattatac tttattgcat    2460 ctttttgtt taattgtatt taagcattgt gcaatcactt gggaaaaata ttaaattatt     2520
aacattgagg tattaataca ttttaagcct tttgttttta aatttctttt cttccagaga    2580
ttgtttaaaa ataatattg acaaaaat                                        2608
```

<210> SEQ ID NO 15
<211> LENGTH: 533
<212> TYPE: PRT
<213> ORGANISM: Homo sapiens

<400> SEQUENCE: 15

Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Ser Tyr Phe Arg Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
        275                 280                 285

Leu His Ile Ala Asp Lys Lys Arg Lys Lys Tyr Leu Asn Asn Lys Tyr
    290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe

```
                325            330            335
Val Tyr Asn Tyr Leu Tyr Leu Ala Asn Leu Arg Glu Asn Trp Glu Glu
            340                345                350
Val Lys Lys Asn Ala Arg Lys Ala Pro Gln Pro Glu Val Arg Arg Tyr
            355                360                365
Val Leu Pro Leu Asn Ile Asp Lys Ala Asp Thr Gly Lys Asn Leu Val
            370                375                380
Thr Leu Pro Asn Thr Thr Ala Thr Ala Ile Leu Cys Ser Asp Glu Thr
385                390                395                400
Ile Trp Leu Glu Pro Glu Val Leu Phe Ser Gly Pro Arg Gln Ala Phe
                405                410                415
Glu Phe Pro Gln Ile Asn Tyr Gln Lys Tyr Cys Gly Lys Pro Tyr Thr
            420                425                430
Tyr Ala Tyr Gly Leu Gly Leu Asn His Phe Val Pro Asp Arg Leu Cys
            435                440                445
Lys Leu Asn Val Lys Thr Lys Glu Thr Trp Val Trp Gln Glu Pro Asp
450                455                460
Ser Tyr Pro Ser Glu Pro Ile Phe Val Ser His Pro Asp Ala Leu Glu
465                470                475                480
Glu Asp Asp Gly Val Val Leu Ser Val Val Ser Pro Gly Ala Gly
                485                490                495
Gln Lys Pro Ala Tyr Leu Leu Ile Leu Asn Ala Lys Asp Leu Ser Glu
            500                505                510
Val Ala Arg Ala Glu Val Glu Ile Asn Ile Pro Val Thr Phe His Gly
            515                520                525
Leu Phe Lys Lys Ser
530
```

<210> SEQ ID NO 16
<211> LENGTH: 1752
<212> TYPE: DNA
<213> ORGANISM: Homo sapiens

<400> SEQUENCE: 16

```
gagcccgatt taacggaaac tgtgggcggt gagaagttcc ttatgacaca ctaatcccaa      60
cctgctgacc ggaccacgcc tccagcggag ggaacctcta gagctccagg acattcaggt     120
accaggtagc cccaaggagg agctgccgac ctggcaggga caaccaaga ctgggggttaa     180
atctcacagc ctgcaagtgg aagagaagaa cttgaaccca ggtccaactt ttgcgccaca     240
gcaggctgcc tcttggtcct gacaggaagt cacaacttgg ccctgacttc ctatcctagg     300
gaaggggccg gctggagagg ccaggacaga gaaagcagat cccttctttt tccaaggact     360
ctgtgtcttc cataggcaac atgtcagaag gggtgggcac gttccgcatg gtacctgaag     420
aggaacagga gctccgtgcc caactggagc agctcacaac caaggaccat ggacctgtct     480
ttggcccgtg cagccagctg ccccgccaca ccttgcagaa ggccaaggat gagctgaacg     540
agagagagga gacccgggag gaggcagtgc gagagctgca ggagatggtg caggcgcagg     600
cggcctcggg ggaggagctg gcggtggccg tggcggagag ggtgcaagag aaggacagcg     660
gcttcttcct gcgcttcatc cgcgcacgga gttcaacgt gggccgtgcc tatgagctgc     720
tcagaggcta tgtgaatttc cggctgcagt accctgagct ctttgacagc ctgtccccag     780
aggctgtccg ctgcaccatt gaagctggct accctggtgt cctctctagt cgggacaagt     840
atggccgagt ggtcatgctc ttcaacattg agaactggca aagtcaagaa atcacctttg     900
```

```
atgagatctt gcaggcatat tgcttcatcc tggagaagct gctggagaat gaggaaactc    960
aaatcaatgg cttctgcatc attgagaact tcaagggctt taccatgcag caggctgcta   1020
gtctccggac ttcagatctc aggaagatgg tggacatgct ccaggattcc ttcccagccc   1080
ggttcaaagc catccacttc atccaccagc catggtactt caccacgacc tacaatgtgg   1140
tcaagccctt cttgaagagc aagctgcttg agagggtctt tgtccacggg gatgaccttt   1200
ctggtttcta ccaggagatc gatgagaaca tcctgccctc tgacttcggg ggcacgctgc   1260
ccaagtatga tggcaaggcc gttgctgagc agctctttgg ccccaggcc caagctgaga    1320 acacagcctt ctgaaaacat ctcctgccag ctgaactgta gttagaatct ctgggcctct   1380
cctcaactgt cctggaccca aggctaggaa agggctgctt gagatgactg tggtccccc    1440 ttagactccc taagcccgag tgagctcagg tgtcaccctg ttctcaagtt gggggatggg   1500
taataaagga gggggaattc ccttgaacaa gaagaactgg ggatagttat atttccacct   1560
gcccttgaag ctttaagaca gtgattttg tgtaaggttg tatttcaaag actcgaattc    1620
attttctcag tcatttcctt tgtaacagag ttttacgact tagagtctgt gaaaacaggc   1680
aaggagcccg ggttaaaata tcccctatt cgcccccaaa atgcaataaa agaagataaa    1740
agagagagga ta                                                        1752
```

<210> SEQ ID NO 17
<211> LENGTH: 317
<212> TYPE: PRT
<213> ORGANISM: Homo sapiens

<400> SEQUENCE: 17

```
Met Ser Glu Gly Val Gly Thr Phe Arg Met Val Pro Glu Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Thr Arg Glu Glu Ala Val Arg
    50                  55                  60

Glu Leu Gln Glu Met Val Gln Ala Gln Ala Ser Gly Glu Glu Leu
65              70                  75                  80

Ala Val Ala Val Ala Glu Arg Val Gln Glu Lys Asp Ser Gly Phe Phe
                85                  90                  95

Leu Arg Phe Ile Arg Ala Arg Lys Phe Asn Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Pro Glu Ala Val Arg Cys Thr Ile Glu Ala Gly Tyr
    130                 135                 140

Pro Gly Val Leu Ser Ser Arg Asp Lys Tyr Gly Arg Val Val Met Leu
145                 150                 155                 160

Phe Asn Ile Glu Asn Trp Gln Ser Gln Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Ser Leu Arg Thr Ser Asp Leu Arg Lys Met Val
    210                 215                 220
```

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
            245                 250                 255

Phe Leu Lys Ser Lys Leu Leu Glu Arg Val Phe Val His Gly Asp Asp
            260                 265                 270

Leu Ser Gly Phe Tyr Gln Glu Ile Asp Glu Asn Ile Leu Pro Ser Asp
        275                 280                 285

Phe Gly Gly Thr Leu Pro Lys Tyr Asp Gly Lys Ala Val Ala Glu Gln
    290                 295                 300

Leu Phe Gly Pro Gln Ala Gln Ala Glu Asn Thr Ala Phe
305                 310                 315

<210> SEQ ID NO 18
<211> LENGTH: 3027
<212> TYPE: DNA
<213> ORGANISM: Homo sapiens

<400> SEQUENCE: 18
cagcgttcag gctgccccctt cttggctggg aagggcgctg aagaaacaac gcccaggacc      60
aggactatcc cctgctcaag ctgtgattcc gagacccctg ccaccactac tgcattcacg     120
gggatcccag gctagtggga ctcgacatgg gtagcccccca gggcagctcc ctacagcttg    180
ggccatctgc actttttccca aggccctaag tctccgcctc tgggctcgtt aaggtttggg    240
gtgggagctg tgctgtggga agcaacccgg actacacttg gcaagcatgg cgctactgaa    300
agtcaagttt gaccagaaga gcgggtcaa gttgcccaa gggctctggc tcatgaactg       360
gttctccgtg ttggctggca tcatcatctt cagcctagga ctgttcctga agattgaact    420
ccgaaagagg agcgatgtga tgaataattc tgagagccat tttgtgccca actcattgat    480
agggatgggg gtgctatcct gtgtcttcaa ctcgctggct gggaagatct gctacgacgc    540
cctggaccca gccaagtatg ccagatggaa gccctggctg aagccgtacc tggctatctg    600
tgttctcttc aacatcatcc tcttccttgt ggctctctgc tgctttctgc ttcggggctc    660
gctggagaac ccctgggcc aagggctcaa gaacggcatg aagtactacc gggacacaga    720 caccccctggc aggtgtttca tgaagaagac catcgacatg ctgcagatcg agttcaaatg    780
ctgcggcaac aacggttttc gggactggtt tgagattcag tggatcagca atcgctacct    840
ggacttttcc tccaaagaag tcaaagatcg aatcaagagc aacgtggatg gcggtacct    900 ggtggacggg gtccctttca gctgctgcaa tcctagctcg ccacggccct gcatccagta    960
tcagatcacc aacaactcag cacactacag ttacgaccac cagacggagg agctcaacct   1020
gtgggtgcgt ggctgcaggg ctgccctgct gagctactac agcagcctca tgaactccat   1080
gggtgtcgtc acgctcctca tttggctctt cgaggtgacc attacaattg gctgcgcta   1140 cctacagacg tcgctggatg gtgtgtccaa ccccgaggaa tctgagagcg agagccaggg   1200
ctggctgctg gagaggagcg tgccggagac ctggaaggcc tttctggaga gtgtgaagaa   1260
gctgggcaag gcaaccagg tggaagccga gggcgcagac gcaggccagg ccccagaggc   1320
tggctgaggg ccctggggcc cctccccctcc cgaacactga aaatagtgc actccaagaa   1380 acgtggatct cccctcatc caactccgaa agtctgaatc tcccaaggag ggcaccatct   1440
tacagagact ctccctgacg gtggaattta agtttagggt ccctaaaagc atttgacaca   1500
cagttgttga atgactgacc caaaatgtga atgaagctaa tgtgaatgtg agtgaagctc   1560

```
ccttcaggcc cgctgccata ggatatgccc tcctggtgac tcggggggctg tctcagacga   1620
ctagcccagg acccatcttt ctcacacgga tttagtccca ccctatggcc actggccgta   1680
tctgagggct gctccccttt tagaatttac ctcttatgag ctccatgttg cttcactcta   1740
tccaaagtgt cacttggtgc ataagcacag aaatctgaaa aatggccatg ttgtcttttt   1800
tttttttttt taatgccaag attgacaggt tggccgtttg cttaatgcca gaagttgggg   1860
gaaagttacg cttttctaag aataatggac tcttaaggca ttgagggctc taaacaggat   1920
tctttaatca tggagcaaga gaatttcaag gcaggggatt ttatccccca ccaaaaacac   1980
agtgaaaggc ctgcttttgt gtcccattca catgccctcg gtcactgagt ctggagtgaa   2040
ccacggggttg aggaagtcag gctgttggcg tgtcccagca ccacaccacc cctaaagtgc   2100
caggtgatct cctgtggctc atcggtggaa gcagtggggt aggctgctgc cctgctgtgg   2160
aagaggagca acaatcagac atgagtccac cctttggaga ccaggcctca gctcttggtg   2220
ggcccaggga cacccacaca ggtggccatc acagccccat ggacaacact aattgtccac   2280
agcaaagggc aaggaatcct ctgggagctt cttccgtttc ttcccccag atacccatct   2340
tgaaaaacac tatttctgga atgcttctgc atcaaaggag attctttgag atagcccatc   2400
ttcctgagct agcaaataca ggagtttttca ctttctttag gaaagagaag ctttcagggg   2460
aaggagagaa tgattttgct gacttcccaa gccctggtga ccagaccaag gcagggccca   2520
gcataattcc tccagttgga tgaacattca agagagctcg ttcctacctg gctggagacc   2580
gaggccagaa ggcaaaaacc agaaagggaa cagtccataa cttacctctg cttctgaccg   2640
atggtgtttg gaataggtt actttggact gagtttgggt tctctgctgt cctaagaact   2700
tcagtgtaga gaaataaga cttctggtgc tgctgggta tgttctgggc ttaattcccc   2760
caagcagaag accagatcca agatgtttgg acaccctgtc agacgttggt cccaagttta   2820
attagatttc tgaatctcgt tgaggccaag gaatgatcca tactgaaaaa atgctgagcc   2880
agccatcttt ggcaaaggtc cctgagctct tgctatctct caagagtgct gagaaccacg   2940
gtgaaagtgc tgctctaggc ccacaagtgt aactatgctg ttaacagctg tcaatagata   3000
attaaaattc atactgtatg aaaatca                                       3027

<210> SEQ ID NO 19
<211> LENGTH: 346
<212> TYPE: PRT
<213> ORGANISM: Homo sapiens

<400> SEQUENCE: 19

Met Ala Leu Leu Lys Val Lys Phe Asp Gln Lys Lys Arg Val Lys Leu
1               5                   10                  15

Ala Gln Gly Leu Trp Leu Met Asn Trp Phe Ser Val Leu Ala Gly Ile
            20                  25                  30

Ile Ile Phe Ser Leu Gly Leu Phe Leu Lys Ile Glu Leu Arg Lys Arg
        35                  40                  45

Ser Asp Val Met Asn Asn Ser Glu Ser His Phe Val Pro Asn Ser Leu
    50                  55                  60

Ile Gly Met Gly Val Leu Ser Cys Val Phe Asn Ser Leu Ala Gly Lys
65                  70                  75                  80

Ile Cys Tyr Asp Ala Leu Asp Pro Ala Lys Tyr Ala Arg Trp Lys Pro
                85                  90                  95

Trp Leu Lys Pro Tyr Leu Ala Ile Cys Val Leu Phe Asn Ile Ile Leu
            100                 105                 110
```

```
Phe Leu Val Ala Leu Cys Cys Phe Leu Leu Arg Gly Ser Leu Glu Asn
                115                 120                 125

Thr Leu Gly Gln Gly Leu Lys Asn Gly Met Lys Tyr Tyr Arg Asp Thr
    130                 135                 140

Asp Thr Pro Gly Arg Cys Phe Met Lys Lys Thr Ile Asp Met Leu Gln
145                 150                 155                 160

Ile Glu Phe Lys Cys Cys Gly Asn Asn Gly Phe Arg Asp Trp Phe Glu
                165                 170                 175

Ile Gln Trp Ile Ser Asn Arg Tyr Leu Asp Phe Ser Ser Lys Glu Val
                180                 185                 190

Lys Asp Arg Ile Lys Ser Asn Val Asp Gly Arg Tyr Leu Val Asp Gly
                195                 200                 205

Val Pro Phe Ser Cys Cys Asn Pro Ser Ser Pro Arg Pro Cys Ile Gln
    210                 215                 220

Tyr Gln Ile Thr Asn Asn Ser Ala His Tyr Ser Tyr Asp His Gln Thr
225                 230                 235                 240

Glu Glu Leu Asn Leu Trp Val Arg Gly Cys Arg Ala Ala Leu Leu Ser
                245                 250                 255

Tyr Tyr Ser Ser Leu Met Asn Ser Met Gly Val Val Thr Leu Leu Ile
                260                 265                 270

Trp Leu Phe Glu Val Thr Ile Thr Ile Gly Leu Arg Tyr Leu Gln Thr
                275                 280                 285

Ser Leu Asp Gly Val Ser Asn Pro Glu Glu Ser Glu Ser Glu Ser Gln
                290                 295                 300

Gly Trp Leu Leu Glu Arg Ser Val Pro Glu Thr Trp Lys Ala Phe Leu
305                 310                 315                 320

Glu Ser Val Lys Lys Leu Gly Lys Gly Asn Gln Val Glu Ala Glu Gly
                325                 330                 335

Ala Asp Ala Gly Gln Ala Pro Glu Ala Gly
                340                 345

<210> SEQ ID NO 20
<211> LENGTH: 1767
<212> TYPE: DNA
<213> ORGANISM: Homo sapiens

<400> SEQUENCE: 20
gtcagctggg tgactcatac atctgtgaga ccctccgtat ggagaccggg gcggggggtg      60
ttgcttaatg cttagaactg ctgaaactac cagttcactg tctcagcact aatccaactc     120
tgctccttaa gtgggatttg cttttagac attgagacct ggatgctggg catcctcgct     180 agatcccta caaattcccc acatacgtag gccaggagcc tcagcggtgc cccttcaggc     240
tcatctggca agacggtacc agcttgctca gaacaggggc tggctattca tcatctcaga     300
gcatagagac cctctccttg ccacccggcc cttcccacct ggttggtgac aaatcacaag     360
gtggtagaag ttgccaggga cagataacat ggcagccagc gggaagacca gcaagtccga     420
accgaaccat gttatcttca gaagatctcc ccgggacaaa tcggtgacca tctacctggg     480
gaacagagac tacatagacc atgtcagcca agtccagcct gtggatggtg tcgtgttggt     540
tgatcctgat cttgtgaagg gaagaaagt gtatgtcact ctgacctgcg ccttccgcta     600
tggccaagag gacattgacg tgatcggctt gaccttccgc agggacctgt acttctcccg     660
ggtccaggtg tatcctcctg tgggggccgc gagcaccccc acaaaactgc aagagagcct     720
gcttaaaaag ctggggagca acacgtaccc ctttctcctg acgtttcctg actacttgcc     780
```

```
ctgttcagtg atgttgcagc cagctccaca agattcaggg aagtcctgtg gggttgactt    840
tgaggtcaaa gcattcgcca cagacagcac cgatgccgaa gaggacaaaa tccccaagaa    900
gagctccgtg cgattactga tccgcaaagt acagcatgcc ccacttgaga tgggtcccca    960
gccccgagct gaggcggcct ggcagttctt catgtctgac aagcccctgc accttgcggt   1020
ctctctcaac aaagagatct atttccatgg ggagcccatc cctgtgaccg tgactgtcac   1080
caataacaca gagaagaccg tgaagaagat taaagcattc gtggaacagg tggccaatgt   1140
ggttctctac tcgagtgatt attacgtcaa gcccgtggct atggaggaag cgcaagaaaa   1200
agtgccacca acagcacttt tgaccaagac gctgacgctg ctgcccttgc tggctaacaa   1260
tcgagaaagg agaggcattg ccctggatgg gaaaatcaag cacgaggaca caaaccttgc   1320
ctccagcacc atcattaagg agggcataga ccggaccgtc ctgggaatcc tggtgtctta   1380
ccagatcaag gtgaagctca cagtgtcagg ctttctggga gagctcacct ccagtgaagt   1440
cgccactgag gtcccattcc gcctcatgca ccctcagcct gaggacccag ctaaggaaag   1500
ttatcaggat gcaaatttag tttttgagga gtttgctcgc ataatctga aagatgcagg   1560 agaagctgag gaggggaaga gagacaagaa tgacgttgat gagtgaagat gtcggctcag   1620
gatgccggaa aatgacctgt agttaccagt gcaacgagca aagccccaca gtttagtcct   1680
ttggagttat gctgcgtatg aaaggatgag tcttcttccg agaaataaag cttgtttgtt   1740
ctcccctgga aaaaaaaaaa aaaaaaa                                      1767
```

<210> SEQ ID NO 21
<211> LENGTH: 405
<212> TYPE: PRT
<213> ORGANISM: Homo sapiens

<400> SEQUENCE: 21

```
Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45

Val Leu Val Asp Pro Asp Leu Val Lys Gly Lys Lys Val Tyr Val Thr
    50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
```

```
                    195                 200                 205
Leu Ala Val Ser Leu Asn Lys Glu Ile Tyr Phe His Gly Glu Pro Ile
    210                 215                 220
Pro Val Thr Val Thr Val Thr Asn Asn Thr Glu Lys Thr Val Lys Lys
225                 230                 235                 240
Ile Lys Ala Phe Val Glu Gln Val Ala Asn Val Val Leu Tyr Ser Ser
                245                 250                 255
Asp Tyr Tyr Val Lys Pro Val Ala Met Glu Glu Ala Gln Glu Lys Val
            260                 265                 270
Pro Pro Asn Ser Thr Leu Thr Lys Thr Leu Thr Leu Leu Pro Leu Leu
        275                 280                 285
Ala Asn Asn Arg Glu Arg Arg Gly Ile Ala Leu Asp Gly Lys Ile Lys
    290                 295                 300
His Glu Asp Thr Asn Leu Ala Ser Ser Thr Ile Ile Lys Glu Gly Ile
305                 310                 315                 320
Asp Arg Thr Val Leu Gly Ile Leu Val Ser Tyr Gln Ile Lys Val Lys
                325                 330                 335
Leu Thr Val Ser Gly Phe Leu Gly Glu Leu Thr Ser Ser Glu Val Ala
            340                 345                 350
Thr Glu Val Pro Phe Arg Leu Met His Pro Gln Pro Glu Asp Pro Ala
        355                 360                 365
Lys Glu Ser Tyr Gln Asp Ala Asn Leu Val Phe Glu Glu Phe Ala Arg
    370                 375                 380
His Asn Leu Lys Asp Ala Gly Glu Ala Glu Glu Gly Lys Arg Asp Lys
385                 390                 395                 400
Asn Asp Val Asp Glu
                405

<210> SEQ ID NO 22
<211> LENGTH: 2483
<212> TYPE: DNA
<213> ORGANISM: Homo sapiens

<400> SEQUENCE: 22
agttgattgc aggtcctcct ggggccagaa gggtgcctgg gaggccaggt tctggggatc      60
ccctccatcc agaagaacca cctgctcact ctgtcccttc gcctgctgct gggaccatgg     120
gggctggggc cagtgctgag gagaagcact ccagggagct ggaaaagaag ctgaaagagg     180
acgctgagaa ggatgctcga accgtgaagc tgctgcttct gggtgccggt gagtccggga     240
agagccacca cgtcaagcag atgaagatta ccaccagga cgggtactcg ctggaagagt     300
gcctcgagtt tatcgccatc atctacggca acacgttgca gtccatcctg ccatcgtac      360 gcgccatgac cacactcaac atccagtacg agactctgc acgccaggac gacgcccgga     420
agctgatgca catggcagac actatcgagg agggcacgat gcccaaggag atgtcggaca     480
tcatccagcg gctgtggaag gactccggta ccaggcctg ttttgagcgc gcctcggagt     540
accagctcaa cgactcggcg ggctactacc tctccgacct ggagcgcctg gtaacccgg      600 gctacgtgcc caccgagcag gacgtgctgc gctcgcgagt caagaccact ggcatcatcg     660
agacgcagtt ctccttcaag gatctcaact tccggatgtt cgatgtgggc gggcagcgct     720
cggagcgcaa gaagtggatc cactgcttcg agggcgtgac ctgcatcatc ttcatcgcgg     780
cgctgagcgc ctacgacatg gtgctagtgg aggacgacga agtgaaccgc atgcacgaga     840
gcctgcacct gttcaacagc atctgcaacc accgctactt cgccacgacg tccatcgtgc     900
```

```
tcttccttaa caagaaggac gtcttcttcg agaagatcaa gaaggcgcac ctcagcatct    960
gtttcccgga ctacgatgga cccaacacct acgaggacgc cggcaactac atcaaggtgc   1020
agttcctcga gctcaacatg cggcgcgacg tgaaggagat ctattcccac atgacgtgcg   1080
ccaccgacac gcagaacgtc aaatttgtct tcgacgctgt caccgacatc atcatcaagg   1140
agaacctcaa agactgtggc ctcttctgag gccagggcct gtgctgcagt cggggacaag   1200
gagcttccgt ctggcaaggc cggggcacaa tttgcactcc cctcagctag acgcacagac   1260
tcagcaataa acctttgcat caggctccag ctgtcctttc ttggtggagg acttaattat   1320
cacaagtcat gggcatttat taagtgccca gtgctgggtt gggcatgaag tgggaagatg   1380
gcccctccca ggaagaagta cctggcctga caaggtgggg cactcttggg ggtatgggac   1440
caactcatgg cttttcacgg gagttgagga gagaggagct gtggaaaata ttcactggga   1500
cagtcttgga tcaagaggga gttttgaggt ggaggctcat tctggcaggg accgtagtgt   1560
ctaccagccc cagaaacatg ggcttatggc cacaggagtt cagtggagca agagcagggg   1620
aggagagacg tggacaggtg cccaaagcca gtcgagggc ctgggctttc tcagaaggtg   1680
atggagagtc ttggaagccc tcgaggcagg aacataattg cagggctggg attagggtga   1740
gggaagtgag gcacactcac cttgggtgca acatttaagg cgatgccaaa aaatttagta   1800
accaaggtaa ataatattag gataatattt ttaaaaatca aatgaatgca aaaccccaca   1860
atgaatgaaa tatcaaaatc aacagagga tcaaacagag gcatgctaag atatattggg   1920
gcttgaagca aagggaaaac tatttgttgc tatatgtttg tagggatttt ttgccagttt   1980
taaaaataca tgtatcataa agtttactat ctcagccact tgccggtgta tagtttggtg   2040
gtgttaagta cattcataat gttgtacaac caccgcaact gttcatctcc agaactcctt   2100
tcctcttgta aaactgtaac tctgtaccca tgaaaaaata accccccatt cctgccttcc   2160
cccggctcct ggcatccacc attctacttt ccatctctat gaatgtgact gctctaagtg   2220
cctcagatgt gtgggtccat gaagtctttg tcttttttgca actggcttat ttcacttagc   2280
atcatgtctt caaggtttat tcatgtgtag catatggcag aatctccttc cttttttaagg   2340
ttgaataata ttccattgta tatattccac actttgttta tttattcatc tattgatgaa   2400
tggttacatc tgccttttgg ctattgtgaa taatgctgct atgaacatgg gtgtacaaat   2460
ctctcaaaaa aaaaaaaaaa aaa                                            2483
```

<210> SEQ ID NO 23
<211> LENGTH: 350
<212> TYPE: PRT
<213> ORGANISM: Homo sapiens

<400> SEQUENCE: 23

Met Gly Ala Gly Ala Ser Ala Glu Glu Lys His Ser Arg Glu Leu Glu
1               5                   10                  15

Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
        35                  40                  45

Met Lys Ile Ile His Gln Asp Gly Tyr Ser Leu Glu Glu Cys Leu Glu
    50                  55                  60

Phe Ile Ala Ile Ile Tyr Gly Asn Thr Leu Gln Ser Ile Leu Ala Ile
65                  70                  75                  80

Val Arg Ala Met Thr Thr Leu Asn Ile Gln Tyr Gly Asp Ser Ala Arg
                85                  90                  95

Gln Asp Asp Ala Arg Lys Leu Met His Met Ala Asp Thr Ile Glu Glu
                100                 105                 110

Gly Thr Met Pro Lys Glu Met Ser Asp Ile Ile Gln Arg Leu Trp Lys
                115                 120                 125

Asp Ser Gly Ile Gln Ala Cys Phe Glu Arg Ala Ser Glu Tyr Gln Leu
                130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
                165                 170                 175

Thr Thr Gly Ile Ile Glu Thr Gln Phe Ser Phe Lys Asp Leu Asn Phe
                180                 185                 190

Arg Met Phe Asp Val Gly Gly Gln Arg Ser Glu Arg Lys Lys Trp Ile
                195                 200                 205

His Cys Phe Glu Gly Val Thr Cys Ile Ile Phe Ile Ala Ala Leu Ser
                210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
                245                 250                 255

Thr Thr Ser Ile Val Leu Phe Leu Asn Lys Lys Asp Val Phe Phe Glu
                260                 265                 270

Lys Ile Lys Lys Ala His Leu Ser Ile Cys Phe Pro Asp Tyr Asp Gly
                275                 280                 285

Pro Asn Thr Tyr Glu Asp Ala Gly Asn Tyr Ile Lys Val Gln Phe Leu
                290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
                340                 345                 350

<210> SEQ ID NO 24
<211> LENGTH: 201
<212> TYPE: PRT
<213> ORGANISM: Homo sapiens

<400> SEQUENCE: 24

Met Gly Asn Val Met Glu Gly Lys Ser Val Glu Glu Leu Ser Ser Thr
1               5                   10                  15

Glu Cys His Gln Trp Tyr Lys Lys Phe Met Thr Glu Cys Pro Ser Gly
                20                  25                  30

Gln Leu Thr Leu Tyr Glu Phe Arg Gln Phe Phe Gly Leu Lys Asn Leu
                35                  40                  45

Ser Pro Ser Ala Ser Gln Tyr Val Glu Gln Met Phe Glu Thr Phe Asp
            50                  55                  60

Phe Asn Lys Asp Gly Tyr Ile Asp Phe Met Glu Tyr Val Ala Ala Leu
65              70                  75                  80

Ser Leu Val Leu Lys Gly Lys Val Glu Gln Lys Leu Arg Trp Tyr Phe
                85                  90                  95

Lys Leu Tyr Asp Val Asp Gly Asn Gly Cys Ile Asp Arg Asp Glu Leu
                100                 105                 110

Leu Thr Ile Ile Gln Ala Ile Arg Ala Ile Asn Pro Cys Ser Asp Thr

```
                115                 120                 125
Thr Met Thr Ala Glu Glu Phe Thr Asp Thr Val Phe Ser Lys Ile Asp
        130                 135                 140

Val Asn Gly Asp Gly Glu Leu Ser Leu Glu Glu Phe Ile Glu Gly Val
145                 150                 155                 160

Gln Lys Asp Gln Met Leu Leu Asp Thr Leu Thr Arg Ser Leu Asp Leu
                165                 170                 175

Thr Arg Ile Val Arg Arg Leu Gln Asn Gly Glu Gln Asp Glu Glu Gly
            180                 185                 190

Ala Asp Glu Ala Ala Glu Ala Ala Gly
        195                 200

<210> SEQ ID NO 25
<211> LENGTH: 1103
<212> TYPE: PRT
<213> ORGANISM: Homo sapiens

<400> SEQUENCE: 25

Met Thr Ala Cys Ala Arg Arg Ala Gly Gly Leu Pro Asp Pro Gly Leu
1               5                   10                  15

Cys Gly Pro Ala Trp Trp Ala Pro Ser Leu Pro Arg Leu Pro Arg Ala
            20                  25                  30

Leu Pro Arg Leu Pro Leu Leu Leu Leu Leu Leu Leu Gln Pro Pro
        35                  40                  45

Ala Leu Ser Ala Val Phe Thr Val Gly Val Leu Gly Pro Trp Ala Cys
    50                  55                  60

Asp Pro Ile Phe Ser Arg Ala Arg Pro Asp Leu Ala Ala Arg Leu Ala
65                  70                  75                  80

Ala Ala Arg Leu Asn Arg Asp Pro Gly Leu Ala Gly Gly Pro Arg Phe
                85                  90                  95

Glu Val Ala Leu Leu Pro Glu Pro Cys Arg Thr Pro Gly Ser Leu Gly
            100                 105                 110

Ala Val Ser Ser Ala Leu Ala Arg Val Ser Gly Leu Val Gly Pro Val
        115                 120                 125

Asn Pro Ala Ala Cys Arg Pro Ala Glu Leu Leu Ala Glu Glu Ala Gly
        130                 135                 140

Ile Ala Leu Val Pro Trp Gly Cys Pro Trp Thr Gln Ala Glu Gly Thr
145                 150                 155                 160

Thr Ala Pro Ala Val Thr Pro Ala Ala Asp Ala Leu Tyr Ala Leu Leu
                165                 170                 175

Arg Ala Phe Gly Trp Ala Arg Val Ala Leu Val Thr Ala Pro Gln Asp
            180                 185                 190

Leu Trp Val Glu Ala Gly Arg Ser Leu Ser Thr Ala Leu Arg Ala Arg
        195                 200                 205

Gly Leu Pro Val Ala Ser Val Thr Ser Met Glu Pro Leu Asp Leu Ser
        210                 215                 220

Gly Ala Arg Glu Ala Leu Arg Lys Val Arg Asp Gly Pro Arg Val Thr
225                 230                 235                 240

Ala Val Ile Met Val Met His Ser Val Leu Leu Gly Gly Glu Glu Gln
                245                 250                 255

Arg Tyr Leu Leu Glu Ala Ala Glu Glu Leu Gly Leu Thr Asp Gly Ser
            260                 265                 270

Leu Val Phe Leu Pro Phe Asp Thr Ile His Tyr Ala Leu Ser Pro Gly
        275                 280                 285
```

```
Pro Glu Ala Leu Ala Ala Leu Ala Asn Ser Ser Gln Leu Arg Arg Ala
    290                 295                 300

His Asp Ala Val Leu Thr Leu Thr Arg His Cys Pro Ser Glu Gly Ser
305                 310                 315                 320

Val Leu Asp Ser Leu Arg Arg Ala Gln Glu Arg Arg Glu Leu Pro Ser
                325                 330                 335

Asp Leu Asn Leu Gln Gln Val Ser Pro Leu Phe Gly Thr Ile Tyr Asp
                340                 345                 350

Ala Val Phe Leu Leu Ala Arg Gly Val Ala Glu Ala Arg Ala Ala Ala
            355                 360                 365

Gly Gly Arg Trp Val Ser Gly Ala Ala Val Ala Arg His Ile Arg Asp
370                 375                 380

Ala Gln Val Pro Gly Phe Cys Gly Asp Leu Gly Gly Asp Glu Glu Pro
385                 390                 395                 400

Pro Phe Val Leu Leu Asp Thr Asp Ala Ala Gly Asp Arg Leu Phe Ala
                405                 410                 415

Thr Tyr Met Leu Asp Pro Ala Arg Gly Ser Phe Leu Ser Ala Gly Thr
            420                 425                 430

Arg Met His Phe Pro Arg Gly Gly Ser Ala Pro Gly Pro Asp Pro Ser
            435                 440                 445

Cys Trp Phe Asp Pro Asn Asn Ile Cys Gly Gly Leu Glu Pro Gly
    450                 455                 460

Leu Val Phe Leu Gly Phe Leu Val Val Gly Met Gly Leu Ala Gly
465                 470                 475                 480

Ala Phe Leu Ala His Tyr Val Arg His Arg Leu Leu His Met Gln Met
                485                 490                 495

Val Ser Gly Pro Asn Lys Ile Ile Leu Thr Val Asp Asp Ile Thr Phe
            500                 505                 510

Leu His Pro His Gly Gly Thr Ser Arg Lys Val Ala Gln Gly Ser Arg
            515                 520                 525

Ser Ser Leu Gly Ala Arg Ser Met Ser Asp Ile Arg Ser Gly Pro Ser
530                 535                 540

Gln His Leu Asp Ser Pro Asn Ile Gly Val Tyr Glu Gly Asp Arg Val
545                 550                 555                 560

Trp Leu Lys Lys Phe Pro Gly Asp Gln His Ile Ala Ile Arg Pro Ala
                565                 570                 575

Thr Lys Thr Ala Phe Ser Lys Leu Gln Glu Leu Arg His Glu Asn Val
            580                 585                 590

Ala Leu Tyr Leu Gly Leu Phe Leu Ala Arg Gly Ala Glu Gly Pro Ala
            595                 600                 605

Ala Leu Trp Glu Gly Asn Leu Ala Val Val Ser Glu His Cys Thr Arg
610                 615                 620

Gly Ser Leu Gln Asp Leu Leu Ala Gln Arg Glu Ile Lys Leu Asp Trp
625                 630                 635                 640

Met Phe Lys Ser Ser Leu Leu Leu Asp Leu Ile Lys Gly Ile Arg Tyr
                645                 650                 655

Leu His His Arg Gly Val Ala His Gly Arg Leu Lys Ser Arg Asn Cys
            660                 665                 670

Ile Val Asp Gly Arg Phe Val Leu Lys Ile Thr Asp His Gly His Gly
            675                 680                 685

Arg Leu Leu Glu Ala Gln Lys Val Leu Pro Glu Pro Arg Ala Glu
690                 695                 700

Asp Gln Leu Trp Thr Ala Pro Glu Leu Leu Arg Asp Pro Ala Leu Glu
```

-continued

```
            705                 710                 715                 720
        Arg Arg Gly Thr Leu Ala Gly Asp Val Phe Ser Leu Ala Ile Ile Met
                        725                 730                 735
        Gln Glu Val Val Cys Arg Ser Ala Pro Tyr Ala Met Leu Glu Leu Thr
                        740                 745                 750
        Pro Glu Glu Val Val Gln Arg Val Arg Ser Pro Pro Leu Cys Arg
                        755                 760                 765
        Pro Leu Val Ser Met Asp Gln Ala Pro Val Glu Cys Ile Leu Leu Met
                        770                 775                 780
        Lys Gln Cys Trp Ala Glu Gln Pro Glu Leu Arg Pro Ser Met Asp His
        785                 790                 795                 800
        Thr Phe Asp Leu Phe Lys Asn Ile Asn Lys Gly Arg Lys Thr Asn Ile
                        805                 810                 815
        Ile Asp Ser Met Leu Arg Met Leu Glu Gln Tyr Ser Ser Asn Leu Glu
                        820                 825                 830
        Asp Leu Ile Arg Glu Arg Thr Glu Leu Glu Leu Glu Lys Gln Lys
                        835                 840                 845
        Thr Asp Arg Leu Leu Thr Gln Met Leu Pro Pro Ser Val Ala Glu Ala
        850                 855                 860
        Leu Lys Thr Gly Thr Pro Val Glu Pro Glu Tyr Phe Glu Gln Val Thr
        865                 870                 875                 880
        Leu Tyr Phe Ser Asp Ile Val Gly Phe Thr Thr Ile Ser Ala Met Ser
                        885                 890                 895
        Glu Pro Ile Glu Val Val Asp Leu Leu Asn Asp Leu Tyr Thr Leu Phe
                        900                 905                 910
        Asp Ala Ile Ile Gly Ser His Asp Val Tyr Lys Val Glu Thr Ile Gly
                        915                 920                 925
        Asp Ala Tyr Met Val Ala Ser Gly Leu Pro Gln Arg Asn Gly Gln Arg
                        930                 935                 940
        His Ala Ala Glu Ile Ala Asn Met Ser Leu Asp Ile Leu Ser Ala Val
        945                 950                 955                 960
        Gly Thr Phe Arg Met Arg His Met Pro Glu Val Pro Val Arg Ile Arg
                        965                 970                 975
        Ile Gly Leu His Ser Gly Pro Cys Val Ala Gly Val Val Gly Leu Thr
                        980                 985                 990
        Met Pro Arg Tyr Cys Leu Phe Gly Asp Thr Val Asn Thr Ala Ser Arg
                        995                 1000                1005
        Met Glu Ser Thr Gly Leu Pro Tyr Arg Ile His Val Asn Leu Ser
            1010                1015                1020
        Thr Val Gly Ile Leu Arg Ala Leu Asp Ser Gly Tyr Gln Val Glu
            1025                1030                1035
        Leu Arg Gly Arg Thr Glu Leu Lys Gly Lys Gly Ala Glu Asp Thr
            1040                1045                1050
        Phe Trp Leu Val Gly Arg Arg Gly Phe Asn Lys Pro Ile Pro Lys
            1055                1060                1065
        Pro Pro Asp Leu Gln Pro Gly Ser Ser Asn His Gly Ile Ser Leu
            1070                1075                1080
        Gln Glu Ile Pro Pro Glu Arg Arg Arg Lys Leu Glu Lys Ala Arg
            1085                1090                1095
        Pro Gly Gln Phe Ser
            1100

<210> SEQ ID NO 26
```

```
<211> LENGTH: 676
<212> TYPE: PRT
<213> ORGANISM: Homo sapiens

<400> SEQUENCE: 26

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Arg Lys Lys Thr Lys Lys Asp Ala Ile Val Val Asp
130                 135                 140

Pro Ser Ser Asn Leu Tyr Tyr Arg Trp Leu Thr Ala Ile Ala Leu Pro
145                 150                 155                 160

Val Phe Tyr Asn Trp Tyr Leu Leu Ile Cys Arg Ala Cys Phe Asp Glu
                165                 170                 175

Leu Gln Ser Glu Tyr Leu Met Leu Trp Leu Val Leu Asp Tyr Ser Ala
            180                 185                 190

Asp Val Leu Tyr Val Leu Asp Val Leu Val Arg Ala Arg Thr Gly Phe
        195                 200                 205

Leu Glu Gln Gly Leu Met Val Ser Asp Thr Asn Arg Leu Trp Gln His
210                 215                 220

Tyr Lys Thr Thr Thr Gln Phe Lys Leu Asp Val Leu Ser Leu Val Pro
225                 230                 235                 240

Thr Asp Leu Ala Tyr Leu Lys Val Gly Thr Asn Tyr Pro Glu Val Arg
                245                 250                 255

Phe Asn Arg Leu Leu Lys Phe Ser Arg Leu Phe Glu Phe Phe Asp Arg
            260                 265                 270

Thr Glu Thr Arg Thr Asn Tyr Pro Asn Met Phe Arg Ile Gly Asn Leu
        275                 280                 285

Val Leu Tyr Ile Leu Ile Ile Ile His Trp Asn Ala Cys Ile Tyr Phe
290                 295                 300

Ala Ile Ser Lys Phe Ile Gly Phe Gly Thr Asp Ser Trp Val Tyr Pro
305                 310                 315                 320

Asn Ile Ser Ile Pro Glu His Gly Arg Leu Ser Arg Lys Tyr Ile Tyr
                325                 330                 335

Ser Leu Tyr Trp Ser Thr Leu Thr Leu Thr Thr Ile Gly Glu Thr Pro
            340                 345                 350

Pro Pro Val Lys Asp Glu Glu Tyr Leu Phe Val Val Asp Phe Leu
        355                 360                 365

Val Gly Val Leu Ile Phe Ala Thr Ile Val Gly Asn Val Gly Ser Met
370                 375                 380

Ile Ser Asn Met Asn Ala Ser Arg Ala Glu Phe Gln Ala Lys Ile Asp
```

```
385                 390                 395                 400
Ser Ile Lys Gln Tyr Met Gln Phe Arg Lys Val Thr Lys Asp Leu Glu
            405                 410                 415

Thr Arg Val Ile Arg Trp Phe Asp Tyr Leu Trp Ala Asn Lys Lys Thr
            420                 425                 430

Val Asp Glu Lys Glu Val Leu Lys Ser Leu Pro Asp Lys Leu Lys Ala
            435                 440                 445

Glu Ile Ala Ile Asn Val His Leu Asp Thr Leu Lys Lys Val Arg Ile
            450                 455                 460

Phe Gln Asp Cys Glu Ala Gly Leu Leu Val Glu Leu Val Leu Lys Leu
465                 470                 475                 480

Arg Pro Thr Val Phe Ser Pro Gly Asp Tyr Ile Cys Lys Lys Gly Asp
            485                 490                 495

Ile Gly Lys Glu Met Tyr Ile Ile Asn Glu Gly Lys Leu Ala Val Val
            500                 505                 510

Ala Asp Asp Gly Val Thr Gln Phe Val Val Leu Ser Asp Gly Ser Tyr
            515                 520                 525

Phe Gly Glu Ile Ser Ile Leu Asn Ile Lys Gly Ser Lys Ser Gly Asn
            530                 535                 540

Arg Arg Thr Ala Asn Ile Arg Ser Ile Gly Tyr Ser Asp Leu Phe Cys
545                 550                 555                 560

Leu Ser Lys Asp Asp Leu Met Glu Ala Leu Thr Glu Tyr Pro Glu Ala
            565                 570                 575

Lys Lys Ala Leu Glu Glu Lys Gly Arg Gln Ile Leu Met Lys Asp Asn
            580                 585                 590

Leu Ile Asp Glu Glu Leu Ala Arg Ala Gly Ala Asp Pro Lys Asp Leu
            595                 600                 605

Glu Glu Lys Val Glu Gln Leu Gly Ser Ser Leu Asp Thr Leu Gln Thr
            610                 615                 620

Arg Phe Ala Arg Leu Leu Ala Glu Tyr Asn Ala Thr Gln Met Lys Met
625                 630                 635                 640

Lys Gln Arg Leu Ser Gln Leu Glu Ser Gln Val Lys Gly Gly Gly Asp
            645                 650                 655

Lys Pro Leu Ala Asp Gly Glu Val Pro Gly Asp Ala Thr Lys Thr Glu
            660                 665                 670

Asp Lys Gln Gln
            675

<210> SEQ ID NO 27
<211> LENGTH: 694
<212> TYPE: PRT
<213> ORGANISM: Homo sapiens

<400> SEQUENCE: 27

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Glu Glu Thr Ser Ser Val Leu Gln Pro
            35                  40                  45

Gly Ile Ala Met Glu Thr Arg Gly Leu Ala Asp Ser Gly Gln Gly Ser
            50                  55                  60

Phe Thr Gly Gln Gly Ile Ala Arg Leu Ser Arg Leu Ile Phe Leu Leu
65                  70                  75                  80
```

-continued

Arg Arg Trp Ala Ala Arg His Val His His Gln Asp Gln Gly Pro Asp
            85                  90                  95

Ser Phe Pro Asp Arg Phe Arg Gly Ala Glu Leu Lys Glu Val Ser Ser
        100                 105                 110

Gln Glu Ser Asn Ala Gln Ala Asn Val Gly Ser Gln Glu Pro Ala Asp
        115                 120                 125

Arg Gly Arg Ser Ala Trp Pro Leu Ala Lys Cys Asn Thr Asn Thr Ser
        130                 135                 140

Asn Asn Thr Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
                180                 185                 190

Asp Glu Leu Gln Ser Glu Tyr Leu Met Leu Trp Leu Val Leu Asp Tyr
        195                 200                 205

Ser Ala Asp Val Leu Tyr Val Leu Asp Val Leu Arg Ala Arg Thr
        210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
                260                 265                 270

Val Arg Phe Asn Arg Leu Leu Lys Phe Ser Arg Leu Phe Glu Phe Phe
        275                 280                 285

Asp Arg Thr Glu Thr Arg Thr Asn Tyr Pro Asn Met Phe Arg Ile Gly
        290                 295                 300

Asn Leu Val Leu Tyr Ile Leu Ile Ile His Trp Asn Ala Cys Ile
305                 310                 315                 320

Tyr Phe Ala Ile Ser Lys Phe Ile Gly Phe Gly Thr Asp Ser Trp Val
                325                 330                 335

Tyr Pro Asn Ile Ser Ile Pro Glu His Gly Arg Leu Ser Arg Lys Tyr
                340                 345                 350

Ile Tyr Ser Leu Tyr Trp Ser Thr Leu Thr Leu Thr Thr Ile Gly Glu
                355                 360                 365

Thr Pro Pro Pro Val Lys Asp Glu Glu Tyr Leu Phe Val Val Val Asp
        370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
                420                 425                 430

Leu Glu Thr Arg Val Ile Arg Trp Phe Asp Tyr Leu Trp Ala Asn Lys
                435                 440                 445

Lys Thr Val Asp Glu Lys Glu Val Leu Lys Ser Leu Pro Asp Lys Leu
        450                 455                 460

Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys

```
                500             505             510
Gly Asp Ile Gly Lys Glu Met Tyr Ile Ile Asn Glu Gly Lys Leu Ala
            515                 520                 525

Val Val Ala Asp Asp Gly Val Thr Gln Phe Val Val Leu Ser Asp Gly
            530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
            580                 585                 590

Glu Ala Lys Lys Ala Leu Glu Glu Lys Gly Arg Gln Ile Leu Met Lys
            595                 600                 605

Asp Asn Leu Ile Asp Glu Glu Leu Ala Arg Ala Gly Ala Asp Pro Lys
            610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
            660                 665                 670

Gly Asp Lys Pro Leu Ala Asp Gly Glu Val Pro Gly Asp Ala Thr Lys
            675                 680                 685

Thr Glu Asp Lys Gln Gln
            690

<210> SEQ ID NO 28
<211> LENGTH: 354
<212> TYPE: PRT
<213> ORGANISM: Homo sapiens

<400> SEQUENCE: 28

Met Gly Ser Gly Ala Ser Ala Glu Asp Lys Glu Leu Ala Lys Arg Ser
1               5                   10                  15

Lys Glu Leu Glu Lys Lys Leu Gln Glu Asp Ala Asp Lys Glu Ala Lys
            20                  25                  30

Thr Val Lys Leu Leu Leu Leu Gly Ala Gly Glu Ser Gly Lys Ser Thr
        35                  40                  45

Ile Val Lys Gln Met Lys Ile Ile His Gln Asp Gly Tyr Ser Pro Glu
    50                  55                  60

Glu Cys Leu Glu Phe Lys Ala Ile Ile Tyr Gly Asn Val Leu Gln Ser
65                  70                  75                  80

Ile Leu Ala Ile Ile Arg Ala Met Thr Thr Leu Gly Ile Asp Tyr Ala
                85                  90                  95

Glu Pro Ser Cys Ala Asp Asp Gly Arg Gln Leu Asn Asn Leu Ala Asp
            100                 105                 110

Ser Ile Glu Glu Gly Thr Met Pro Pro Glu Leu Val Glu Val Ile Arg
        115                 120                 125

Arg Leu Trp Lys Asp Gly Gly Val Gln Ala Cys Phe Glu Arg Ala Ala
    130                 135                 140

Glu Tyr Gln Leu Asn Asp Ser Ala Ser Tyr Tyr Leu Asn Gln Leu Glu
145                 150                 155                 160

Arg Ile Thr Asp Pro Glu Tyr Leu Pro Ser Glu Gln Asp Val Leu Arg
                165                 170                 175
```

-continued

Ser Arg Val Lys Thr Thr Gly Ile Ile Glu Thr Lys Phe Ser Val Lys
            180                 185                 190

Asp Leu Asn Phe Arg Met Phe Asp Val Gly Gly Gln Arg Ser Glu Arg
            195                 200                 205

Lys Lys Trp Ile His Cys Phe Glu Gly Val Thr Cys Ile Ile Phe Cys
210                 215                 220

Ala Ala Leu Ser Ala Tyr Asp Met Val Leu Val Glu Asp Asp Glu Val
225                 230                 235                 240

Asn Arg Met His Glu Ser Leu His Leu Phe Asn Ser Ile Cys Asn His
                245                 250                 255

Lys Phe Phe Ala Ala Thr Ser Ile Val Leu Phe Leu Asn Lys Lys Asp
            260                 265                 270

Leu Phe Glu Glu Lys Ile Lys Lys Val His Leu Ser Ile Cys Phe Pro
            275                 280                 285

Glu Tyr Asp Gly Asn Asn Ser Tyr Asp Asp Ala Gly Asn Tyr Ile Lys
            290                 295                 300

Ser Gln Phe Leu Asp Leu Asn Met Arg Lys Asp Val Lys Glu Ile Tyr
305                 310                 315                 320

Ser His Met Thr Cys Ala Thr Asp Thr Gln Asn Val Lys Phe Val Phe
                325                 330                 335

Asp Ala Val Thr Asp Ile Ile Ile Lys Glu Asn Leu Lys Asp Cys Gly
            340                 345                 350

Leu Phe

<210> SEQ ID NO 29
<211> LENGTH: 858
<212> TYPE: PRT
<213> ORGANISM: Homo sapiens

<400> SEQUENCE: 29

Met Gly Glu Ile Asn Gln Val Ala Val Glu Lys Tyr Leu Glu Glu Asn
1               5                   10                  15

Pro Gln Phe Ala Lys Glu Tyr Phe Asp Arg Lys Leu Arg Val Glu Val
            20                  25                  30

Leu Gly Glu Ile Phe Lys Asn Ser Gln Val Pro Val Gln Ser Ser Met
            35                  40                  45

Ser Phe Ser Glu Leu Thr Gln Val Glu Glu Ser Ala Leu Cys Leu Glu
    50                  55                  60

Leu Leu Trp Thr Val Gln Glu Gly Gly Thr Pro Glu Gln Gly Val
65                  70                  75                  80

His Arg Ala Leu Gln Arg Leu Ala His Leu Gln Ala Asp Arg Cys
                85                  90                  95

Ser Met Phe Leu Cys Arg Ser Arg Asn Gly Ile Pro Glu Val Ala Ser
            100                 105                 110

Arg Leu Leu Asp Val Thr Pro Thr Ser Lys Phe Glu Asp Asn Leu Val
            115                 120                 125

Gly Pro Asp Lys Glu Val Val Phe Pro Leu Asp Ile Gly Ile Val Gly
            130                 135                 140

Trp Ala Ala His Thr Lys Lys Thr His Asn Val Pro Asp Val Lys Lys
145                 150                 155                 160

Asn Ser His Phe Ser Asp Phe Met Asp Lys Gln Thr Gly Tyr Val Thr
                165                 170                 175

Lys Asn Leu Leu Ala Thr Pro Ile Val Val Gly Lys Glu Val Leu Ala
            180                 185                 190

-continued

```
Val Ile Met Ala Val Asn Lys Val Asn Ala Ser Glu Phe Ser Lys Gln
        195                 200                 205
Asp Glu Glu Val Phe Ser Lys Tyr Leu Asn Phe Val Ser Ile Ile Leu
        210                 215                 220
Arg Leu His His Thr Ser Tyr Met Tyr Asn Ile Glu Ser Arg Arg Ser
225                 230                 235                 240
Gln Ile Leu Met Trp Ser Ala Asn Lys Val Phe Glu Glu Leu Thr Asp
                245                 250                 255
Val Glu Arg Gln Phe His Lys Ala Leu Tyr Thr Val Arg Ser Tyr Leu
            260                 265                 270
Asn Cys Glu Arg Tyr Ser Ile Gly Leu Leu Asp Met Thr Lys Glu Lys
        275                 280                 285
Glu Phe Tyr Asp Glu Trp Pro Ile Lys Leu Gly Glu Val Glu Pro Tyr
    290                 295                 300
Lys Gly Pro Lys Thr Pro Asp Gly Arg Glu Val Asn Phe Tyr Lys Ile
305                 310                 315                 320
Ile Asp Tyr Ile Leu His Gly Lys Glu Ile Lys Val Ile Pro Thr
                325                 330                 335
Pro Pro Ala Asp His Trp Thr Leu Ile Ser Gly Leu Pro Thr Tyr Val
            340                 345                 350
Ala Glu Asn Gly Phe Ile Cys Asn Met Met Asn Ala Pro Ala Asp Glu
        355                 360                 365
Tyr Phe Thr Phe Gln Lys Gly Pro Val Asp Glu Thr Gly Trp Val Ile
    370                 375                 380
Lys Asn Val Leu Ser Leu Pro Ile Val Asn Lys Lys Glu Asp Ile Val
385                 390                 395                 400
Gly Val Ala Thr Phe Tyr Asn Arg Lys Asp Gly Lys Pro Phe Asp Glu
                405                 410                 415
His Asp Glu Tyr Ile Thr Glu Thr Leu Thr Gln Phe Leu Gly Trp Ser
            420                 425                 430
Leu Leu Asn Thr Asp Thr Tyr Asp Lys Met Asn Lys Leu Glu Asn Arg
        435                 440                 445
Lys Asp Ile Ala Gln Glu Met Leu Met Asn Gln Thr Lys Ala Thr Pro
    450                 455                 460
Glu Glu Ile Lys Ser Ile Leu Lys Phe Gln Glu Lys Leu Asn Val Asp
465                 470                 475                 480
Val Ile Asp Asp Cys Glu Lys Gln Leu Val Ala Ile Leu Lys Glu
                485                 490                 495
Asp Leu Pro Asp Pro Arg Ser Ala Glu Leu Tyr Glu Phe Arg Phe Ser
            500                 505                 510
Asp Phe Pro Leu Thr Glu His Gly Leu Ile Lys Cys Gly Ile Arg Leu
        515                 520                 525
Phe Phe Glu Ile Asn Val Val Glu Lys Phe Lys Val Pro Val Glu Val
    530                 535                 540
Leu Thr Arg Trp Met Tyr Thr Val Arg Lys Gly Tyr Arg Ala Val Thr
545                 550                 555                 560
Tyr His Asn Trp Arg His Gly Phe Asn Val Gly Gln Thr Met Phe Thr
                565                 570                 575
Leu Leu Met Thr Gly Arg Leu Lys Lys Tyr Tyr Thr Asp Leu Glu Ala
            580                 585                 590
Phe Ala Met Leu Ala Ala Ala Phe Cys His Asp Ile Asp His Arg Gly
        595                 600                 605
Thr Asn Asn Leu Tyr Gln Met Lys Ser Thr Ser Pro Leu Ala Arg Leu
```

```
                610            615            620

His Gly Ser Ser Ile Leu Glu Arg His His Leu Glu Tyr Ser Lys Thr
625                 630                 635                 640

Leu Leu Gln Asp Glu Ser Leu Asn Ile Phe Gln Asn Leu Asn Lys Arg
                645                 650                 655

Gln Phe Glu Thr Val Ile His Leu Phe Glu Val Ala Ile Ile Ala Thr
            660                 665                 670

Asp Leu Ala Leu Tyr Phe Lys Lys Arg Thr Met Phe Gln Lys Ile Val
            675                 680                 685

Asp Ala Cys Glu Gln Met Gln Thr Glu Glu Ala Ile Lys Tyr Val
            690                 695                 700

Thr Val Asp Pro Thr Lys Lys Glu Ile Ile Met Ala Met Met Met Thr
705                 710                 715                 720

Ala Cys Asp Leu Ser Ala Ile Thr Lys Pro Trp Glu Val Gln Ser Gln
                725                 730                 735

Val Ala Leu Met Val Ala Asn Glu Phe Trp Glu Gln Gly Asp Leu Glu
                740                 745                 750

Arg Thr Val Leu Gln Gln Gln Pro Ile Pro Met Met Asp Arg Asn Lys
                755                 760                 765

Arg Asp Glu Leu Pro Lys Leu Gln Val Gly Phe Ile Asp Phe Val Cys
770                 775                 780

Thr Phe Val Tyr Lys Glu Phe Ser Arg Phe His Lys Glu Ile Thr Pro
785                 790                 795                 800

Met Leu Ser Gly Leu Gln Asn Asn Arg Val Glu Trp Lys Ser Leu Ala
                805                 810                 815

Asp Glu Tyr Asp Ala Lys Met Lys Val Ile Glu Glu Glu Ala Lys Lys
                820                 825                 830

Gln Glu Gly Gly Ala Glu Lys Ala Ala Glu Asp Ser Gly Gly Gly Asp
                835                 840                 845

Asp Lys Lys Ser Lys Thr Cys Leu Met Leu
        850                 855

<210> SEQ ID NO 30
<211> LENGTH: 83
<212> TYPE: PRT
<213> ORGANISM: Homo sapiens

<400> SEQUENCE: 30

Met Ser Asp Asn Thr Thr Leu Pro Ala Pro Ala Ser Asn Gln Gly Pro
1               5                   10                  15

Thr Thr Pro Arg Lys Gly Pro Pro Lys Phe Lys Gln Arg Gln Thr Arg
                20                  25                  30

Gln Phe Lys Ser Lys Pro Pro Lys Lys Gly Val Lys Gly Phe Gly Asp
            35                  40                  45

Asp Ile Pro Gly Met Glu Gly Leu Gly Thr Asp Ile Thr Val Ile Cys
        50                  55                  60

Pro Trp Glu Ala Phe Ser His Leu Glu Leu His Glu Leu Ala Gln Phe
65                  70                  75                  80

Gly Ile Ile

<210> SEQ ID NO 31
<211> LENGTH: 299
<212> TYPE: PRT
<213> ORGANISM: Homo sapiens

<400> SEQUENCE: 31
```

```
Met Met Ala Tyr Met Asn Pro Gly Pro His Tyr Ser Val Asn Ala Leu
1               5                   10                  15

Ala Leu Ser Gly Pro Ser Val Asp Leu Met His Gln Ala Val Pro Tyr
                20                  25                  30

Pro Ser Ala Pro Arg Lys Gln Arg Arg Glu Arg Thr Thr Phe Thr Arg
            35                  40                  45

Ser Gln Leu Glu Glu Leu Glu Ala Leu Phe Ala Lys Thr Gln Tyr Pro
        50                  55                  60

Asp Val Tyr Ala Arg Glu Val Ala Leu Lys Ile Asn Leu Pro Glu
65                  70                  75                  80

Ser Arg Val Gln Val Trp Phe Lys Asn Arg Arg Ala Lys Cys Arg Gln
                85                  90                  95

Gln Arg Gln Gln Gln Lys Gln Gln Gln Pro Pro Gly Gly Gln Ala
            100                 105                 110

Lys Ala Arg Pro Ala Lys Arg Lys Ala Gly Thr Ser Pro Arg Pro Ser
            115                 120                 125

Thr Asp Val Cys Pro Asp Pro Leu Gly Ile Ser Asp Ser Tyr Ser Pro
130                 135                 140

Pro Leu Pro Gly Pro Ser Gly Ser Pro Thr Thr Ala Val Ala Thr Val
145                 150                 155                 160

Ser Ile Trp Ser Pro Ala Ser Glu Ser Pro Leu Pro Glu Ala Gln Arg
                165                 170                 175

Ala Gly Leu Val Ala Ser Gly Pro Ser Leu Thr Ser Ala Pro Tyr Ala
            180                 185                 190

Met Thr Tyr Ala Pro Ala Ser Ala Phe Cys Ser Ser Pro Ser Ala Tyr
        195                 200                 205

Gly Ser Pro Ser Ser Tyr Phe Ser Gly Leu Asp Pro Tyr Leu Ser Pro
210                 215                 220

Met Val Pro Gln Leu Gly Gly Pro Ala Leu Ser Pro Leu Ser Gly Pro
225                 230                 235                 240

Ser Val Gly Pro Ser Leu Ala Gln Ser Pro Thr Ser Leu Ser Gly Gln
                245                 250                 255

Ser Tyr Gly Ala Tyr Ser Pro Val Asp Ser Leu Glu Phe Lys Asp Pro
            260                 265                 270

Thr Gly Thr Trp Lys Phe Thr Tyr Asn Pro Met Asp Pro Leu Asp Tyr
            275                 280                 285

Lys Asp Gln Ser Ala Trp Lys Phe Gln Ile Leu
        290                 295

<210> SEQ ID NO 32
<211> LENGTH: 809
<212> TYPE: PRT
<213> ORGANISM: Homo sapiens

<400> SEQUENCE: 32

Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
                20                  25                  30

Pro Ser Asn Gln Ser Gln Gln Thr Ala Gln Glu Glu Asn Lys Gly
            35                  40                  45

Glu Glu Lys Ser Leu Lys Thr Lys Ser Thr Pro Val Thr Ser Glu Glu
        50                  55                  60

Pro His Thr Asn Ile Gln Asp Lys Leu Ser Lys Lys Asn Ser Ser Gly
```

```
              65                  70                  75                  80
Asp Leu Thr Thr Asn Pro Asp Pro Gln Asn Ala Ala Glu Pro Thr Gly
                         85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
            115                 120                 125

Asp Ala Gln Leu His Asn Leu Val Lys Arg Met Arg Gln Arg Thr Ala
            130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Val Lys Glu Ser
                165                 170                 175

Asp Asp Lys Pro Thr Glu His Tyr Tyr Arg Leu Leu Trp Phe Lys Val
                180                 185                 190

Lys Lys Met Pro Leu Thr Glu Tyr Leu Lys Arg Ile Lys Leu Pro Asn
                195                 200                 205

Ser Ile Asp Ser Tyr Thr Asp Arg Leu Tyr Leu Leu Trp Leu Leu Leu
            210                 215                 220

Val Thr Leu Ala Tyr Asn Trp Asn Cys Trp Phe Ile Pro Leu Arg Leu
225                 230                 235                 240

Val Phe Pro Tyr Gln Thr Ala Asp Asn Ile His Tyr Trp Leu Ile Ala
                245                 250                 255

Asp Ile Ile Cys Asp Ile Ile Tyr Leu Tyr Asp Met Leu Phe Ile Gln
                260                 265                 270

Pro Arg Leu Gln Phe Val Arg Gly Gly Asp Ile Ile Val Asp Ser Asn
            275                 280                 285

Glu Leu Arg Lys His Tyr Arg Thr Ser Thr Lys Phe Gln Leu Asp Val
            290                 295                 300

Ala Ser Ile Ile Pro Phe Asp Ile Cys Tyr Leu Phe Phe Gly Phe Asn
305                 310                 315                 320

Pro Met Phe Arg Ala Asn Arg Met Leu Lys Tyr Thr Ser Phe Phe Glu
                325                 330                 335

Phe Asn His His Leu Glu Ser Ile Met Asp Lys Ala Tyr Ile Tyr Arg
            340                 345                 350

Val Ile Arg Thr Thr Gly Tyr Leu Leu Phe Ile Leu His Ile Asn Ala
            355                 360                 365

Cys Val Tyr Tyr Trp Ala Ser Asn Tyr Glu Gly Ile Gly Thr Thr Arg
            370                 375                 380

Trp Val Tyr Asp Gly Glu Gly Asn Glu Tyr Leu Arg Cys Tyr Tyr Trp
385                 390                 395                 400

Ala Val Arg Thr Leu Ile Thr Ile Gly Gly Leu Pro Glu Pro Gln Thr
                405                 410                 415

Leu Phe Glu Ile Val Phe Gln Leu Leu Asn Phe Phe Ser Gly Val Phe
                420                 425                 430

Val Phe Ser Ser Leu Ile Gly Gln Met Arg Asp Val Ile Gly Ala Ala
            435                 440                 445

Thr Ala Asn Gln Asn Tyr Phe Arg Ala Cys Met Asp Asp Thr Ile Ala
            450                 455                 460

Tyr Met Asn Asn Tyr Ser Ile Pro Lys Leu Val Gln Lys Arg Val Arg
465                 470                 475                 480

Thr Trp Tyr Glu Tyr Thr Trp Asp Ser Gln Arg Met Leu Asp Glu Ser
                485                 490                 495
```

```
Asp Leu Leu Lys Thr Leu Pro Thr Thr Val Gln Leu Ala Leu Ala Ile
            500                 505                 510

Asp Val Asn Phe Ser Ile Ile Ser Lys Val Asp Leu Phe Lys Gly Cys
            515                 520                 525

Asp Thr Gln Met Ile Tyr Asp Met Leu Leu Arg Leu Lys Ser Val Leu
            530                 535                 540

Tyr Leu Pro Gly Asp Phe Val Cys Lys Gly Glu Ile Gly Lys Glu
545                 550                 555                 560

Met Tyr Ile Ile Lys His Gly Glu Val Gln Val Leu Gly Gly Pro Asp
            565                 570                 575

Gly Thr Lys Val Leu Val Thr Leu Lys Ala Gly Ser Val Phe Gly Glu
            580                 585                 590

Ile Ser Leu Leu Ala Ala Gly Gly Asn Arg Arg Thr Ala Asn Val
    595                 600                 605

Val Ala His Gly Phe Ala Asn Leu Leu Thr Leu Asp Lys Lys Thr Leu
            610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
            645                 650                 655

Pro Pro Arg Lys Asp Leu Ala Leu Leu Phe Pro Pro Lys Glu Glu Thr
            660                 665                 670

Pro Lys Leu Phe Lys Thr Leu Leu Gly Gly Thr Gly Lys Ala Ser Leu
            675                 680                 685

Ala Arg Leu Leu Lys Leu Lys Arg Glu Gln Ala Ala Gln Lys Lys Glu
            690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
            725                 730                 735

Asn Glu Asp Lys Asp Lys Gly Arg Glu Pro Glu Lys Pro Leu Asp
            740                 745                 750

Arg Pro Glu Cys Thr Ala Ser Pro Ile Ala Val Glu Glu Pro His
            755                 760                 765

Ser Val Arg Arg Thr Val Leu Pro Arg Gly Thr Ser Arg Gln Ser Leu
            770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
                805

<210> SEQ ID NO 33
<211> LENGTH: 610
<212> TYPE: PRT
<213> ORGANISM: Homo sapiens

<400> SEQUENCE: 33

Met Pro Leu Thr Glu Tyr Leu Lys Arg Ile Lys Leu Pro Asn Ser Ile
1               5                   10                  15

Asp Ser Tyr Thr Asp Arg Leu Tyr Leu Leu Trp Leu Leu Leu Val Thr
                20                  25                  30

Leu Ala Tyr Asn Trp Asn Cys Cys Phe Ile Pro Leu Arg Leu Val Phe
            35                  40                  45

Pro Tyr Gln Thr Ala Asp Asn Ile His Tyr Trp Leu Ile Ala Asp Ile
```

-continued

```
                50                  55                  60
Ile Cys Asp Ile Ile Tyr Leu Tyr Asp Met Leu Phe Ile Gln Pro Arg
 65                  70                  75                  80
Leu Gln Phe Val Arg Gly Gly Asp Ile Ile Val Asp Ser Asn Glu Leu
                     85                  90                  95
Arg Lys His Tyr Arg Thr Ser Thr Lys Phe Gln Leu Asp Val Ala Ser
                    100                 105                 110
Ile Ile Pro Phe Asp Ile Cys Tyr Leu Phe Gly Phe Asn Pro Met
                115                 120                 125
Phe Arg Ala Asn Arg Met Leu Lys Tyr Thr Ser Phe Phe Glu Phe Asn
                130                 135                 140
His His Leu Glu Ser Ile Met Asp Lys Ala Tyr Ile Tyr Arg Val Ile
145                 150                 155                 160
Arg Thr Thr Gly Tyr Leu Leu Phe Ile Leu His Ile Asn Ala Cys Val
                    165                 170                 175
Tyr Tyr Trp Ala Ser Asn Tyr Glu Gly Ile Gly Thr Thr Arg Trp Val
                180                 185                 190
Tyr Asp Gly Glu Gly Asn Glu Tyr Leu Arg Cys Tyr Tyr Trp Ala Val
                195                 200                 205
Arg Thr Leu Ile Thr Ile Gly Gly Leu Pro Glu Pro Gln Thr Leu Phe
                210                 215                 220
Glu Ile Val Phe Gln Leu Leu Asn Phe Ser Gly Val Phe Val Phe
225                 230                 235                 240
Ser Ser Leu Ile Gly Gln Met Arg Asp Val Ile Gly Ala Ala Thr Ala
                    245                 250                 255
Asn Gln Asn Tyr Phe Arg Ala Cys Met Asp Asp Thr Ile Ala Tyr Met
                260                 265                 270
Asn Asn Tyr Ser Ile Pro Lys Leu Val Gln Lys Arg Val Arg Thr Trp
                275                 280                 285
Tyr Glu Tyr Thr Trp Asp Ser Gln Arg Met Leu Asp Glu Ser Asp Leu
                290                 295                 300
Leu Lys Thr Leu Pro Thr Thr Val Gln Leu Ala Leu Ala Ile Asp Val
305                 310                 315                 320
Asn Phe Ser Ile Ile Ser Lys Val Asp Leu Phe Lys Gly Cys Asp Thr
                    325                 330                 335
Gln Met Ile Tyr Asp Met Leu Leu Arg Leu Lys Ser Val Leu Tyr Leu
                340                 345                 350
Pro Gly Asp Phe Val Cys Lys Lys Gly Glu Ile Gly Lys Glu Met Tyr
                355                 360                 365
Ile Ile Lys His Gly Glu Val Gln Val Leu Gly Gly Pro Asp Gly Thr
370                 375                 380
Lys Val Leu Val Thr Leu Lys Ala Gly Ser Val Leu Ala Ala Gly
385                 390                 395                 400
Gly Gly Asn Arg Arg Thr Ala Asn Val Val Ala His Gly Phe Ala Asn
                    405                 410                 415
Leu Leu Thr Leu Asp Lys Lys Thr Leu Gln Glu Ile Leu Val His Tyr
                420                 425                 430
Pro Asp Ser Glu Arg Ile Leu Met Lys Lys Ala Arg Val Leu Leu Lys
                435                 440                 445
Gln Lys Ala Lys Thr Ala Glu Ala Thr Pro Pro Arg Lys Asp Leu Ala
                450                 455                 460
Leu Leu Phe Pro Pro Lys Glu Glu Thr Pro Lys Leu Phe Lys Thr Leu
465                 470                 475                 480
```

Leu Gly Gly Thr Gly Lys Ala Ser Leu Ala Arg Leu Lys Leu Lys
            485                 490                 495

Arg Glu Gln Ala Ala Gln Lys Lys Glu Asn Ser Glu Gly Glu Glu
            500                 505                 510

Glu Gly Lys Glu Asn Glu Asp Lys Gln Lys Glu Asn Glu Asp Lys Gln
            515                 520                 525

Lys Glu Asn Glu Asp Lys Gly Lys Glu Asn Glu Asp Lys Asp Lys Gly
            530                 535                 540

Arg Glu Pro Glu Glu Lys Pro Leu Asp Arg Pro Glu Cys Thr Ala Ser
545                 550                 555                 560

Pro Ile Ala Val Glu Glu Glu Pro His Ser Val Arg Arg Thr Val Leu
            565                 570                 575

Pro Arg Gly Thr Ser Arg Gln Ser Leu Ile Ile Ser Met Ala Pro Ser
            580                 585                 590

Ala Glu Gly Gly Glu Glu Val Leu Thr Ile Glu Val Lys Glu Lys Ala
            595                 600                 605

Lys Gln
    610

<210> SEQ ID NO 34
<211> LENGTH: 7100
<212> TYPE: DNA
<213> ORGANISM: Homo sapiens

<400> SEQUENCE: 34

| | | | | |
|---|---|---|---|---|
| gacatactga | gaataaatcc | aaagacatta | gtttctttgc | acgaaatgag | gttacatatc | 60 |
| cagtgacatt | tatttgagct | atttaaacaa | cttaaacatc | tttttctttt | cttaataagg | 120 |
| gacgtttcaa | gttgtggtct | cagccaaaat | gagtgatacc | ccttctactg | gtttttccat | 180 |
| cattcatcct | acgtcttctg | aaggtcaagt | tccacccoct | cgccatttga | gcctcactca | 240 |
| tcctgttgtg | gccaagcgaa | tcagtttcta | caagagcgga | gaccccaat | tcggcgggt | 300 |
| cagggtggtg | gtcaaccctc | gctcctttaa | gtcctttgat | gctctgctgg | ataacttgtc | 360 |
| caggaaggtg | cccctccctt | ttggagtgag | gaacatcagc | acccctcggg | gcaggcacag | 420 |
| catcacgcgc | ctggaggagc | tggaggacgg | cgagtcctac | ctatgttccc | acggcaggaa | 480 |
| ggtgcagcct | gtagacctgg | acaaagcccg | tcggcgcccg | cggccctggc | tcagcagccg | 540 |
| ggccattagc | gcgcactcac | cgccccaccc | cgtagccgtc | gctgctcccg | gcatgccccg | 600 |
| ccccccacgg | agcctagtgg | tcttcaggaa | tggcgaccc | aagacgaggc | gtgcggttct | 660 |
| tctgagcagg | agggtcaccc | agagcttcga | ggcatttcta | cagcacctga | cagaggtcat | 720 |
| gcagcgccct | gtggtcaagc | tgtacgctac | ggacggaagg | agggttccca | gcctccaggc | 780 |
| agtgatcctg | agctctggag | ctgtggtggc | ggcaggaagg | gagccattta | aaccaggaaa | 840 |
| ttatgacatc | caaaaatact | tgcttcctgc | tagattacca | gggatctctc | agcgtgtgta | 900 |
| ccccaaggga | aatgcaaagt | cagaaagcag | aaagataagc | acacatatgt | cttcaagctc | 960 |
| aaggtcccag | atttattctg | tttcttctga | gaaaacacat | aataatgatt | gctacttaga | 1020 |
| ctattctttt | gttcctgaaa | agtacttggc | cttagaaaag | aatgattctc | agaatttacc | 1080 |
| aatatatcct | tctgaagatg | atattgagaa | atcaattatt | tttaatcaag | acggcactat | 1140 |
| gacagttgag | atgaaagttc | gattcagaat | aaaagaggaa | gaaaccataa | aatggacaac | 1200 |
| tactgtcagt | aaaactggtc | cttctaataa | tgatgaaaag | agtgagatga | gttttccagg | 1260 |
| aagaacagaa | agtcgatcat | ctggtttaaa | gcttgcagca | tgttcattct | ctgcagatgt | 1320 |

-continued

```
gtcacctatg gagcgaagca gtaatcaaga gggcagtttg gcagaggaga taaacattca    1380
aatgacagat caagtggctg aaacttgcag ttctgctagt tgggagaatg ctactgtgga    1440
cacagatatc atccagggaa ctcaagacca agcaaagcat cgttttttata ggcccccta c   1500 acctggacta agaagagtga gacaaaagaa atctgtgatt ggcagtgtga ccttagtatc    1560
tgaaactgag gttcaagaga aaatgattgg acagttttca tatagtgaag aaagggaaag    1620
tggggaaaac aagtctgagt atcacatgtt tacacattct tgcagtaaaa tgtcatcagt    1680
atctaacaaa ccagtacttg ttcagatcaa taacaatgat caaatggagg agtcatcatt    1740 agaagaaaa aaggaaaaca gtctgcttaa gtcaagtgca ataagtgctg gtgttataga     1800
aattacaagt cagaagatgt tagagatgtc acataataat ggtttgccat caactatatc    1860
aaataactca attgtggagg aagatgtagt tgattgtgtg gtattggaca acaaaactgg    1920
tatcaagaac ttcaaaactt atggtaacac caatgatagg ttcagtccta tttcagcaga    1980
tgcaacccat ttttcaagta ataactctgg aactgacaaa aatatttctg aggctccagc    2040
ttcagaagca tcctctactg tcactgcaag aattgacaga ctaattaatg aatttgctca    2100
gtgtggttta acaaaacttc caaaaaatga aagaagatt ttgtcatctg ttgccagcaa     2160
aaagaagaaa aaatctcgac agcaagcaat aaattccagg tatcaagatg gacagcttgc    2220
aaccaaagga attcttaata agaatgagag aataaacaca aaggtagaa ttacaaagga     2280 aatgatagtg caagattcag atagtcccct taaaggaggg atactttgtg aggaagacct    2340
ccagaaaagt gatactgtaa ttgaatcaaa tacttttttgt tccaaaagta atctcaattc    2400
cacgatttcc aagaatttcc atagaaataa attaaatact actcaaaatt ccaaggttca    2460 aggacttttta accaaaagaa aatctagatc actaaataaa ataagcttag gagcacctaa    2520 aaaagagaa atcggtcaaa gagataaagt gtttcctcac aatgaatcta aatattgcaa     2580
aagtactttt gaaaacaaaa gtttatttca tgtatttaac atccttgagc aaaaacccaa    2640
agatttttat gcaccgcaat ctcaagcaga agtggcatct gggtatttga gaggaatggc    2700
aaagaagagt ttagtttcaa aagttactga ttcacacata actttaaaaa gccagaaaaa    2760
acgtaaaggg gataaagtga aagcaagtgc tattttaagt aaacaacatg ctacaaccag    2820
ggcaaattct ttagcttctt tgaaaaaacc tgattttcct gaggctattg ctcatcattc    2880
aattcaaaat tatatacaga gttggttgca gaacataaat ccatatccaa cttta aagcc   2940 tataaaatca gctccagtat gtagaaatga acgagtgtg gtaaattgta gcaataatag     3000
tttttcaggg aatgatcccc atacaaattc tggaaaaata agtaattttg ttatggaaag    3060
taataagcac ataactaaaa ttgccggttt gacaggagat aatctatgta agagggaga    3120 taagtctttt attgccaatg acactggtga agaagatctc catgagacac aggttggatc    3180
tctgaatgat gcttatttgg ttcccctgca tgaacactgt actttgtcac agtcagctat    3240
taatgatcat aatactaaaa gtcatatagc tgctgaaaaa tcaggaccag agaaaaaact    3300
tgtttaccag gaaataaacc tagctagaaa aaggcaaagt gtagaggctg ccattcaagt    3360
agatcctata gaagaggaaa ctccaaaaga cctcttacca gtcctgatgc ttcaccaatt    3420
gcaagcttca gttcctggta ttcacaagac tcagaatgga gttgttcaaa tgccaggttc    3480
acttgcaggt gttccctttc attctgcaat atgtaattca tccactaatc tccttctagc    3540
ttggctcttg gtgctaaacc taagggaag tatgaatagc ttctgtcaag ttgatgctca    3600
caaggctacc aacaaatctt cagaaacact tgcattgttg gagattctaa agcacataggc  3660
```

| | |
|---|---|
| tatcacagag gaagctgatg acttgaaagc tgctgttgcc aatttagtgg agtcaactac | 3720 |
| aagccacttt ggactcagtg agaaagaaca agacatggtt ccaatagatc tttctgcaaa | 3780 |
| ttgttccacg gtcaacattc agagtgttcc taagtgcagt gaaaatgaaa gaacacaagg | 3840 |
| aatctcctct ttggatggag gttgctctgc cagtgaggca tgtgccctg aagtctgtgt | 3900 |
| tttggaagtg acttgctctc catgtgagat gtgcactgta aataaggctt attctccaaa | 3960 |
| agagacatgt aacccagtg acactttttt tcctagtgat ggttatggtg tggatcagac | 4020 |
| ttctatgaat aaggcttgtt tcctaggaga ggtctgttca cttactgata ctgtgttttc | 4080 |
| tgataaggct tgtgctcaaa aggagaacca tacctatgag ggagcttgcc caattgatga | 4140 |
| gacctacgtt cctgtcaatg tctgcaatac cattgactt ttaaactcca agaaaacac | 4200 |
| atatactgat aacttggatt caactgaaga gttagaaaga ggtgatgaca ttcagaaaga | 4260 |
| tctaaatatt ttgacagacc ctgaatataa aaatggattt aatacattgg tgtcacatca | 4320 |
| aaatgtcagt aatttaagct cctgtggcct ttgcctaagt gaaaaagaag cagaacttga | 4380 |
| taagaaacat agttctctag atgatttga aaattgttca ctaaggaagt ttcaggatga | 4440 |
| aaatgcatat acttcctttg atatggaaga accacggact tctgaagaac caggctcaat | 4500 |
| aaccaacagc atgacatcaa gtgaaagaaa catttcagaa ttggaatctt ttgaagaatt | 4560 |
| agaaaaccat gacactgata tctttaatac agtggtaaat ggaggagagc aagccactga | 4620 |
| agaattaatc caagaagagg tagaggctag taaaacttta gaattgatag acatctctag | 4680 |
| taagaatatt atggaagaaa aaagaatgaa cggtataatt tatgaaataa tcagtaagag | 4740 |
| gctggcaaca ccaccatctt tagatttttg ctatgattct aagcaaaata gtgaaaagga | 4800 |
| gaccaatgaa ggagaaacta agatggtaaa aatgatggtg aaaactatgg aaactggaag | 4860 |
| ttattcagag tcctctcctg atttaaaaaa atgcatcaaa agtccagtga cttctgattg | 4920 |
| gtcagactat cggcctgaca gtgacagtga gcagccatat aaaacatcca gtgatgatcc | 4980 |
| caatgacagt ggcgaactta cccaagagaa agaatataac ataggatttg ttaaagggc | 5040 |
| aatagaaaaa ctgtacggta aagcagatat tatcaaacca tcttttttc ctgggtctac | 5100 |
| ccgcaaatct caggttttgtc cttataattc tgtggaattt cagtgttcca ggaaagcaag | 5160 |
| tcttatgat tctgaagggc agtcattgg ctcttctgaa caggtatcta gtagttcatc | 5220 |
| tatgttgcag gaattccagg aggaaagaca agataagtgt gatgttagtg ctgtgaggga | 5280 |
| caattattgt aggggtgaca ttgtagaacc tggtacaaaa caaaatgatg atagcagaat | 5340 |
| cctcacagac atagaggaag gagtactgat tgacaaggc aaatggcttc tgaaagaaaa | 5400 |
| tcatttgcta aggatgtcat ctgaaaatcc tggcatgtgt ggcaatgcag acaccacatc | 5460 |
| agtggacacc ctacttgata taacagcag tgaggtacca tattcacatt ttggtaatt | 5520 |
| ggccccaggc ccaacgatgg atgaactctc ctcttcagaa ctcgaggaac tgactcaacc | 5580 |
| ccttgaacta aaatgcaatt actttaacat gcctcatggt agtgactcag aaccttttca | 5640 |
| tgaggacttg ctggatgttc gcaatgaaac ctgtgccaag gaaagaatag caaatcatca | 5700 |
| tacagaggag aagggtagtc atcagtcaga aagagtatgc acatctgtca ctcattcctt | 5760 |
| tatttctgct ggtaacaaag tctaccctgt ctctgatgat gctattaaaa accaaccatt | 5820 |
| gcctggcagt aatatgattc atggtacact tcaggaagct gactctttgg ataaactgta | 5880 |
| tgctcttttgt ggtcaacatt gcccaatact aactgttatt atccaaccca tgaatgagga | 5940 |
| agaccgagga tttgcatatc gcaaagaatc tgatattgaa aatttcttgg gttttatttt | 6000 |
| atggatgaaa atacacccat atttacttca gacagacaaa aatgtgttca gggaagagaa | 6060 |

```
caataaagca agtatgagac aaaatcttat tgataatgcc attggtgata tatttgatca    6120
gttttatttc agtaacacat ttgacttgat gggtaaaaga agaaaacaaa aaagaattaa    6180
cttcttgggg ttagaggaag aaggtaattt aaagaaattt caaccagatt tgaaggaaag    6240
gttttgtatg aatttcttgc acacatcatt gttagttgtg ggtaatgtgg attcaaatac    6300
acaagacctc agcggtcaga caaatgaaat ctttaaagca gtcgatgaga ataacaactt    6360 attaataac agattccagg gctcaagaac aaatctcaac caagtagtaa gagaaaatat     6420
caactgtcat tacttctttg aaatgcttgg tcaagcttgc ctcttagata tttgccaagt    6480
tgagacctcc ttaaatatta gcaacagaaa tattttagaa ctttgtatgt ttgagggtga    6540
aaatcttttc atttgggaag aggaagacat attaaattta actgatcttg aaagcagtag    6600
agaacaagaa gatttataat tcaatatca gcacactcat tctttgtcaa ttcattttt      6660 cccatgagat gaagcacatg tgacgaatac ggactagata acctctaaga attttccact    6720
tcttcaaaat gaacttactc tagaaagctt acccttggat aaccagtttg actttcataa    6780
tgtctctgtt ttttgttttt ccaacaatta cagactcagg ttctcttatt ttggaagttt    6840
ctatctggtt ttgttctgaa cttacatttt ttttttttt ggtatctatg attttttttg     6900
ctcagggcat caaaatgtgc taaggacaag aattatatcc ttttttaaaaa atgttgttag   6960 cttggtgtaa aatgtatatt gactgtattg gtgaataaat tgaatagaca taacctcaaa    7020
gtacttcact tattcttttt aactactgat ttgataaaaa gtatgattat aagatatcca    7080
cgacaatctc atagtttctt                                                7100

<210> SEQ ID NO 35
<211> LENGTH: 2156
<212> TYPE: PRT
<213> ORGANISM: Homo sapiens

<400> SEQUENCE: 35

Met Ser Asp Thr Pro Ser Thr Gly Phe Ser Ile Ile His Pro Thr Ser
1               5                   10                  15

Ser Glu Gly Gln Val Pro Pro Arg His Leu Ser Leu Thr His Pro
            20                  25                  30

Val Val Ala Lys Arg Ile Ser Phe Tyr Lys Ser Gly Asp Pro Gln Phe
        35                  40                  45

Gly Gly Val Arg Val Val Asn Pro Arg Ser Phe Lys Ser Phe Asp
    50                  55                  60

Ala Leu Leu Asp Asn Leu Ser Arg Lys Val Pro Leu Pro Phe Gly Val
65                  70                  75                  80

Arg Asn Ile Ser Thr Pro Arg Gly Arg His Ser Ile Thr Arg Leu Glu
                85                  90                  95

Glu Leu Glu Asp Gly Glu Ser Tyr Leu Cys Ser His Gly Arg Lys Val
            100                 105                 110

Gln Pro Val Asp Leu Asp Lys Ala Arg Arg Pro Arg Pro Trp Leu
        115                 120                 125

Ser Ser Arg Ala Ile Ser Ala His Ser Pro Pro His Pro Val Ala Val
130                 135                 140

Ala Ala Pro Gly Met Pro Arg Pro Pro Arg Ser Leu Val Val Phe Arg
145                 150                 155                 160

Asn Gly Asp Pro Lys Thr Arg Arg Ala Val Leu Leu Ser Arg Arg Val
                165                 170                 175

Thr Gln Ser Phe Glu Ala Phe Leu Gln His Leu Thr Glu Val Met Gln
```

-continued

```
                180                 185                 190
Arg Pro Val Val Lys Leu Tyr Ala Thr Asp Gly Arg Val Pro Ser
            195                 200                 205
Leu Gln Ala Val Ile Leu Ser Ser Gly Ala Val Ala Ala Gly Arg
        210                 215                 220
Glu Pro Phe Lys Pro Gly Asn Tyr Asp Ile Gln Lys Tyr Leu Leu Pro
225                 230                 235                 240
Ala Arg Leu Pro Gly Ile Ser Gln Arg Val Tyr Pro Lys Gly Asn Ala
            245                 250                 255
Lys Ser Glu Ser Arg Lys Ile Ser Thr His Met Ser Ser Ser Arg
        260                 265                 270
Ser Gln Ile Tyr Ser Val Ser Ser Glu Lys Thr His Asn Asn Asp Cys
    275                 280                 285
Tyr Leu Asp Tyr Ser Phe Val Pro Glu Lys Tyr Leu Ala Leu Glu Lys
        290                 295                 300
Asn Asp Ser Gln Asn Leu Pro Ile Tyr Pro Ser Glu Asp Asp Ile Glu
305                 310                 315                 320
Lys Ser Ile Ile Phe Asn Gln Asp Gly Thr Met Thr Val Glu Met Lys
            325                 330                 335
Val Arg Phe Arg Ile Lys Glu Glu Thr Ile Lys Trp Thr Thr Thr
        340                 345                 350
Val Ser Lys Thr Gly Pro Ser Asn Asn Asp Glu Lys Ser Glu Met Ser
            355                 360                 365
Phe Pro Gly Arg Thr Glu Ser Arg Ser Ser Gly Leu Lys Leu Ala Ala
        370                 375                 380
Cys Ser Phe Ser Ala Asp Val Ser Pro Met Glu Arg Ser Ser Asn Gln
385                 390                 395                 400
Glu Gly Ser Leu Ala Glu Glu Ile Asn Ile Gln Met Thr Asp Gln Val
            405                 410                 415
Ala Glu Thr Cys Ser Ser Ala Ser Trp Glu Asn Ala Thr Val Asp Thr
        420                 425                 430
Asp Ile Ile Gln Gly Thr Gln Asp Gln Ala Lys His Arg Phe Tyr Arg
        435                 440                 445
Pro Pro Thr Pro Gly Leu Arg Arg Val Arg Gln Lys Lys Ser Val Ile
        450                 455                 460
Gly Ser Val Thr Leu Val Ser Glu Thr Glu Val Gln Glu Lys Met Ile
465                 470                 475                 480
Gly Gln Phe Ser Tyr Ser Glu Glu Arg Glu Ser Gly Glu Asn Lys Ser
            485                 490                 495
Glu Tyr His Met Phe Thr His Ser Cys Ser Lys Met Ser Ser Val Ser
            500                 505                 510
Asn Lys Pro Val Leu Val Gln Ile Asn Asn Asp Gln Met Glu Glu
            515                 520                 525
Ser Ser Leu Glu Arg Lys Lys Glu Asn Ser Leu Leu Lys Ser Ser Ala
        530                 535                 540
Ile Ser Ala Gly Val Ile Glu Ile Thr Ser Gln Lys Met Leu Glu Met
545                 550                 555                 560
Ser His Asn Asn Gly Leu Pro Thr Ile Ser Asn Asn Ser Ile Val
            565                 570                 575
Glu Glu Asp Val Val Asp Cys Val Val Leu Asp Asn Lys Thr Gly Ile
            580                 585                 590
Lys Asn Phe Lys Thr Tyr Gly Asn Thr Asn Asp Arg Phe Ser Pro Ile
        595                 600                 605
```

```
Ser Ala Asp Ala Thr His Phe Ser Asn Asn Ser Gly Thr Asp Lys
    610                 615                 620

Asn Ile Ser Glu Ala Pro Ala Ser Glu Ala Ser Ser Thr Val Thr Ala
625                 630                 635                 640

Arg Ile Asp Arg Leu Ile Asn Glu Phe Ala Gln Cys Gly Leu Thr Lys
                645                 650                 655

Leu Pro Lys Asn Glu Lys Lys Ile Leu Ser Ser Val Ala Ser Lys Lys
                660                 665                 670

Lys Lys Lys Ser Arg Gln Gln Ala Ile Asn Ser Arg Tyr Gln Asp Gly
            675                 680                 685

Gln Leu Ala Thr Lys Gly Ile Leu Asn Lys Asn Glu Arg Ile Asn Thr
690                 695                 700

Lys Gly Arg Ile Thr Lys Glu Met Ile Val Gln Asp Ser Asp Ser Pro
705                 710                 715                 720

Leu Lys Gly Gly Ile Leu Cys Glu Gly Asp Leu Gln Lys Ser Asp Thr
                725                 730                 735

Val Ile Glu Ser Asn Thr Phe Cys Ser Lys Ser Asn Leu Asn Ser Thr
                740                 745                 750

Ile Ser Lys Asn Phe His Arg Asn Lys Leu Asn Thr Thr Gln Asn Ser
            755                 760                 765

Lys Val Gln Gly Leu Leu Thr Lys Arg Lys Ser Arg Ser Leu Asn Lys
770                 775                 780

Ile Ser Leu Gly Ala Pro Lys Lys Arg Glu Ile Gly Gln Arg Asp Lys
785                 790                 795                 800

Val Phe Pro His Asn Glu Ser Lys Tyr Cys Lys Ser Thr Phe Glu Asn
                805                 810                 815

Lys Ser Leu Phe His Val Phe Asn Ile Leu Glu Gln Lys Pro Lys Asp
            820                 825                 830

Phe Tyr Ala Pro Gln Ser Gln Ala Glu Val Ala Ser Gly Tyr Leu Arg
            835                 840                 845

Gly Met Ala Lys Lys Ser Leu Val Ser Lys Val Thr Asp Ser His Ile
850                 855                 860

Thr Leu Lys Ser Gln Lys Lys Arg Lys Gly Asp Lys Val Lys Ala Ser
865                 870                 875                 880

Ala Ile Leu Ser Lys Gln His Ala Thr Thr Arg Ala Asn Ser Leu Ala
                885                 890                 895

Ser Leu Lys Lys Pro Asp Phe Pro Glu Ala Ile Ala His His Ser Ile
                900                 905                 910

Gln Asn Tyr Ile Gln Ser Trp Leu Gln Asn Ile Asn Pro Tyr Pro Thr
            915                 920                 925

Leu Lys Pro Ile Lys Ser Ala Pro Val Cys Arg Asn Glu Thr Ser Val
930                 935                 940

Val Asn Cys Ser Asn Asn Ser Phe Ser Gly Asn Asp Pro His Thr Asn
945                 950                 955                 960

Ser Gly Lys Ile Ser Asn Phe Val Met Glu Ser Asn Lys His Ile Thr
                965                 970                 975

Lys Ile Ala Gly Leu Thr Gly Asp Asn Leu Cys Lys Glu Gly Asp Lys
            980                 985                 990

Ser Phe Ile Ala Asn Asp Thr Gly  Glu Glu Asp Leu His  Glu Thr Gln
                995                 1000                1005

Val Gly  Ser Leu Asn Asp Ala  Tyr Leu Val Pro Leu  His Glu His
    1010                1015                1020
```

```
Cys Thr Leu Ser Gln Ser Ala Ile Asn Asp His Asn Thr Lys Ser
    1025                1030                1035

His Ile Ala Ala Glu Lys Ser Gly Pro Glu Lys Lys Leu Val Tyr
    1040                1045                1050

Gln Glu Ile Asn Leu Ala Arg Lys Arg Gln Ser Val Glu Ala Ala
    1055                1060                1065

Ile Gln Val Asp Pro Ile Glu Glu Thr Pro Lys Asp Leu Leu
    1070                1075                1080

Pro Val Leu Met Leu His Gln Leu Gln Ala Ser Val Pro Gly Ile
    1085                1090                1095

His Lys Thr Gln Asn Gly Val Val Gln Met Pro Gly Ser Leu Ala
    1100                1105                1110

Gly Val Pro Phe His Ser Ala Ile Cys Asn Ser Ser Thr Asn Leu
    1115                1120                1125

Leu Leu Ala Trp Leu Leu Val Leu Asn Leu Lys Gly Ser Met Asn
    1130                1135                1140

Ser Phe Cys Gln Val Asp Ala His Lys Ala Thr Asn Lys Ser Ser
    1145                1150                1155

Glu Thr Leu Ala Leu Leu Glu Ile Leu Lys His Ile Ala Ile Thr
    1160                1165                1170

Glu Glu Ala Asp Asp Leu Lys Ala Ala Val Ala Asn Leu Val Glu
    1175                1180                1185

Ser Thr Thr Ser His Phe Gly Leu Ser Glu Lys Glu Gln Asp Met
    1190                1195                1200

Val Pro Ile Asp Leu Ser Ala Asn Cys Ser Thr Val Asn Ile Gln
    1205                1210                1215

Ser Val Pro Lys Cys Ser Glu Asn Glu Arg Thr Gln Gly Ile Ser
    1220                1225                1230

Ser Leu Asp Gly Gly Cys Ser Ala Ser Glu Ala Cys Ala Pro Glu
    1235                1240                1245

Val Cys Val Leu Glu Val Thr Cys Ser Pro Cys Glu Met Cys Thr
    1250                1255                1260

Val Asn Lys Ala Tyr Ser Pro Lys Glu Thr Cys Asn Pro Ser Asp
    1265                1270                1275

Thr Phe Phe Pro Ser Asp Gly Tyr Gly Val Asp Gln Thr Ser Met
    1280                1285                1290

Asn Lys Ala Cys Phe Leu Gly Glu Val Cys Ser Leu Thr Asp Thr
    1295                1300                1305

Val Phe Ser Asp Lys Ala Cys Ala Gln Lys Glu Asn His Thr Tyr
    1310                1315                1320

Glu Gly Ala Cys Pro Ile Asp Glu Thr Tyr Val Pro Val Asn Val
    1325                1330                1335

Cys Asn Thr Ile Asp Phe Leu Asn Ser Lys Glu Asn Thr Tyr Thr
    1340                1345                1350

Asp Asn Leu Asp Ser Thr Glu Glu Leu Glu Arg Gly Asp Asp Ile
    1355                1360                1365

Gln Lys Asp Leu Asn Ile Leu Thr Asp Pro Glu Tyr Lys Asn Gly
    1370                1375                1380

Phe Asn Thr Leu Val Ser His Gln Asn Val Ser Asn Leu Ser Ser
    1385                1390                1395

Cys Gly Leu Cys Leu Ser Glu Lys Glu Ala Glu Leu Asp Lys Lys
    1400                1405                1410

His Ser Ser Leu Asp Asp Phe Glu Asn Cys Ser Leu Arg Lys Phe
```

```
            1415                1420                1425

Gln Asp Glu Asn Ala Tyr Thr Ser Phe Asp Met Glu Glu Pro Arg
    1430                1435                1440

Thr Ser Glu Glu Pro Gly Ser Ile Thr Asn Ser Met Thr Ser Ser
    1445                1450                1455

Glu Arg Asn Ile Ser Glu Leu Glu Ser Phe Glu Glu Leu Glu Asn
    1460                1465                1470

His Asp Thr Asp Ile Phe Asn Thr Val Val Asn Gly Gly Glu Gln
    1475                1480                1485

Ala Thr Glu Glu Leu Ile Gln Glu Val Glu Ala Ser Lys Thr
    1490                1495                1500

Leu Glu Leu Ile Asp Ile Ser Ser Lys Asn Ile Met Glu Glu Lys
    1505                1510                1515

Arg Met Asn Gly Ile Ile Tyr Glu Ile Ile Ser Lys Arg Leu Ala
    1520                1525                1530

Thr Pro Pro Ser Leu Asp Phe Cys Tyr Asp Ser Lys Gln Asn Ser
    1535                1540                1545

Glu Lys Glu Thr Asn Glu Gly Glu Thr Lys Met Val Lys Met Met
    1550                1555                1560

Val Lys Thr Met Glu Thr Gly Ser Tyr Ser Glu Ser Ser Pro Asp
    1565                1570                1575

Leu Lys Lys Cys Ile Lys Ser Pro Val Thr Ser Asp Trp Ser Asp
    1580                1585                1590

Tyr Arg Pro Asp Ser Asp Ser Glu Gln Pro Tyr Lys Thr Ser Ser
    1595                1600                1605

Asp Asp Pro Asn Asp Ser Gly Glu Leu Thr Gln Glu Lys Glu Tyr
    1610                1615                1620

Asn Ile Gly Phe Val Lys Arg Ala Ile Glu Lys Leu Tyr Gly Lys
    1625                1630                1635

Ala Asp Ile Ile Lys Pro Ser Phe Phe Pro Gly Ser Thr Arg Lys
    1640                1645                1650

Ser Gln Val Cys Pro Tyr Asn Ser Val Glu Phe Gln Cys Ser Arg
    1655                1660                1665

Lys Ala Ser Leu Tyr Asp Ser Glu Gly Gln Ser Phe Gly Ser Ser
    1670                1675                1680

Glu Gln Val Ser Ser Ser Ser Met Leu Gln Glu Phe Gln Glu
    1685                1690                1695

Glu Arg Gln Asp Lys Cys Asp Val Ser Ala Val Arg Asp Asn Tyr
    1700                1705                1710

Cys Arg Gly Asp Ile Val Glu Pro Gly Thr Lys Gln Asn Asp Asp
    1715                1720                1725

Ser Arg Ile Leu Thr Asp Ile Glu Glu Gly Val Leu Ile Asp Lys
    1730                1735                1740

Gly Lys Trp Leu Leu Lys Glu Asn His Leu Leu Arg Met Ser Ser
    1745                1750                1755

Glu Asn Pro Gly Met Cys Gly Asn Ala Asp Thr Thr Ser Val Asp
    1760                1765                1770

Thr Leu Leu Asp Asn Asn Ser Ser Glu Val Pro Tyr Ser His Phe
    1775                1780                1785

Gly Asn Leu Ala Pro Gly Pro Thr Met Asp Glu Leu Ser Ser Ser
    1790                1795                1800

Glu Leu Glu Glu Leu Thr Gln Pro Leu Glu Leu Lys Cys Asn Tyr
    1805                1810                1815
```

Phe Asn Met Pro His Gly Ser Asp Ser Glu Pro Phe His Glu Asp
    1820            1825                1830

Leu Leu Asp Val Arg Asn Glu Thr Cys Ala Lys Glu Arg Ile Ala
    1835            1840                1845

Asn His His Thr Glu Glu Lys Gly Ser His Gln Ser Glu Arg Val
    1850            1855                1860

Cys Thr Ser Val Thr His Ser Phe Ile Ser Ala Gly Asn Lys Val
    1865            1870                1875

Tyr Pro Val Ser Asp Asp Ala Ile Lys Asn Gln Pro Leu Pro Gly
    1880            1885                1890

Ser Asn Met Ile His Gly Thr Leu Gln Glu Ala Asp Ser Leu Asp
    1895            1900                1905

Lys Leu Tyr Ala Leu Cys Gly Gln His Cys Pro Ile Leu Thr Val
    1910            1915                1920

Ile Ile Gln Pro Met Asn Glu Glu Asp Arg Gly Phe Ala Tyr Arg
    1925            1930                1935

Lys Glu Ser Asp Ile Glu Asn Phe Leu Gly Phe Tyr Leu Trp Met
    1940            1945                1950

Lys Ile His Pro Tyr Leu Leu Gln Thr Asp Lys Asn Val Phe Arg
    1955            1960                1965

Glu Glu Asn Asn Lys Ala Ser Met Arg Gln Asn Leu Ile Asp Asn
    1970            1975                1980

Ala Ile Gly Asp Ile Phe Asp Gln Phe Tyr Phe Ser Asn Thr Phe
    1985            1990                1995

Asp Leu Met Gly Lys Arg Arg Lys Gln Lys Arg Ile Asn Phe Leu
    2000            2005                2010

Gly Leu Glu Glu Glu Gly Asn Leu Lys Lys Phe Gln Pro Asp Leu
    2015            2020                2025

Lys Glu Arg Phe Cys Met Asn Phe Leu His Thr Ser Leu Leu Val
    2030            2035                2040

Val Gly Asn Val Asp Ser Asn Thr Gln Asp Leu Ser Gly Gln Thr
    2045            2050                2055

Asn Glu Ile Phe Lys Ala Val Asp Glu Asn Asn Asn Leu Leu Asn
    2060            2065                2070

Asn Arg Phe Gln Gly Ser Arg Thr Asn Leu Asn Gln Val Val Arg
    2075            2080                2085

Glu Asn Ile Asn Cys His Tyr Phe Phe Glu Met Leu Gly Gln Ala
    2090            2095                2100

Cys Leu Leu Asp Ile Cys Gln Val Glu Thr Ser Leu Asn Ile Ser
    2105            2110                2115

Asn Arg Asn Ile Leu Glu Leu Cys Met Phe Glu Gly Glu Asn Leu
    2120            2125                2130

Phe Ile Trp Glu Glu Glu Asp Ile Leu Asn Leu Thr Asp Leu Glu
    2135            2140                2145

Ser Ser Arg Glu Gln Glu Asp Leu
    2150            2155

<210> SEQ ID NO 36
<211> LENGTH: 3950
<212> TYPE: DNA
<213> ORGANISM: Homo sapiens

<400> SEQUENCE: 36
atgtcacatc tggtggaccc tacatcagga gacttgccag ttagagacat agatgctata      60

```
cctctggtgc taccagcctc aaaaggtaag aatatgaaaa ctcaaccacc cttgagcagg      120
atgaaccggg aggaattgga ggacagtttc tttcgacttc gcgaagatca catgttggtg      180
aaggagcttt cttggaagca acaggatgag atcaaaaggc tgaggaccac cttgctgcgg      240
ttgaccgctg ctggccggga cctgcgggtc gcggaggagg cggcgccgct ctcggagacc      300
gcaaggcgcg ggcagaaggc gggatggcgg cagcgcctct ccatgcacca gcgccccag      360 atgcaccgac tgcaagggca tttccactgc gtcggccctg ccagccccg ccgcgcccag      420 cctcgcgtcc aagtgggaca cagacagctc cacacagccg gtgcaccggt gccggagaaa      480
cccaagaggg ggccaaggga caggctgagc tacacagccc ctccatcgtt taaggagcat      540
gcgacaaatg aaaacagagg tgaagtagcc agtaaaccca gtgaacttgt ttctggttct      600
aacagcataa tttctttcag cagtgtcata agtatggcta aacccattgg tctatgcatg      660
cctaacagtg cccacatcat ggccagcaat accatgcaag tggaagagcc acccaagtct      720
cctgagaaaa tgtggcctaa agatgaaaat tttgaacaga gaagctcatt ggagtgtgct      780
cagaaggctg cagagcttcg agcttccatt aaagagaagg tagagctgat tcgacttaag      840
aagctcttac atgaaagaaa tgcttcattg gttatgacaa agcacaatt aacagaagtt      900 caagaggcat acgaaacctt gctccagaag aatcagggaa tcctgagtgc agcccatgag      960
gccctcctca gcaagtgaa tgagctcagg gcagagctga aggaagaaag caagaaggct     1020
gtgagcttga agagccaact ggaagatgtg tctatcttgc agatgactct gaaggagttt     1080
caggagagag ttgaagattt ggaaaaagaa cgaaaattgc tgaatgacaa ttatgacaaa     1140
ctcttagaaa gcatgctgga cagcagtgac agctccagtc agccccactg gagcaacgag     1200
ctcatagcgg aacagctaca gcagcaagtc tctcagctgc aggatcagct ggatgctgag     1260
ctggaggaca agagaaaagt tttacttgag ctgtccaggg agaaagccca aaatgaggat     1320
ctgaagcttg aagtcaccaa catacttcag aagcataaac aggaagtaga gctcctccaa     1380
aatgcagcca caatttccca acctcctgac aggcaatctg aaccagccac tcacccagct     1440
gtattgcaag agaacactca gatcgagcca agtgaaccca aaaaccaaga agaaagaaa      1500 ctgtcccagg tgctaaatga gttgcaagta tcacacgcag agaccacatt ggaactagaa     1560
aagaccaggg acatgcttat tctgcagcgc aaaatcaacg tgtgttatca ggaggaactg     1620
gaggcaatga tgacaaaagc tgacaatgat aatagagatc acaaagaaaa gctggagagg     1680
ttgactcgac tactagacct caagaataac cgtatcaagc agctggaagg tatttaaga      1740 agccatgacc ttccaacatc tgaacagctc aaagatgttg cttatggcac ccgaccgttg     1800
tcgttatgtt tggaaacact gccagcccat ggagatgagg ataaagtgga tatttctctg     1860
ctgcatcagg gtgagaatct ttttgaactg cacatccacc aggccttcct gacatctgcc     1920
gccctagctc aggctggaga tacccaacct accactttct gcacctattc cttctatgac     1980
tttgaaaccc actgtacccc attatctgtg gggccacagc ccctctatga cttcacctcc     2040
cagtatgtga tggagacaga ttcgcttttc ttacactacc ttcaagaggc ttcagcccgg     2100
cttgacatac accaggccat ggccagtgaa cacagcactc ttgctgcagg atggatttgc     2160
tttgacaggg tgctagagac tgtggagaaa gtccatggct tggccacact gattggagct     2220
ggtggagaag agttcggggt tctagagtac tggatgaggc tgcgtttccc cataaaaccc     2280
agcctacagg cgtgcaataa acgaaagaaa gcccaggtct acctgtcaac cgatgtgctt     2340
ggaggccgga aggcccagga agaggagttc agatcggagt cttgggaacc tcagaacgag     2400
```

| | |
|---|---|
| ctgtggattg aaatcaccaa gtgctgtggc ctccggagtc gatggctggg aactcaaccc | 2460 |
| agtccatatg ctgtgtaccg cttcttcacc ttttctgacc atgacactgc catcattcca | 2520 |
| gccagtaaca acccctactt tagagaccag gctcgattcc cagtgcttgt gacctctgac | 2580 |
| ctggaccatt atctgagacg ggaggccttg tctatacatg ttttttgatga tgaagactta | 2640 |
| gagcctggct cgtatcttgg ccgagcccga gtgcctttac tgcctcttgc aaaaaatgaa | 2700 |
| tctatcaaag gtgattttaa cctcactgac cctgcagaga aacccaacgg atctattcaa | 2760 |
| gtgcaactgg attggaagtt ccctacata cccctgaga gcttcctgaa accagaagct | 2820 |
| cagactaagg ggaaggatac caaggacagt tcaaagatct catctgaaga ggaaaaggct | 2880 |
| tcatttcctt cccaggatca gatggcatct cctgaggttc ccattgaagc tggccagtat | 2940 |
| cgatctaaga gaaaacctcc tcatggggga gaaagaaagg agaaggagca ccaggttgtg | 3000 |
| agctactcaa gaagaaaaca tggcaaaaga ataggtgttc aaggaaagaa tagaatggag | 3060 |
| tatcttagcc ttaacatctt aaatggaaat acaccagagc aggtgaatta cactgagtgg | 3120 |
| aagttctcag agactaacag cttcataggt gatggcttta aaaatcagca cgaggaagag | 3180 |
| gaaatgacat tatcccattc agcactgaaa cagaaggaac ctctacatcc tgtaaatgac | 3240 |
| aaagaatcct ctgaacaagg ttctgaagtc agtgaagcac aaactaccga cagtgatgat | 3300 |
| gtcatagtgc cacccatgtc tcagaaatat cctaaggcag attcagagaa gatgtgcatt | 3360 |
| gaaattgtct ccctggcctt ctacccagag cagaagtgta tgtctgatga aacataaaa | 3420 |
| caggtgtatg tggagtacaa attctacgac ctacccttgt cggagacaga gactccagtg | 3480 |
| tccctaagga agcctagggc aggagaagaa atccactttc actttagcaa ggtaatagac | 3540 |
| ctggacccac aggagcagca aggccgaagg cggtttctgt tcgacatgct gaatggacaa | 3600 |
| gatcctgatc aaggacattt aaagtttaca gtggtaagtg atcctctgga tgaagaaaag | 3660 |
| aaagaatgtg aagaagtggg atatgcatat cttcaactgt ggcagatcct ggagtcagga | 3720 |
| agagatattc tagagcaaga gctagacatt gttagccctg aagatctggc tacccccaata | 3780 |
| ggaaggctga aggtttccct tcaagcagct gctgtcctcc atgctatta caaggagatg | 3840 |
| actgaagatt tgttttcatg aaggaacaag tgctattcca atctaaaagt ctctgaggga | 3900 |
| accatagtaa aaagtctctt ataaagttag cttgctataa catgaaaaaa | 3950 |

<210> SEQ ID NO 37
<211> LENGTH: 1286
<212> TYPE: PRT
<213> ORGANISM: Homo sapiens

<400> SEQUENCE: 37

```
Met Ser His Leu Val Asp Pro Thr Ser Gly Asp Leu Pro Val Arg Asp
1               5                   10                  15

Ile Asp Ala Ile Pro Leu Val Leu Pro Ala Ser Lys Gly Lys Asn Met
            20                  25                  30

Lys Thr Gln Pro Pro Leu Ser Arg Met Asn Arg Glu Glu Leu Glu Asp
        35                  40                  45

Ser Phe Phe Arg Leu Arg Glu Asp His Met Leu Val Lys Glu Leu Ser
    50                  55                  60

Trp Lys Gln Gln Asp Glu Ile Lys Arg Leu Arg Thr Thr Leu Leu Arg
65                  70                  75                  80

Leu Thr Ala Ala Gly Arg Asp Leu Arg Val Ala Glu Glu Ala Ala Pro
                85                  90                  95

Leu Ser Glu Thr Ala Arg Arg Gly Gln Lys Ala Gly Trp Arg Gln Arg
```

-continued

```
                100                 105                 110
Leu Ser Met His Gln Arg Pro Gln Met His Arg Leu Gln Gly His Phe
            115                 120                 125
His Cys Val Gly Pro Ala Ser Pro Arg Arg Ala Gln Pro Arg Val Gln
        130                 135                 140
Val Gly His Arg Gln Leu His Thr Ala Gly Ala Pro Val Pro Glu Lys
145                 150                 155                 160
Pro Lys Arg Gly Pro Arg Asp Arg Leu Ser Tyr Thr Ala Pro Pro Ser
                165                 170                 175
Phe Lys Glu His Ala Thr Asn Glu Asn Arg Gly Glu Val Ala Ser Lys
            180                 185                 190
Pro Ser Glu Leu Val Ser Gly Ser Asn Ser Ile Ile Ser Phe Ser Ser
        195                 200                 205
Val Ile Ser Met Ala Lys Pro Ile Gly Leu Cys Met Pro Asn Ser Ala
210                 215                 220
His Ile Met Ala Ser Asn Thr Met Gln Val Glu Glu Pro Pro Lys Ser
225                 230                 235                 240
Pro Glu Lys Met Trp Pro Lys Asp Glu Asn Phe Glu Gln Arg Ser Ser
                245                 250                 255
Leu Glu Cys Ala Gln Lys Ala Ala Glu Leu Arg Ala Ser Ile Lys Glu
            260                 265                 270
Lys Val Glu Leu Ile Arg Leu Lys Lys Leu Leu His Glu Arg Asn Ala
        275                 280                 285
Ser Leu Val Met Thr Lys Ala Gln Leu Thr Glu Val Gln Glu Ala Tyr
    290                 295                 300
Glu Thr Leu Leu Gln Lys Asn Gln Gly Ile Leu Ser Ala Ala His Glu
305                 310                 315                 320
Ala Leu Leu Lys Gln Val Asn Glu Leu Arg Ala Glu Leu Lys Glu Glu
                325                 330                 335
Ser Lys Lys Ala Val Ser Leu Lys Ser Gln Leu Glu Asp Val Ser Ile
            340                 345                 350
Leu Gln Met Thr Leu Lys Glu Phe Gln Glu Arg Val Glu Asp Leu Glu
        355                 360                 365
Lys Glu Arg Lys Leu Leu Asn Asp Asn Tyr Asp Lys Leu Leu Glu Ser
    370                 375                 380
Met Leu Asp Ser Ser Asp Ser Ser Ser Gln Pro His Trp Ser Asn Glu
385                 390                 395                 400
Leu Ile Ala Glu Gln Leu Gln Gln Gln Val Ser Gln Leu Gln Asp Gln
                405                 410                 415
Leu Asp Ala Glu Leu Glu Asp Lys Arg Lys Val Leu Leu Glu Leu Ser
            420                 425                 430
Arg Glu Lys Ala Gln Asn Glu Asp Leu Lys Leu Glu Val Thr Asn Ile
        435                 440                 445
Leu Gln Lys His Lys Gln Glu Val Glu Leu Leu Gln Asn Ala Ala Thr
    450                 455                 460
Ile Ser Gln Pro Pro Asp Arg Gln Ser Glu Pro Ala Thr His Pro Ala
465                 470                 475                 480
Val Leu Gln Glu Asn Thr Gln Ile Glu Pro Ser Glu Pro Lys Asn Gln
                485                 490                 495
Glu Glu Lys Lys Leu Ser Gln Val Leu Asn Glu Leu Gln Val Ser His
            500                 505                 510
Ala Glu Thr Thr Leu Glu Leu Glu Lys Thr Arg Asp Met Leu Ile Leu
        515                 520                 525
```

```
Gln Arg Lys Ile Asn Val Cys Tyr Gln Glu Glu Leu Glu Ala Met Met
            530                 535                 540

Thr Lys Ala Asp Asn Asp Asn Arg Asp His Lys Glu Lys Leu Glu Arg
545                 550                 555                 560

Leu Thr Arg Leu Leu Asp Leu Lys Asn Asn Arg Ile Lys Gln Leu Glu
                565                 570                 575

Gly Ile Leu Arg Ser His Asp Leu Pro Thr Ser Glu Gln Leu Lys Asp
            580                 585                 590

Val Ala Tyr Gly Thr Arg Pro Leu Ser Leu Cys Leu Glu Thr Leu Pro
        595                 600                 605

Ala His Gly Asp Glu Asp Lys Val Asp Ile Ser Leu Leu His Gln Gly
610                 615                 620

Glu Asn Leu Phe Glu Leu His Ile His Gln Ala Phe Leu Thr Ser Ala
625                 630                 635                 640

Ala Leu Ala Gln Ala Gly Asp Thr Gln Pro Thr Thr Phe Cys Thr Tyr
                645                 650                 655

Ser Phe Tyr Asp Phe Glu Thr His Cys Thr Pro Leu Ser Val Gly Pro
            660                 665                 670

Gln Pro Leu Tyr Asp Phe Thr Ser Gln Tyr Val Met Glu Thr Asp Ser
            675                 680                 685

Leu Phe Leu His Tyr Leu Gln Glu Ala Ser Ala Arg Leu Asp Ile His
        690                 695                 700

Gln Ala Met Ala Ser Glu His Ser Thr Leu Ala Ala Gly Trp Ile Cys
705                 710                 715                 720

Phe Asp Arg Val Leu Glu Thr Val Glu Lys Val His Gly Leu Ala Thr
                725                 730                 735

Leu Ile Gly Ala Gly Gly Glu Glu Phe Gly Val Leu Glu Tyr Trp Met
            740                 745                 750

Arg Leu Arg Phe Pro Ile Lys Pro Ser Leu Gln Ala Cys Asn Lys Arg
        755                 760                 765

Lys Lys Ala Gln Val Tyr Leu Ser Thr Asp Val Leu Gly Gly Arg Lys
770                 775                 780

Ala Gln Glu Glu Glu Phe Arg Ser Glu Ser Trp Glu Pro Gln Asn Glu
785                 790                 795                 800

Leu Trp Ile Glu Ile Thr Lys Cys Cys Gly Leu Arg Ser Arg Trp Leu
                805                 810                 815

Gly Thr Gln Pro Ser Pro Tyr Ala Val Tyr Arg Phe Thr Phe Ser
            820                 825                 830

Asp His Asp Thr Ala Ile Ile Pro Ala Ser Asn Pro Tyr Phe Arg
        835                 840                 845

Asp Gln Ala Arg Phe Pro Val Leu Val Thr Ser Asp Leu Asp His Tyr
850                 855                 860

Leu Arg Arg Glu Ala Leu Ser Ile His Val Phe Asp Asp Glu Asp Leu
865                 870                 875                 880

Glu Pro Gly Ser Tyr Leu Gly Arg Ala Arg Val Pro Leu Leu Pro Leu
                885                 890                 895

Ala Lys Asn Glu Ser Ile Lys Gly Asp Phe Asn Leu Thr Asp Pro Ala
            900                 905                 910

Glu Lys Pro Asn Gly Ser Ile Gln Val Gln Leu Asp Trp Lys Phe Pro
        915                 920                 925

Tyr Ile Pro Pro Glu Ser Phe Leu Lys Pro Glu Ala Gln Thr Lys Gly
930                 935                 940
```

-continued

```
Lys Asp Thr Lys Asp Ser Ser Lys Ile Ser Ser Glu Glu Glu Lys Ala
945                 950                 955                 960

Ser Phe Pro Ser Gln Asp Gln Met Ala Ser Pro Glu Val Pro Ile Glu
            965                 970                 975

Ala Gly Gln Tyr Arg Ser Lys Arg Lys Pro Pro His Gly Gly Glu Arg
        980                 985                 990

Lys Glu Lys Glu His Gln Val Val Ser Tyr Ser Arg Arg Lys His Gly
    995                 1000                1005

Lys Arg Ile Gly Val Gln Gly Lys Asn Arg Met Glu Tyr Leu Ser
    1010                1015                1020

Leu Asn Ile Leu Asn Gly Asn Thr Pro Glu Gln Val Asn Tyr Thr
    1025                1030                1035

Glu Trp Lys Phe Ser Glu Thr Asn Ser Phe Ile Gly Asp Gly Phe
    1040                1045                1050

Lys Asn Gln His Glu Glu Glu Met Thr Leu Ser His Ser Ala
    1055                1060                1065

Leu Lys Gln Lys Glu Pro Leu His Pro Val Asn Asp Lys Glu Ser
    1070                1075                1080

Ser Glu Gln Gly Ser Glu Val Ser Glu Ala Gln Thr Thr Asp Ser
    1085                1090                1095

Asp Asp Val Ile Val Pro Pro Met Ser Gln Lys Tyr Pro Lys Ala
    1100                1105                1110

Asp Ser Glu Lys Met Cys Ile Glu Ile Val Ser Leu Ala Phe Tyr
    1115                1120                1125

Pro Glu Ala Glu Val Met Ser Asp Glu Asn Ile Lys Gln Val Tyr
    1130                1135                1140

Val Glu Tyr Lys Phe Tyr Asp Leu Pro Leu Ser Glu Thr Glu Thr
    1145                1150                1155

Pro Val Ser Leu Arg Lys Pro Arg Ala Gly Glu Glu Ile His Phe
    1160                1165                1170

His Phe Ser Lys Val Ile Asp Leu Asp Pro Gln Glu Gln Gln Gly
    1175                1180                1185

Arg Arg Arg Phe Leu Phe Asp Met Leu Asn Gly Gln Asp Pro Asp
    1190                1195                1200

Gln Gly His Leu Lys Phe Thr Val Val Ser Asp Pro Leu Asp Glu
    1205                1210                1215

Glu Lys Lys Glu Cys Glu Glu Val Gly Tyr Ala Tyr Leu Gln Leu
    1220                1225                1230

Trp Gln Ile Leu Glu Ser Gly Arg Asp Ile Leu Glu Gln Glu Leu
    1235                1240                1245

Asp Ile Val Ser Pro Glu Leu Ala Thr Pro Ile Gly Arg Leu
    1250                1255                1260

Lys Val Ser Leu Gln Ala Ala Ala Val Leu His Ala Ile Tyr Lys
    1265                1270                1275

Glu Met Thr Glu Asp Leu Phe Ser
    1280                1285

<210> SEQ ID NO 38
<211> LENGTH: 7221
<212> TYPE: DNA
<213> ORGANISM: Homo sapiens

<400> SEQUENCE: 38
cgggcggcct cttgtgtgag ggcctgtggg attctccgga tatggccgga gtgtttcctt    60
```

-continued

```
atcgagggcc gggtaacccg gtgcctggcc ctctagcccc gctaccggac tacatgtcgg    120
aggagaagct gcaggagaaa gctcgaaaat ggcagcaatt gcaggccaag cgctatgcag    180
aaaagcggaa gtttgggttt gtggatgccc agaaggaaga catgccccca gaacatgtca    240
gggagatcat tcgagaccat ggagacatga ccaacaggaa gttccgccat gacaaaaggg    300
tttacttggg tgccctaaag tacatgcccc acgcagtcct caaactcctg gagaacatgc    360
ctatgccttg ggagcagatt cgggatgtgc cgtgctgta ccacatcact ggagccattt     420
ccttcgtcaa tgagattccc tgggtcattg aacctgtcta catctcccag tgggggtcaa    480
tgtggattat gatgcgccga gaaaaaagag ataggaggca tttcaagaga atgcgttttc    540
ccccttttga tgatgaggag ccgcccttgg actatgctga caacatccta aatgttgagc    600
cactggaggc cattcagcta gagctggacc ctgaggagga cgcccctgtg ttggactggt    660
tctatgacca ccagccgttg agggacagca ggaagtatgt aaatggctcc acttaccagc    720
gctggcagtt cacactacct atgatgtcaa ctctctaccg cctggctaat cagctcctga    780
cagacttggt ggatgacaac tacttctacc tgtttgattt gaaggccttc tttacgtcca    840
aggcactcaa tatggccatt cctggaggcc ccaaatttga acctcttgtt cgagacatca    900
acctacagga tgaagactgg aatgaattca atgatattaa caagattatc atccggcagc    960
ctatccggac tgagtacaag attgcttttc cttacttgta caacaatctt ccacaccatg   1020
tccacctcac ctggtaccat actcccaatg ttgtattcat caaaactgaa gatcctgact   1080
tgccagcttt ctactttgac cctttgatca acccaatctc ccataggcac tcagtcaaga   1140
gccaggaacc attgccggat gatgatgagg aatttgagct cccggagttt gtggagccct   1200
tcctgaagga cacacccctc tatacagaca atacagccaa tggcattgcc ctgctctggg   1260
ccccgcggcc cttcaaccta cgctctggtc gcacccgtcg ggccctggac atacccttg    1320 tcaagaactg gtatcgggag cattgtcctg ccgggcagcc tgtgaaagtg agggtctcct   1380
accagaagct gcttaagtac tatgtgctga atgccctgaa gcatcggccc cctaaggctc   1440
aaaagaagag gtatttgttc cgctccttca agccaccaa attctttcag tccacaaagc    1500
tggactgggt ggagggttgg ctccaggttt gccgccaggg ctacaacatg ctcaaccttc   1560
tcattcaccg caaaaaccte aactacctgc acctggacta caacttcaac ctcaagcctg   1620
tgaaaacgct caccaccaag gaaagaaaga atctcgtttt gggaatgct ttccacctgt    1680 gtcgggaagt tctgcgtttg actaagctgg tggtggatag tcacgtgcag tatcggctgg   1740
gcaatgtgga tgccttccag ctggcagatg gattgcagta tatatttgcc catgttgggc   1800
agttgacggg catgtatcga tacaaataca agctgatgcg acagattcgc gtgtgcaagg   1860
acctgaagca tctcatctat tatcgtttca acacaggccc tgtagggaag gtcctggct    1920 gtggcttctg ggctgccggt tggcgagtct ggctcttttt catgcgtggc attacccctt   1980
tattagagcg atggcttggc aacctcctgg cccggcagtt tgaaggtcga cactcaaagg   2040
gggtggcaaa gacagtaaca aagcagcgag tggagtcaca ttttgaccct tgagctgcggg  2100 cagctgtgat gcatgatatt ctggacatga tgcctgaggg gatcaagcag aacaaggccc   2160
ggacaatcct gcagcacctc agtgaagcct ggcgctgctg gaaagccaac attccctgga   2220
aggtccctgg gctgccgacg cccatagaga atatgatcct tcgatacgtg aaggccaagg   2280
ctgactggtg gaccaacact gcccactaca accgagaacg gatccgccga ggggccactg   2340 tggacaaagac tgtttgtaaa aagaatctgg gccgcctcac ccggctctat ctgaggcag    2400 aacaggagcg gcagcacaac tacctgaagg acgggcctta catcacagcg gaggaaacag   2460
```

| | |
|---|---|
| tggcagtata taccaccaca gtgcattggt tggaaagccg caggttttca cccatcccat | 2520 |
| tcccccact ctcctataag catgacacca agttgctcat cttggcattg gagcggctca | 2580 |
| aggaagctta tagtgtgaag tctcggttga accagtctca gagggaggag ctaggtctga | 2640 |
| tcgagcaggc ctacgataac ctccacgagg cgctgtcccg cataaagcgt cacctcctca | 2700 |
| cacagagagc cttcaaagag gtgggcattg agttcatgga tctgtatagc cacctcgttc | 2760 |
| cagtatatga tgttgagccc ctggagaaga taactgatgc ttacctggac cagtacctgt | 2820 |
| ggtatgaagc cgacaagcgc cgcctgttcc caccctggat taagcctgca gacacagaac | 2880 |
| cacctccact gcttgtttac aagtggtgtc aaggcatcaa taacctgcag gacgtgtggg | 2940 |
| agacgagtga aggcgagtgc aatgtcatgc tggaatcccg ctttgagaag atgtatgaga | 3000 |
| agatcgactt gactctgctc aacaggctcg tgcgcctcat cgtggaccac aacatagccg | 3060 |
| actacatgac agccaagaac aacgtcgtca tcaactataa ggacatgaac catacgaatt | 3120 |
| catatgggat catcagaggc ctgcagtttg cctcattcat agtgcagtat tatggcctgg | 3180 |
| tgatggattt gcttgtattg ggattgcacc gggccagtga gatggctggg cccctcaga | 3240 |
| tgccaaatga cttcctcagt ttccaggaca tagccactga ggctgcccac cccatccgtc | 3300 |
| tcttctgcag atacattgat cgcatccata ttttttcag gttcacagca gatgaggctc | 3360 |
| gggacctgat tcaacgttac ctgacagagc accctgaccc caataatgaa acatcgttg | 3420 |
| gctataataa caagaagtgc tggccccgag atgcccgcat gcgcctcatg aaacatgatg | 3480 |
| ttaacttagg ccgggcggta ttctgggaca tcaagaaccg cttgccacgg tcagtgacta | 3540 |
| cagttcagtg ggagaacagc ttcgtgtctg tgtacagtaa ggacaacccc aacctgctgt | 3600 |
| tcaacatgtg tggcttcgag tgccgcatcc tgcctaagtg ccgcaccagc tatgaggagt | 3660 |
| tcacccacaa ggacggggtc tggaacctgc agaatgaggt tactaaggag cgcacagctc | 3720 |
| agtgtttcct gcgtgtggac gatgagtcaa tgcagcgctt ccacaaccgc gtgcgtcaga | 3780 |
| ttctcatggc ctctgggtcc accaccttca ccaagattgt gaataagtgg aatacagctc | 3840 |
| tcattggcct tatgacatac tttcgggagg ctgtggtgaa cacccaagag ctcttggact | 3900 |
| tactggtgaa gtgtgagcac aaaatccaga cacgtatcaa gattggactc aactccaaga | 3960 |
| tgccaagtcg gttccccccg gttgtgttct acacccctaa ggagttgggt ggactcggca | 4020 |
| tgctctcaat gggccatgtg ctcatccccc aatccgacct caggtggtcc aaacagacag | 4080 |
| atgtaggtat cacacacttt cgttcaggaa tgagccatga agaagaccag ctcattccca | 4140 |
| acttgtaccg ctacatacag ccatgggaga gcgagttcat tgattctcag cgggtctggg | 4200 |
| ctgagtactc actcaagaga caagaggcca ttgctcagaa cagacgcctg actttagaag | 4260 |
| acctagaaga ttcatgggat cgtggcattc ctcgaatcaa taccctcttc cagaaggacc | 4320 |
| ggcacacact ggcttatgat aagggctggc gtgtcagaac tgactttaag cagtatcagg | 4380 |
| ttttgaagca gaatccgttc tggtggacac caccgcggca tgatgggaag ctctggaacc | 4440 |
| tgaacaacta ccgtacagac atgatccagg ccctgggcgg tgtggaaggc attctggaac | 4500 |
| acacactctt taagggcact tacttcccta cctgggaggg gcttttctgg gagaaggcca | 4560 |
| gtggctttga ggaatctatg aagtggaaga agctaactaa tgctcagcga tcaggactga | 4620 |
| accagattcc caatcgtaga ttcacccttct ggtggtcccc gaccattaat cgagccaatg | 4680 |
| tatatgtagg ctttcaggtg cagctagacc tgacgggtat cttcatgcac ggcaagatcc | 4740 |
| ccacgctgaa gatctctctc atccagatct tccgagctca cttgtggcag aagatccatg | 4800 |

```
agagcattgt tatggactta tgtcaggtgt ttgaccagga acttgatgca ctggaaattg    4860
agacagtaca aaaggagaca atccatcccc gaaagtcata taagatgaac tcttcctgtg    4920
cagatatcct gctctttgcc tcctataagt ggaatgtctc ccggccctca ttgctggctg    4980
actccaagga tgtgatggac agcaccacca cccagaaata ctggattgac atccagttgc    5040
gctgggggga ctatgattcc cacgacattg agcgctacgc ccgggccaag ttcctggact    5100
acaccaccga caacatgagt atctacccctt cgcccacagg tgtactcatc gccattgacc    5160
tggcctataa cttgcacagt gcctatggaa actggttccc aggcagcaag cctctcatac    5220
aacaggccat ggccaagatc atgaaggcaa accctgccct gtatgtgtta cgtgaacgga    5280
tccgcaaggg gctacagctc tattcatctg aacccactga gccttatttg tcttctcaga    5340
actatggtga gctcttctcc aaccagatta tctggtttgt ggatgacacc aacgtctaca    5400
gagtgactat tcacaagacc tttgaaggga acttgacaac caagcccatc aacggagcca    5460
tcttcatctt caacccacgc acagggcagc tgttcctcaa gataatccac acgtccgtgt    5520
gggcgggaca gaagcgtttg gggcagttgg ctaagtggaa gacagctgag gaggtggccg    5580
ccctgatccg atctctgcct gtggaggagc agcccaagca gatcattgtc accaggaagg    5640
acatgctgga cccactggag gtgcacttac tggacttccc caatattgtc atcaaaggat    5700
cggagctcca actccctttc caggcgtgtc tcaaggtgga aaaattcggg gatctcatcc    5760
ttaaagccac tgagcccag atggttctct tcaacctcta tgacgactgg ctcaagacta    5820
tttcatctta cacggccttc tcccgtctca tcctgattct gcgtgcccta catgtgaaca    5880
acgatcgggc aaaagtgatc ctgaagccag acaagactac tattacagaa ccacaccaca    5940
tctggcccac tctgactgac gaagaatgga tcaaggtcga ggtgcagctc aaggatctga    6000
tcttggctga ctacggcaag aaaaacaatg tgaacgtggc atcactgaca caatcagaaa    6060
ttcgagacat catcctgggt atggagatct cggcaccgtc acagcagcgg cagcagatcg    6120
ctgagatcga gaagcagacc aaggaacaat cgcagctgac ggcaacacag actcgcactg    6180
tcaacaagca tggcgatgag atcatcacct ccaccaccag caactatgag acccagactt    6240
tctcatccaa gactgagtgg agggtcaggg ccatctctgc tgccaacctg cacctaagga    6300
ccaatcacat ctatgtttca tctgacgaca tcaaggagac tggctacacc tacatccttc    6360
ccaagaatgt gcttaagaag ttcatctgca tatctgacct tcgggcccaa attgcaggat    6420
acctatatgg ggtgagccca ccagataacc cccaggtgaa ggagatccgc tgcattgtga    6480
tggtgccgca gtggggcact caccagaccg tgcacctgcc tggccagctg ccccagcatg    6540
agtacctcaa ggagatggaa cccttaggtt ggatccacac tcagcccaat gagtccccgc    6600
agttatcacc ccaggatgtc accacccatg ccaagatcat ggctgacaac ccatcttggg    6660
atggcgagaa gaccattatc atcacatgca gcttcacgcc aggctcctgt acactgacgg    6720
cctacaagct gaccctagt ggctacgaat ggggccgcca gaacacagac aagggcaaca    6780
accccaaggg ctacctgcct tcacactatg agagggtgca gatgctgctg tcggaccgtt    6840
tccttggctt cttcatggtc cctgcccagt cctcgtggaa ctacaacttc atgggtgttc    6900
ggcatgaccc caacatgaaa tatgagctac agctggcgaa ccccaaagag ttctaccacg    6960
aggtgcacag gccctctcac ttcctcaact tgctctcct gcaggagggg gaggtttact    7020
ctgcggatcg ggaggacctg tatgcctgac cgtttccctg cctcctgctt cagcctcccg    7080
aggccgaagc ctcagcccct ccagacaggc cgctgacatt cagcagtttg gcctcttttcc    7140
ctctgtctgt gcttgtgttg ttgacctcct gatggcttgt catcctgaat aaaatataat    7200
``` aataaattt gtataaatag g                                    7221

<210> SEQ ID NO 39
<211> LENGTH: 2335
<212> TYPE: PRT
<213> ORGANISM: Homo sapiens

<400> SEQUENCE: 39

Met Ala Gly Val Phe Pro Tyr Arg Gly Pro Gly Asn Pro Val Pro Gly
1               5                   10                  15

Pro Leu Ala Pro Leu Pro Asp Tyr Met Ser Glu Glu Lys Leu Gln Glu
            20                  25                  30

Lys Ala Arg Lys Trp Gln Gln Leu Gln Ala Lys Arg Tyr Ala Glu Lys
        35                  40                  45

Arg Lys Phe Gly Phe Val Asp Ala Gln Lys Glu Asp Met Pro Pro Glu
    50                  55                  60

His Val Arg Glu Ile Ile Arg Asp His Gly Asp Met Thr Asn Arg Lys
65                  70                  75                  80

Phe Arg His Asp Lys Arg Val Tyr Leu Gly Ala Leu Lys Tyr Met Pro
                85                  90                  95

His Ala Val Leu Lys Leu Leu Glu Asn Met Pro Met Pro Trp Glu Gln
            100                 105                 110

Ile Arg Asp Val Pro Val Leu Tyr His Ile Thr Gly Ala Ile Ser Phe
        115                 120                 125

Val Asn Glu Ile Pro Trp Val Ile Glu Pro Val Tyr Ile Ser Gln Trp
    130                 135                 140

Gly Ser Met Trp Ile Met Met Arg Arg Glu Lys Arg Asp Arg His
145                 150                 155                 160

Phe Lys Arg Met Arg Phe Pro Pro Phe Asp Asp Glu Glu Pro Pro Leu
                165                 170                 175

Asp Tyr Ala Asp Asn Ile Leu Asn Val Glu Pro Leu Glu Ala Ile Gln
            180                 185                 190

Leu Glu Leu Asp Pro Glu Glu Asp Ala Pro Val Leu Asp Trp Phe Tyr
        195                 200                 205

Asp His Gln Pro Leu Arg Asp Ser Arg Lys Tyr Val Asn Gly Ser Thr
    210                 215                 220

Tyr Gln Arg Trp Gln Phe Thr Leu Pro Met Met Ser Thr Leu Tyr Arg
225                 230                 235                 240

Leu Ala Asn Gln Leu Leu Thr Asp Leu Val Asp Asp Asn Tyr Phe Tyr
                245                 250                 255

Leu Phe Asp Leu Lys Ala Phe Phe Thr Ser Lys Ala Leu Asn Met Ala
            260                 265                 270

Ile Pro Gly Gly Pro Lys Phe Glu Pro Leu Val Arg Asp Ile Asn Leu
        275                 280                 285

Gln Asp Glu Asp Trp Asn Glu Phe Asn Asp Ile Asn Lys Ile Ile Ile
    290                 295                 300

Arg Gln Pro Ile Arg Thr Glu Tyr Lys Ile Ala Phe Pro Tyr Leu Tyr
305                 310                 315                 320

Asn Asn Leu Pro His His Val His Leu Thr Trp Tyr His Thr Pro Asn
                325                 330                 335

Val Val Phe Ile Lys Thr Glu Asp Pro Asp Leu Pro Ala Phe Tyr Phe
            340                 345                 350

Asp Pro Leu Ile Asn Pro Ile Ser His Arg His Ser Val Lys Ser Gln
        355                 360                 365

```
Glu Pro Leu Pro Asp Asp Glu Glu Phe Glu Leu Pro Glu Phe Val
    370                 375                 380

Glu Pro Phe Leu Lys Asp Thr Pro Leu Tyr Thr Asp Asn Thr Ala Asn
385                 390                 395                 400

Gly Ile Ala Leu Leu Trp Ala Pro Arg Pro Phe Asn Leu Arg Ser Gly
                405                 410                 415

Arg Thr Arg Arg Ala Leu Asp Ile Pro Leu Val Lys Asn Trp Tyr Arg
            420                 425                 430

Glu His Cys Pro Ala Gly Gln Pro Val Lys Val Arg Val Ser Tyr Gln
            435                 440                 445

Lys Leu Leu Lys Tyr Tyr Val Leu Asn Ala Leu Lys His Arg Pro Pro
        450                 455                 460

Lys Ala Gln Lys Lys Arg Tyr Leu Phe Arg Ser Phe Lys Ala Thr Lys
465                 470                 475                 480

Phe Phe Gln Ser Thr Lys Leu Asp Trp Val Glu Gly Trp Leu Gln Val
                485                 490                 495

Cys Arg Gln Gly Tyr Asn Met Leu Asn Leu Leu Ile His Arg Lys Asn
            500                 505                 510

Leu Asn Tyr Leu His Leu Asp Tyr Asn Phe Asn Leu Lys Pro Val Lys
            515                 520                 525

Thr Leu Thr Thr Lys Glu Arg Lys Lys Ser Arg Phe Gly Asn Ala Phe
    530                 535                 540

His Leu Cys Arg Glu Val Leu Arg Leu Thr Lys Leu Val Val Asp Ser
545                 550                 555                 560

His Val Gln Tyr Arg Leu Gly Asn Val Asp Ala Phe Gln Leu Ala Asp
                565                 570                 575

Gly Leu Gln Tyr Ile Phe Ala His Val Gly Gln Leu Thr Gly Met Tyr
            580                 585                 590

Arg Tyr Lys Tyr Lys Leu Met Arg Gln Ile Arg Val Cys Lys Asp Leu
        595                 600                 605

Lys His Leu Ile Tyr Tyr Arg Phe Asn Thr Gly Pro Val Gly Lys Gly
    610                 615                 620

Pro Gly Cys Gly Phe Trp Ala Ala Gly Trp Arg Val Trp Leu Phe Phe
625                 630                 635                 640

Met Arg Gly Ile Thr Pro Leu Leu Glu Arg Trp Leu Gly Asn Leu Leu
                645                 650                 655

Ala Arg Gln Phe Glu Gly Arg His Ser Lys Gly Val Ala Lys Thr Val
            660                 665                 670

Thr Lys Gln Arg Val Glu Ser His Phe Asp Leu Glu Leu Arg Ala Ala
    675                 680                 685

Val Met His Asp Ile Leu Asp Met Met Pro Glu Gly Ile Lys Gln Asn
    690                 695                 700

Lys Ala Arg Thr Ile Leu Gln His Leu Ser Glu Ala Trp Arg Cys Trp
705                 710                 715                 720

Lys Ala Asn Ile Pro Trp Lys Val Pro Gly Leu Pro Thr Pro Ile Glu
                725                 730                 735

Asn Met Ile Leu Arg Tyr Val Lys Ala Lys Ala Asp Trp Trp Thr Asn
            740                 745                 750

Thr Ala His Tyr Asn Arg Glu Arg Ile Arg Arg Gly Ala Thr Val Asp
        755                 760                 765

Lys Thr Val Cys Lys Lys Asn Leu Gly Arg Leu Thr Arg Leu Tyr Leu
    770                 775                 780
```

-continued

```
Lys Ala Glu Gln Glu Arg Gln His Asn Tyr Leu Lys Asp Gly Pro Tyr
785                 790                 795                 800

Ile Thr Ala Glu Glu Thr Val Ala Val Tyr Thr Thr Thr Val His Trp
                805                 810                 815

Leu Glu Ser Arg Arg Phe Ser Pro Ile Pro Phe Pro Pro Leu Ser Tyr
            820                 825                 830

Lys His Asp Thr Lys Leu Leu Ile Leu Ala Leu Glu Arg Leu Lys Glu
                835                 840                 845

Ala Tyr Ser Val Lys Ser Arg Leu Asn Gln Ser Gln Arg Glu Glu Leu
    850                 855                 860

Gly Leu Ile Glu Gln Ala Tyr Asp Asn Leu His Glu Ala Leu Ser Arg
865                 870                 875                 880

Ile Lys Arg His Leu Leu Thr Gln Arg Ala Phe Lys Glu Val Gly Ile
                885                 890                 895

Glu Phe Met Asp Leu Tyr Ser His Leu Val Pro Val Tyr Asp Val Glu
                900                 905                 910

Pro Leu Glu Lys Ile Thr Asp Ala Tyr Leu Asp Gln Tyr Leu Trp Tyr
            915                 920                 925

Glu Ala Asp Lys Arg Arg Leu Phe Pro Pro Trp Ile Lys Pro Ala Asp
930                 935                 940

Thr Glu Pro Pro Pro Leu Leu Val Tyr Lys Trp Cys Gln Gly Ile Asn
945                 950                 955                 960

Asn Leu Gln Asp Val Trp Glu Thr Ser Glu Gly Glu Cys Asn Val Met
                965                 970                 975

Leu Glu Ser Arg Phe Glu Lys Met Tyr Glu Lys Ile Asp Leu Thr Leu
            980                 985                 990

Leu Asn Arg Leu Val Arg Leu Ile Val Asp His Asn Ile Ala Asp Tyr
        995                 1000                1005

Met Thr Ala Lys Asn Asn Val Val Ile Asn Tyr Lys Asp Met Asn
    1010                1015                1020

His Thr Asn Ser Tyr Gly Ile Ile Arg Gly Leu Gln Phe Ala Ser
    1025                1030                1035

Phe Ile Val Gln Tyr Tyr Gly Leu Val Met Asp Leu Leu Val Leu
    1040                1045                1050

Gly Leu His Arg Ala Ser Glu Met Ala Gly Pro Pro Gln Met Pro
    1055                1060                1065

Asn Asp Phe Leu Ser Phe Gln Asp Ile Ala Thr Glu Ala Ala His
    1070                1075                1080

Pro Ile Arg Leu Phe Cys Arg Tyr Ile Asp Arg Ile His Ile Phe
    1085                1090                1095

Phe Arg Phe Thr Ala Asp Glu Ala Arg Asp Leu Ile Gln Arg Tyr
    1100                1105                1110

Leu Thr Glu His Pro Asp Pro Asn Asn Glu Asn Ile Val Gly Tyr
    1115                1120                1125

Asn Asn Lys Lys Cys Trp Pro Arg Asp Ala Arg Met Arg Leu Met
    1130                1135                1140

Lys His Asp Val Asn Leu Gly Arg Ala Val Phe Trp Asp Ile Lys
    1145                1150                1155

Asn Arg Leu Pro Arg Ser Val Thr Thr Val Gln Trp Glu Asn Ser
    1160                1165                1170

Phe Val Ser Val Tyr Ser Lys Asp Asn Pro Asn Leu Leu Phe Asn
    1175                1180                1185

Met Cys Gly Phe Glu Cys Arg Ile Leu Pro Lys Cys Arg Thr Ser
```

```
                1190                1195                1200
Tyr Glu Glu Phe Thr His Lys Asp Gly Val Trp Asn Leu Gln Asn
    1205                1210                1215
Glu Val Thr Lys Glu Arg Thr Ala Gln Cys Phe Leu Arg Val Asp
    1220                1225                1230
Asp Glu Ser Met Gln Arg Phe His Asn Arg Val Arg Gln Ile Leu
    1235                1240                1245
Met Ala Ser Gly Ser Thr Thr Phe Thr Lys Ile Val Asn Lys Trp
    1250                1255                1260
Asn Thr Ala Leu Ile Gly Leu Met Thr Tyr Phe Arg Glu Ala Val
    1265                1270                1275
Val Asn Thr Gln Glu Leu Leu Asp Leu Leu Val Lys Cys Glu His
    1280                1285                1290
Lys Ile Gln Thr Arg Ile Lys Ile Gly Leu Asn Ser Lys Met Pro
    1295                1300                1305
Ser Arg Phe Pro Pro Val Val Phe Tyr Thr Pro Lys Glu Leu Gly
    1310                1315                1320
Gly Leu Gly Met Leu Ser Met Gly His Val Leu Ile Pro Gln Ser
    1325                1330                1335
Asp Leu Arg Trp Ser Lys Gln Thr Asp Val Gly Ile Thr His Phe
    1340                1345                1350
Arg Ser Gly Met Ser His Glu Glu Asp Gln Leu Ile Pro Asn Leu
    1355                1360                1365
Tyr Arg Tyr Ile Gln Pro Trp Glu Ser Glu Phe Ile Asp Ser Gln
    1370                1375                1380
Arg Val Trp Ala Glu Tyr Ser Leu Lys Arg Gln Glu Ala Ile Ala
    1385                1390                1395
Gln Asn Arg Arg Leu Thr Leu Glu Asp Leu Glu Asp Ser Trp Asp
    1400                1405                1410
Arg Gly Ile Pro Arg Ile Asn Thr Leu Phe Gln Lys Asp Arg His
    1415                1420                1425
Thr Leu Ala Tyr Asp Lys Gly Trp Arg Val Arg Thr Asp Phe Lys
    1430                1435                1440
Gln Tyr Gln Val Leu Lys Gln Asn Pro Phe Trp Trp Thr His Gln
    1445                1450                1455
Arg His Asp Gly Lys Leu Trp Asn Leu Asn Asn Tyr Arg Thr Asp
    1460                1465                1470
Met Ile Gln Ala Leu Gly Gly Val Glu Gly Ile Leu Glu His Thr
    1475                1480                1485
Leu Phe Lys Gly Thr Tyr Phe Pro Thr Trp Glu Gly Leu Phe Trp
    1490                1495                1500
Glu Lys Ala Ser Gly Phe Glu Ser Met Lys Trp Lys Lys Leu
    1505                1510                1515
Thr Asn Ala Gln Arg Ser Gly Leu Asn Gln Ile Pro Asn Arg Arg
    1520                1525                1530
Phe Thr Leu Trp Trp Ser Pro Thr Ile Asn Arg Ala Asn Val Tyr
    1535                1540                1545
Val Gly Phe Gln Val Gln Leu Asp Leu Thr Gly Ile Phe Met His
    1550                1555                1560
Gly Lys Ile Pro Thr Leu Lys Ile Ser Leu Ile Gln Ile Phe Arg
    1565                1570                1575
Ala His Leu Trp Gln Lys Ile His Glu Ser Ile Val Met Asp Leu
    1580                1585                1590
```

-continued

Cys Gln Val Phe Asp Gln Glu Leu Asp Ala Leu Glu Ile Glu Thr
1595                1600                1605

Val Gln Lys Glu Thr Ile His Pro Arg Lys Ser Tyr Lys Met Asn
1610                1615                1620

Ser Ser Cys Ala Asp Ile Leu Leu Phe Ala Ser Tyr Lys Trp Asn
1625                1630                1635

Val Ser Arg Pro Ser Leu Leu Ala Asp Ser Lys Asp Val Met Asp
1640                1645                1650

Ser Thr Thr Thr Gln Lys Tyr Trp Ile Asp Ile Gln Leu Arg Trp
1655                1660                1665

Gly Asp Tyr Asp Ser His Asp Ile Glu Arg Tyr Ala Arg Ala Lys
1670                1675                1680

Phe Leu Asp Tyr Thr Thr Asp Asn Met Ser Ile Tyr Pro Ser Pro
1685                1690                1695

Thr Gly Val Leu Ile Ala Ile Asp Leu Ala Tyr Asn Leu His Ser
1700                1705                1710

Ala Tyr Gly Asn Trp Phe Pro Gly Ser Lys Pro Leu Ile Gln Gln
1715                1720                1725

Ala Met Ala Lys Ile Met Lys Ala Asn Pro Ala Leu Tyr Val Leu
1730                1735                1740

Arg Glu Arg Ile Arg Lys Gly Leu Gln Leu Tyr Ser Ser Glu Pro
1745                1750                1755

Thr Glu Pro Tyr Leu Ser Ser Gln Asn Tyr Gly Glu Leu Phe Ser
1760                1765                1770

Asn Gln Ile Ile Trp Phe Val Asp Asp Thr Asn Val Tyr Arg Val
1775                1780                1785

Thr Ile His Lys Thr Phe Glu Gly Asn Leu Thr Thr Lys Pro Ile
1790                1795                1800

Asn Gly Ala Ile Phe Ile Phe Asn Pro Arg Thr Gly Gln Leu Phe
1805                1810                1815

Leu Lys Ile Ile His Thr Ser Val Trp Ala Gly Gln Lys Arg Leu
1820                1825                1830

Gly Gln Leu Ala Lys Trp Lys Thr Ala Glu Glu Val Ala Ala Leu
1835                1840                1845

Ile Arg Ser Leu Pro Val Glu Glu Gln Pro Lys Gln Ile Ile Val
1850                1855                1860

Thr Arg Lys Asp Met Leu Asp Pro Leu Glu Val His Leu Leu Asp
1865                1870                1875

Phe Pro Asn Ile Val Ile Lys Gly Ser Glu Leu Gln Leu Pro Phe
1880                1885                1890

Gln Ala Cys Leu Lys Val Glu Lys Phe Gly Asp Leu Ile Leu Lys
1895                1900                1905

Ala Thr Glu Pro Gln Met Val Leu Phe Asn Leu Tyr Asp Asp Trp
1910                1915                1920

Leu Lys Thr Ile Ser Ser Tyr Thr Ala Phe Ser Arg Leu Ile Leu
1925                1930                1935

Ile Leu Arg Ala Leu His Val Asn Asn Asp Arg Ala Lys Val Ile
1940                1945                1950

Leu Lys Pro Asp Lys Thr Thr Ile Thr Glu Pro His His Ile Trp
1955                1960                1965

Pro Thr Leu Thr Asp Glu Glu Trp Ile Lys Val Glu Val Gln Leu
1970                1975                1980

| | | | | | | | | | | |
|---|---|---|---|---|---|---|---|---|---|---|
|Lys|Asp|Leu|Ile|Leu|Ala|Asp|Tyr|Gly|Lys|Asn Asn Val Asn|
| |1985| | | |1990| | | |1995| |
|Val|Ala|Ser|Leu|Thr|Gln|Ser|Glu|Ile|Arg|Asp Ile Ile Leu Gly|
| |2000| | | |2005| | | |2010| |
|Met|Glu|Ile|Ser|Ala|Pro|Ser|Gln|Gln|Arg|Gln Gln Ile Ala Glu|
| |2015| | | |2020| | | |2025| |
|Ile|Glu|Lys|Gln|Thr|Lys|Glu|Gln|Ser|Gln|Leu Thr Ala Thr Gln|
| |2030| | | |2035| | | |2040| |
|Thr|Arg|Thr|Val|Asn|Lys|His|Gly|Asp|Glu|Ile Ile Thr Ser Thr|
| |2045| | | |2050| | | |2055| |
|Thr|Ser|Asn|Tyr|Glu|Thr|Gln|Thr|Phe|Ser|Ser Lys Thr Glu Trp|
| |2060| | | |2065| | | |2070| |
|Arg|Val|Arg|Ala|Ile|Ser|Ala|Ala|Asn|Leu|His Leu Arg Thr Asn|
| |2075| | | |2080| | | |2085| |
|His|Ile|Tyr|Val|Ser|Ser|Asp|Asp|Ile|Lys|Glu Thr Gly Tyr Thr|
| |2090| | | |2095| | | |2100| |
|Tyr|Ile|Leu|Pro|Lys|Asn|Val|Leu|Lys|Lys|Phe Ile Cys Ile Ser|
| |2105| | | |2110| | | |2115| |
|Asp|Leu|Arg|Ala|Gln|Ile|Ala|Gly|Tyr|Leu|Tyr Gly Val Ser Pro|
| |2120| | | |2125| | | |2130| |
|Pro|Asp|Asn|Pro|Gln|Val|Lys|Glu|Ile|Arg|Cys Ile Val Met Val|
| |2135| | | |2140| | | |2145| |
|Pro|Gln|Trp|Gly|Thr|His|Gln|Thr|Val|His|Leu Pro Gly Gln Leu|
| |2150| | | |2155| | | |2160| |
|Pro|Gln|His|Glu|Tyr|Leu|Lys|Glu|Met|Glu|Pro Leu Gly Trp Ile|
| |2165| | | |2170| | | |2175| |
|His|Thr|Gln|Pro|Asn|Glu|Ser|Pro|Gln|Leu|Ser Pro Gln Asp Val|
| |2180| | | |2185| | | |2190| |
|Thr|Thr|His|Ala|Lys|Ile|Met|Ala|Asp|Asn|Pro Ser Trp Asp Gly|
| |2195| | | |2200| | | |2205| |
|Glu|Lys|Thr|Ile|Ile|Ile|Thr|Cys|Ser|Phe|Thr Pro Gly Ser Cys|
| |2210| | | |2215| | | |2220| |
|Thr|Leu|Thr|Ala|Tyr|Lys|Leu|Thr|Pro|Ser|Gly Tyr Glu Trp Gly|
| |2225| | | |2230| | | |2235| |
|Arg|Gln|Asn|Thr|Asp|Lys|Gly|Asn|Asn|Pro|Lys Gly Tyr Leu Pro|
| |2240| | | |2245| | | |2250| |
|Ser|His|Tyr|Glu|Arg|Val|Gln|Met|Leu|Leu|Ser Asp Arg Phe Leu|
| |2255| | | |2260| | | |2265| |
|Gly|Phe|Phe|Met|Val|Pro|Ala|Gln|Ser|Ser|Trp Asn Tyr Asn Phe|
| |2270| | | |2275| | | |2280| |
|Met|Gly|Val|Arg|His|Asp|Pro|Asn|Met|Lys|Tyr Glu Leu Gln Leu|
| |2285| | | |2290| | | |2295| |
|Ala|Asn|Pro|Lys|Glu|Phe|Tyr|His|Glu|Val|His Arg Pro Ser His|
| |2300| | | |2305| | | |2310| |
|Phe|Leu|Asn|Phe|Ala|Leu|Leu|Gln|Glu|Gly|Glu Val Tyr Ser Ala|
| |2315| | | |2320| | | |2325| |
|Asp|Arg|Glu|Asp|Leu|Tyr|Ala| | | | |
| |2330| | | |2335| | | | | |

<210> SEQ ID NO 40
<211> LENGTH: 7972
<212> TYPE: DNA
<213> ORGANISM: Homo sapiens

<400> SEQUENCE: 40

```
atttgaagtc ctcgttccac gccttctcat catcctgaac accgagctct gggactccgg    60
cggagaatct aaacgtaaag catcaccac ggtcgtgaac tgtaggctct cctggcatcc    120
gggatcttat tctggccttg gcggagttgg ggatggtgtc gcctagcagc cgctgccgct    180
ttggcttgct cgggaccatt tggctggacc cagagtccgc gtggaaccgc gatagggatc    240
tgtcagggcc cgcggccggg tccagcttgg tggttgcggt agtgagaggc ctccgctggt    300
tgccaggctt ggtctagagg tggagcacag tgaaagaatt caagatgcca cctaatataa    360
actggaaaga aataatgaaa gttgacccag atgacctgcc ccgtcaagaa gaactggcag    420
ataatttatt gatttcctta tccaaggtgg aagtaaatga gctaaaaagt gaaaagcaag    480
aaaatgtgat acacctttc agaattactc agtcactaat gaagatgaaa gctcaagaag    540
tggagctggc tttggaagaa gtagaaaaag ctggagaaga caagcaaaa tttgaaaatc    600 aattaaaaac taaagtaatg aaactggaaa atgaactgga gatggctcag cagtctgcag    660
gtggacgaga tactcggttt ttacgtaatg aaatttgcca acttgaaaaa caattagaac    720
aaaaagatag agaattggag gacatggaaa aggagttgga gaaagagaag aaagttaatg    780
agcaattggc tcttcgaaat gaggaggcag aaaatgaaaa cagcaaatta agaagagaga    840
acaaacgtct aaagaaaaag aatgaacaac tttgtcagga tattattgac taccagaaac    900
aaatagattc acagaaagaa acactttat caagaagagg ggaagacagt gactaccgat    960
cacagttgtc taaaaaaac tatgagctta ccaatatct tgatgaaatt cagactttaa    1020
cagaagctaa tgagaaaatt gaagttcaga atcaagaaat gagaaaaaat ttagaagagt    1080
ctgtacagga aatggagaag atgactgatg aatataatag aatgaaagct attgtgcatc    1140
agacagataa tgtaatagat cagttaaaaa aagaaaacga tcattatcaa cttcaagtgc    1200
aggagcttac agatcttctg aaatcaaaaa atgaagaaga tgatccaatt atggtagctg    1260
tcaatgcaaa agtagaagaa tggaagctaa ttttgtcttc taaagatgat gaaattattg    1320
agtatcagca aatgttacat aacctaaggg agaaacttaa gaatgctcag cttgatgctg    1380
ataaaagtaa tgttatggct ctacagcagg gtatacagga acgagacagt caaattaaga    1440
tgctcaccga acaagtagaa caatatacaa aagaaatgga aaagaatact tgtattattg    1500
aagatttgaa aaatgagctc caaagaaaca aaggtgcttc aacccttcct caacagactc    1560
atatgaaaat tcagtcaacg ttagacattt taaaagagaa aactaaagag ctgagagaa    1620 cagctgaact ggctgaggct gatgctaggg aaaaggataa agaattagtt gaggctctga    1680
agaggttaaa agattatgaa tcgggagtat atggtttaga agatgctgtc gttgaaataa    1740
agaattgtaa aaaccaaatt aaaataagag atcgagagat tgaaatatta acaaaggaaa    1800
tcaataaact tgaattgaag atcagtgatt tccttgatga aaatgaggca cttagagagc    1860
gtgtgggcct tgaaccaaag acaatgattg atttaactga atttagaaat agcaaacact    1920
taaaacagca gcagtacaga gctgaaaacc agattctttt gaaagagatt gaaagtctag    1980
aggaagaacg acttgatctg aaaaaaaaaa ttcgtcaaat ggctcaagaa agaggaaaaa    2040
gaagtgcaac ttcaggatta accactgagg acctgaacct aactgaaaac atttctcaag    2100
gagatagaat aagtgaaaga aaattggatt tattgagcct caaaaatatg agtgaagcac    2160
aatcaaagaa tgaatttctt tcaagagaac taattgaaaa agaaagagat ttagaaagga    2220
gtaggacagt gatagccaaa tttcagaata aattaaaaga attagttgaa gaaaataagc    2280
aacttgaaga aggtatgaaa gaaatattgc aagcaattaa ggaaatgcag aaagatcctg    2340
```

```
atgttaaagg aggagaaaca tctctaatta tccctagcct tgaaagacta gttaatgcta    2400
tagaatcaaa gaatgcagaa ggaatctttg atgcgagtct gcatttgaaa gcccaagttg    2460
atcagcttac cggaagaaat gaagaattaa gacaggagct cagggaatct cggaaagagg    2520
ctataaatta ttcacagcag ttggcaaaag ctaatttaaa gatagaccat cttgaaaaag    2580
aaactagtct tttacgacaa tcagaaggat cgaatgttgt ttttaaagga attgacttac    2640
ctgatgggat agcaccatct agtgccagta tcattaattc tcagaatgaa tatttaatac    2700
atttgttaca ggaactagaa aataaagaaa aaaagttaaa gaatttagaa gattctcttg    2760
aagattacaa cagaaaattt gctgtaattc gtcatcaaca aagtttgttg tataaagaat    2820
acctaagtga aaaggagacc tggaaaacag aatctaaaac aataaaagag gaaaagagaa    2880
aacttgagga tcaagtccaa caagatgcta taaaagtaaa agaatataat aatttgctca    2940
atgctcttca gatggattcg gatgaaatga aaaaaatact tgcagaaaat agtaggaaaa    3000
ttactgtttt gcaagtgaat gaaaaatcac ttataaggca atatacaacc ttagtagaat    3060
tggagcgaca acttagaaaa gaaaatgaga agcaaaagaa tgaattgttg tcaatggagg    3120
ctgaagtttg tgaaaaaatt gggtgtttgc aaagatttaa ggaaatggcc attttcaaga    3180
ttgcagctct ccaaaaagtt gtagataata gtgtttcttt gtctgaacta gaactggcta    3240
ataaacagta caatgaactg actgctaagt acagggacat cttgcaaaaa gataatatgc    3300
ttgttcaaag aacaagtaac ttggaacacc tggagtgtga aaacatctcc ttaaaagaac    3360
aagtggagtc tataaataaa gaactggaga ttaccaagga aaaacttcac actattgaac    3420
aagcctggga acaggaaact aaattaggta atgaatctag catggataag gcaagaaat     3480 caataaccaa cagtgacatt gttttccattt caaaaaaaat aactatgctg gaaatgaagg    3540
aattaaatga aaggcagcgg gctgaacatt gtcaaaaaat gtatgaacac ttacggactt    3600
cgttaaagca aatggaggaa cgtaattttg aattggaaac caaatttgct gagcttacca    3660
aaatcaattt ggatgcacag aaggtggaac agatgttaag agatgaatta gctgatagtg    3720
tgagcaaggc agtaagtgat gctgataggc aacggattct agaattagag aagaatgaaa    3780
tggaactaaa agttgaagtg tcaaaactga gagagatttc tgatattgcc agaagacaag    3840
ttgaaatttt gaatgcacaa caacaatcta gggacaagga agtagagtcc ctcagaatgc    3900
aactgctaga ctatcaggca cagtctgatg aaaagtcgct cattgccaag ttgcaccaac    3960
ataatgtctc tcttcaactg agtgaggcta ctgctcttgg taagttggag tcaattacat    4020
ctaaactgca gaagatggag gcctacaact tgcgcttaga gcagaaactt gatgaaaaag    4080
aacaggctct ctattatgct cgtttggagg aagaaacag agcaaaacat ctgcgccaaa    4140
caattcagtc tctacgacga cagtttagtg gagctttacc cttggcacaa caggaaaagt    4200
tctccaaaac aatgattcaa ctacaaaatg acaaacttaa gataatgcaa gaaatgaaaa    4260
attctcaaca agaacataga aatatggaga caaaacatt ggagatggaa ttaaaattaa    4320
agggcctgga agagttaata agcacttttaa aggataccaa aggagcccaa aagtaatca    4380 actggcatat gaaaatagaa gaacttcgtc ttcaagaact taaactaaat cgggaattag    4440
tcaaggataa agaagaaata aaatatttga ataacataat ttctgaatat gaacgtacaa    4500
tcagcagtct tgaagaagaa attgtgcaac agaacaagtt tcatgaagaa agacaaatgg    4560
cctgggatca aagagaagtt gacctggaac gccaactaga cattttttgac cgtcagcaaa    4620 atgaaatact aaatgcggca caaaagtttg aagaagctac aggatcaatc cctgaccta     4680 gtttgcccct tccaaatcaa cttgagatcg ctctaaggaa aattaaggag aacattcgaa    4740
```

```
taattctaga aacacgggca acttgcaaat cactagaaga gaaactaaaa gagaaagaat   4800
ctgctttaag gttagcagaa caaaatatac tgtcaagaga caaagtaatc aatgaactga   4860
ggcttcgatt gcctgccact gcagaaagag aaaagctcat agctgagcta ggcagaaaag   4920
agatggaacc aaaatctcac cacacattga aaattgctca tcaaaccatt gcaaacatgc   4980
aagcaaggtt aaatcaaaaa gaagaagtat taaagaagta tcaacgtctt ctagaaaaag   5040
ccagagagga gcaaagagaa attgtgaaga aacatgagga agaccttcat attcttcatc   5100
acagattaga actacaggct gatagttcac taaataaatt caaacaaacg gcttgggatt   5160
taatgaaaca gtctcccact ccagttccta ccaacaagca ttttattcgt ctggctgaga   5220
tggaacagac agtagcagaa caagatgact ctctttcctc actcttggtc aaactaaaga   5280
aagtatcaca agatttggag agacaaagag aaatcactga attaaaagta aaagaatttg   5340
aaaatatcaa attacagctt caagaaaacc atgaagatga agtgaaaaaa gtaaaagcgg   5400
aagtagagga tttaaagtat cttctggacc agtcacaaaa ggagtcacag tgtttaaaat   5460
ctgaacttca ggctcaaaaa gaagcaaatt caagagctcc aacaactaca atgagaaatc   5520
tagtagaacg gctaaagagc caattagcct tgaaggagaa acaacagaaa gcacttagtc   5580
gggcactttt agaactccgg gcagaaatga cagcagctgc tgaagaacgt attatttctg   5640
caacttctca aaaagaggcc catctcaatg ttcaacaaat cgttgatcga catactagag   5700
agctaaagac acaagttgaa gatttaaatg aaaatctttt aaaattgaaa gaagcactta   5760
aaacaagtaa aaacagagaa aactcactaa ctgataattt gaatgactta aataatgaac   5820
tgcaaaagaa acaaaaagcc tataataaaa tacttagaga gaaagaggaa attgatcaag   5880
agaatgatga actgaaaagg caaattaaaa gactaaccag tggattacag ggcaaacccc   5940
tgacagataa taaacaaagt ctaattgaag aactccaaag gaaagttaaa aaactagaga   6000
accaattaga gggaaaggtg gaggaagtag acctaaaacc tatgaaagaa aagaatgcta   6060
aagaagaatt aattaggtgg gaagaaggta aaaagtggca agccaaaata gaaggaattc   6120
gaaacaagtt aaaagagaaa gagggggaag tctttacttt aacaaagcag ttgaatactt   6180
tgaaggatct ttttgccaaa gccgataaag agaaacttac tttgcagagg aaactaaaaa   6240
caactggcat gactgttgat caggttttgg gaatacgagc tttggagtca gaaaaagaat   6300
tggaagaatt aaaaaagaga aatcttgact agaaaatgta tatattgtat atgagggccc   6360
accaagctct tcctcgagat tctgttgtag aagatttaca tttacaaaat agatacctcc   6420
aagaaaaact tcatgcttta gaaaaacagt tttcaaagga tacatattct aagccttcaa   6480
tttcaggaat agagtcagat gatcattgtc agagagaaca ggagcttcag aaggaaaact   6540
tgaagttgtc atctgaaaat attgaactga aatttcagct tgaacaagca ataaagatt   6600
tgccaagatt aaagaatcaa gtcagagatt tgaaggaaat gtgtgaattt cttaagaaag   6660
aaaaagcaga agttcagcgg aaacttggcc atgttagagg gtctggtaga agtgaaagaa   6720
caatcccaga actggaaaaa accattggtt taatgaaaaa agtagttgaa aaagtccaga   6780
gagaaaatga acagttgaaa aaagcatcag gaatattgac tagtgaaaaa atggctaata   6840
ttgagcagga aaatgaaaaa ttgaaggctg aattagaaaa acttaaagct catcttgggc   6900
atcagttgag catgcactat gaatccaaga ccaaaggcac agaaaaaatt attgctgaaa   6960
atgaaaggct tcgtaaagaa cttaaaaaag aaactgatgc tgcagagaaa ttacggatag   7020
caaagaataa tttagagata ttaaatgaga agatgacagt tcaactagaa gagactggta   7080
```

```
agagattgca gtttgcagaa agcagaggtc cacagcttga aggtgctgac agtaagagct      7140
ggaaatccat tgtggttaca agaatgtatg aaaccaagtt aaaagaattg gaaactgata      7200
ttgccaaaaa aaatcaaagc attactgacc ttaaacagct tgtaaaagaa gcaacagaga      7260
gagaacaaaa agttaacaaa tacaatgaag accttgaaca acagattaag attcttaaac      7320
atgttcctga aggtgctgag acagagcaag gccttaaacg ggagcttcaa gttcttagat      7380
tagctaatca tcagctggat aaagagaaag cagaattaat ccatcagata gaagctaaca      7440
aggaccaaag tggagctgaa agcaccatac ctgatgctga tcaactaaag gaaaaaataa      7500
aagatctaga gacacagctc aaaatgtcag atctagaaaa gcagcatttg aaggaggaaa      7560
taaagaagct gaaaaagaa ctggaaaatt ttgatccttc attttttgaa gaaattgaag      7620
atcttaagta taattacaag gaagaagtga agaagaatat tctcttagaa gagaaggtaa      7680
aaaaactttc agaacaattg ggagttgaat taactagccc tgttgctgct tctgaagagt      7740
ttgaagatga agaagaaagt cctgttaatt tccccattta ctaaaggtca cctataaact      7800
ttgtttcatt taactattta ttaactttat aagttaaata tacttggaaa taagcagttc      7860
tccgaactgt agtatttcct tctcactacc ttgtaccttt atacttagat tggaattctt      7920
aataaataaa attatgtgaa attttcaact tattaaaaaa aaaaaaaaa aa              7972
```

<210> SEQ ID NO 41
<211> LENGTH: 2479
<212> TYPE: PRT
<213> ORGANISM: Homo sapiens

<400> SEQUENCE: 41

```
Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220
```

```
Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
            245                 250                 255

Tyr Asn Arg Met Lys Ala Ile Val His Gln Thr Asp Asn Val Ile Asp
        260                 265                 270

Gln Leu Lys Lys Glu Asn Asp His Tyr Gln Leu Gln Val Gln Glu Leu
    275                 280                 285

Thr Asp Leu Leu Lys Ser Lys Asn Glu Glu Asp Pro Ile Met Val
290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Cys Ile
370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
    530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
        595                 600                 605

Asn Glu Phe Leu Ser Arg Glu Leu Ile Glu Lys Glu Arg Asp Leu Glu
    610                 615                 620

Arg Ser Arg Thr Val Ile Ala Lys Phe Gln Asn Lys Leu Lys Glu Leu
625                 630                 635                 640
```

```
Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
            675                 680                 685

Lys Asn Ala Glu Gly Ile Phe Asp Ala Ser Leu His Leu Lys Ala Gln
            690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
            725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
            755                 760                 765

Ile Ala Pro Ser Ser Ala Ser Ile Ile Asn Ser Gln Asn Glu Tyr Leu
            770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
            805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
            835                 840                 845

Asp Gln Val Gln Gln Asp Ala Ile Lys Val Lys Glu Tyr Asn Asn Leu
850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
            885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
            915                 920                 925

Cys Glu Lys Ile Gly Cys Leu Gln Arg Phe Lys Glu Met Ala Ile Phe
            930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
            965                 970                 975

Arg Asp Ile Leu Gln Lys Asp Asn Met Leu Val Gln Arg Thr Ser Asn
            980                 985                 990

Leu Glu His Leu Glu Cys Glu Asn Ile Ser Leu Lys Glu Gln Val Glu
            995                 1000                1005

Ser Ile Asn Lys Glu Leu Glu Ile Thr Lys Glu Lys Leu His Thr
            1010                1015                1020

Ile Glu Gln Ala Trp Glu Gln Glu Thr Lys Leu Gly Asn Glu Ser
            1025                1030                1035

Ser Met Asp Lys Ala Lys Lys Ser Ile Thr Asn Ser Asp Ile Val
            1040                1045                1050

Ser Ile Ser Lys Lys Ile Thr Met Leu Glu Met Lys Glu Leu Asn
```

-continued

```
              1055                1060                1065
Glu Arg Gln Arg Ala Glu His Cys Gln Lys Met Tyr Glu His Leu
       1070                1075                1080
Arg Thr Ser Leu Lys Gln Met Glu Glu Arg Asn Phe Glu Leu Glu
       1085                1090                1095
Thr Lys Phe Ala Glu Leu Thr Lys Ile Asn Leu Asp Ala Gln Lys
       1100                1105                1110
Val Glu Gln Met Leu Arg Asp Glu Leu Ala Asp Ser Val Ser Lys
       1115                1120                1125
Ala Val Ser Asp Ala Asp Arg Gln Arg Ile Leu Glu Leu Glu Lys
       1130                1135                1140
Asn Glu Met Glu Leu Lys Val Glu Val Ser Lys Leu Arg Glu Ile
       1145                1150                1155
Ser Asp Ile Ala Arg Arg Gln Val Glu Ile Leu Asn Ala Gln Gln
       1160                1165                1170
Gln Ser Arg Asp Lys Glu Val Glu Ser Leu Arg Met Gln Leu Leu
       1175                1180                1185
Asp Tyr Gln Ala Gln Ser Asp Glu Lys Ser Leu Ile Ala Lys Leu
       1190                1195                1200
His Gln His Asn Val Ser Leu Gln Leu Ser Glu Ala Thr Ala Leu
       1205                1210                1215
Gly Lys Leu Glu Ser Ile Thr Ser Lys Leu Gln Lys Met Glu Ala
       1220                1225                1230
Tyr Asn Leu Arg Leu Glu Gln Lys Leu Asp Glu Lys Glu Gln Ala
       1235                1240                1245
Leu Tyr Tyr Ala Arg Leu Glu Gly Arg Asn Arg Ala Lys His Leu
       1250                1255                1260
Arg Gln Thr Ile Gln Ser Leu Arg Arg Gln Phe Ser Gly Ala Leu
       1265                1270                1275
Pro Leu Ala Gln Gln Glu Lys Phe Ser Lys Thr Met Ile Gln Leu
       1280                1285                1290
Gln Asn Asp Lys Leu Lys Ile Met Gln Glu Met Lys Asn Ser Gln
       1295                1300                1305
Gln Glu His Arg Asn Met Glu Asn Lys Thr Leu Glu Met Glu Leu
       1310                1315                1320
Lys Leu Lys Gly Leu Glu Glu Leu Ile Ser Thr Leu Lys Asp Thr
       1325                1330                1335
Lys Gly Ala Gln Lys Val Ile Asn Trp His Met Lys Ile Glu Glu
       1340                1345                1350
Leu Arg Leu Gln Glu Leu Lys Leu Asn Arg Glu Leu Val Lys Asp
       1355                1360                1365
Lys Glu Glu Ile Lys Tyr Leu Asn Asn Ile Ile Ser Glu Tyr Glu
       1370                1375                1380
Arg Thr Ile Ser Ser Leu Glu Glu Ile Val Gln Gln Asn Lys
       1385                1390                1395
Phe His Glu Glu Arg Gln Met Ala Trp Asp Gln Arg Glu Val Asp
       1400                1405                1410
Leu Glu Arg Gln Leu Asp Ile Phe Asp Arg Gln Gln Asn Glu Ile
       1415                1420                1425
Leu Asn Ala Ala Gln Lys Phe Glu Glu Ala Thr Gly Ser Ile Pro
       1430                1435                1440
Asp Pro Ser Leu Pro Leu Pro Asn Gln Leu Glu Ile Ala Leu Arg
       1445                1450                1455
```

```
Lys Ile Lys Glu Asn Ile Arg Ile Ile Leu Glu Thr Arg Ala Thr
    1460            1465                1470

Cys Lys Ser Leu Glu Glu Lys Leu Lys Glu Lys Glu Ser Ala Leu
    1475            1480                1485

Arg Leu Ala Glu Gln Asn Ile Leu Ser Arg Asp Lys Val Ile Asn
    1490            1495                1500

Glu Leu Arg Leu Arg Leu Pro Ala Thr Ala Glu Arg Glu Lys Leu
    1505            1510                1515

Ile Ala Glu Leu Gly Arg Lys Glu Met Glu Pro Lys Ser His His
    1520            1525                1530

Thr Leu Lys Ile Ala His Gln Thr Ile Ala Asn Met Gln Ala Arg
    1535            1540                1545

Leu Asn Gln Lys Glu Glu Val Leu Lys Lys Tyr Gln Arg Leu Leu
    1550            1555                1560

Glu Lys Ala Arg Glu Glu Gln Arg Glu Ile Val Lys Lys His Glu
    1565            1570                1575

Glu Asp Leu His Ile Leu His His Arg Leu Glu Leu Gln Ala Asp
    1580            1585                1590

Ser Ser Leu Asn Lys Phe Lys Gln Thr Ala Trp Asp Leu Met Lys
    1595            1600                1605

Gln Ser Pro Thr Pro Val Pro Thr Asn Lys His Phe Ile Arg Leu
    1610            1615                1620

Ala Glu Met Glu Gln Thr Val Ala Glu Gln Asp Asp Ser Leu Ser
    1625            1630                1635

Ser Leu Leu Val Lys Leu Lys Lys Val Ser Gln Asp Leu Glu Arg
    1640            1645                1650

Gln Arg Glu Ile Thr Glu Leu Lys Val Lys Glu Phe Glu Asn Ile
    1655            1660                1665

Lys Leu Gln Leu Gln Glu Asn His Glu Asp Glu Val Lys Lys Val
    1670            1675                1680

Lys Ala Glu Val Glu Asp Leu Lys Tyr Leu Leu Asp Gln Ser Gln
    1685            1690                1695

Lys Glu Ser Gln Cys Leu Lys Ser Glu Leu Gln Ala Gln Lys Glu
    1700            1705                1710

Ala Asn Ser Arg Ala Pro Thr Thr Thr Met Arg Asn Leu Val Glu
    1715            1720                1725

Arg Leu Lys Ser Gln Leu Ala Leu Lys Glu Lys Gln Gln Lys Ala
    1730            1735                1740

Leu Ser Arg Ala Leu Leu Glu Leu Arg Ala Glu Met Thr Ala Ala
    1745            1750                1755

Ala Glu Glu Arg Ile Ile Ser Ala Thr Ser Gln Lys Glu Ala His
    1760            1765                1770

Leu Asn Val Gln Gln Ile Val Asp Arg His Thr Arg Glu Leu Lys
    1775            1780                1785

Thr Gln Val Glu Asp Leu Asn Glu Asn Leu Leu Lys Leu Lys Glu
    1790            1795                1800

Ala Leu Lys Thr Ser Lys Asn Arg Glu Asn Ser Leu Thr Asp Asn
    1805            1810                1815

Leu Asn Asp Leu Asn Asn Glu Leu Gln Lys Lys Gln Lys Ala Tyr
    1820            1825                1830

Asn Lys Ile Leu Arg Glu Lys Glu Glu Ile Asp Gln Glu Asn Asp
    1835            1840                1845
```

-continued

```
Glu Leu Lys Arg Gln Ile Lys Arg Leu Thr Ser Gly Leu Gln Gly
    1850                1855                1860

Lys Pro Leu Thr Asp Asn Lys Gln Ser Leu Ile Glu Glu Leu Gln
1865                1870                1875

Arg Lys Val Lys Lys Leu Glu Asn Gln Leu Glu Gly Lys Val Glu
    1880                1885                1890

Glu Val Asp Leu Lys Pro Met Lys Glu Lys Asn Ala Lys Glu Glu
    1895                1900                1905

Leu Ile Arg Trp Glu Glu Gly Lys Lys Trp Gln Ala Lys Ile Glu
    1910                1915                1920

Gly Ile Arg Asn Lys Leu Lys Glu Lys Glu Gly Glu Val Phe Thr
    1925                1930                1935

Leu Thr Lys Gln Leu Asn Thr Leu Lys Asp Leu Phe Ala Lys Ala
    1940                1945                1950

Asp Lys Glu Lys Leu Thr Leu Gln Arg Lys Leu Lys Thr Thr Gly
    1955                1960                1965

Met Thr Val Asp Gln Val Leu Gly Ile Arg Ala Leu Glu Ser Glu
    1970                1975                1980

Lys Glu Leu Glu Glu Leu Lys Lys Arg Asn Leu Asp Leu Glu Asn
    1985                1990                1995

Asp Ile Leu Tyr Met Arg Ala His Gln Ala Leu Pro Arg Asp Ser
    2000                2005                2010

Val Val Glu Asp Leu His Leu Gln Asn Arg Tyr Leu Gln Glu Lys
    2015                2020                2025

Leu His Ala Leu Glu Lys Gln Phe Ser Lys Asp Thr Tyr Ser Lys
    2030                2035                2040

Pro Ser Ile Ser Gly Ile Glu Ser Asp Asp His Cys Gln Arg Glu
    2045                2050                2055

Gln Glu Leu Gln Lys Glu Asn Leu Lys Leu Ser Ser Glu Asn Ile
    2060                2065                2070

Glu Leu Lys Phe Gln Leu Glu Gln Ala Asn Lys Asp Leu Pro Arg
    2075                2080                2085

Leu Lys Asn Gln Val Arg Asp Leu Lys Glu Met Cys Glu Phe Leu
    2090                2095                2100

Lys Lys Glu Lys Ala Glu Val Gln Arg Lys Leu Gly His Val Arg
    2105                2110                2115

Gly Ser Gly Arg Ser Gly Lys Thr Ile Pro Glu Leu Glu Lys Thr
    2120                2125                2130

Ile Gly Leu Met Lys Lys Val Val Glu Lys Val Gln Arg Glu Asn
    2135                2140                2145

Glu Gln Leu Lys Lys Ala Ser Gly Ile Leu Thr Ser Glu Lys Met
    2150                2155                2160

Ala Asn Ile Glu Gln Glu Asn Glu Lys Leu Lys Ala Glu Leu Glu
    2165                2170                2175

Lys Leu Lys Ala His Leu Gly His Gln Leu Ser Met His Tyr Glu
    2180                2185                2190

Ser Lys Thr Lys Gly Thr Glu Lys Ile Ile Ala Glu Asn Glu Arg
    2195                2200                2205

Leu Arg Lys Glu Leu Lys Lys Glu Thr Asp Ala Ala Glu Lys Leu
    2210                2215                2220

Arg Ile Ala Lys Asn Asn Leu Glu Ile Leu Asn Glu Lys Met Thr
    2225                2230                2235

Val Gln Leu Glu Glu Thr Gly Lys Arg Leu Gln Phe Ala Glu Ser
```

```
        2240              2245              2250
Arg Gly Pro Gln Leu Glu Gly Ala Asp Ser Lys Ser Trp Lys Ser
        2255              2260              2265

Ile Val Val Thr Arg Met Tyr Glu Thr Lys Leu Lys Glu Leu Glu
        2270              2275              2280

Thr Asp Ile Ala Lys Lys Asn Gln Ser Ile Thr Asp Leu Lys Gln
        2285              2290              2295

Leu Val Lys Glu Ala Thr Arg Glu Gln Lys Val Asn Lys Tyr
        2300              2305              2310

Asn Glu Asp Leu Glu Gln Gln Ile Lys Ile Leu Lys His Val Pro
        2315              2320              2325

Glu Gly Ala Glu Thr Glu Gln Gly Leu Lys Arg Glu Leu Gln Val
        2330              2335              2340

Leu Arg Leu Ala Asn His Gln Leu Asp Lys Glu Lys Ala Glu Leu
        2345              2350              2355

Ile His Gln Ile Glu Ala Asn Lys Asp Gln Ser Gly Ala Glu Ser
        2360              2365              2370

Thr Ile Pro Asp Ala Asp Gln Leu Lys Glu Lys Ile Lys Asp Leu
        2375              2380              2385

Glu Thr Gln Leu Lys Met Ser Asp Leu Glu Lys Gln His Leu Lys
        2390              2395              2400

Glu Glu Ile Lys Lys Leu Lys Lys Glu Leu Glu Asn Phe Asp Pro
        2405              2410              2415

Ser Phe Phe Glu Glu Ile Glu Asp Leu Lys Tyr Asn Tyr Lys Glu
        2420              2425              2430

Glu Val Lys Lys Asn Ile Leu Leu Glu Glu Lys Val Lys Lys Leu
        2435              2440              2445

Ser Glu Gln Leu Gly Val Glu Leu Thr Ser Pro Val Ala Ala Ser
        2450              2455              2460

Glu Glu Phe Glu Asp Glu Glu Ser Pro Val Asn Phe Pro Ile
        2465              2470              2475

Tyr
```

<210> SEQ ID NO 42
<211> LENGTH: 2625
<212> TYPE: DNA
<213> ORGANISM: Homo sapiens

<400> SEQUENCE: 42

```
actcgaccgg gctgcgctca ctgcccagcc ggggccccgg gagcctccag gctcccgccc    60
gccctgagct gcggcctccg catggagggg ccactcactc caccaccgct gcagggaggc   120
ggagccgccg ctgttccgga gcccggagcc cggcaacacc cggacacga gacgcggcg    180
cagcggtaca gcgcccgact gctgcaggcc ggctacgagc ccgagagccc tagattggac   240
ctcgctacac acccgacgac accccgttca gaactatctt cagtggtctt actggcaggt   300
gttggtgtcc agatggatcg ccttcgcagg gctagcatgg cggactacct gatcagcggc   360
ggcaccggct acgtgcccga ggatgggctc accgcgcagc agctcttcgc cagcgccgac   420
ggcctcacct acaacgactt cctgattctc ccaggattca tagacttcat agctgatgag   480
gtggacctga cctcagccct gacccggaag atcacgctga agacgccact gatctcctcc   540
cccatggaca ctgtgacaga ggctgacatg gccattgcca tggctctgat ggaggtatt   600
ggtttcattc accacaactg cacccagag ttccaggcca acgaggtgcg gaaggtcaag   660
```

```
aagtttgaac agggcttcat cacggaccct gtggtgctga gcccctcgca cactgtgggc    720
gatgtgctgg aggccaagat gcggcatggc ttctctggca tccccatcac tgagacgggc    780
accatgggca gcaagctggt gggcatcgtc acctcccgag acatcgactt tcttgctgag    840
aaggaccaca ccaccctcct cagtgaggtg atgacgccaa ggattgaact ggtggtggct    900
ccagcaggtg tgacgttgaa agaggcaaat gagatcctgc agcgtagcaa gaaagggaag    960
ctgcctatcg tcaatgattg cgatgagctg gtggccatca tcgcccgcac cgacctgaag   1020
aagaaccgag actaccctct ggcctccaag gattcccaga agcagctgct ctgtggggca   1080
gctgtgggca cccgtgagga tgacaaatac cgtctggacc tgctcaccca ggcgggcgtc   1140
gacgtcatag tcttggactc gtcccaaggg aattcggtgt atcagatcgc catggtgcat   1200
tacatcaaac agaagtaccc ccacctccag gtgattgggg ggaacgtggt gacagcagcc   1260
caggccaaga acctgattga tgctggtgtg gacgggctgc gcgtgggcat gggctgcggc   1320
tccatctgca tcacccagga agtgatggcc tgtggtcggc cccagggcac tgctgtgtac   1380
aaggtggctg agtatgcccg cgcctttggt gtgcccatca tagccgatgg cggcatccag   1440
accgtgggac acgtggtcaa ggccctggcc cttggagcct ccacagtgat gatgggctcc   1500
ctgctggccg ccactacgga ggcccctggc gagtacttct tctcagacgg ggtgcggctc   1560
aagaagtacc ggggcatggg ctcactggat gccatggaga agagcagcag cagccagaaa   1620
cgatacttca gcgaggggga taaagtgaag atcgcgcagg gtgtctcggg ctccatccag   1680
gacaaaggat ccattcagaa gttcgtgccc tacctcatag caggcatcca acacggctgc   1740
caggatatcg gggcccgcag cctgtctgtc cttcggtcca tgatgtactc aggagagctc   1800
aagtttgaga gcggaccat gtcggcccag attgagggtg tgtccatgg cctgcactct   1860 tacgaaaagc ggctgtactg aggacagcgg tggaggccga ggtggtggag gggatgcacc   1920
ccagtgtcca cttttgggca cagcctccct ccataactga gtggtccaca gatttgcact   1980
acgggttctc cagctccttt ccaggcagag aggaggggag gtcctgaggg gactgctgcc   2040
cctcactcgg catcccctgc agagtcagga ctgctcccgg ggccaggctg ccctgggagc   2100 cccctccga gccagccag ccaggctctc aggccctgcg cctgcctcag gtctttcttg   2160
ctgcagcctg ctccagcctg gcccccaccc caggggcagg cggcccctcc tggcttctcc   2220
tgtagggcac ctccctgccc ctagcctccc aggaaatggt gctctcctgg ccctgcctct   2280
ggcccttccc gggccgctgc ccctcagcca tgtggcactt ctgagctcct gacctaggcc   2340
aagggggagt ctctgccccc ttccccggcc ctgggctacc cttgggtcct gctcctcagg   2400
ccgctcccct gtccctggcc atgggtagga gactgccctg gtcatggccg cctgcctgtc   2460
attcctgact caccaccgtc cccaggtgaa ccattcctcc cttctcctca gctgcagtcg   2520
aaggctttaa ctttgcacac ttgggatcac agttgcgtca ttgtgtatta aatacttgga   2580
ataaatcaag caggtctcaa cgcctccact aaaaaaaaaa aaaaa              2625
```

<210> SEQ ID NO 43
<211> LENGTH: 599
<212> TYPE: PRT
<213> ORGANISM: Homo sapiens

<400> SEQUENCE: 43

```
Met Glu Gly Pro Leu Thr Pro Pro Leu Gln Gly Gly Gly Ala Ala
1               5                   10                  15

Ala Val Pro Glu Pro Gly Ala Arg Gln His Pro Gly His Glu Thr Ala
            20                  25                  30
```

```
Ala Gln Arg Tyr Ser Ala Arg Leu Leu Gln Ala Gly Tyr Glu Pro Glu
        35                  40                  45

Ser Pro Arg Leu Asp Leu Ala Thr His Pro Thr Thr Pro Arg Ser Glu
    50                  55                  60

Leu Ser Ser Val Val Leu Leu Ala Gly Val Gly Val Gln Met Asp Arg
65                  70                  75                  80

Leu Arg Arg Ala Ser Met Ala Asp Tyr Leu Ile Ser Gly Gly Thr Gly
                85                  90                  95

Tyr Val Pro Glu Asp Gly Leu Thr Ala Gln Gln Leu Phe Ala Ser Ala
            100                 105                 110

Asp Gly Leu Thr Tyr Asn Asp Phe Leu Ile Leu Pro Gly Phe Ile Asp
            115                 120                 125

Phe Ile Ala Asp Glu Val Asp Leu Thr Ser Ala Leu Thr Arg Lys Ile
        130                 135                 140

Thr Leu Lys Thr Pro Leu Ile Ser Ser Pro Met Asp Thr Val Thr Glu
145                 150                 155                 160

Ala Asp Met Ala Ile Ala Met Ala Leu Met Gly Gly Ile Gly Phe Ile
                165                 170                 175

His His Asn Cys Thr Pro Glu Phe Gln Ala Asn Glu Val Arg Lys Val
            180                 185                 190

Lys Lys Phe Glu Gln Gly Phe Ile Thr Asp Pro Val Val Leu Ser Pro
        195                 200                 205

Ser His Thr Val Gly Asp Val Leu Glu Ala Lys Met Arg His Gly Phe
    210                 215                 220

Ser Gly Ile Pro Ile Thr Glu Thr Gly Thr Met Gly Ser Lys Leu Val
225                 230                 235                 240

Gly Ile Val Thr Ser Arg Asp Ile Asp Phe Leu Ala Glu Lys Asp His
                245                 250                 255

Thr Thr Leu Leu Ser Glu Val Met Thr Pro Arg Ile Glu Leu Val Val
            260                 265                 270

Ala Pro Ala Gly Val Thr Leu Lys Glu Ala Asn Glu Ile Leu Gln Arg
        275                 280                 285

Ser Lys Lys Gly Lys Leu Pro Ile Val Asn Asp Cys Asp Glu Leu Val
    290                 295                 300

Ala Ile Ile Ala Arg Thr Asp Leu Lys Lys Asn Arg Asp Tyr Pro Leu
305                 310                 315                 320

Ala Ser Lys Asp Ser Gln Lys Gln Leu Leu Cys Gly Ala Ala Val Gly
                325                 330                 335

Thr Arg Glu Asp Asp Lys Tyr Arg Leu Asp Leu Leu Thr Gln Ala Gly
            340                 345                 350

Val Asp Val Ile Val Leu Asp Ser Ser Gln Gly Asn Ser Val Tyr Gln
        355                 360                 365

Ile Ala Met Val His Tyr Ile Lys Gln Lys Tyr Pro His Leu Gln Val
    370                 375                 380

Ile Gly Gly Asn Val Val Thr Ala Ala Gln Ala Lys Asn Leu Ile Asp
385                 390                 395                 400

Ala Gly Val Asp Gly Leu Arg Val Gly Met Gly Cys Gly Ser Ile Cys
                405                 410                 415

Ile Thr Gln Glu Val Met Ala Cys Gly Arg Pro Gln Gly Thr Ala Val
            420                 425                 430

Tyr Lys Val Ala Glu Tyr Ala Arg Arg Phe Gly Val Pro Ile Ile Ala
        435                 440                 445
```

Asp Gly Gly Ile Gln Thr Val Gly His Val Val Lys Ala Leu Ala Leu
    450                 455                 460

Gly Ala Ser Thr Val Met Met Gly Ser Leu Leu Ala Ala Thr Thr Glu
465                 470                 475                 480

Ala Pro Gly Glu Tyr Phe Phe Ser Asp Gly Val Arg Leu Lys Lys Tyr
                485                 490                 495

Arg Gly Met Gly Ser Leu Asp Ala Met Glu Lys Ser Ser Ser Ser Gln
            500                 505                 510

Lys Arg Tyr Phe Ser Glu Gly Asp Lys Val Lys Ile Ala Gln Gly Val
        515                 520                 525

Ser Gly Ser Ile Gln Asp Lys Gly Ser Ile Gln Lys Phe Val Pro Tyr
    530                 535                 540

Leu Ile Ala Gly Ile Gln His Gly Cys Gln Asp Ile Gly Ala Arg Ser
545                 550                 555                 560

Leu Ser Val Leu Arg Ser Met Met Tyr Ser Gly Glu Leu Lys Phe Glu
                565                 570                 575

Lys Arg Thr Met Ser Ala Gln Ile Glu Gly Gly Val His Gly Leu His
            580                 585                 590

Ser Tyr Glu Lys Arg Leu Tyr
        595

<210> SEQ ID NO 44
<211> LENGTH: 2981
<212> TYPE: DNA
<213> ORGANISM: Homo sapiens

<400> SEQUENCE: 44

```
gctgggtaaa tcccagagtc tcagccgcct aagtgtcttc cccggaggtg agattatctc    60
cgcctgtgct ggacacctcc ctttctcctg cagccatgga tgccgctctg ctcctgaacg   120
tggaaggggt caagaaaacc attctgcacg ggggcacggg cgagctccca aacttcatca   180
ccggatcccg agtgatcttt catttccgca ccatgaaatg tgatgaggag cggacagtca   240
ttgacgacag tcggcaggtg ggccagccca tgcacatcat catcggaaac atgttcaagc   300
tcgaggtctg ggagatcctg cttacctcca tgcgggtgca cgaggtggcc gagttctggt   360
gcgacaccat ccacacgggg gtctacccca tcctatcccg gagcctgagg cagatggccc   420
agggcaagga ccccacagag tggcacgtgc acacgtgcgg gctggccaac atgttcgcct   480
accacacgct gggctacgag gacctggacg agctgcagaa ggagcctcag cctctggtct   540
ttgtgatcga gctgctgcag gttgatgccc cgagtgatta ccagagggag acctggaacc   600
tgagcaatca tgagaagatg aaggcggtgc ccgtcctcca cggagaggga atcggctct   660
tcaagctggg ccgctacgag gaggcctctt ccaagtacca ggaggccatc atctgcctaa   720
ggaacctgca gaccaaggag aagccatggg aggtgcagtg gctgaagctg agaagatga   780
tcaatactct gatcctcaac tactgccagt gcctgctgaa gaggaggag tactatgagg   840
tgctggagca caccagtgat attctccggc caccccagg catcgtgaag gcctactacg   900
tgcgtgcccg ggctcacgca gaggtgtgga atgaggccga ggccaaggcg acctccaga   960
aagtgctgga gctggagccg tccatgcaga aggcggtgcg cagggagctg aggctgctgg  1020
agaaccgcat ggcggagaag caggaggagg agcggctgcg ctgccggaac atgctgagcc  1080
agggtgccac gcagcctccc gcagagccac ccacagagcc acccgcacag tcatccacag  1140
agccacctgc agagccaccc acagccatct gcagagct gtccgcaggg cccctgcag  1200
agccagccac agagccaccc ccgtccccag ggcactcgct gcagcactga gccccctgag  1260
```

```
gcccacagcc acccaggcag ggagcaagtg gcctggtcac ttctggttcg attgaccagg   1320
atcgtggtgt cacttttaa aatttaaaat taattttga aatcaaagtc agacacaccc    1380
atggtaaaaa aaaaaaaaa aacaatccca agggtacaga agagcttatg aataaaagta   1440
gttttctcct ctaccctct cattccttcc gtgccatggt tttaattgac cctgttttta   1500
attcttctgg tagttttctc tatttccaag taatctgttt aaatcagttt ctagatttta   1560
ccccatgtca atgacaaatg aggatttgat gctctgatcc tttctcatgc ctgatacccc   1620
tccctgtctc cccatttgg atagttacat ttggggtca tctcggtgat ttttgtaact    1680
ttacgcagga cacttagagc tctctagaat cccactgact ttagtgggtc ttgatgtagg   1740
gtgggcaagc ccgacactg gagcttagcc tgagagggtt cttggcctcc cccaggaaag   1800
atttcaaagg caagcgccag tgtagggta aagaaaaaca gctgtggtcg ggcacggtgg   1860
ctcacgccta aatcccagc actttgggag gccgaggcgg gtggatcacc tgaggtcagg   1920
agttccagac cagcctggcc aacatggtga aaccctcatct ctactaaaaa tacaaaaaaa   1980
ctagctgggc gtggtggcgg gcgcctataa tcccagctac ttgggaggct gaggcaggag   2040
aattgattga acctgggagg cggaggttgc agtgagccaa gatcacgtca ttgcactcca   2100
gcctggtcaa caagagtaaa acttcatctc aaaaacaaa acaaacaaa acaacaaca     2160 aaaaacaaaa gaaaaacaaa caaaaccaaa accaaaacag ctgtattgaa gctgcagtgt   2220
tgcagctctg tgactgccct gcagagcagg gctaccccat aggcagcgag cagcagctca   2280
gggcagttct gcagtcagat ttatacccac ttttaattac atgtagatta aggagctgca   2340
tatacaaaga tttctaggga aggagtagta acttctgggt cctggggtct ttgccacgga   2400
acagggcagt atgccagggt gttgccacgg caatggtaaa ctgacatggc accctggggg   2460
tcatgcctta gggaaagccg cttccactcg ccctgttttt agctcatctt caagttagtc   2520
tggtgtccaa gctccaccgc ctgcctcagt ctggtgacct ccttctgtgt ctgatgagca   2580
tggcagcgtt gggaccttcc ccttccaact ctctccctcc tcttcgtcct ccctaaagga   2640
cgggtacgag gagggctat cacgccagcg acatcctcta gcaccaccca ggtgtgtggg    2700
gtggggcagg ggggcgacga agtatccagc ccagggccac gtagtcaact gccaagggct   2760
tcctgggctt ctcttctgcc ccagagcttg tctccaccca gcagggttc ccccagcgct    2820 aactgtatcc ctaaagttct gatgtacttt acttttccat cttccttgtt gttaacatct   2880
accttctgct ctgtaagcaa aactaaatct tctgtgcttt gtccataggt tgattctaca   2940
atctgaaaat caataaacag catttgcatg aaaaaaaaa a                        2981
```

<210> SEQ ID NO 45
<211> LENGTH: 384
<212> TYPE: PRT
<213> ORGANISM: Homo sapiens

<400> SEQUENCE: 45

Met Asp Ala Ala Leu Leu Leu Asn Val Glu Gly Val Lys Lys Thr Ile
1               5                   10                  15

Leu His Gly Gly Thr Gly Glu Leu Pro Asn Phe Ile Thr Gly Ser Arg
            20                  25                  30

Val Ile Phe His Phe Arg Thr Met Lys Cys Asp Glu Glu Arg Thr Val
        35                  40                  45

Ile Asp Asp Ser Arg Gln Val Gly Gln Pro Met His Ile Ile Ile Gly
    50                  55                  60

```
Asn Met Phe Lys Leu Glu Val Trp Glu Ile Leu Leu Thr Ser Met Arg
 65                  70                  75                  80

Val His Glu Val Ala Glu Phe Trp Cys Asp Thr Ile His Thr Gly Val
                 85                  90                  95

Tyr Pro Ile Leu Ser Arg Ser Leu Arg Gln Met Ala Gln Gly Lys Asp
            100                 105                 110

Pro Thr Glu Trp His Val His Thr Cys Gly Leu Ala Asn Met Phe Ala
        115                 120                 125

Tyr His Thr Leu Gly Tyr Glu Asp Leu Asp Glu Leu Gln Lys Glu Pro
    130                 135                 140

Gln Pro Leu Val Phe Val Ile Glu Leu Leu Gln Val Asp Ala Pro Ser
145                 150                 155                 160

Asp Tyr Gln Arg Glu Thr Trp Asn Leu Ser Asn His Glu Lys Met Lys
                165                 170                 175

Ala Val Pro Val Leu His Gly Glu Gly Asn Arg Leu Phe Lys Leu Gly
            180                 185                 190

Arg Tyr Glu Glu Ala Ser Ser Lys Tyr Gln Glu Ala Ile Ile Cys Leu
        195                 200                 205

Arg Asn Leu Gln Thr Lys Glu Lys Pro Trp Glu Val Gln Trp Leu Lys
    210                 215                 220

Leu Glu Lys Met Ile Asn Thr Leu Ile Leu Asn Tyr Cys Gln Cys Leu
225                 230                 235                 240

Leu Lys Lys Glu Glu Tyr Tyr Glu Val Leu Glu His Thr Ser Asp Ile
                245                 250                 255

Leu Arg His His Pro Gly Ile Val Lys Ala Tyr Tyr Val Arg Ala Arg
            260                 265                 270

Ala His Ala Glu Val Trp Asn Glu Ala Glu Ala Lys Ala Asp Leu Gln
        275                 280                 285

Lys Val Leu Glu Leu Glu Pro Ser Met Gln Lys Ala Val Arg Arg Glu
    290                 295                 300

Leu Arg Leu Leu Glu Asn Arg Met Ala Gly Lys Gln Glu Glu Glu Arg
305                 310                 315                 320

Leu Arg Cys Arg Asn Met Leu Ser Gln Gly Ala Thr Gln Pro Pro Ala
                325                 330                 335

Glu Pro Pro Thr Glu Pro Pro Ala Gln Ser Ser Thr Glu Pro Pro Ala
            340                 345                 350

Glu Pro Pro Thr Ala Pro Ser Ala Glu Leu Ser Ala Gly Pro Pro Ala
        355                 360                 365

Glu Pro Ala Thr Glu Pro Pro Ser Pro Gly His Ser Leu Gln His
    370                 375                 380
```

<210> SEQ ID NO 46
<211> LENGTH: 1934
<212> TYPE: DNA
<213> ORGANISM: Homo sapiens

<400> SEQUENCE: 46

| | |
|---|---|
| gggcacaagc aatcctccct tctcagcttc ctgagtggcc aggactacag aggactgtat | 60 |
| gctgttctta aggactctct gcttcctgga caagctcaag ctaaggacta catctcccag | 120 |
| caggctgtgc tctgacagct cttggattta aataggattc tgggctctgc tcagagtcag | 180 |
| gctgctgctc agcacccagg acggagagga gcagagaagc agcagaagca gccaagagct | 240 |
| ggagccagac caggaacctg agccagagct ggggttgaag ctggagcagc agcaaaagca | 300 |
| acagcagcta cagaagttgg aacgatgctg gtcaccttgg gactgctcac ctccttcttc | 360 |

```
tcgttcctgt atatggtagc tccatccatc aggaagttct ttgctggtgg agtgtgtaga    420
acaaatgtgc agcttcctgg caaggtagtg gtgatcactg cgccaacac  gggcattggc    480 aaggagacgg ccagagagct cgctagccga ggagcccgag tctatattgc ctgcagagat    540
gtactgaagg gggagtctgc tgccagtgaa atccgagtgg atacaaagaa ctcccaggtg    600
ctggtgcgga aattggacct atccgacacc aaatctatcc gagcctttgc tgagggcttt    660
ctggcagagg aaaagcagct ccatattctg atcaacaatg cgggagtaat gatgtgtcca    720
tattccaaga cagctgatgg ctttgaaacc cacctgggag tcaaccacct gggccacttc    780
ctcctcacct acctgctcct ggagcggcta aaggtgtctg cccctgcacg ggtggttaat    840
gtgtcctcgg tggctcacca cattggcaag attcccttcc acgacctcca gagcgagaag    900
cgctacagca ggggttttgc ctattgccac agcaagctgg ccaatgtgct ttttactcgt    960
gagctggcca gaggctccaa ggcaccgggg tcaccacct  acgcagtgca cccaggcgtc   1020
gtccgctctg agctggtccg gcactcctcc ctgctctgcc tgctctggcg gctcttctcc   1080
ccctttgtca agacggcacg ggaggggggcg cagaccagcc tgcactgcgc cctggctgag   1140
ggcctggagc ccctgagtgg caagtacttc agtgactgca agaggacctg ggtgtctcca   1200
agggcccgaa ataacaaaac agctgagcgc ctatggaatg tcagctgtga gcttctagga   1260
atccggtggg agtagctggt ggaagagctg cagctttatc aggcccaatc catgccataa   1320
tgaacaggga ccaaggagaa ggccaaccct aaaggattgt cctcttggcc agctggtgct   1380
gcgaatcctg cctgctctga tcctcttgac ccttctggga atgtttgcac acctgacact   1440
cttgtgagac tggcttatgg catgagttgt ggacacctat agagtgttct tctctaagac   1500
ctggaaagtc agcaaccctc tgggggcagc aggactgggc agatcccagg ctgggcatgg   1560
gggtggcaga agagcccgag aaattgggtc agttccctca tcagcaccag aggctcagct   1620
gaggcaagaa gagcaccatc actgcctatt tctaggggct atacactcca actcttggtt   1680
gatctctttc tttttaaaaa tatttgccac caccctggag tctagaccaa cacacaaaga   1740
tcctggctaa ccctggccta tttagattcc ttcctctcac ctggaccttc ccatttcaat   1800
catgcagatg gtttctttt  gtaaagagtt ccgtttgcct ttcaattttt agagaaaata   1860
aagactgcat tcatctcaaa aaaaaaaaaa aaaaaaaaaa aaaaaaaaaa aaaaaaaaaa   1920
aaaaaaaaaa aaaa                                                     1934
```

<210> SEQ ID NO 47
<211> LENGTH: 316
<212> TYPE: PRT
<213> ORGANISM: Homo sapiens

<400> SEQUENCE: 47

Met Leu Val Thr Leu Gly Leu Leu Thr Ser Phe Phe Ser Phe Leu Tyr
1               5                   10                  15

Met Val Ala Pro Ser Ile Arg Lys Phe Phe Ala Gly Gly Val Cys Arg
            20                  25                  30

Thr Asn Val Gln Leu Pro Gly Lys Val Val Ile Thr Gly Ala Asn
        35                  40                  45

Thr Gly Ile Gly Lys Glu Thr Ala Arg Glu Leu Ala Ser Arg Gly Ala
    50                  55                  60

Arg Val Tyr Ile Ala Cys Arg Asp Val Leu Lys Gly Glu Ser Ala Ala
65                  70                  75                  80

Ser Glu Ile Arg Val Asp Thr Lys Asn Ser Gln Val Leu Val Arg Lys

```
                85                  90                  95
Leu Asp Leu Ser Asp Thr Lys Ser Ile Arg Ala Phe Ala Glu Gly Phe
            100                 105                 110
Leu Ala Glu Glu Lys Gln Leu His Ile Leu Ile Asn Asn Ala Gly Val
            115                 120                 125
Met Met Cys Pro Tyr Ser Lys Thr Ala Asp Gly Phe Glu Thr His Leu
            130                 135                 140
Gly Val Asn His Leu Gly His Phe Leu Leu Thr Tyr Leu Leu Leu Glu
145                 150                 155                 160
Arg Leu Lys Val Ser Ala Pro Ala Arg Val Val Asn Val Ser Ser Val
                165                 170                 175
Ala His His Ile Gly Lys Ile Pro Phe His Asp Leu Gln Ser Glu Lys
                180                 185                 190
Arg Tyr Ser Arg Gly Phe Ala Tyr Cys His Ser Lys Leu Ala Asn Val
                195                 200                 205
Leu Phe Thr Arg Glu Leu Ala Lys Arg Leu Gln Gly Thr Gly Val Thr
            210                 215                 220
Thr Tyr Ala Val His Pro Gly Val Val Arg Ser Glu Leu Val Arg His
225                 230                 235                 240
Ser Ser Leu Leu Cys Leu Leu Trp Arg Leu Phe Ser Pro Phe Val Lys
                245                 250                 255
Thr Ala Arg Glu Gly Ala Gln Thr Ser Leu His Cys Ala Leu Ala Glu
            260                 265                 270
Gly Leu Glu Pro Leu Ser Gly Lys Tyr Phe Ser Asp Cys Lys Arg Thr
            275                 280                 285
Trp Val Ser Pro Arg Ala Arg Asn Asn Lys Thr Ala Glu Arg Leu Trp
            290                 295                 300
Asn Val Ser Cys Glu Leu Leu Gly Ile Arg Trp Glu
305                 310                 315

<210> SEQ ID NO 48
<211> LENGTH: 4729
<212> TYPE: DNA
<213> ORGANISM: Homo sapiens

<400> SEQUENCE: 48
agtctaggcc tccgcctccg ttaccctgga gcccaggtta ccgccgctgc cacccaggag    60
ccccgatcct cgcctctgtc ccatccttgt gttcaaacct cccgcatctc ggcaacctcg   120
gcacccgccc ggcagcctcc gcaggaacca ggcacccgct ctttggcggt cagacgccga   180
ggccccagct gggagtttgg tcctaagagg gaaggcaagg aggcgggacg ccgcatcggc   240
tctgctgaag agcctgcggg ttggaggtgg gctttgaagt gggcgtggag acggcggggg   300
aggtggaggt gcgagtataa atgatcaacc agaaattatc ttcaaaggaa taaaaccaga   360
agtatgtaaa taaaaagccc aagataaaga aacagaaaag ctgacactac atgaagcaga   420
gggcaaaaaa gtttatcttc tggatgccaa tgtgaattgt ggtctacaaa tacattgtgg   480
agaaaataga ttgcacagaa atgaatatta tcaggatctg aagactgtga aaatgttttt   540
cagtattgtc atagtctcct ctggagaaaa taatctgtga aattatgtga atagagacca   600
ttttcaaaa caatggggga aagagcagga agtccaggta ctgatcaaga agaaaggca   660
ggcaaacacc attattctta cttatctgat tttgaaacgc cacagtcttc tggccgatca   720
tcgctggtca gttcttcacc tgcaagtgtt aggagaaaaa atcctaaaag acaaacttca   780
gatggccaag tacatcacca agcccctcgg aaaccaagcc ctaagggtct accaaacaga   840
```

-continued

```
aagggagtcc gagtgggatt tcgctcccag agcctcaata gagagccact tcggaaagat    900
actgatcttg ttacaaaacg gattctgtct gcaagactgc taaaaatcaa tgagttgcag    960
aatgaagtat ctgaactcca ggtcaagtta gctgagctgc taaaagaaaa taaatctttg   1020
aaaaggcttc agtacagaca ggagaaagcc ctgaataagt tgaagatgc cgaaaatgaa   1080
atctcacaac ttatatttcg tcataacaat gagattacag cactcaaaga acgcttaaga   1140
aaatctcaag agaagaacg ggcaactgag aaaagggtaa aagatacaga aagtgaacta   1200
tttaggacaa aattttcctt acagaaactg aaagagatct ctgaagctag acacctacct   1260
gaacgagatg atttggcaaa gaaactagtt tcagcagagt taaagttaga tgacaccgag   1320
agaagaatta aggagctatc gaaaaacctt gaactgagta ctaacagttt ccaacgacag   1380
ttgcttgctg aaaggaaaag ggcatatgag gctcatgatg aaaataaagt tcttcaaaag   1440
gaggtacagc gactatatca caaattaaag gaaaaggaga gagaactgga tataaaaaat   1500
atatattcta atcgtctgcc aaagtcctct ccaaataaag agaagaact tgcattaaga   1560
aaaaatgctg catgccagag tgattttgca gacctgtgta caaaaggagt acaaaccatg   1620
gaagacttca agccagaaga atatccttta actccagaaa caattatgtg ttacgaaaac   1680
aaatgggaag aaccaggaca tcttactttg gacttgcaat ctcaaaagca agacaggcat   1740
ggagaagcag ggattctaaa cccaattatg gaaagaaag aaaaatttgt tacagatgaa   1800
gaactccatg tcgtaaaaca ggaggttgaa aagctggagg atgaatggga aagagaagaa   1860
cttgataaaa agcaaaaaga aaaggcatct ttactggaaa gagaagaaaa gccagagtgg   1920
gaaactggaa ggtaccaact aggaatgtat ccaattcaga atatggataa attgcaagga   1980
gaggaagaag aaagactgaa gagagaaatg ctacttgcta aactgaatga aattgacaga   2040
gaactccaag attctcgaaa tctaaaatac cctgttttgc cattgttacc tgattttgaa   2100
tcaaaactac actccccaga gagaagcccc aaaacataca ggttctctga atcctcagag   2160
agattattta atgggcatca tttgcaagac atcagtttct caactccaaa aggagaaggt   2220
cagaattcag gaaatgttag aagtccagcc tcccctaatg agttcgcatt tggtagctac   2280
gtgccttcgt ttgcaaaaac atcagagagg tcaaatccat ttagtcaaaa aagtagtttt   2340
ttggatttcc aaagaaacag tatgaaaaaa cttagtaaag atggtgtaga tttaattaca   2400
agaaaagaga aaaagctaa tttgatggaa cagttatttg gtgccagtgg tagcagcacc   2460
atttcctcca aaagcagtga cccaaattct gtggcttcca gtaaaggaga cattgaccct   2520
ctaaattttc tccctgggaa taaaggcagc agagatcaag aacatgatga agatgaaggc   2580
ttttcctca gtgaaggaag aagttttaat ccaaataggc accgattaaa acatgcagac   2640
gataaaccag cagtaaaagc agctgattct gtagaagatg aaattgaaga agtagcactg   2700
agatgactga ctagagtata cattttttct aattgtaaat attgaaatat tttaatacag   2760
tatttattat aaacatttag acttttaat gctaaaatgt ccttattaag gaatgatttt   2820
taatagctaa atacaatgca gttaaaaaga agtagatcat acatacacca catagatagt   2880
ttgccaagaa tgaaggaggc tttttttgaat gaaaccaaaa ataaaaatat gtcttgaaaa   2940
atgaaataga ttttaactct tcatccagtg ctatggcaag tttaactgca ctggaggtgg   3000
tattcctttt ctacttttat tcctatttat gtatttattt ttaatcatat tctcactgtg   3060
ctaaatacag tcttcccact aattgttgaa tgaaaattaa gggtgaaagt ctgtgttggg   3120
aagtgtagct ccggatggtg gagaaccagt gcttcttagg agcccttccc tttatggata   3180
```

```
gggccagggg tccctatctt acgtggcagt cctaagctac tcttgagtga tagcagtcac    3240
aacattggga tttcccattc ctctgaaagt acccacagct aaacactact catttcccaa    3300
tttcagtatt tactgaaatc acttacctac aattctgtta gaatattatg ttgagttcgg    3360
aagacatttc tctgtttgca aggacagtta gttgctctct gtcatagccc gcagaagctt    3420
ggctacagtg taattcctct ccttgttctc ctacactctt tgtatctcag tgactgggtg    3480
taagatttca tgccaaatgc aaggaatagt ggaaatacat accaactgca aagaatagaa    3540
aaactttatc ccaatatatt atagaaagat cttcagttca attatgtcca gagtaatata    3600
atttggcaat gttaatgctt ttaagatttg aacttgtcct caaaccaagg agacaacaat    3660
agtgtaatac tattggactt acaggattag ttttaaagca actttgaata gaagtgtttc    3720
agacatagga cttctgcctt gttgactaga gtggatagtt ttctgtttaa atgcattggt    3780
cttttggctg tttgtaattc acttcagctt atagagaagt tgatgacctt ggatcatgct    3840
gggtatgatt ggtctttaaa aagcagtaat ataccaccag cccaaggaga aaacattgtt    3900
aaaatgaaga gtggtggaaa tagtgtgttg ggaagaataa aaaatttaga ttggcactta    3960
ttctaaagtg agctgttttt ttcaagaatt tactagcatt tgctcgtagt atgatttctg    4020
acgccagtca tatatactga tgaggggaag gagttactgt gttattctga gttcttataa    4080
atgcatatta ttgaatttca ttgcatgact attttgtcaag acttacctgg ttaggtctcc    4140
aattaaaaga tgtaccacct gtcatcttct aaattgtgtt cctttcattt attgggaaca    4200
gaatctctca aaagtgctaa actatattaa aaagttttct taatagattt gtatgtctga    4260
tatgtataac catttactat aatatgttgc aaatcattct aatatatgta aaacaatatt    4320
atttgtaatg cagttattgg taaaatatta tgtaatgtta attttgttcc tagctgctaa    4380
tttttctgcc aaaagtattc taattttcag gttgttttaa aggcttttaa aacttttag     4440
ttaagttttt tattcacgtc atttaaatta gttttttgct ttttttctac ctgataatct    4500
ctttaacaag atgcaacaag acagaattat taaaattaaa cctaaagtta agttacagat    4560
ttaaaggcat tatgatatta agcattaaaa ttggagatta aaatgtacaa aacagggttt    4620
tccttatgaa caaaccttac agggtaaatt gttttttttt ctaaatgtca ttaaatttat    4680
ttgtactcag aactgttact aataaaaatt aaaaatgcaa aaaaaaaaa                 4729
```

<210> SEQ ID NO 49
<211> LENGTH: 697
<212> TYPE: PRT
<213> ORGANISM: Homo sapiens

<400> SEQUENCE: 49

Met Gly Glu Arg Ala Gly Ser Pro Gly Thr Asp Gln Glu Arg Lys Ala
1               5                   10                  15

Gly Lys His His Tyr Ser Tyr Leu Ser Asp Phe Glu Thr Pro Gln Ser
            20                  25                  30

Ser Gly Arg Ser Ser Leu Val Ser Ser Pro Ala Ser Val Arg Arg
        35                  40                  45

Lys Asn Pro Lys Arg Gln Thr Ser Asp Gly Gln Val His His Gln Ala
    50                  55                  60

Pro Arg Lys Pro Ser Pro Lys Gly Leu Pro Asn Arg Lys Gly Val Arg
65                  70                  75                  80

Val Gly Phe Arg Ser Gln Ser Leu Asn Arg Glu Pro Leu Arg Lys Asp
                85                  90                  95

Thr Asp Leu Val Thr Lys Arg Ile Leu Ser Ala Arg Leu Leu Lys Ile

```
                100                 105                 110
Asn Glu Leu Gln Asn Glu Val Ser Glu Leu Gln Val Lys Leu Ala Glu
            115                 120                 125

Leu Leu Lys Glu Asn Lys Ser Leu Lys Arg Leu Gln Tyr Arg Gln Glu
        130                 135                 140

Lys Ala Leu Asn Lys Phe Glu Asp Ala Glu Asn Glu Ile Ser Gln Leu
145                 150                 155                 160

Ile Phe Arg His Asn Asn Glu Ile Thr Ala Leu Lys Glu Arg Leu Arg
                165                 170                 175

Lys Ser Gln Glu Lys Glu Arg Ala Thr Glu Lys Arg Val Lys Asp Thr
            180                 185                 190

Glu Ser Glu Leu Phe Arg Thr Lys Phe Ser Leu Gln Lys Leu Lys Glu
        195                 200                 205

Ile Ser Glu Ala Arg His Leu Pro Glu Arg Asp Leu Ala Lys Lys
    210                 215                 220

Leu Val Ser Ala Glu Leu Lys Leu Asp Asp Thr Glu Arg Arg Ile Lys
225                 230                 235                 240

Glu Leu Ser Lys Asn Leu Glu Leu Ser Thr Asn Ser Phe Gln Arg Gln
                245                 250                 255

Leu Leu Ala Glu Arg Lys Arg Ala Tyr Glu Ala His Asp Glu Asn Lys
            260                 265                 270

Val Leu Gln Lys Glu Val Gln Arg Leu Tyr His Lys Leu Lys Glu Lys
        275                 280                 285

Glu Arg Glu Leu Asp Ile Lys Asn Ile Tyr Ser Asn Arg Leu Pro Lys
    290                 295                 300

Ser Ser Pro Asn Lys Glu Lys Glu Leu Ala Leu Arg Lys Asn Ala Ala
305                 310                 315                 320

Cys Gln Ser Asp Phe Ala Asp Leu Cys Thr Lys Gly Val Gln Thr Met
                325                 330                 335

Glu Asp Phe Lys Pro Glu Glu Tyr Pro Leu Thr Pro Glu Thr Ile Met
            340                 345                 350

Cys Tyr Glu Asn Lys Trp Glu Glu Pro Gly His Leu Thr Leu Asp Leu
        355                 360                 365

Gln Ser Gln Lys Gln Asp Arg His Gly Glu Ala Gly Ile Leu Asn Pro
    370                 375                 380

Ile Met Glu Arg Glu Glu Lys Phe Val Thr Asp Glu Glu Leu His Val
385                 390                 395                 400

Val Lys Gln Glu Val Glu Lys Leu Glu Asp Glu Trp Glu Arg Glu Glu
                405                 410                 415

Leu Asp Lys Lys Gln Lys Glu Lys Ala Ser Leu Leu Glu Arg Glu Glu
            420                 425                 430

Lys Pro Glu Trp Glu Thr Gly Arg Tyr Gln Leu Gly Met Tyr Pro Ile
        435                 440                 445

Gln Asn Met Asp Lys Leu Gln Gly Glu Glu Glu Arg Leu Lys Arg
    450                 455                 460

Glu Met Leu Leu Ala Lys Leu Asn Glu Ile Asp Arg Glu Leu Gln Asp
465                 470                 475                 480

Ser Arg Asn Leu Lys Tyr Pro Val Leu Pro Leu Leu Pro Asp Phe Glu
                485                 490                 495

Ser Lys Leu His Ser Pro Glu Arg Ser Pro Lys Thr Tyr Arg Phe Ser
            500                 505                 510

Glu Ser Ser Glu Arg Leu Phe Asn Gly His His Leu Gln Asp Ile Ser
        515                 520                 525
```

```
Phe Ser Thr Pro Lys Gly Glu Gly Gln Asn Ser Gly Asn Val Arg Ser
        530                 535                 540

Pro Ala Ser Pro Asn Glu Phe Ala Phe Gly Ser Tyr Val Pro Ser Phe
545                 550                 555                 560

Ala Lys Thr Ser Glu Arg Ser Asn Pro Phe Ser Gln Lys Ser Ser Phe
                565                 570                 575

Leu Asp Phe Gln Arg Asn Ser Met Glu Lys Leu Ser Lys Asp Gly Val
            580                 585                 590

Asp Leu Ile Thr Arg Lys Glu Lys Lys Ala Asn Leu Met Glu Gln Leu
        595                 600                 605

Phe Gly Ala Ser Gly Ser Ser Thr Ile Ser Ser Lys Ser Ser Asp Pro
    610                 615                 620

Asn Ser Val Ala Ser Ser Lys Gly Asp Ile Asp Pro Leu Asn Phe Leu
625                 630                 635                 640

Pro Gly Asn Lys Gly Ser Arg Asp Gln Glu His Asp Glu Asp Glu Gly
                645                 650                 655

Phe Phe Leu Ser Glu Gly Arg Ser Phe Asn Pro Asn Arg His Arg Leu
            660                 665                 670

Lys His Ala Asp Asp Lys Pro Ala Val Lys Ala Ala Asp Ser Val Glu
        675                 680                 685

Asp Glu Ile Glu Glu Val Ala Leu Arg
    690                 695

<210> SEQ ID NO 50
<211> LENGTH: 3771
<212> TYPE: DNA
<213> ORGANISM: Artificial Sequence
<220> FEATURE:
<223> OTHER INFORMATION: pR2.1 from ATG to L-opsin gene

<400> SEQUENCE: 50
ccagggtgag attatgaggc tgagctgaga atatcaagac tgtaccgagt agggggcctt      60
ggcaagtgtg gagagcccgg cagctggggc agagggcgga gtacggtgtg cgtttacgga     120
cctcttcaaa cgaggtagga aggtcagaag tcaaaaaggg aacaaatgat gtttaaccac     180
acaaaaatga aaatccaatg gttggatatc cattccaaat acacaaaggc aacggataag     240
tgatccgggc caggcacaga aggccatgca cccgtaggat tgcactcaga gctcccaaat     300
gcataggaat agaagggtgg gtgcaggagg ctgagggggtg gggaagggc atgggtgttt     360
catgaggaca gagcttccgt ttcatgcaat gaaaagagtt tggagacgga tggtggtgac     420
tggactatac acttacacac ggtagcgatg gtacactttg tattatgtat attttaccac     480
gatcttttta aagtgtcaaa ggcaaatggc caaatggttc cttgtcctat agctgtagca     540
gccatcggct gttagtgaca aagcccctga gtcaagatga cagcagcccc cataactcct     600
aatcggctct cccgcgtgga gtcatttagg agtagtcgca ttagagacaa gtccaacatc     660
taatcttcca ccctggccag ggcccagct ggcagcgagg gtgggagact ccgggcagag     720
cagagggcgc tgacattggg gcccggcctg gcttgggtcc ctctggcctt tccccagggg     780
ccctcttttcc ttggggcttt cttggccgc cactgctccc gctcctctcc ccatcccca     840
ccccctcacc ccctcgttct tcatatcctt ctctagtgct ccctccactt tcatccaccc     900
ttctgcaaga gtgtgggacc acaaatgagt tttcacctgg cctggggaca cacgtgcccc     960
cacaggtgct gagtgacttt ctaggacagt aatctgcttt aggctaaaat ggacttgat    1020
cttctgttag ccctaatcat caattagcag agccggtgaa ggtgcagaac ctaccgcctt    1080
```

```
tccaggcctc ctcccacctc tgccacctcc actctccttc ctgggatgtg ggggctggca   1140
cacgtgtggc ccagggcatt ggtgggattg cactgagctg ggtcattagc gtaatcctgg   1200
acaagggcag acagggcgag cggagggcca gctccggggc tcaggcaagg ctgggggctt   1260
cccccagaca ccccactcct cctctgctgg accccccactt catagggcac ttcgtgttct   1320
caaagggctt ccaaatagca tggtggcctt ggatgcccag ggaagcctca gagttgctta   1380
tctccctcta gacagaaggg gaatctcggt caagagggag aggtcgccct gttcaaggcc   1440
acccagccag ctcatggcgg taatgggaca aggctggcca gccatcccac cctcagaagg   1500
gacccggtgg ggcaggtgat ctcagaggag gctcacttct gggtctcaca ttcttggatc   1560
cggttccagg cctcggccct aaatagtctc cctgggcttt caagagaacc acatgagaaa   1620
ggaggattcg ggctctgagc agtttcacca cccaccccccc agtctgcaaa tcctgacccg   1680
tgggtccacc tgccccaaag gcggacgcag acagtagaa gggaacagag aacacataaa   1740
cacagagagg gccacagcgg ctcccacagt caccgccacc ttcctggcgg ggatgggtgg   1800
ggcgtctgag tttggttccc agcaaatccc tctgagccgc ccttgcgggc tcgcctcagg   1860 agcagggag caagaggtgg gaggaggagg tctaagtccc aggcccaatt aagagatcag   1920
gtagtgtagg gtttgggagc ttttaaggtg aagaggcccg ggctgatccc acaggccagt   1980
ataaagcgcc gtgaccctca ggtgatgcgc cagggccggc tgccgtcggg gacagggctt   2040
tccatagcca tgctagagga tccggtactc gaggaactga aaaccagaa agttaactgg   2100 taagtttagt cttttttgtct tttatttcag gtcccggatc cggtggtggt gcaaatcaaa   2160
gaactgctcc tcagtggatg ttgcctttac ttctaggcct gtacggaagt gttacttctg   2220
ctctaaaagc tgcggaattg tacccgcggc cgcgggacag ggctttccat agccatggcc   2280
cagcagtgga gcctccaaag gctcgcaggc cgccatccgc aggacagcta tgaggacagc   2340
acccagtcca gcatcttcac ctacaccaac agcaactcca ccagaggccc cttcgaaggc   2400
ccgaattacc acatcgctcc cagatgggtg taccacctca ccagtgtctg gatgatcttt   2460
gtggtcactg catccgtctt cacaaatggg cttgtgctgg cggccaccat gaagttcaag   2520
aagctgcgcc acccgctgaa ctggatcctg gtgaacctgg cggtcgctga cctagcagag   2580
accgtcatcg ccagcactat cagcattgtg aaccaggtct ctggctactt cgtgctgggc   2640
caccctatgt gtgtcctgga gggctacacc gtctccctgt gtgggatcac aggtctctgg   2700
tctctggcca tcatttcctg ggagagatgg atggtggtct gcaagccctt tggcaatgtg   2760
agatttgatg ccaagctggc catcgtgggc attgccttct cctggatctg gtctgctgtg   2820
tggacagccc cgcccatctt tggttggagc aggtactggc cccacggcct gaagacttca   2880
tgcggcccag acgtgttcag cggcagctcg taccccgggg tgcagtctta catgattgtc   2940
ctcatggtca cctgctgcat catcccactc gctatcatca tgctctgcta cctccaagtg   3000
tggctggcca tccgagcggt ggcaaagcag cagaaagagt ctgaatccac ccagaaggca   3060
gagaaggaag tgacgcgcat ggtggtggtg atgatctttg cgtactgcgt ctgctggggca   3120 ccctacacct tcttcgcatg ctttgctgct gccaaccctg gttacgcctt ccaccctttg   3180
atggctgcct gccggcctta ctttgccaaa agtgccacta tctacaaccc cgttatctat   3240
gtctttatga accggcagtt tcgaaactgc atcttgcagc ttttcgggaa gaaggttgac   3300
gatggctctg aactctccag cgcctccaaa acggaggtcc aactgtgtc ctcgacccag   3360 gtagggccta actgaggtct gcctcctacc catcccgccc accggggctt tggccacctc   3420
```

| | |
|---|---|
| tccttttcccc ctccttctcc atccctgtaa aataaatgta atttatctttt gccaaaacca | 3480 |
| aaaaaaacgg aattcgtaat catgtcatag ctgtttcctg tgtgaaattg ttatccgctc | 3540 |
| acaattccac acaacatacg aggcggccgc gcggatccag acatgataag atacattgat | 3600 |
| gagtttggac aaaccacaac tagaatgcag tgaaaaaaat gctttatttg tgaaatttgt | 3660 |
| gatgctattg ctttatttgt aaccattata agctgcaata aacaagttaa caacaacaat | 3720 |
| tgcattcatt ttatgtttca ggttcagggg gaggtgtggg aggttttta g | 3771 |

<210> SEQ ID NO 51
<211> LENGTH: 36
<212> TYPE: DNA
<213> ORGANISM: Homo sapiens

<400> SEQUENCE: 51

| | |
|---|---|
| gacttgatct tctgttagcc ctaatcatca attagc | 36 |

<210> SEQ ID NO 52
<211> LENGTH: 1565
<212> TYPE: DNA
<213> ORGANISM: Homo sapiens

<400> SEQUENCE: 52

| | |
|---|---|
| cctacagcag ccagggtgag attatgaggc tgagctgaga atatcaagac tgtaccgagt | 60 |
| agggggcctt ggcaagtgtg gagagcccgg cagctgggc agaggcgga gtacggtgtg | 120 |
| cgtttacgga cctcttcaaa cgaggtagga aggtcagaag tcaaaagggg aacaaatgat | 180 |
| gtttaaccac acaaaatga aatccaatg gttggatatc cattccaaat acacaaaggc | 240 |
| aacggataag tgatccgggc caggcacaga aggccatgca cccgtaggat tgcactcaga | 300 |
| gctcccaaat gcataggaat agaagggtgg gtgcaggagg ctgaggggtg gggaaagggc | 360 |
| atgggtgttt catgaggaca gagcttccgt ttcatgcaat gaaaagagtt tggagacgga | 420 |
| tggtggtgac tggactatac acttacacac ggtagcgatg gtacactttg tattatgtat | 480 |
| attttaccac gatctttta aagtgtcaaa ggcaaatggc caaatggttc cttgtcctat | 540 |
| agctgtagca gccatcggct gttagtgaca aagcccctga gtcaagatga cagcagcccc | 600 |
| cataactcct aatcggctct cccgcgtgga gtcatttagg agtagtcgca ttagagacaa | 660 |
| gtccaacatc taatcttcca ccctggccag ggcccagct ggcagcgagg gtgggagact | 720 |
| ccgggcagag cagagggcgc tgacattggg gcccggcctg gcttgggtcc ctctggcctt | 780 |
| tccccagggg ccctctttcc ttggggcttt cttgggccgc cactgctccc gctcctctcc | 840 |
| ccccatccca cccctcacc ccctcgttct tcatatcctt ctctagtgct ccctccactt | 900 |
| tcatccaccc ttctgcaaga gtgtgggacc acaaatgagt tttcacctgg cctggggaca | 960 |
| cacgtgcccc cacaggtgct gagtgacttt ctaggacagt aatctgcttt aggctaaaat | 1020 |
| gggacttgat cttctgttag ccctaatcat caattagcag agccggtgaa ggtgcagaac | 1080 |
| ctaccgcctt tccaggcctc ctcccacctc tgccacctcc actctccttc ctgggatgtg | 1140 |
| ggggctggca cacgtgtggc ccagggcatt ggtgggattg cactgagctg ggtcattagc | 1200 |
| gtaatcctgg acaagggcag acagggcgag cggaggccca gctccggggc tcaggcaagg | 1260 |
| ctgggggctt ccccagaca ccccactcct cctctgctgg acccccactt cataggcac | 1320 |
| ttcgtgttct caagggctt ccaaatagca tggtggcctt ggatgccag ggaagcctca | 1380 |
| gagttgctta tctccctcta gacagaaggg gaatctcggt caagagggag aggtcgccct | 1440 |
| gttcaaggcc acccagccag ctcatggcgg taatgggaca aggctggcca gccatcccac | 1500 |

```
cctcagaagg acccggtgg ggcaggtgat ctcagaggag gctcacttct gggtctcaca    1560
ttctt                                                                1565

<210> SEQ ID NO 53
<211> LENGTH: 491
<212> TYPE: DNA
<213> ORGANISM: Homo sapiens

<400> SEQUENCE: 53
ggttccaggc ctcggcccta aatagtctcc ctgggctttc aagagaacca catgagaaag      60
gaggattcgg gctctgagca gtttcaccac ccacccccca gtctgcaaat cctgacccgt     120
gggtccacct gccccaaagg cggacgcagg acagtagaag gaacagaga acacataaac      180 acagagaggg ccacagcggc tcccacagtc accgccacct tcctggcggg gatgggtggg     240
gcgtctgagt ttggttccca gcaaatccct ctgagccgcc cttgcgggct cgcctcagga    300
gcaggggagc aagaggtggg aggaggaggt ctaagtccca ggcccaatta agagatcagg    360
tagtgtaggg tttgggagct tttaaggtga agaggcccgg gctgatccca caggccagta    420
taaagcgccg tgaccctcag gtgatgcgcc agggccggct gccgtcgggg acagggcttt    480
ccatagccat g                                                         491

<210> SEQ ID NO 54
<211> LENGTH: 491
<212> TYPE: DNA
<213> ORGANISM: Homo sapiens

<400> SEQUENCE: 54
agtagaaacg gggttttcacc atgttagtca ggctggtcgg gaactcctga cctcaggaga     60
tctacccgcc ttggcctccc aaagtgctgg gattacaggc gtgtgccact gtgcccagcc    120 acttttttt agacagagtc ttggtctgtt gcccaggcta gagttcagtg gcgccatctc     180
agctcactgc aacctccgcc tcccagattc aagcgattct cctgcctcga cctcccagta    240
gctgggatta caggtttcca gcaaatccct ctgagccgcc ccggggggct cgcctcagga    300
gcaaggaagc aaggggtggg aggaggaggt ctaagtccca ggcccaatta agagatcaga    360
tggtgtagga tttgggagct tttaaggtga agaggcccgg gctgatccca ctggccggta    420
taaagcaccg tgaccctcag gtgacgcacc agggccggct gccgtcgggg acagggcttt    480
ccatagccat g                                                         491

<210> SEQ ID NO 55
<211> LENGTH: 239
<212> TYPE: DNA
<213> ORGANISM: Homo sapiens

<400> SEQUENCE: 55
ggtttccagc aaatccctct gagccgcccc cggggctcg cctcaggagc aaggaagcaa      60
ggggtgggag gaggaggtct aagtcccagg cccaattaag agatcagatg gtgtaggatt    120
tgggagcttt taaggtgaag aggcccgggc tgatcccact ggccggtata aagcaccgtg    180
accctcaggt gacgcaccag ggccggctgc cgtcggggac agggctttcc atagccatg    239

<210> SEQ ID NO 56
<211> LENGTH: 169
<212> TYPE: RNA
<213> ORGANISM: Artificial Sequence
<220> FEATURE:
```

<223> OTHER INFORMATION: Synthesized 5'UTR

<400> SEQUENCE: 56

```
gccagggccg cugccgucg gggacagggc uuuccauagc caugcuagag gauccgguac    60
ucgaggaacu gaaaaaccag aaaguuaacu ggccuguacg gaaguguuac uucugcucua   120
aaagcugcgg aauuguaccc gcggccgcgg gacagggcuu uccauagcc              169
```

<210> SEQ ID NO 57
<211> LENGTH: 77
<212> TYPE: RNA
<213> ORGANISM: Artificial Sequence
<220> FEATURE:
<223> OTHER INFORMATION: Synthesized 5'UTR

<400> SEQUENCE: 57

```
gcaccagggc cggcugccgu cggggacagg gcuuccaua gcccaggccu cuagagagga    60
guaucagugc cgccacc                                                  77
```

<210> SEQ ID NO 58
<211> LENGTH: 213
<212> TYPE: DNA
<213> ORGANISM: Homo sapiens

<400> SEQUENCE: 58

```
aacggctagc ctgaggagct gctgcgacag tccactacct ttttcgagag tgactcccgt    60
tgtcccaagg cttcccagag cgaacctgtg cggctgcagg caccggcgcg tcgagtttcc   120
ggcgtccgga aggaccgagc tcttctcgcg gatccagtgt tccgtttcca gcccccaatc   180
tcagagccga gccgacagag agcagggaac cgc                                213
```

<210> SEQ ID NO 59
<211> LENGTH: 97
<212> TYPE: DNA
<213> ORGANISM: Artificial Sequence
<220> FEATURE:
<223> OTHER INFORMATION: pR2.1 intron sequence

<400> SEQUENCE: 59

```
gtaagtttag tcttttttgtc ttttatttca ggtcccggat ccggtggtgg tgcaaatcaa    60
agaactgctc ctcagtggat gttgccttta cttctag                            97
```

<210> SEQ ID NO 60
<211> LENGTH: 133
<212> TYPE: DNA
<213> ORGANISM: Artificial Sequence
<220> FEATURE:
<223> OTHER INFORMATION: MNTC intron sequence

<400> SEQUENCE: 60

```
gtaagtatca aggttacaag acaggtttaa ggagaccaat agaaactggg cttgtcgaga    60
cagagaagac tcttgcgttt ctgataggca cctattggtc ttactgacat ccactttgcc   120
tttctctcca cag                                                      133
```

<210> SEQ ID NO 61
<211> LENGTH: 1095
<212> TYPE: DNA
<213> ORGANISM: Homo sapiens

<400> SEQUENCE: 61

```
atggcccagc agtggagcct ccaaaggctc gcaggccgcc atccgcagga cagctatgag    60
```

```
gacagcaccc agtccagcat cttcacctac accaacagca actccaccag aggcccttc      120 gaaggcccga attaccacat cgctcccaga tgggtgtacc acctcaccag tgtctggatg     180
atctttgtgg tcactgcatc cgtcttcaca aatgggcttg tgctggcggc caccatgaag    240
ttcaagaagc tgcgccaccc gctgaactgg atcctggtga acctggcggt cgctgaccta    300
gcagagaccg tcatcgccag cactatcagc attgtgaacc aggtctctgg ctacttcgtg    360
ctgggccacc ctatgtgtgt cctggagggc tacaccgtct ccctgtgtgg gatcacaggt    420
ctctggtctc tggccatcat ttcctgggag aggtggctgg tggtgtgcaa gccctttggc    480
aatgtgagat ttgatgccaa gctggccatc gtgggcattg ccttctcctg gatctggtct    540
gctgtgtgga cagccccgcc catctttggt tggagcaggt actggcccca cggcctgaag    600
acttcatgcg gccagacgt gttcagcggc agctcgtacc ccggggtgca gtcttacatg     660
attgtcctca tggtcacctg ctgcatcatc ccactcgcta tcatcatgct ctgctacctc    720
caagtgtggc tggccatccg agcggtggca aagcagcaga aagagtctga atccacccag    780
aaggcagaga aggaagtgac gcgcatggtg gtggtgatga tctttgcgta ctgcgtctgc    840
tgggacccct acaccttctt cgcatgcttt gctgctgcca accctggtta cgccttccac    900
cctttgatgg ctgccctgcc ggcctacttt gccaaaagtg ccactatcta caacccgtt    960 atctatgtct ttatgaaccg gcagtttcga aactgcatct tgcagctttt cgggaagaag    1020
gttgacgatg gctctgaact ctccagcgcc tccaaaacgg aggtctcatc tgtgtcctcg    1080
gtatcgcctg catga                                                      1095
```

<210> SEQ ID NO 62
<211> LENGTH: 1095
<212> TYPE: DNA
<213> ORGANISM: Homo sapiens

<400> SEQUENCE: 62

```
atggcccagc agtggagcct ccaaaggctc gcaggccgcc atccgcagga cagctatgag     60
gacagcaccc agtccagcat cttcacctac accaacagca actccaccag aggcccttc     120 gaaggcccga attaccacat cgctcccaga tgggtgtacc acctcaccag tgtctggatg    180
atctttgtgg tcattgcatc cgtcttcaca aatgggcttg tgctggcggc caccatgaag    240
ttcaagaagc tgcgccaccc gctgaactgg atcctggtga acctggcggt cgctgacctg    300
gcagagaccg tcatcgccag cactatcagc gttgtgaacc aggtctatgg ctacttcgtg    360
ctgggccacc ctatgtgtgt cctggagggc tacaccgtct ccctgtgtgg gatcacaggt    420
ctctggtctc tggccatcat ttcctgggag agatggatgg tggtctgcaa gccctttggc    480
aatgtgagat ttgatgccaa gctggccatc gtgggcattg ccttctcctg gatctgggct    540
gctgtgtgga cagccccgcc catctttggt tggagcaggt actggcccca cggcctgaag    600
acttcatgcg gccagacgt gttcagcggc agctcgtacc ccggggtgca gtcttacatg     660
attgtcctca tggtcacctg ctgcatcacc ccactcagca tcatcgtgct ctgctacctc    720
caagtgtggc tggccatccg agcggtggca aagcagcaga aagagtctga atccacccag    780
aaggcagaga aggaagtgac gcgcatggtg gtggtgatga tctttgcatt ctgcttctgc    840 tgggaccat acgccttctt cgcatgcttt gctgctgcca accctggcta cccttccac     900 cctttgatgg ctgccctgcc ggccttcttt gccaaaagtg ccactatcta caacccgtt    960 atctatgtct ttatgaaccg gcagtttcga aactgcatct tgcagctttt cgggaagaag    1020
```

```
gttgacgatg gctctgaact ctccagcgcc tccaaaacgg aggtctcatc tgtgtcctcg   1080
gtatcgcctg catga                                                    1095

<210> SEQ ID NO 63
<211> LENGTH: 1092
<212> TYPE: DNA
<213> ORGANISM: Homo sapiens

<400> SEQUENCE: 63
atggcccagc agtggagcct ccaaaggctc gcaggccgcc atccgcagga cagctatgag   60
gacagcaccc agtccagcat cttcacctac accaacagca actccaccag aggccccttc  120
gaaggcccga attaccacat cgctcccaga tgggtgtacc cctcaccag tgtctggatg   180 atctttgtgg tcattgcatc cgtcttcaca aatgggcttg tgctggcggc caccatgaag  240
ttcaagaagc tgcgccaccc gctgaactgg atcctggtga acctggcggt cgctgacctg  300
gcagagaccg tcatcgccag cactatcagc gttgtgaacc aggtctatgg ctacttcgtg  360
ctgggccacc ctatgtgtgt cctggagggc tacaccgtct ccctgtgtgg atcacaggt   420 ctctggtctc tggccatcat ttcctgggag agatggctgg tggtctgcaa gcccttggc   480 aatgtgagat ttgatgccaa gctggccatc gtgggcattg ccttctcctg gatctgggct  540
gctgtgtgga cagccccgcc catctttggt tggagcaggt actggcccta cggcctgaag  600
acttcatgcg gccagacgt gttcagcggc agctcgtacc ccggggtgca gtcttacatg  660
attgtcctca tggtcacctg ctgcatcacc ccactcagca tcatcgtgct ctgctacctc  720
caagtgtggc tggccatccg agcggtggca aagcagcaga aagagtctga atccacccag  780
aaggcagaga aggaagtgac gcgcatggtg gtggtgatgg tcctggcatt ctgcttctgc  840
tggggaccat acgccttctt cgcatgcttt gctgctgcca accctggcta ccccttccac  900
cctttgatgg ctgccctgcc gtcctacttt gccaaaagtg ccactatcta caaccccgtt  960
atctatgtct ttatgaaccg gcagtttcga aactgcatct gcagcttttt cgggaagaag  1020
gttgacgatg gctctgaact ctccagcgcc tccaaaacgg aggtctcatc tgtgtcctcg  1080
gtatcgcctg ca                                                       1092

<210> SEQ ID NO 64
<211> LENGTH: 1092
<212> TYPE: DNA
<213> ORGANISM: Homo sapiens

<400> SEQUENCE: 64
atggcccagc agtggagcct gcagcggctg gccggccggc accccagga cagctacgag   60 gacagcaccc agagcagcat cttcacctac accaacagca cagcacccg ggcccttc    120 gagggcccca actaccacat cgcccccgg tgggtgtacc cctgaccag cgtgtggatg   180 atcttcgtgg tgatcgccag cgtgttcacc aacggcctgg tgctggccgc caccatgaag  240
ttcaagaagc tgcggcaccc cctgaactgg atcctggtga acctggccgt ggccgacctg  300
gccgagaccg tgatcgccag caccatcagc gtggtgaacc aggtgtacgg ctacttcgtg  360
ctgggccacc ccatgtgcgt gctggagggc tacaccgtga gcctgtgcgg catcaccggc  420
ctgtggagcc tggccatcat cagctgggag cggtggctgg tggtgtgcaa gcccttcggc  480
aacgtgcggt tcgacgccaa gctggccatc gtgggcatcg ccttcagctg gatctgggcc  540
gccgtgtgga ccgcccccc catcttcggc tggagcggt actggcccta cggcctgaag  600
accagctgcg gccccgacgt gttcagcggc agcagctacc ccggcgtgca gagctacatg  660
```

```
atcgtgctga tggtgacctg ctgcatcacc cccctgagca tcatcgtgct gtgctacctg    720
caggtgtggc tggccatccg ggccgtggcc aagcagcaga aggagagcga gagcacccag    780
aaggccgaga aggaggtgac ccggatggtg gtggtgatgg tgctggcctt ctgcttctgc    840
tggggcccct acgccttctt cgcctgcttc gccgccgcca accccggcta ccccttccac    900
cccctgatgg ccgccctgcc cagctacttc gccaagagcg ccaccatcta caaccccgtg    960
atctacgtgt tcatgaaccg gcagttccgg aactgcatcc tgcagctgtt cggcaagaag   1020
gtggacgacg gcagcgagct gagcagcgcc agcaagaccg aggtgagcag cgtgagcagc   1080
gtgagccccg cc                                                      1092

<210> SEQ ID NO 65
<211> LENGTH: 1092
<212> TYPE: DNA
<213> ORGANISM: Homo sapiens

<400> SEQUENCE: 65
atggcccagc agtggagcct gcagcggctg gccggccggc accccagga cagctacgag      60 gacagcaccc agagcagcat cttcacctac accaacagca cagcacccg gggccccttc     120 gagggcccca actaccacat cgccccccgg tgggtgtacc acctgaccag cgtgtggatg    180
atcttcgtgg tgatcgccag cgtgttcacc aacggcctgg tgctggccgc cacaatgaag    240
ttcaagaagc tgcggcaccc cctgaactgg atcctggtga acctggccgt ggccgacctg    300
gccgagaccg tgatcgccag cacaatcagc gtggtgaacc aggtgtacgg ctacttcgtg    360
ctgggccacc ccatgtgcgt gctggagggc tacaccgtga gcctgtgcgg catcaccggc    420
ctgtggagcc tggccatcat cagctgggag cggtggctgg tggtgtgcaa gcccttcggc    480
aacgtgcggt tcgacgccaa gctggctatc gtgggaatcg ccttcagctg gatctgggcc    540
gccgtgtgga ccgccccccc tatcttcggc tggagccggt actggcccta cggcctgaag    600
accagctgcg gccccgacgt gttcagcggc agcagctacc ccggcgtgca gagctacatg    660
atcgtgctga tggtgacctg ctgcatcacc cccctgagca tcatcgtgct gtgctacctg    720
caggtgtggc tggccatccg ggccgtggcc aagcagcaga aggagagcga gagcacccag    780
aaggccgaga aggaggtgac ccggatggtg gtggtgatgg tgctggcctt ctgcttctgc    840
tggggcccct acgccttctt cgcctgcttc gccgccgcca accccggcta ccccttccac    900
cccctgatgg ccgccctgcc cagctacttc gccaagagcg ccaccatcta caaccccgtg    960
atctacgtgt tcatgaaccg gcagttccgg aactgcatcc tgcagctgtt cggcaagaag   1020
gtggacgacg gcagcgagct gagcagcgcc agcaagaccg aggtgtcaag cgtgagcagc   1080
gtgagccccg cc                                                      1092

<210> SEQ ID NO 66
<211> LENGTH: 1047
<212> TYPE: DNA
<213> ORGANISM: Homo sapiens

<400> SEQUENCE: 66
atgagaaaaa tgtcggagga agagttttat ctgttcaaaa atatctcttc agtggggccg      60
tgggatgggc ctcagtacca cattgcccct gtctgggcct tctacctcca ggcagctttc     120
atgggcactg tcttccttat agggttccca ctcaatgcca tggtgctggt ggccacactg    180
cgctacaaaa agttgcggca gccctcaac tacattctgg tcaacgtgtc cttcggaggc    240
```

```
ttcctcctct gcatcttctc tgtcttccct gtcttcgtcg ccagctgtaa cggatacttc      300
gtcttcggtc gccatgtttg tgctttggag ggcttcctgg gcactgtagc aggtctggtt      360
acaggatggt cactggcctt cctggccttt gagcgctaca ttgtcatctg taagcccttc      420
ggcaacttcc gcttcagctc caagcatgca ctgacggtgg tcctggctac ctggaccatt      480
ggtattggcg tctccatccc acccttcttt ggctggagcc ggttcatccc tgagggcctg      540
cagtgttcct gtggccctga ctggtacacc gtgggcacca ataccgcag cgagtccat       600 acgtggttcc tcttcatctt ctgcttcatt gtgcctctct ccctcatctg cttctcctac      660
actcagctgc tgagggccct gaaagctgtt gcagctcagc agcaggagtc agctacgacc      720
cagaaggctg aacgggaggt gagccgcatg gtggttgtga tggtaggatc cttctgtgtc      780
tgctacgtgc cctacgcggc cttcgccatg tacatggtca acaaccgtaa ccatgggctg      840
gacttacggc ttgtcaccat tccttcattc ttctccaaga gtgcttgcat ctacaatccc      900
atcatctact gcttcatgaa taagcagttc aagcttgca tcatgaagat ggtgtgtggg      960
aaggccatga cagatgaatc cgacacatgc agctcccaga aaacagaagt ttctactgtc     1020
tcgtctaccc aagttggccc caactga                                         1047
```

<210> SEQ ID NO 67
<211> LENGTH: 1064
<212> TYPE: DNA
<213> ORGANISM: Homo sapiens

<400> SEQUENCE: 67

```
acccagtcga gcatcttcac ctataccaac agcaacagta ccagaggtcc ctttgaaggc       60
cccaattatc acattgctcc caggtgggtg taccacctca ccagcgcctg gatgatcttt      120
gtggtcattg catcagtctt cactaatggg cttgtgctgg cagccaccat acggttcaag      180
aagctgcgcc atcctctgaa ttggattctg gtgaacttgg caattgctga cctaatagag      240
accatcattg ctggcactat cagtgttgtg aaccaaatct atggctactt cgtactaggc      300
caccctctgt gcgtcgtgga aggctacatt gtcgccctgt gtggcatcac aggcctctgg      360
tccctggccg ttatttcctg ggagaggtgg ctggtggtct gcaagccctt tggcaatatg      420
agatttgatg ctaagctggc cactgtggga atcatcttt cttgggtctg ggctgctgtg      480
tggacagccc caccaatctt tggttggagc aggtactggc cttatggcct gaagacatcc      540
tgtggtccag acgtgttcag cggcacttcg tatcctgggg ttcagtctta tatgatggtt      600
ctcatggtca cgtgctgcat cttcccactt agcatcatcg tgctctgcta cctccaagtg      660
tggctggcca tccgagcagt agcaaagcaa caaaaagaat ctgagtctac ccagaaggct     720
gagaaggagg tgacacgcat ggtgcttgtg atgatcttcg catactgcat ctgctggggc      780
ccctacgctg tctttgcatg ctttgctact gcccaccctg gctatgcatt ccacccactt      840
gtggcctccc taccatctta ctttgcgaaa agtgccacta tctacaaccc cattatctat      900
gtctttatga accgacagtt tcaaaactgc atcttacagc tctttggaaa gaaggttgat     960
gatagctctg aacttgccag tacctccaaa acagaaacct catctgaagc cgaattccag     1020
cacactggcg gccgtactag tgatccgagt cgtagcctgg accc                      1064
```

<210> SEQ ID NO 68
<211> LENGTH: 1041
<212> TYPE: DNA
<213> ORGANISM: Homo sapiens

<400> SEQUENCE: 68

```
atgtcaggag aggatgactt ttacctgttt cagaatatct cttcggtggg gccctgggat      60
gggcctcagt accaccttgc tcctgtctgg gccttccgcc tccaggcagc cttcatggga     120
tttgtcttct ttgtggggac cccactcaat gccatagtgc tggtggccac actgcattac     180
aaaaagttgc gacagcccct caactatatt ctggtcaatg tatccctcgg ggcttcctc      240 ttctgcatct tctctgtctt cacagtcttc atcgccagct gtcacggata cttcctcttt     300
ggtcgccatg tttgtgctct ggaggccttc ttgggctctg tagcaggtct agtgacagga     360
tggtcattgg ctttcctggc ttttgaacgc tacgttgtca tctgtaaacc cttcggcagc     420
atccgcttca actccaagca tgcactgatg gtggtcctgg ctacttggat tattggtatc     480
ggggtgtcca tcccacccct ttttggctgg agcaggttca tccctgaggg cctgcagtgc     540
tcctgtggcc cagactggta cactgtgggc accaagtatc gaagcgagta ctacacctgg     600
ttcctcttca tcttctgttt catcattcct ctttccctca tctgcttctc ctactcccag     660
ttgctgagga ctctcagagc tgtggcagct cagcagcaag agtctgctac gacacaaaag     720
gctgaacggg aggtgagtca tatggtggtg gtgatggtgg atccttctg tctctgctac      780 gtgccctatg ctgccctggc catgtacatg gtcaacaatc ggaaccacgg gctggactta     840
cggcttgtca ccatccccgc cttctttttcc aagagctcct gtgtctacaa ccccatcatc    900
tactgcttca tgaataagca gttccgggct tgcattctgg agatggtgtg caggaagccc     960
atggcagacg aatctgacgt gtctggctct cagaaaacag aagtttctac tgtctcttct    1020
agcaaagttg gccctcactg a                                              1041
```

<210> SEQ ID NO 69
<211> LENGTH: 930
<212> TYPE: DNA
<213> ORGANISM: Artificial Sequence
<220> FEATURE:
<223> OTHER INFORMATION: Synthetic construct channel rhodopsin

<400> SEQUENCE: 69

```
atggactatg gcggcgcttt gtctgccgtc ggacgcgaac ttttgttcgt tactaatcct      60
gtggtggtga acgggtccgt cctggtccct gaggatcaat gttactgtgc cggatggatt     120
gaatctcgcg gcacgaacgg cgctcagacc gcgtcaaatg tcctgcagtg gcttgcagca     180
ggattcagca ttttgctgct gatgttctat gcctaccaaa cctggaaatc tacatgcggc     240
tgggaggaga tctatgtgtg cgccattgaa atggttaagg tgattctcga gttctttttt     300
gagtttaaga atccctctat gctctacctt gccacaggac accgggtgca gtggctgcgc     360
tatgcagagt ggctgctcac ttgtcctgtc atccttatcc acctgagcaa cctcaccggc     420
ctgagcaacg actacagcag gagaaccatg ggactccttg tctcagacat cgggactatc     480
gtgtgggggg ctaccagcgc catggcaacc ggctatgtta aagtcatctt cttttgtctt     540
ggattgtgct atggcgcgaa cacatttttt cacgccgcca agcatatata cgagggttat     600
catactgtgc caaagggtcg gtgccgccag gtcgtgaccg gcatggcatg gctgttttc      660 gtgagctggg gtatgttccc aattctcttc attttggggc ccgaaggttt tggcgtcctg     720
agcgtctatg gctccaccgt aggtcacacg attattgatc tgatgagtaa aaattgttgg     780
gggttgttgg acactacct gcgcgtcctg atccacgagc acatattgat tcacggagat     840
atccgcaaaa ccaccaaact gaacatcggc ggaacggaga tcgaggtcga gactctcgtc     900
gaagacgaag ccgaggccgg agccgtgcca                                     930
```

<210> SEQ ID NO 70
<211> LENGTH: 924
<212> TYPE: DNA
<213> ORGANISM: Artificial Sequence
<220> FEATURE:
<223> OTHER INFORMATION: Synthetic construct halorodopsin

<400> SEQUENCE: 70

| atgagggta cgcccctgct cctcgtcgtc tctctgttct ctctgcttca ggacacagag | 60 |
| accctgcctc ccgtgaccga gagtgccgtg gcccttcaag ccgaggttac ccaaagggag | 120 |
| ttgttcgagt tcgtgctgaa cgacccttg cttgcaagca gtctctatat caacatcgca | 180 |
| cttgcaggac tgagtatact gctgttcgtt tttatgaccc gaggactcga tgatccacgg | 240 |
| gcaaaactta ttgctgtgtc aaccatcctt gtgcctgtcg tcagcattgc ctcctacact | 300 |
| ggattggcga gcggcctgac aatttccgtt cttgaaatgc cagcgggcca ttttgcagaa | 360 |
| ggcagctcag tgatgctggg aggagaagag gtagatggtg tagtcaccat gtgggacgg | 420 |
| tatctcacct gggcactttc cacgcccatg attctcctcg ctctgggtct cctggccgga | 480 |
| agcaatgcta caaagctctt cacagctatc actttcgata tcgctatgtg cgtgactggc | 540 |
| cttgccgcgg ccctgactac ctcctcccac ctcatgagat ggttctggta cgctatcagt | 600 |
| tgtgcatgct ttctggtggt cttgtatatc ctgctggtgg agtgggcaca ggacgccaaa | 660 |
| gccgcgggaa ccgctgacat gttcaatacc ctgaagctgt tgacagtagt gatgtggctg | 720 |
| gggtatccaa ttgtgtgggc tcttggagtc gagggtatcg cggtgttgcc cgttggggtg | 780 |
| acgagctggg gatattcttt cctggatatc gtggcaaagt acattttcgc attcttgctc | 840 |
| ctgaactatc tgacgtcaaa cgaatctgtc gtgtccggca gcattttgga tgttccatct | 900 |
| gcttctggga ccccggctga tgat | 924 |

<210> SEQ ID NO 71
<211> LENGTH: 717
<212> TYPE: DNA
<213> ORGANISM: Artificial Sequence
<220> FEATURE:
<223> OTHER INFORMATION: Synthetic construct enhanced green fluorecent
    protein

<400> SEQUENCE: 71

| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctgggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaag | 717 |

<210> SEQ ID NO 72

```
<211> LENGTH: 7
<212> TYPE: DNA
<213> ORGANISM: Artificial Sequence
<220> FEATURE:
<223> OTHER INFORMATION: Translation initiation sequence

<400> SEQUENCE: 72 accatgg                                                                   7

<210> SEQ ID NO 73
<211> LENGTH: 13
<212> TYPE: DNA
<213> ORGANISM: Artificial Sequence
<220> FEATURE:
<223> OTHER INFORMATION: Translation initiation sequence
<220> FEATURE:
<221> NAME/KEY: misc_feature
<222> LOCATION: (7)..(7)
<223> OTHER INFORMATION: n is A or G

<400> SEQUENCE: 73
gccgccncca tgg                                                           13

<210> SEQ ID NO 74
<211> LENGTH: 221
<212> TYPE: DNA
<213> ORGANISM: Artificial Sequence
<220> FEATURE:
<223> OTHER INFORMATION: Synthetic construct pR2.1 poly A

<400> SEQUENCE: 74
agacatgata agatacattg atgagtttgg acaaaccaca actagaatgc agtgaaaaaa        60
atgctttatt tgtgaaattt gtgatgctat tgctttattt gtaaccatta taagctgcaa       120
taaacaagtt aacaacaaca attgcattca ttttatgttt caggttcagg gggagatgtg       180
ggaggttttt taaagcaagt aaaacctcta caaatgtggt a                          221

<210> SEQ ID NO 75
<211> LENGTH: 85
<212> TYPE: DNA
<213> ORGANISM: Homo sapiens

<400> SEQUENCE: 75
tgaggtctgc ctcctaccca tcccgcccac cggggctttg ccacctctc ctttcccct         60 ccttctccat ccctgtaaaa taaat                                              85

<210> SEQ ID NO 76
<211> LENGTH: 103
<212> TYPE: DNA
<213> ORGANISM: Homo sapiens

<400> SEQUENCE: 76
cccgggtggc atccctgtga cccctcccca gtgcctctcc tggccttgga agttgccact        60
ccagtgccca ccagccttgt cctaataaaa ttaagttgca tca                        103

<210> SEQ ID NO 77
<211> LENGTH: 225
<212> TYPE: DNA
<213> ORGANISM: Artificial Sequence
<220> FEATURE:
<223> OTHER INFORMATION: Synthetic construct  poly A region

<400> SEQUENCE: 77
tgtgccttct agttgccagc catctgttgt ttgcccctcc cccgtgcctt ccttgaccct        60
```

```
ggaaggtgcc actcccactg tcctttccta ataaaatgag gaaattgcat cgcattgtct    120
gagtaggtgt cattctattc tgggggggtgg ggtggggcag dacagcaagg gggaggattg    180
ggaagacaat agcaggcatg ctggggatgc ggtgggctct atggc                    225
```

<210> SEQ ID NO 78
<211> LENGTH: 502
<212> TYPE: DNA
<213> ORGANISM: Artificial Sequence
<220> FEATURE:
<223> OTHER INFORMATION: Synthetic construct  poly A region

<400> SEQUENCE: 78

```
gtgcaggctg cctatcagaa ggtggtggct ggtgtggcca atgccctggc tcacaaatac     60
cactgagatc tttttccctc tgccaaaaat tatggggaca tcatgaagcc ccttgagcat    120
ctgacttctg gctaataaag gaaatttatt ttcattgcaa tagtgtgttg gaattttttg    180
tgtctctcac tcggaaggac atatgggagg gcaaatcatt taaaacatca gaatgagtat    240
ttggtttaga gtttggcaac atatgccata tgctggctgc catgaacaaa ggtggctata    300
aagaggtcat cagtatatga aacagccccc tgctgtccat tccttattcc atagaaaagc    360
cttgacttga ggttagattt tttttatatt ttgttttgtg ttattttttt ctttaacatc    420
cctaaaattt tccttacatg ttttactagc cagatttttc ctcctctcct gactactccc    480
agtcatagct gtccctcttc tc                                             502
```

<210> SEQ ID NO 79
<211> LENGTH: 496
<212> TYPE: DNA
<213> ORGANISM: Homo sapiens

<400> SEQUENCE: 79

```
ggatccggtt ccaggcctcg gccctaaata gtctccctgg gctttcaaga gaaccacatg     60
agaaaggagg attcgggctc tgagcagttt caccacccac cccccagtct gcaaatcctg    120
acccgtgggt ccacctgccc caaaggcgga cgcaggacag tagaagggaa cagagaacac    180
ataaacacag agagggccac agcggctccc acagtcaccg ccaccttcct ggcggggatg    240
ggtggggcgt ctgagtttgg ttcccagcaa atccctctga gccgcccttg cgggctcgcc    300
tcaggagcag gggagcaaga ggtggggagga ggaggtctaa gtcccaggcc caattaagag    360
atcaggtagt gtagggtttg ggagcttttta aggtgaagag gcccgggctg atcccacagg    420
ccagtataaa gcgccgtgac cctcaggtga tgccagggcc ggctgccgtc ggggacaggg    480
ctttccatag ccatgg                                                    496
```

<210> SEQ ID NO 80
<211> LENGTH: 149
<212> TYPE: DNA
<213> ORGANISM: Homo sapiens

<400> SEQUENCE: 80

```
ccagcaaatc cctctgagcc gccccggggg gctcgcctca ggagcaagga agcaagggggt     60 gggaggagga ggtctaagtc ccaggcccaa ttaagagatc agatggtgta ggatttggga    120
gcttttaagg tgaagaggcc cgggctgat                                      149
```

<210> SEQ ID NO 81
<211> LENGTH: 434
<212> TYPE: DNA

<213> ORGANISM: Homo sapiens

<400> SEQUENCE: 81

| | | | | | |
|---|---|---|---|---|---|
| ggatccggtt | ccaggcctcg | gccctaaata | gtctccctgg | gctttcaaga | gaaccacatg | 60 |
| agaaaggagg | attcgggctc | tgagcagttt | caccacccac | cccccagtct | gcaaatcctg | 120 |
| acccgtgggt | ccacctgccc | caaaggcgga | cgcaggacag | tagaagggaa | cagagaacac | 180 |
| ataaacacag | agagggccac | agcggctccc | acagtcaccg | ccaccttcct | ggcggggatg | 240 |
| ggtggggcgt | ctgagtttgg | ttcccagcaa | atccctctga | gccgcccttg | cgggctcgcc | 300 |
| tcaggagcag | gggagcaaga | ggtgggagga | ggaggtctaa | gtcccaggcc | caattaagag | 360 |
| atcaggtagt | gtagggtttg | ggagctttta | aggtgaagag | gcccgggctg | atcccacagg | 420 |
| ccagtataaa | gcgc | | | | | 434 |

<210> SEQ ID NO 82
<211> LENGTH: 263
<212> TYPE: DNA
<213> ORGANISM: Homo sapiens

<400> SEQUENCE: 82

| ggatccggtt | ccaggcctcg | gccctaaata | gtctccctgg | gctttcaaga | gaaccacatg | 60 |
|---|---|---|---|---|---|---|
| agaaaggagg | attcgggctc | tgagcagttt | caccacccac | cccccagtct | gcaaatcctg | 120 |
| acccgtgggt | ccacctgccc | caaaggcgga | cgcaggacag | tagaagggaa | cagagaacac | 180 |
| ataaacacag | agagggccac | agcggctccc | acagtcaccg | ccaccttcct | ggcggggatg | 240 |
| ggtggggcgt | ctgagtttgg | ttc | | | | 263 |

<210> SEQ ID NO 83
<211> LENGTH: 171
<212> TYPE: DNA
<213> ORGANISM: Homo sapiens

<400> SEQUENCE: 83

| ccagcaaatc | cctctgagcc | gcccttgcgg | gctcgcctca | ggagcagggg | agcaagaggt | 60 |
|---|---|---|---|---|---|---|
| gggaggagga | ggtctaagtc | ccaggcccaa | ttaagagatc | aggtagtgta | gggtttggga | 120 |
| gcttttaagg | tgaagaggcc | cgggctgatc | ccacaggcca | gtataaagcg | c | 171 |

<210> SEQ ID NO 84
<211> LENGTH: 102
<212> TYPE: DNA
<213> ORGANISM: Artificial Sequence
<220> FEATURE:
<223> OTHER INFORMATION: Synthesized 5'UTR

<400> SEQUENCE: 84

| cccactggcc | ggtataaagc | accgtgaccc | tcaggtgacg | caccagggcc | ggctgccgtc | 60 |
|---|---|---|---|---|---|---|
| ggggacaggg | ctttccatag | cccaggccca | gagaggagac | ag | | 102 |

<210> SEQ ID NO 85
<211> LENGTH: 85
<212> TYPE: DNA
<213> ORGANISM: Artificial Sequence
<220> FEATURE:
<223> OTHER INFORMATION: Synthesized 5'UTR

<400> SEQUENCE: 85

| cccactggcc | ggtataaagc | accgtgaccc | tcaggtgacg | caccagggcc | ggctgccgtc | 60 |
|---|---|---|---|---|---|---|
| ggggacaggg | ctttccatag | cccag | | | | 85 |

<210> SEQ ID NO 86
<211> LENGTH: 17
<212> TYPE: DNA
<213> ORGANISM: Artificial Sequence
<220> FEATURE:
<223> OTHER INFORMATION: Synthesized 5'UTR

<400> SEQUENCE: 86
gcccagagag gagacag                                                17

<210> SEQ ID NO 87
<211> LENGTH: 185
<212> TYPE: DNA
<213> ORGANISM: Artificial Sequence
<220> FEATURE:
<223> OTHER INFORMATION: Synthesized 5'UTR construct

<400> SEQUENCE: 87
cgtgaccctc aggtgatgcg ccagggccgg ctgccgtcgg ggacagggct ttccatagcc    60
atgctagagg atccggtact cgaggaactg aaaaaccaga aagttaactg gcctgtacgg   120
aagtgttact tctgctctaa aagctgcgga attgtacccg cggccgcggg acagggcttt   180
ccata                                                              185

<210> SEQ ID NO 88
<211> LENGTH: 110
<212> TYPE: DNA
<213> ORGANISM: Artificial Sequence
<220> FEATURE:
<223> OTHER INFORMATION: Synthesized 5'UTR construct

<400> SEQUENCE: 88
cgtgaccctc aggtgatgcg ccagggccgg ctgccgtcgg ggacagggct ttccatagcc    60
atgctagagg atccggtact cgaggaactg aaaaaccaga aagttaactg                110

<210> SEQ ID NO 89
<211> LENGTH: 75
<212> TYPE: DNA
<213> ORGANISM: Artificial Sequence
<220> FEATURE:
<223> OTHER INFORMATION: Synthesized 5'UTR construct

<400> SEQUENCE: 89
gcctgtacgg aagtgttact tctgctctaa aagctgcgga attgtacccg cggccgcggg    60
acagggcttt ccata                                                    75

<210> SEQ ID NO 90
<211> LENGTH: 235
<212> TYPE: DNA
<213> ORGANISM: Artificial Sequence
<220> FEATURE:
<223> OTHER INFORMATION: Synthetic construct  poly A region

<400> SEQUENCE: 90
ggccgcgggg atccagacat gataagatac attgatgagt ttggacaaac cacaactaga    60
atgcagtgaa aaaaatgctt tatttgtgaa atttgtgatg ctattgcttt atttgtaacc   120
attataagct gcaataaaca agttaacaac aacaattgca ttcattttat gtttcaggtt   180 caggggggaga tgtgggaggt tttttaaagc aagtaaaacc tctacaaatg tggta       235

<210> SEQ ID NO 91

```
<211> LENGTH: 152
<212> TYPE: DNA
<213> ORGANISM: Artificial Sequence
<220> FEATURE:
<223> OTHER INFORMATION: Synthetic construct  poly A region

<400> SEQUENCE: 91
ggccgcgggg atccagacat gataagatac attgatgagt ttggacaaac cacaactaga      60
atgcagtgaa aaaaatgctt tatttgtgaa atttgtgatg ctattgcttt atttgtaacc     120
attataagct gcaataaaca agttaacaac aa                                    152

<210> SEQ ID NO 92
<211> LENGTH: 1714
<212> TYPE: DNA
<213> ORGANISM: Homo sapiens

<400> SEQUENCE: 92
cctacagcag ccagggtgag attatgaggc tgagctgaga atatcaagac tgtaccgagt      60
agggggcctt ggcaagtgtg gagagcccgg cagctgggc agaggggcgga gtacggtgtg     120 cgtttacgga cctcttcaaa cgaggtagga aggtcagaag tcaaaaaggg aacaaatgat     180
gtttaaccac acaaaaatga aaatccaatg gttggatatc cattccaaat acacaaaggc     240
aacggataag tgatccgggc caggcacaga aggccatgca cccgtaggat tgcactcaga     300
gctcccaaat gcataggaat agaagggtgg gtgcaggagg ctgaggggtg gggaaagggc     360
atgggtgttt catgaggaca gagcttccgt ttcatgcaat gaaaagagtt tggagacgga     420
tggtggtgac tggactatac acttacacac ggtagcgatg gtacactttg tattatgtat     480
attttaccac gatcttttta aagtgtcaaa ggcaaatggc caaatggttc cttgtcctat     540
agctgtagca gccatcggct gttagtgaca aagcccctga gtcaagatga cagcagcccc     600
cataactcct aatcggctct cccgcgtgga gtcatttagg agtagtcgca ttagagacaa     660
gtccaacatc taatcttcca ccctggccag ggccccagct ggcagcgagg gtgggagact     720
ccgggcagag cagagggcgc tgacattggg gcccggcctg gcttgggtcc ctctggcctt     780
tccccagggg ccctctttcc ttggggcttt cttgggccgc cactgctccc gctcctctcc     840
ccccatccca cccccctcacc ccctcgttct tcatatcctt ctctagtgct ccctccactt     900
tcatccaccc ttctgcaaga gtgtgggacc acaaatgagt tttcacctgg cctggggaca     960
cacgtgcccc cacaggtgct gagtgacttt ctaggacagt aatctgcttt aggctaaaat    1020
gggacttgat cttctgttag ccctaatcat caattagcag agccggtgaa ggtgcagaac    1080
ctaccgcctt tccaggcctc ctcccacctc tgccacctcc actctccttc ctgggatgtg    1140
ggggctggca cacgtgtggc ccagggcatt ggtgggattg cactgagctg ggtcattagc    1200
gtaatcctgg acaagggcag acagggcgag cggagggcca gctccggggc tcaggcaagg    1260 ctggggggctt ccccccagaca ccccactcct cctctgctgg accccacttt catagggcac    1320
ttcgtgttct caaagggctt ccaaatagca tggtggcctt ggatgcccag ggaagcctca    1380
gagttgctta tctccctcta gacagaaggg gaatctcggt caagagggag aggtcgccct    1440
gttcaaggcc acccagccag ctcatggcgg taatgggaca aggctggcca gccatcccac    1500
cctcagaagg gacccggtgg ggcaggtgat ctcagaggag gctcacttct gggtctcaca    1560
ttcttccagc aaatccctct gagccgcccc cggggctcg cctcaggagc aaggaagcaa    1620
ggggtgggag gaggaggtct aagtcccagg cccaattaag agatcagatg gtgtaggatt    1680
tgggagcttt taaggtgaag aggcccgggc tgat                                 1714
```

<210> SEQ ID NO 93
<211> LENGTH: 234
<212> TYPE: DNA
<213> ORGANISM: Artificial Sequence
<220> FEATURE:
<223> OTHER INFORMATION: Optimized promoter sequence

<400> SEQUENCE: 93

```
ccagcaaatc cctctgagcc gcccccgggg gctcgcctca ggagcaagga agcaaggggt      60
gggaggagga ggtctaagtc ccaggcccaa ttaagagatc agatggtgta ggatttggga     120
gcttttaagg tgaagaggcc cgggctgatc ccactggccg gtataaagca ccgtgaccct     180
caggtgacgc accagggccg gctgccgtcg ggacagggc tttccatagc ccag            234
```

<210> SEQ ID NO 94
<211> LENGTH: 235
<212> TYPE: DNA
<213> ORGANISM: Artificial Sequence
<220> FEATURE:
<223> OTHER INFORMATION: Optimized intron sequence

<400> SEQUENCE: 94

```
cccactggcc ggtataaagc accgtgaccc tcaggtgacg caccagggcc ggctgccgtc      60
ggggacaggg cttttccatag cccaggtaag tatcaaggtt acaagacagg tttaaggaga    120
ccaatagaaa ctgggcttgt cgagacagag aagactcttg cgtttctgat aggcacctat    180
tggtcttact gacatccact ttgcctttct ctccacaggc cagagagga gacag           235
```

<210> SEQ ID NO 95
<211> LENGTH: 1958
<212> TYPE: DNA
<213> ORGANISM: Artificial Sequence
<220> FEATURE:
<223> OTHER INFORMATION: Cassette comprising optimized enhance,
      optimized promoter, optimized 5'UTR, optimized intron, optimized
      kozak and optimized polyA region

<400> SEQUENCE: 95

```
cctacagcag ccagggtgag attatgaggc tgagctgaga atatcaagac tgtaccgagt      60
agggggcctt gcaagtgtg gagagcccgg cagctgggc agaggcgga gtacggtgtg       120 cgtttacgga cctcttcaaa cgaggtagga aggtcagaag tcaaaagggg aacaaatgat    180
gtttaaccac acaaaaatga aaatccaatg gttggatatc cattccaaat acacaaaggc    240
aacggataag tgatccgggc caggcacaga aggccatgca cccgtaggat tgcactcaga    300
gctcccaaat gcataggaat agaagggtgg gtgcaggagg ctgaggggtg gggaaagggc    360
atgggtgttt catgaggaca gagcttccgt ttcatgcaat gaaaagagtt tggagacgga    420
tggtggtgac tggactatac acttacacac ggtagcgatg gtacactttg tattatgtat    480
attttaccac gatctttta aagtgtcaaa ggcaaatggc caaatggttc cttgtcctat     540
agctgtagca gccatcggct gttagtgaca aagcccctga gtcaagatga cagcagcccc    600
cataactcct aatcggctct cccgcgtgga gtcatttagg agtagtcgca ttagagacaa    660
gtccaacatc taatcttcca ccctggccag ggccccagct ggcagcgagg gtgggagact    720 ccggcagag cagagggcgc tgacattggg gcccggcctg gcttgggtcc ctctggcctt    780
tccccagggg ccctctttcc ttggggcttt cttgggccgc cactgctccc gctcctctcc    840
ccccatccca cccccctcacc ccctcgttct tcatatcctt ctctagtgct ccctccactt    900
```

-continued

```
tcatccaccc ttctgcaaga gtgtgggacc acaaatgagt tttcacctgg cctggggaca      960
cacgtgcccc cacaggtgct gagtgacttt ctaggacagt aatctgcttt aggctaaaat     1020
gggacttgat cttctgttag ccctaatcat caattagcag agccggtgaa ggtgcagaac     1080
ctaccgcctt tccaggcctc ctcccacctc tgccacctcc actctccttc ctgggatgtg     1140
ggggctggca cacgtgtggc ccagggcatt ggtgggattg cactgagctg ggtcattagc     1200
gtaatcctgg acaagggcag acagggcgag cggagggcca gctccggggc tcaggcaagg     1260
ctgggggctt ccccagaca ccccactcct cctctgctgg accccacttt catagggcac     1320
ttcgtgttct caaagggctt ccaaatagca tggtggcctt ggatgcccag ggaagcctca     1380
gagttgctta tctccctcta gacagaaggg gaatctcggt caagagggag aggtcgccct     1440
gttcaaggcc acccagccag ctcatggcgg taatgggaca aggctggcca gccatcccac     1500
cctcagaagg gacccggtgg ggcaggtgat ctcagaggag gctcacttct gggtctcaca     1560
ttcttccagc aaatccctct gagccgcccc cgggggctcg cctcaggagc aaggaagcaa     1620
ggggtgggag gaggaggtct aagtcccagg cccaattaag agatcagatg gtgtaggatt     1680
tgggagcttt taaggtgaag aggcccgggc tgatcccact ggccggtata aagcaccgtg     1740
accctcaggt gacgcaccag ggccggctgc cgtcggggac agggctttcc atagcccagg     1800
taagtatcaa ggttacaaga caggtttaag gagaccaata gaaactgggc ttgtcgagac     1860
agagaagact cttgcgtttc tgataggcac ctattggtct tactgacatc cactttgcct     1920
ttctctccac aggcccagag aggagacagg ccgccacc                             1958
```

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 96

Leu Gly Glu Thr Thr Arg Pro
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 97

Asn Glu Thr Ile Thr Arg Pro
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 98

Lys Ala Gly Gln Ala Asn Asn
1               5

<210> SEQ ID NO 99
<211> LENGTH: 7
<212> TYPE: PRT

```
<213> ORGANISM: Artificial Sequence
<220> FEATURE:
<223> OTHER INFORMATION: Synthetic peptide insertion in the AAV GH loop

<400> SEQUENCE: 99

Lys Asp Pro Lys Thr Thr Asn
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 100

Lys Asp Thr Asp Thr Thr Arg
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 101

Arg Ala Gly Gly Ser Val Gly
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 102

Ala Val Asp Thr Thr Lys Phe
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide insertion in the AAV GH loop

<400> SEQUENCE: 103

Ser Thr Gly Lys Val Pro Asn
1               5
```

COMPOSITIONS AND METHODS FOR ENHANCED GENE EXPRESSION IN CONE CELLS

CROSS REFERENCE TO RELATED APPLICATIONS

Pursuant to 35 U.S.C. § 119 (e), this application claims priority to the filing dates of U.S. Provisional Patent Application Ser. No. 61/954,330 filed Mar. 17, 2014; and U.S. Provisional Patent Application Ser. No. 62/127,185 filed Mar. 2, 2015, the full disclosures of which are herein incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is AVBI_005_02US_ST25.txt. The text file is 308 KB, was created on Mar. 17, 2015, and is being submitted electronically via EFS-Web.

FIELD OF THE INVENTION

This invention pertains to gene therapy of retinal disorders.

BACKGROUND OF THE INVENTION

Vision disorders of the eye often relate to known primary defects in cone cells. These include macular dystrophies such as Stargardt's macular dystrophy, cone dystrophy, cone-rod dystrophy, Spinocerebellar ataxia type 7, and Bardet-Biedl syndrome-1, as well as color vision disorders, including achromotopsia, blue cone monochromacy, and protan, deutan, and tritan defects.

In addition to those disorders where the known cause is intrinsic to cone photoreceptors, there are vision disorders of the central macula (within primates) that may be treated by targeting cone cells. These include age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, and X-linked retinoschisis.

A promising approach to treating and preventing ophthalmic disease that addresses the limitations of existing treatment is delivery of therapeutic agents to the eye with a gene therapy vector such as an adeno-associated virus (AAV). AAV is a 4.7 kb, single stranded DNA virus. Recombinant vectors based on AAV are associated with excellent clinical safety, since wild-type AAV is nonpathogenic and has no etiologic association with any known diseases. In addition, AAV offers the capability for highly efficient gene delivery and sustained transgene expression in numerous tissues, including eye, muscle, lung, and brain. Furthermore, AAV has shown promise in human clinical trials. One example is Leber's congenital amaurosis in which patients treated with a therapeutic delivered by a single subretinal administration of an rAAV vector have experienced sustained clinical benefit from expression of the therapeutic agent for more than four years from the initial date of treatment.

A number of challenges remain with regard to designing polynucleotide cassettes and expression vectors for use in gene therapy to treat eye disease generally and cone cells specifically. One significant challenge is obtaining sufficient expression of the transgene in target cells, especially in cone cells of the retina. A longstanding unmet need in the art has been sufficiently robust expression of transgenes following gene transfer. In some cases, more efficient expression is required for the efficacy of certain vectors, for example plasmid DNA vectors. In other cases, more efficient gene expression cassettes are desirable to allow for a lower therapeutic dose that has a more favorable safety profile or a less invasive route of administration (e.g., intravitreal vs. subretinal). In some settings, efficient expression has been achieved using a strong, ubiquitous promoter, but it is often desirable to have high transgene expression using a nucleic acid expression cassette that is only expressed in target cell types.

Previous efforts to express transgenes in cone cells, for example as disclosed in US patent application US 2012/0172419, showed some promise, but often the expression levels were lower than optimal or not cell specific. Given that a number of vision disorders result from primary defects in cone cells, specific expression of transgenes in cone cells, with high expression levels, would represent a meaningful advance in the art. Therefore, there remains a need for improved methods and optimized nucleic acid cassettes and vectors for expressing genes in cone cells.

SUMMARY OF THE INVENTION

The present disclosure provides polynucleotide cassettes, expression vectors and methods for the expression of a gene in cone cells.

In some aspects of the invention, polynucleotide cassettes are provided for the expression of a transgene in cone cells of a mammalian retina. In some embodiments, the expression of the transgene is enhanced expression. In certain embodiments, the expression of the coding sequence is greater than expression of the transgene operably linked to SEQ ID NO:1. In some embodiments, the expression of the transgene is cone-specific.

In some embodiments, the polynucleotide cassette comprises a promoter region, wherein the promoter region promotes the expression of a gene in retinal cone cells; and a polyadenylation site. In some embodiments, the expression is specifically in cone cells. In some such embodiments, the promoter region comprises a polynucleotide sequence having a sequence identity of 85% or more to a sequence selected from the group consisting of SEQ ID NO:1, SEQ ID NO:2, SEQ ID NO:3, SEQ ID NO:53, SEQ ID NO:54, SEQ ID NO:55, SEQ ID NO:79, SEQ ID NO:80, SEQ ID NO:81. SEQ ID NO:82, and SEQ ID NO:83, or a functional fragment thereof. In some embodiments, the promoter region is less than 492 nucleotides in length. In some embodiments, the promoter region consists essentially of a polynucleotide sequence having a sequence identity of 85% or more to the full length of SEQ ID NO:55 or a functional fragment thereof.

In some embodiments, the polynucleotide cassette comprises a polynucleotide sequence encoding an untranslated region 5' for a coding sequence, referred to herein as a 5'UTR. In some such embodiments, the 5'UTR comprises a sequence having a sequence identity of 85% or more to a sequence selected from the group consisting of SEQ ID NO:56, SEQ ID NO:57, SEQ ID NO:58, SEQ ID NO:84, SEQ ID NO:85, SEQ ID NO:86, SEQ ID NO:87, SEQ ID NO:88, and SEQ ID NO:89, or a fragment thereof. In some embodiments, some or all of the 5'UTR sequence is comprised by a promoter region as disclosed in, for example, SEQ ID NO:1, SEQ ID NO:2, SEQ ID NO:3, SEQ ID NO:53, SEQ ID NO:54, SEQ ID NO:55, or SEQ ID NO:79. In some embodiments, the 5'UTR sequence is heterologous to the promoter sequence. In some embodiments, the 5'UTR consists essentially of a sequence having a sequence identity of 85% or more to the full length of SEQ ID NO:85 or SEQ ID NO:86, or a fragment thereof. In some embodiments, the 5'UTR does not comprise a polynucleotide ATG.

In some embodiments, the polynucleotide cassette comprises an intron. In some such embodiments, the intron comprises a sequence having a sequence identity of 85% or more to a sequence selected from the group consisting of SEQ ID NO:5, SEQ ID NO:59, and SEQ ID NO:60. In certain embodiments, the intron is located within the polynucleotide sequence encoding a 5'UTR.

In some embodiments, the polynucleotide cassette comprises a translation initiation sequence. In some such embodiments, the translation initiation sequence comprises a polynucleotide sequence consisting essentially of SEQ ID NO:72 or SEQ ID NO:73.

In some embodiments, the polynucleotide cassette comprises an enhancer sequence. In some such embodiments, the enhancer sequence comprises a polynucleotide sequence having a sequence identity of 85% or more to SEQ ID NO:52 or a functional fragment thereof. In certain embodiments, the enhancer sequence consists essentially of a sequence having a sequence identity of 85% or more to the full length of SEQ ID NO:51.

In some embodiments, the polynucleotide cassette comprises a coding sequence operably linked to the promoter. In some embodiments, the coding sequence is heterologous to the promoter region and/or the 5'UTR sequence. In some embodiments, the coding sequence encodes a polypeptide having a sequence identity of at least 85%, 90%, or 95% to SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, and a polymorph of SEQ ID NO:11 selected from the group consisting of: (i) Thr65Ile (ii) Ile111Val (iii) Ser116Tyr (iv) Leu153Met (v) Ile171Val (vi) Ala174Val (vii) Ile178Val (viii) Ser180Ala (ix) Ile230Thr (x) Ala233Ser (xi) Val236Met (xii) Ile274Val (xiii) Phe275Leu (xiv) Tyr277Phe (xv) Val279Phe (xvi) Thr285Ala (xvii) Pro298Ala; and (xviii) Tyr309Phe. In some embodiments, the coding sequence has a sequence identity of at least 85%, 90%, or 95% to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, or SEQ ID NO:71. In some embodiments, the sequence between the transcription initiation site and the end of coding sequence does not contain an open reading frame, other than the transgene open reading frame, that is more than 500 nucleotides in length. In some embodiments, the sequence between the transcription initiation site and the end of coding sequence does not contain an open reading frame, other than the transgene open reading frame, that is more than 273 nucleotides in length. In some embodiments, the sequence between the transcription initiation site and the end of coding sequence does not contain an open reading frame, other than the transgene open reading frame, that is more than 250 nucleotides in length. In some embodiments, at least one open reading frame of the coding sequence has been removed.

In some embodiments, the polynucleotide comprises a promoter region, wherein the promoter region promotes the expression of a gene in retinal cone cells; a 5' untranslated region; an intron; a translation initiation sequence; a coding sequence operatively linked to the promoter region; and a polyadenlyation site. In some embodiments, the polynucleotide comprises a promoter region, wherein the promoter region promotes the expression of a gene specifically in retinal cone cells; a 5' untranslated region; an intron; a translation initiation sequence; a coding sequence operatively linked to the promoter region; and a polyadenlyation site.

In some aspects of the invention, gene delivery vectors are provided comprising a polynucleotide cassette of the present invention. In some embodiments, the gene delivery vector is a recombinant adeno-associated virus, wherein the recombinant adeno-associated virus comprises an AAV capsid protein. In some embodiments, the AAV capsid protein is a wild type AAV capsid protein. In other embodiments, the AAV capsid protein is a variant AAV capsid protein. In certain embodiments, the variant AAV capsid protein comprises a peptide insertion in the AAV GH loop selected from the group consisting of LGETTRP (SEQ ID NO:96), NETITRP (SEQ ID NO:97), KAGQANN (SEQ ID NO:98), KDPKTTN (SEQ ID NO:99), KDTDTTR (SEQ ID NO:100), RAGGSVG (SEQ ID NO:101), AVDTTKF (SEQ ID NO:102), and STGKVPN (SEQ ID NO:103).

In some aspects of the invention, pharmaceutical compositions are provided comprising a polynucleotide cassette of the invention and a pharmaceutical excipient. In some embodiments, the pharmaceutical composition comprises a gene delivery vector of the invention and a pharmaceutical excipient.

In some aspects of the invention, methods are provided for expressing a transgene in cone cells. In some embodiments, the method comprises contacting one or more cone cells with an effective amount of a polynucleotide cassette of the invention or a gene delivery vector of the invention, wherein the transgene is expressed at detectable levels in the one or more cone cells. In some embodiments, the method is in vitro. In other embodiments, the method is in vivo. In certain such embodiments, the contacting comprises injection of the polynucleotide cassette or gene delivery vector into the vitreous of a mammal eye. In other such emobidments, the method comprises injection of the polynucleotide cassette or gene delivery vector into the subretinal space of a mammal eye. In some embodiments, the method further comprises detecting the expression of the trangene in cone cells, wherein expression is detected in 80% or more of the cone cells. In some embodiments, the expression is specific for cone cells.

In some aspects of the invention, methods are provided for the treatment or prophylaxis of a cone cell disorder in a mammal in need of treatment or prophylaxis for a cone cell disorder. In some embodiments, the method comprises administering to the eye of the mammal an effective amount of a pharmaceutical composition of the invention, wherein the coding sequence encodes a therapeutic gene product. In some embodiments, the administering comprises injecting the pharmaceutical composition into the vitreous of the mammal eye. In other such embodiments, the method comprises injecting the pharmaceutical composition into the subretinal space of a mammal eye.

In some embodiments, the cone cell disorder is a color vision disorder. In certain embodiments, the color vision disorder is selected from the group consisting of achromotopsia, blue cone monochromacy, a protan defect, a deutan defect, and a tritan defect. In some such embodiments, the method further comprises detecting a change in the disease symptoms, wherein the change comprises an increase in the ability of the mammal to perceive a color. In some embodiments, the cone cell disorder is a macular dystrophy. In certain embodiments, the macular dystrophy is selected from the group consisting of Stargardt's macular dystrophy, cone dystrophy, cone-rod dystrophy, Spinocerebellar ataxia type 7, and Bardet-Biedl syndrome-1. In some embodiments, the cone cell disorder is a vision disorder of the central macula. In certain embodiments, vision disorder of the central macula is selected from the group consisting of age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, rod-cone dystrophy, Leber's congenital amaurosis, and X-linked retinoschisis. In some such embodiments, the method further comprises detecting a change in the disease symptoms. In some such embodiments, the change comprises a stabilization in the health of the cone cells and/or a reduction in the rate of visual acuity loss of the mammal. In certain such embodiments, the change comprises an improvement in the health of the cone cells and/or an improvement in the visual acuity of the mammal.

BRIEF DESCRIPTION OF THE DRAWINGS

The novel features of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7 illustrates robust and cone-specific gene expression in the cones of a mouse retina following intravitreal injection of AAV-delivery MNTC.GFP. (a-b) Examples of GFP fluorescence 11 weeks after mice received intravitreal injections of $5.04 \times 10^{10}$ vector genomes via intravitreal injection. (c-e) retinas were harvested for histology 14 weeks after injection and cone outersegments were labeled with an antibody to L/M opsin (red). In (c) the red channel is turned off so only the native GFP is visible, (d) is the same image with the red channel on to allow visualization of cone outersegments. Comparison of (c) and (d) shows that most if not all cones were transduced by the virus. (e) Image from the same retina as in c and d from different angle showing profiles of cone photoreceptors.

Figures 1A, 1B:
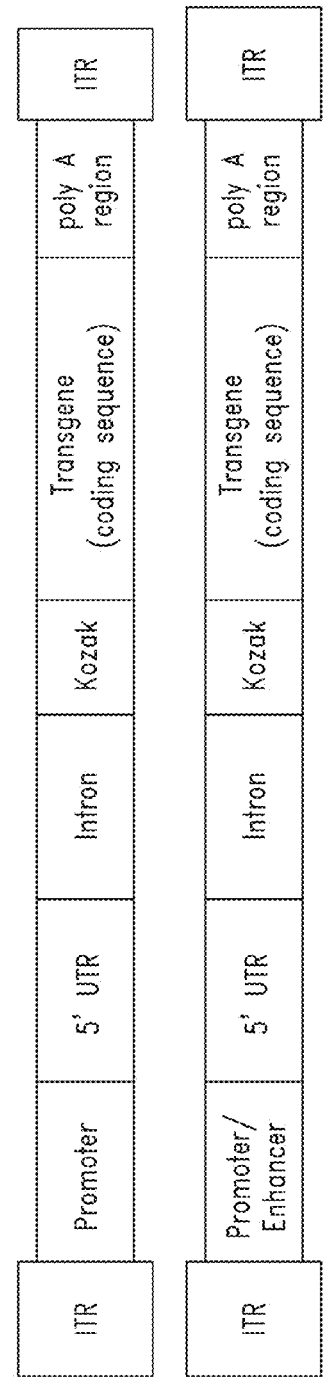
FIG. 1A depicts the schematic overview of polynucleotide cassettes for enhanced expression of a transgene in cone cells.
FIG. 1B depicts a schematic overview of viral vectors comprising polynucleotide cassettes for enhanced expression of a transgene in cone cells.
Figure 2:
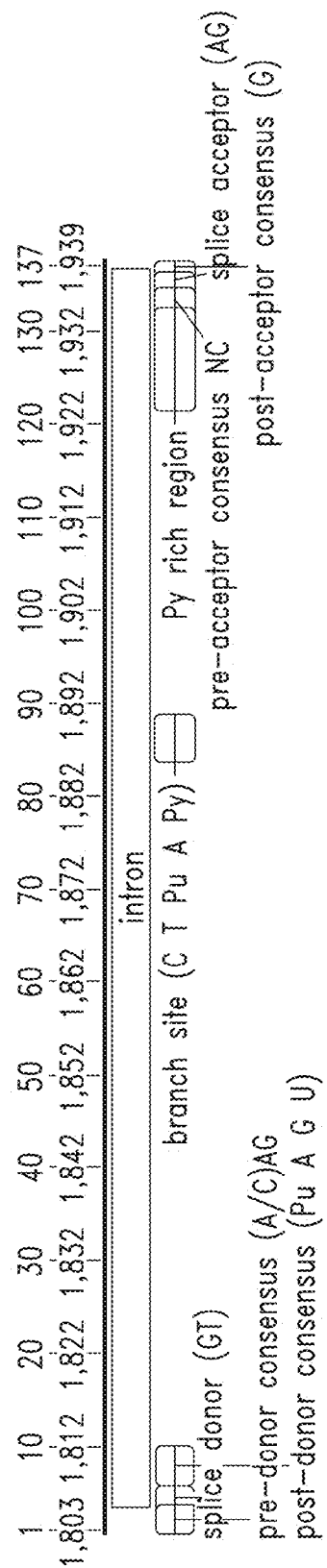
FIG. 2 depicts an example intron containing canonical features, including consensus sequences for the splice donor (A/C) A G G T Pu A G U; branch site C T Pu A Py; Py-rich region; and acceptor N C A G G.

7m8.MNTC.GFP into animals 271 and 472; AAV2-7m8.pR2.1.GFP into animals 500 and 509). Retinas were visualized in vivo at (a) 2 weeks, (b) 4 weeks, (c) 8 weeks, and (d) 12 weeks for GFP using a fundus fluorescence camera (a, b, c, d) or autofluorescence on Heidelberg Spectralis OCT (a, b; data not shown for weeks 8 and 12). OD, oculus dexter (right eye). OS, oculus sinister (left eye).

FIGS. 10A-10D demonstrate the contribution of each of the optimized pMNTC elements to the more robust expression observed. (a) The pMNTC and pR2.1 expression cassettes. (b) The experimental expression cassettes, in which each element in pMNTC is replaced one-by-one by the corresponding element in pR2.1. (c,d) Expression of the luciferase transgene in the retinas of gerbils intravitreally injected with each of the test articles (n=6-8 eyes per construct) as detected (c) 4 weeks and (d) 8 weeks after injection by IVIS imaging. "7m8.CMV" served as the positive control.

DEFINITIONS

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes, and other gene delivery vehicles.

The term "AAV" is an abbreviation for adeno-associated virus, and may be used to refer to the virus itself or derivatives thereof. The term covers all subtypes and both naturally occurring and recombinant forms, except where required otherwise. The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as a "rAAV vector particle" or simply a "rAAV vector". Thus, production of rAAV particle necessarily includes production of rAAV vector, as such a vector is contained within a rAAV particle.

The term "replication defective" as used herein relative to an AAV viral vector of the invention means the AAV vector cannot independently replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate further.

An "AAV variant" or "AAV mutant" as used herein refers to a viral particle composed of: a) a variant AAV capsid protein, where the variant AAV capsid protein comprises at least one amino acid difference (e.g., amino acid substitution, amino acid insertion, amino acid deletion) relative to a corresponding parental AAV capsid protein, and where the variant capsid protein confers increased infectivity of a retinal cell compared to the infectivity of the retinal cell by an AAV virion comprising the corresponding parental AAV capsid protein, where the AAV capsid protein does not comprise an amino acid sequence present in a naturally occurring AAV capsid protein; and b) a heterologous nucleic acid comprising a nucleotide sequence encoding a heterologous gene product.

The abbreviation "rAAV" refers to recombinant adeno-associated virus, also referred to as a recombinant AAV vector (or "rAAV vector"). A "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

As used herein, the term "gene" or "coding sequence" refers to a nucleotide sequence in vitro or in vivo that encodes a gene product. In some instances, the gene consists or consists essentially of coding sequence, that is, sequence that encodes the gene product. In other instances, the gene comprises additional, non-coding, sequence. For example, the gene may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, a "therapeutic gene" refers to a gene that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

As used herein, a transgene is a gene that is delivered to a cell by a vector.

As used herein, the term "gene product" refers to the desired expression product of a polynucleotide sequence such as a polypeptide, peptide, protein or interfering RNA including short interfering RNA (siRNA), miRNA or small hairpin RNA (shRNA).

As used herein, the terms "polypeptide," "peptide," and "protein" refer to polymers of amino acids of any length. The terms also encompass an amino acid polymer that has been modified; for example, disulfide bond formation, glycosylation, lipidation, phosphorylation, or conjugation with a labeling component.

By "comprising" it is meant that the recited elements are required in, for example, the composition, method, kit, etc., but other elements may be included to form the, for example, composition, method, kit etc. within the scope of the claim. For example, an expression cassette "comprising" a gene encoding a therapeutic polypeptide operably linked to a promoter is an expression cassette that may include other elements in addition to the gene and promoter, e.g. polyadenylation sequence, enhancer elements, other genes, linker domains, etc.

By "consisting essentially of", it is meant a limitation of the scope of the, for example, composition, method, kit, etc., described to the specified materials or steps that do not materially affect the basic and novel characteristic(s) of the, for example, composition, method, kit, etc. For example, an expression cassette "consisting essentially of" a gene encoding a therapeutic polypeptide operably linked to a promoter and a polyadenylation sequence may include additional sequences, e.g. linker sequences, so long as they do not materially affect the transcription or translation of the gene. As another example, a variant, or mutant, polypeptide fragment "consisting essentially of" a recited sequence has the amino acid sequence of the recited sequence plus or minus about 10 amino acid residues at the boundaries of the sequence based upon the full length naïve polypeptide from which it was derived, e.g. 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of", it is meant the exclusion from the composition, method, or kit of any element, step, or ingredient not specified in the claim. For example, an expression cassette "consisting of" a gene encoding a therapeutic polypeptide operably linked to a promoter, and a polyadenylation sequence consists only of the promoter, polynucleotide sequence encoding the therapeutic polypeptide, and polyadenyation sequence. As another example, a polypeptide "consisting of" a recited sequence contains only the recited sequence.

As used herein, the terms "sequence identity," e.g. "% sequence identity," refers to the degree of identity between two or more polynucleotides when aligned using a nucleotide sequence alignment program; or between two or more polypeptide sequences when aligned using an amino acid sequence alignment program. Similarly, the term "identical" or percent "identity" when used herein in the context of two or more nucleotide or amino acid sequences refers to two sequences that are the same or have a specified percentage of amino acid residues or nucleotides when compared and aligned for maximum correspondence, for example as measured using a sequence comparison algorithm, e.g. the Smith-Waterman algorithm, etc., or by visual inspection. For example, the percent identity between two amino acid sequences may be determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. As another example, the percent identity between two nucleotide sequences may be determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4. The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, Nucleic Acids Res, 25: 3389-3402). When utilizing BLAST and Gapped BLAST programs, the default parameters of the respective programs (e.g., XBLAST and NBLAST) can be used.

The term "% homology" is used interchangeably herein with the term "% identity" herein and refers to the level of nucleic acid or amino acid sequence identity between two or more aligned sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence.

As used herein, the terms "complement" and "complementary" refer to two antiparallel nucleotide sequences capable of pairing with one another upon formation of hydrogen bonds between the complementary base residues in the antiparallel nucleotide sequences. For example, an shRNA might be complementary, i.e. 100% complementary, or substantially complementary, e.g. 80% complementary, 85% complementary, 90% complementary, 95% complementary, 98% complementary, or more to a target sequence. The term "expression" as used herein encompasses the transcription and/or translation of an endogenous gene, a transgene or a coding sequence in a cell.

An "expression vector" as used herein encompasses a vector, e.g. plasmid, minicircle, viral vector, liposome, and the like as discussed above or as known in the art, comprising a polynucleotide which encodes a gene product of interest, and is used for effecting the expression of a gene product in an intended target cell. An expression vector also comprises control elements operatively linked to the encoding region to facilitate expression of the gene product in the target. The combination of control elements, e.g. promoters, enhancers, UTRs, miRNA targeting sequences, etc., and a gene or genes to which they are operably linked for expression is sometimes referred to as an "expression cassette." Many such control elements are known and available in the art or can be readily constructed from components that are available in the art.

A "promoter" as used herein encompasses a DNA sequence that directs the binding of RNA polymerase and thereby promotes RNA synthesis, i.e., a minimal sequence sufficient to direct transcription. Promoters and corresponding protein or polypeptide expression may be ubiquitous, meaning strongly active in a wide range of cells, tissues and species or cell-type specific, tissue-specific, or species specific. Promoters may "constitutive," meaning continually active, or "inducible," meaning the promoter can be activated or deactivated by the presence or absence of biotic or abiotic factors. Also included in the nucleic acid constructs or vectors of the invention are enhancer sequences that may or may not be contiguous with the promoter sequence. Enhancer sequences influence promoter-dependent gene expression and may be located in the 5' or 3' regions of the native gene.

An "enhancer" as used herein encompasses a cis-acting element that stimulates or inhibits transcription of adjacent genes. An enhancer that inhibits transcription also is termed a "silencer". Enhancers can function (i.e., can be associated with a coding sequence) in either orientation, over distances of up to several kilobase pairs (kb) from the coding sequence and from a position downstream of a transcribed region.

A "termination signal sequence" as used herein encompasses any genetic element that causes RNA polymerase to terminate transcription, such as for example a polyadenylation signal sequence.

A "polyadenylation signal sequence" as used herein encompasses a recognition region necessary for endonuclease cleavage of an RNA transcript that is followed by the polyadenylation consensus sequence AATAAA. A polyadenylation signal sequence provides a "polyA site", i.e. a site on a RNA transcript to which adenine residues will be added by post-transcriptional polyadenylation.

As used herein, the terms "operatively linked" or "operably linked" refers to a juxtaposition of genetic elements, e.g. promoter, enhancer, termination signal sequence, polyadenylation sequence, etc., wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained. As used herein, the term "heterologous" means derived from a genotypically distinct entity from that of the rest of the entity to which it is being compared. For example, a polynucleotide introduced by genetic engineering techniques into a plasmid or vector derived from a different species is a heterologous polynucleotide. As another example, a promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The term "endogenous" as used herein with reference to a nucleotide molecule or gene product refers to a nucleic acid sequence, e.g. gene or genetic element, or gene product, e.g. RNA, protein, that is naturally occurring in or associated with a host virus or cell.

The term "native" as used herein refers to a nucleotide sequence, e.g. gene, or gene product, e.g. RNA, protein, that is present in a wildtype virus or cell. The term "variant" as used herein refers to a mutant of a reference polynucleotide or polypeptide sequence, for example a native polynucleotide or polypeptide sequence, i.e. having less than 100% sequence identity with the reference polynucleotide or polypeptide sequence. Put another way, a variant comprises at least one amino acid difference (e.g., amino acid substitution, amino acid insertion, amino acid deletion) relative to a reference polynucleotide sequence, e.g. a native polynucleotide or polypeptide sequence. For example, a variant may be a polynucleotide having a sequence identity of 70% or more with a full length native polynucleotide sequence, e.g. an identity of 75% or 80% or more, such as 85%, 90%, or 95% or more, for example, 98% or 99% identity with the full length native polynucleotide sequence. As another example, a variant may be a polypeptide having a sequence identity of 70% or more with a full length native polypeptide sequence, e.g. an identity of 75% or 80% or more, such as 85%, 90%, or 95% or more, for example, 98% or 99% identity with the full length native polypeptide sequence. Variants may also include variant fragments of a reference, e.g. native, sequence sharing a sequence identity of 70% or more with a fragment of the reference, e.g. native, sequence, e.g. an identity of 75% or 80% or more, such as 85%, 90%, or 95% or more, for example, 98% or 99% identity with the native sequence.

As used herein, the terms "biological activity" and "biologically active" refer to the activity attributed to a particular biological element in a cell. For example, the "biological activity" of an "immunoglobulin", "antibody" or fragment or variant thereof refers to the ability to bind an antigenic determinant and thereby facilitate immunological function. As another example, the biological activity of a polypeptide or functional fragment or variant thereof refers to the abilty of the polypeptide or functional fragment or variant thereof to carry out its native functions of, e.g., binding, enzymatic activity, etc. As a third example, the biological activity of a gene regulatory element, e.g. promoter, enhancer, kozak sequence, and the like, refers to the ability of the regulatory element or functional fragment or variant thereof to regulate, i.e. promote, enhance, or activate the translation of, respectively, the expression of the gene to which it is operably linked.

The terms "administering" or "introducing", as used herein refer to delivery of a vector for recombinant protein expression to a cell, to cells and/or organs of a subject, or to a subject. Such administering or introducing may take place in vivo, in vitro or ex vivo. A vector for expression of a gene product may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

"Transformation" is typically used to refer to bacteria comprising heterologous DNA or cells which express an oncogene and have therefore been converted into a continuous growth mode such as tumor cells. A vector used to "transform" a cell may be a plasmid, virus or other vehicle.

Typically, a cell is referred to as "transduced", "infected"; "transfected" or "transformed" dependent on the means used for administration, introduction or insertion of heterologous DNA (i.e., the vector) into the cell. The terms "transduced", "transfected" and "transformed" may be used interchangeably herein regardless of the method of introduction of heterologous DNA.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

The terms "treatment", "treating" and the like are used herein to generally mean obtaining a desired pharmacologic and/or physiologic effect. The effect may be prophylactic in terms of completely or partially preventing a disease or symptom thereof, e.g. reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b)

inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The various compositions and methods of the invention are described below. Although particular compositions and methods are exemplified herein, it is understood that any of a number of alternative compositions and methods are applicable and suitable for use in practicing the invention. It will also be understood that an evaluation of the expression constructs and methods of the invention may be carried out using procedures standard in the art.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

All publications mentioned herein are incorporated herein by reference to disclose and describe the methods and/or materials in connection with which the publications are cited. It is understood that the present disclosure supersedes any disclosure of an incorporated publication to the extent there is a contradiction.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing-herein is to be construed as an admission that the present invention is not entitled to antedate such publication by virtue of prior invention. Further, the dates of publication provided may be different from the actual publication dates which may need to be independently confirmed.

Unless otherwise indicated, all terms used herein have the same meaning as they would to one skilled in the art and the practice of the present invention will employ, conventional techniques of microbiology and recombinant DNA technology, which are within the knowledge of those of skill of the art.

DETAILED DESCRIPTION OF THE INVENTION

The present disclosure provides polynucleotide cassettes and expression vectors for the expression of a gene in cone cells. Also provided are methods for the use of these compositions in promoting the expression of a gene in cone cells, for example, in an individual, e.g. for the treatment or prophylaxis of a cone cell disorder. These and other objects, advantages, and features of the invention will become apparent to those persons skilled in the art upon reading the details of the compositions and methods as more fully described below.

Compositions

In some aspects of the disclosure, compositions are provided for the expression of a transgene in cone cells. By a "cone cell", also referred to herein as a "cone photoreceptor" or "cone", it is meant the subtype of photoreceptor cells in the retina of the eye that function best in relatively bright light. Cones are sensitive to specific wavelengths of light and hence support the perception of color. In addition, cones respond faster to stimuli than rod photoreceptors, perceiving finer detail and more rapid changes in images than rods, and hence, support high acuity vision for activities where visual detail is of primary importance such as reading and driving. Cones are readily identifiable in cross-sections of the retina by the cone-like shape of their outer segments. They are also readily identifiable by their location in the retina, the highest density of cones existing at the 1.5 mm depression located in the center of the macula of the retina, called the "fovea centralis" or "foveal pit".

In some embodiments of the disclosure, the composition that provides for the expression of a transgene in cone cells is a polynucleotide cassette. By a "polynucleotide cassette" it is meant a polynucleotide sequence comprising two or more polynucleotide sequences, e.g. regulatory elements, translation initiation sequences, coding sequences, termination sequences, etc., typically in operably linkage to one another. Likewise, by a "polynucleotide cassette for the expression of a transgene in a cone cell," it is meant a combination of two or more polynucleotide sequences, e.g. promoter, enhancer, 5'UTR, translation initiation sequence, coding sequence, termination sequences, etc. that promotes the expression of the transgene in a cone cell.

For example, in some embodiments, the polynucleotide cassette comprises:
  (a) a promoter region, wherein the promoter region promotes the expression of a coding sequence in cone cells; and
  (b) a coding sequence operatively linked to the promoter region.

As another example, in some embodiments, the polynucleotide cassette comprises:
  (a) a promoter region, wherein the promoter region promotes the expression of a coding sequence in retinal cone cells;
  (b) a translation initiation sequence; and
  (c) a coding sequence operatively linked to the promoter region.

As a third example, in some embodiments, the polynucleotide cassette comprises:
  (a) a promoter region, wherein the promoter region promotes the expression of a coding sequence in retinal cone cells;
  (b) a 5' untranslated region;
  (c) a translation initiation sequence; and
  (d) a coding sequence operatively linked to the promoter region.

As a fourth example, in some embodiments, the polynucleotide cassette comprises:
  (a) a promoter region, wherein the promoter region promotes the expression of a coding sequence in retinal cone cells;
  (b) a 5' untranslated region;
  (c) an intron;
  (d) a translation initiation sequence; and
  (e) a coding sequence operatively linked to the promoter region.

As a fifth example, in some embodiments, the polynucleotide cassette comprises:
  (a) a promoter region, wherein the promoter region promotes the expression of a coding sequence in retinal cone cells;
  (b) a 5' untranslated region;
  (c) an intron;
  (d) a translation initiation sequence; and
  (e) a polyadenylation sequence.

In some embodiments, the polynucleotide cassettes of the present disclosure provide for enhanced expression of a transgene in cone cells. As demonstrated by the working examples of the present disclosure, the present inventors have discovered a number of polynucleotide elements, i.e. improved elements as compared to those known in the art, which individually and synergistically provide for the enhanced expression of transgenes in cone cells. By "enhanced" it is meant that expression of the transgene is increased, augmented, or stronger, in cone cells carrying the polynucleotide cassettes of the present disclosure relative to in cone cells carrying the transgene operably linked to comparable regulatory elements, e.g. as known in the art. Put another way, expression of the transgene is increased, augmented, or stronger, from the polynucleotide cassettes of the present disclosure relative to expression from a polynucleotide cassette not comprising the one or more optimized elements of the present disclosure, i.e. a reference control. For example, expression of the transgene is enhanced, or augmented, or stronger, in cone cells comprising a polynucleotide cassette comprising a promoter disclosed herein than in cone cells that carry the transgene operably linked to a different promoter, e.g. as known in the art. As another example, expression of the transgene is enhanced, or increased, augmented, or stronger, in cone cells comprising a polynucleotide cassette comprising an enhancer sequence disclosed herein than in cone cells that carry the transgene operably linked to a different enhancer sequence. As another example, expression of the transgene is enhanced, or increased, augmented, or stronger, in cone cells comprising a polynucleotide cassette encoding a 5'UTR disclosed herein than in cone cells that carry the transgene operably linked to a different 5'UTR coding sequence. As another example, expression of the transgene is enhanced, or increased, augmented, or stronger, in cone cells comprising a polynucleotide cassette comprising an intron as disclosed herein than in cone cells that carry the transgene operably linked to a different intronic sequence as known in the art. Exemplary sequences comprising elements (e.g., promoters, enhancer sequences, 5'UTRs, and intons) that may be used as references for comparison include sequences encompassed by the native L-opsin promoter (SEQ ID NO:1) and variants thereof, sequences encompassed by the synthetic promoter pR2.1 (SEQ ID NO:50) and variants thereof (e.g. pR1.7, pR1.5, pR1.1) as disclosed in, e.g. US Application No. 2013/0317091, and sequences encompassed by the IRBP/GNAT2 promoter (US Application No. 2014/0275231).

Without wishing to be bound by theory, enhanced expression of a transgene in cells is believed to be due to a faster build-up of gene product in the cells or a more stable gene product in the cells. Thus, enhanced expression of a transgene by the polynucleotide cassettes of the subject disclosure may be observed in a number of ways. For example, enhanced expression may be observed by detecting the expression of the transgene following contact of the polynucleotide cassette to the cone cells sooner, e.g. 7 days sooner, 2 weeks sooner, 3 weeks sooner, 4 weeks sooner, 8 weeks sooner, 12 weeks sooner, or more, than expression would be detected if the transgene were operably linked to comparable regulatory elements, e.g. as known in the art. Enhanced expression may also be observed as an increase in the amount of gene product per cell. For example, there may be a 2-fold increase or more, e.g. a 3-fold increase or more, a 4-fold increase or more, a 5-fold increase or more, or a 10-fold increase or more in the amount of gene product per cone cell. Enhanced expression may also be observed as an increase in the number of cone cells that express detectable levels of the transgene carried by the polynucleotide cassette. For example, there may be a 2-fold increase or more, e.g. a 3-fold increase or more, a 4-fold increase or more, a 5-fold increase or more, or a 10-fold increase or more in the number of cone cells that express detectable levels of the transgene. As another example, the polynucleotide of the present invention may promote detectable levels of the transgene in a greater percentage of cells as compared to a conventional polynucleotide cassette; for example, where a conventional cassette may promote detectable levels of transgene expression in, for example, less than 5% of the cone cells in a certain region, the polynucleotide of the present invention promotes detectable levels of expression in 5% or more of the cone cells in that region; e.g. 10% or more, 15% or more, 20% or more, 25% or more, 30% or more, 35% or more, 40% or more, or 45% or more, in some instances 50% or more, 55% or more; 60% or more, 65% or more, 70% or more, or 75% or more, for example 80% or more, 85% or more, 90% or more, or 95% or more of the cone cells that are contacted, will express detectable levels of gene product. Enhanced expression may also be observed as an alteration in the viability and/or function of the cone cells, e.g. as measured using assessment tools such as fundus photography, OCT, adaptive optics, cERG, color vision tests, visual acuity tests, and the like, as known in the art and as described herein.

The polynucleotide cassettes of the present disclosure typically comprise a promoter region. Any suitable promoter region or promoter sequence therein can be used in the subject polynucleotide cassettes, so long as the promoter region promotes expression of a coding sequence in retinal cone cells. In some embodiments, the promoter specifically promotes expression of the gene in mammalian retinal cone cell; more preferably primate retinal cone cells; more preferably in Catarrhini retinal cone cells; even more preferably in human retinal cone cells. By "specifically" it is meant that the promoter predominately promotes expression of the gene in the target cells as compared to other cell types. Thus, for example, when a promoter region that specifically promotes expression in cone cells is employed, more than 50% of the expression, for example, at least any of 60%, 65%, 70% or 75% or more of the expression, e.g. at least any of 80%, 85%, 90%, 91%, 92%, 93%, 94%, 95%, 96%, 97%, 97%, 98%, 99%, 99.5%, or more of expression of the gene after delivery of the subject polunucleotide cassette to the eye will be in cone cells.

Exemplary suitable promoter regions include the promoter region for any cone-specific gene, such as a 492 L-opsin promoter region (SEQ ID NO:1), a 491 L-opsin promoter region (SEQ ID NO:53), a 496 L-opsin promoter region (SEQ ID NO:79), an M-opsin promoter region (SEQ ID NO:2, SEQ ID NO:54), a minimal M-opsin promoter region (SEQ ID NO:55, SEQ ID NO:93), a core M-opsin promoter sequence as disclosed for the first time herein (SEQ ID NO:80), an S-opsin promoter region (SEQ ID NO:3), an hRK promoter region, and a cone arrestin promoter region; or portions or variants thereof which retain activity promoting the expression of a gene in cone cells. Nonlimiting examples of portions, or fragments, of promoter regions that find use in the subject polynucleotide cassetttes include promoter sequence immediately upstream of the 5'UTR, and canonical binding sequences for transcription factors as known in the art. Such portions, or fragments, may be readily determined using any convenient method as known in the art or described herein. For example, the promoter sequence immediately upstream of the 5'UTR in SEQ ID NO:54 and SEQ ID NO:55 may readily determined by in silico evaluation of the sequence as consisting essentially of nucleotides 1-406 of SEQ ID NO:54 or nucleotides 1-154 of SEQ ID NO:55 using publicly available tools such as, e.g. the UCSC genome BLAT browser; or by empirical testing through operable linkage with a reporter gene and introduction into cone cells, e.g. as described in the working examples herein. Shorter promoter sequences are, in some embodiments, preferable to longer promoter sequences, as they provide for more space in the vector for other nucleotide elements. In some embodiments, the promoter region is less than 492 base pairs in length. For example, in some embodiments, the functional fragment does not comprise nucleotides 1-10 or more of SEQ ID NO:1, for example, the functional fragment does not comprise nucleotides 1-20 or more, nucleotides 1-30 or more, nucleotides 1-40 or more, nucleotides 1-50 or more of SEQ ID NO:1, e.g. nucleotides 1-60 or more, nucleotides 1-70 or more, nucleotides 1-80 or more, nucleotides 1-90 or more, nucleotides 1-100 or more of SEQ ID NO:1, in some instances nucleotides 1-120 or more, nucleotides 1-140 or more, nucleotides 1-160 or more, nucleotides 1-180 or more, nucleotides 1-200 or more, nucleotides 1-220 or more, nucleotides 1-240 or more, or about nucleotides 1-260 of SEQ ID NO:1. Any suitable method for identifying a promoter region capable of driving expression in mammalian or primate cone cells can be used to identify promoter regions and promoter sequences therein that find use in the polynucleotide cassettes of the present disclosure.

In some embodiments, the promoter region of the subject polynucleotide cassette comprises one of the promoter regions disclosed herein, e.g. a 492 L-opsin promoter region (SEQ ID NO:1), a 491 L-opsin promoter region (SEQ ID NO:53), a 496 L-opsin promoter region (SEQ ID NO:79), an M opsin promoter region (SEQ ID NO:2, SEQ ID NO:54), a minimal M opsin promoter region (SEQ ID NO:55, SEQ ID NO:93), the core M-opsin promoter sequence disclosed herein (SEQ ID NO:80), or the S opsin promoter region (SEQ ID NO:3), or a functional fragment or variant thereof, e.g. a sequence having an identity of 75% or more, e.g. 80% or more, 85% or more, 90% or more, or 95% or more, (e.g., 80%, 85%, 90% Or 95%), to an aforementioned sequence or functional fragment thereof. In some embodiments, the promoter sequence of the subject polynucleotide cassette consists essentially of one of the promoter regions disclosed herein, i.e. SEQ ID NO:1, SEQ ID NO:53, SEQ ID NO:79, SEQ ID NO:2, SEQ ID NO:54, SEQ ID NO:55, SEQ ID NO:93, SEQ ID NO:80, or SEQ ID NO:3, or a functional fragment or variant thereof, e.g. a sequence having an identity of 75% or more, e.g. 80%, or more 85% or more, 90% or more, or 95% or more, (e.g., 80%, 85%, 90% Or 95%), to the full length of an aforementioned sequence plus or minus 1, 2, 3, 4, 5, 6, 7, 8, 9, or 10 nucleotides, or functional fragment thereof. In some embodiments, the promoter region of the subject polynucleotide cassette consists of one of the promoter regions disclosed herein, i.e. SEQ ID NO:1, SEQ ID NO:53, SEQ ID NO:79, SEQ ID NO:2, SEQ ID NO:54, SEQ ID NO:55, SEQ ID NO:93, SEQ ID NO:80, or SEQ ID NO:3, or a functional fragment or variant thereof, e.g. a sequence having an identity of 75% or more, e.g. 80%, 85%, 90%, 95% or more, to the full length of an aforementioned sequence or functional fragment thereof. In certain embodiments, the promoter region consists essentially of SEQ ID NO:74. In some such embodiments, the promoter sequence consists essentially of SEQ ID NO:80. In some embodiments, the promoter results in enhanced expression in cone cells compared to other promoters known in the art, e.g., the synthetic promoters pR2.1, pR1.7, pR1.1, and IRBP/GNAT2.

In some embodiments, the polynucleotide cassette further comprises an enhancer element. Enhancers are nucleic acid elements known in the art to enhance transcription, and can be located anywhere in association with the gene they regulate, e.g. upstream, downstream, within an intron, etc. Any enhancer element can be used in the polynucleotide cassettes and gene therapy vectors of the present disclosure, so long as it enhances expression of the gene when used in combination with the promoter. In a preferred embodiment, the enhancer element is specific for retinal cone cells; more preferably, it is specific for primate retinal cone cells; more preferably in Catarrhini retinal cone cells; even more preferably in human retinal cone cellsBy "specifically" it is meant that the enhancer predominately enhances expression of the gene in the target cells compared to other cell types. Thus, for example, when an enhancer that specifically enhances expression in cone cells is employed, more than 50% of the expression, for example, at least any of 60%, 65%, 70%, 75% or more of the expression, e.g., at least 80%, and preferably 85%, 90%, 91%, 92%, 93%, 94%, 95%, 96%, 97%, 97%, 98%, 99%, 99.5%, or more of expression of the gene after delivery of the vector to the eye will be in cone cells.

Exemplary enhancer regions that find use in the polynucleotide cassettes of the present disclosure include those that comprise, consist essentially of, or consist of the enhancer region for any cone-specific gene or fragments or variants thereof which retain enhancer activity. For example, the L/M minimal opsin enhancer, referred to as the Locus Control Region (LCR) (Wang et al., 1992. Neuron 9: 429-440) (SEQ ID NO:52) can be used to enhance gene expression in cone cells; its absence results in blue cone monochromacy (Nathans et al., 1989; Science, 245: 831-838). The LCR has been shown to be useful in gene therapy, for example with AAV vectors (Li et al., Vision Research 48(2008): 332-338). Furthermore, a functional fragment consisting essentially of a 36 bp "core" LCR sequence has been identified that is necessary and sufficient for expression from the opsin promoter in cone cells (Komaromy et al. Targeting gene expression to cones with human cone opsin promoters in recombinant AAV. Gene Ther. 2008; 15(14): 1049-55) (SEQ ID NO:51). In some embodiments, the enhancer of the polynucleotide cassette comprises SEQ ID NO:51 or SEQ ID NO:52. In certain embodiments, the enhancer of the polynucleotide cassette consists essentially of SEQ ID NO:51 or SEQ ID NO:52.

L/M enhancer elements of 100, 200, 300, 400, 500, 600, 700, 800, 900, 1000, 1100, 1200, 1300, 1400, 1500, 1600, 1700, 1800, 1900, 2000, or more nucleotides that comprise one or more copies of the L/M minimal opsin enhancer, and the full L/M opsin enhancer, or other portions or variants thereof which retain activity enhancing expression of genes in a cone-specific manner find use in the present compositions. Any suitable method for identifying enhancer sequences capable of driving expression in primate cone cells can be used to identify such enhancers, as will be understood by those of skill in the art based on the teachings herein.

The length of the promoter and enhancer regions can be of any suitable length for their intended purpose, and the spacing between the promoter and enhancer regions can be any suitable spacing to promote cone-specific expression of the gene product. In various preferred embodiments, the enhancer is located 0-1500; 0-1250; 0-1000; 0-750; 0-600; 0-500; 0-400; 0-300; 0-200; 0-100; 0-90; 0-80; 0-70; 0-60; 0-50; 0-40; 0-30; 0-20; or 0-10 nucleotides upstream of the promoter. The promoter can be any suitable distance upstream of the encoded gene.

In some embodiments, the subject polynucleotide cassette comprises a sequence encoding a 5' untranslated region, i.e. polynucleotide sequence encoding an untranslated region 5' to the coding sequence, also called the 5'UTR. In an expression cassette, the 5'UTR is known in the art as the sequence between the transcription initiation site and the Kozak sequence where protein translation begins. Secondary mRNA structure of the 5'UTR is known to affect transcription levels. Specifically, for enhanced gene expression, the sequence of the 5'UTR region in the present invention is selected to minimize or avoid secondary structures and upstream AUG (uAUG) codons which are known to decrease translation efficiency due to inefficient ribosome scanning and false translational starts (Kozak, 1995. PNAS 92:2662). See Davuluri et al., Genome Research, 2000: 10 (11); 1807-1816. For example, the 5'UTR sequence from the human gene HSP70 (SEQ ID NO:58) has been identified for its unusual ability to enhance mRNA translation, possibly due to an IRES mechanism (Rubtsova et al., 2003. PNAS 278(25): 22350-22356; Vivinus et al, 2001. Eur J Biochem. 268: 1908-1917). Any 5' UTR can be used, but ideally the sequence of the 5'UTR has minimal secondary mRNA structure and upstream AUG sequences. Put another way, in some embodiments, the sequence between the transcription initiation site and the translation initiation site of the polynucleotide cassette does not contain the polynucleotide ATG. In some embodiments, the 5' UTR comprises, consists essentially, or consists of SEQ ID NO:56, SEQ ID NO:57, SEQ ID NO:58, SEQ ID NO:84, SEQ ID NO:85, SEQ ID NO:86, SEQ ID NO:87, SEQ ID NO:88, or SEQ ID NO:89; or a functional fragment or variant thereof, for example, a polynucleotide sequence having a sequence identity of 85% or more to a sequence selected from the group consisting of SEQ ID NO:56, SEQ ID NO:57, SEQ ID NO:58, SEQ ID NO:84, SEQ ID NO:85, SEQ ID NO:86, SEQ ID NO:87, SEQ ID NO:88, and SEQ ID NO:89, or a fragment thereof. In some embodiments, some or all of the 5'UTR sequence is comprised by a promoter region as disclosed in, for example, SEQ ID NO:1, SEQ ID NO:2, SEQ ID NO:3, SEQ ID NO:53, SEQ ID NO:54, SEQ ID NO:55, or SEQ ID NO:79. In other embodiments, the 5'UTR is not comprised by the promoter region; see, e.g. the core promoter sequence SEQ ID NO:84, which does not encode for 5' UTR sequence. In some embodiments, the 5'UTR sequence is heterologous to the promoter sequence. In various preferred embodiments, the 3' end of the UTR is 0-20; 0-15; 0-10; 0-9; 0-8; 0-7; 0-6; or 0-5 nucleotides upstream of the coding sequence, and its 5' end is 0-20; 0-15; 0-10; 0-9; 0-8; 0-7; 0-6; or 0-5 nucleotides downstream of the proximal promoter region. In some embodiments, the 5'UTR element results in enhanced expression in cone cells compared to other 5'UTRs known in the art, e.g., the 5'UTRs comprised by the synthetic promoters pR2.1, pR1.7, pR1.1, and IRBP/GNAT2.

In some embodiments, the subject polynucleotide cassette further comprises an intron comprising a splice donor/acceptor region. In some embodiments, the intron is located downstream of the promoter region and is located upstream of the translation initiation sequence of the gene, i.e. the intron is located within the 5'UTR. In other embodiments, the intron is located downstream of the translation initiation sequence of the gene, i.e. the intron is located within the coding sequence. As is generally known in the art, introns are DNA polynucleotides that are transcribed into RNA and removed during mRNA processing through intron splicing. Polynucleotide cassettes containing introns generally have higher expression than those without introns. Introns can stimulate expression between 2- and 500-fold (Buchman and Berg, 1988. *Mol Cel Bio,* 8(10): 4395). Efficiently spliced introns contain a pre-splice donor, branchpoint, and Py rich region (Senapathy et al, 1990; Meth. Enzymol. 183, 252-78; Wu and Krainer, 1999; Mol Cell Biol 19(5):3225-36). 5' introns are generally more efficient compared to introns at the 3' end (Huang and Gorman, 1990; Mol Cell Bio, 10:1805). Although introns are known generally to increase the level of gene expression, the specific increase (if any) of a given cDNA is empirical and must be tested; for example the chimeric intron in the pSI vector increases CAT expression by 21-fold, but luciferase expression by only 3-fold.

Any intron can be used in the subject polynucleotide cassettes, so long as it comprises a splice donor/acceptor region recognized in mammalian or in primate cone cells, so that the intron can be spliced out of the resulting mRNA product. In one embodiment, the intron comprises, consists essentially of, or consists of an SV40 intron according to SEQ ID NO:5. In another embodiment, the intron comprises, consists essentially of, or consists of the chimeric intron from pSI (SEQ ID NO:60) or a variant thereof. In another embodiment, the intron comprises, consists essentially of, or consists of the CMV intron A or a variant thereof. In yet another embodiment, the intron comprises, consists essentially of, or consists of the pR2.1 intron (SEQ ID NO:59) or a variant thereof, or alternatively, the rabbit or human beta globin intron (Xu et al, 2001, Gene 272:149; Xu et al. 2002; J Control Rel 81:155) or a variant thereof. In some such embodiments, the intron comprises a sequence having a sequence identity of 85% or more to a sequence selected from the group consisting of SEQ ID NO:5, SEQ ID NO:59, and SEQ ID NO:60. Typically, the intron is heterologous to the promoter region and/or the 5'UTR.

In some embodiments, the intron resides within a 5'UTR. In other words, the DNA sequence encoding the 5'UTR is interrupted by intronic DNA sequence. For example, the coding sequence for the 5'UTR that is SEQ ID NO:84 may be encoded in two parts, e.g. SEQ ID NO:85 and SEQ ID NO:86, with an intronic sequence between them. As another example, the coding sequences for the 5'UTR that is SEQ ID NO:88 may be encoded in two parts, e.g. SEQ ID NO:89 and SEQ ID NO:73, with an intronic sequence between them. In various embodiments, the 3' end of the intron is 0-20; 0-15; 0-10; 0-9; 0-8; 0-7; 0-6; or 0-5 nucleotides upstream of the gene, and its 5' end is 0-20; 0-15; 0-10; 0-9; 0-8; 0-7; 0-6; or 0-5 nucleotides downstream of the proximal promoter region. In other embodiments, the intron resides within the coding sequene of the gene.

In some embodiments, the polynucleotides cassettes of the present disclosure comprise a translation initiation sequence, also know as a "Kozak sequence" or "Kozak translation initiation sequence. This is the nucleic acid sequence where the ribosome attaches and translation begins. Examples include ACCATGG (Kozak, 1986. Cell, 44:283-292) and (GCC)GCC(A/G)CCATGG (Kozak, 1987. Nucl Acid Res; 15(20): 8125) (SEQ ID NO:73). Any suitable Kozak sequence can be used in the polynucleotide cassette, preferably selected to increase expression of the coding sequence in retinal cone cells. In one embodiment, the translation initiation sequence comprises SEQ ID NO:72. In an alternative embodiment, the translation initiation sequence comprises SEQ ID NO:73. In some embodiments, the Kozak element results in enhanced expression in cone cells compared to other Kozak sequences known in the art, e.g., the Kozak sequences comprised by the synthetic promoters pR2.1, pR1.7, pR1.1, and IRBP/GNAT2.

In some aspects of the present invention, the subject polynucleotide cassettes are used to deliver a gene to cone cells of an animal, e.g. to determine the effect that the gene has on cell viability and/or function, to treat a cone cell disorder, etc. Accordingly, in some embodiments, the polynucleotide cassettes of the present disclosure further comprise a gene to be delivered as a transgene to cone cells of an animal in vitro or in vivo. The gene coding sequence is typically operatively linked to the promoter region of the subject polynucleotide cassette, and in instances in which an an enhancer element is present, to the enhancer element of the subject polynucleotide cassette, such that the promoter and optionally enhancer elements promote the expression of the coding sequence or cDNA in cone cells of the subject.

The coding sequence to be expressed in the cone cells can be any polynucleotide sequence, e.g. gene or cDNA that encodes a gene product, e.g. polypeptide or RNA-based therapeutic (siRNA, antisense, ribozyme, shRNA, etc.). The coding sequence may be heterologous to the promoter sequence and/or 5'UTR sequence to which it is operably linked, i.e. not naturally operably associated with it. Alternatively, the coding sequence may be endogenous to the promoter sequence and/or 5'UTR sequence to which it is operably linked, i.e. is associated in nature with that promoter or 5'UTR. The gene product may act intrinsically in the cone cell, or it may act extrinsically, e.g. it may be secreted. For example, when the transgene is a therapeutic gene, the coding sequene may be any gene that encodes a desired gene product or functional fragment or variant thereof that can be used as a therapeutic for treating a cone cell disease or disorder, or as a means to otherwise enhance vision, including but not limited to promoting tetrachromatic color vision. In various preferred embodiments, the transgene encodes a therapeutic protein or functional fragment or variant thereof selected from the group consisting of:

(a) SEQ ID NO:7 (SEQ ID NO:6) *Homo sapiens* opsin 1 (cone pigments), short-wave-sensitive (OPN1SW), mRNA NCBI Reference Sequence: NM_001708.2;

(b) SEQ ID NO:9 (SEQ ID NO:8) *Homo sapiens* opsin 1 (cone pigments), medium-wave-sensitive (OPN1MW), mRNA NCBI Reference Sequence: NM_000513.2;

(c) SEQ ID NO:11 (SEQ ID NO:10) *Homo sapiens* opsin 1 (cone pigments), long-wave-sensitive (OPN1LW), mRNA NCBI Reference Sequence: NM_020061.4;

(d) SEQ ID NO:13 (SEQ ID NO:12) ATP binding cassette retina gene (ABCR) gene (NM_000350);

(e) SEQ ID NO:15 (SEQ ID NO:14) retinal pigmented epithelium-specific 65 kD protein gene (RPE65) (NM._000329);

(f) SEQ ID NO:17 (SEQ ID NO:16) retinal binding protein 1 gene (RLBP1) (NM._000326);

(g) SEQ ID NO:19 (SEQ ID NO:18) peripherin/retinal degeneration slow gene, (NM_000322);

(h) SEQ ID NO:21 (SEQ ID NO:20) arrestin (SAG) (NM_000541);

(i) SEQ ID NO:23 (SEQ ID NO:22) alpha-transducin (GNAT1) (NM_000172);

(j) SEQ ID NO:24 guanylate cyclase activator 1A (GUCA1A) (NP_000400.2);

(k) SEQ ID NO:25 retina specific guanylate cyclase (GUCY2D), (NP_000171.1);

(l) SEQ ID NO:26 & 27 alpha subunit of the cone cyclic nucleotide gated cation channel (CNGA3) (NP_001073347.1 or NP_001289.1);

(m) SEQ ID NO:28 Human cone transducin alpha subunit (incomplete achromotopsia);

(n) SEQ ID NO:29 cone cGMP-specific 3',5'-cyclic phosphodiesterase subunit alpha', protein (cone dystrophy type 4);
(o) SEQ ID NO:30 retinal cone rhodopsin-sensitive cGMP 3',5'-cyclic phosphodiesterase subunit gamma, protein (retinal cone dystrophy type 3A);
(p) SEQ ID NO:31 cone rod homeobox, protein (Cone-rod dystrophy);
(q) SEQ ID NO:32 cone photoreceptor cyclic nucleotide-gated channel beta subunit, protein (achromatopsia);
(r) SEQ ID NO:33 cone photoreceptor cGMP-gated cation channel beta-subunit, protein (total color blindness, for example, among Pingelapese Islanders);
(s) SEQ ID NO:35 (SEQ ID NO:34) retinitis pigmentosa 1 (autosomal dominant) (RP 1);
(t) SEQ ID NO:37 (SEQ ID NO:36) retinitis pigmentosa GTPase regulator interacting protein 1 (RPGRIP 1);
(u) SEQ ID NO:39 (SEQ ID NO:38) PRP8;
(v) SEQ ID NO:41 (SEQ ID NO:40) centrosomal protein 290 kDa (CEP290);
(w) SEQ ID NO:43 (SEQ ID NO:42) IMP (inosine 5'-monophosphate) dehydrogenase 1 (IMPDH1), transcript variant 1;
(x) SEQ ID NO:45 (SEQ ID NO:44) aryl hydrocarbon receptor interacting protein-like 1 (AIPL1), transcript variant 1;
(y) SEQ ID NO:47 (SEQ ID NO:46) retinol dehydrogenase 12 (all-trans/9-cis/11-cis) (RDH12);
(z) SEQ ID NO:49 (SEQ ID NO:48) Leber congenital amaurosis 5 (LCA5), transcript variant 1; and
(aa) exemplary OPN1LW/OPN1MW2 polymorphs (compared to OPN1LW (L opsin) polypeptide sequence; the amino acid to the left of the number is the residue present in the L opsin sequence; the number is the reside number in L opsin, and the reside to the right of the number is the variation from L opsin. Polymorphs according to these embodiments may comprise one or more of the amino acid substitutions selected from Thr65Ile; Ile111Val; Ser116Tyr; Leu153Met; Ile171Val; Ala174Val; Ile178Val; Ser180Ala; Ile230Thr; Ala233Ser; Val236Met; Ile274Val; Phe275Leu; Tyr277Phe; Val279Phe; Thr285Ala; Pro298Ala; Tyr309Phe;
(ab) Additional Opsin Sequence Variation 1 (SEQ ID NO:61);
(ac) Additional Opsin Sequence Variation 2 (SEQ ID NO:62);
(ad) Additional Opsin Sequence Variation 3 (SEQ ID NO:63);
(ae) Additional Opsin Sequence Variation 4 (SEQ ID NO:64);
(af) Additional Opsin Sequence Variation 5 (SEQ ID NO:65);
(ag) Additional Opsin Sequence Variation 6 (SEQ ID NO:65);
(ah) Additional Opsin Sequence Variation 7 (SEQ ID NO:66);
(ai) Additional Opsin Sequence Variation 8 (SEQ ID NO:67);
(aj) Additional Opsin Sequence Variation 9 (SEQ ID NO:68);
(ak) hCHR2 (channel rhodopsin) (SEQ ID NO:69);
(al) NpHR (halorhodopsin) (SEQ ID NO:70); and
(am) eGFP (SEQ ID NO:71).

In some embodiments, the coding sequence encoded by the transgene encodes a polypeptide having at least 85% sequence identity to a polypeptide encoded by a sequence disclosed above or herein, for example at least 90% sequence identity, e.g. at least 95% sequence identity, at least 98% sequence identity, or at least 99% sequence identity. Thus, for example, the coding sequence encodes a cone opsin having at least 85%, at least 90%, at least 95% identity, at least 98% sequence identity, or at least 99% sequence identity, to the polypeptide encoded by OPN1LW, OPN1MW, or OPN1SW. In some embodiments, the coding sequence has a sequence identity of at least 85%, 90%, 95%, 98% or at least 99% to SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, or SEQ ID NO:71.

The proteins recited in (a)-(c) and (aa-aj) are all involved in color vision. The exemplary polymorphs include ones at positions 65, 116, 180, 230, 233, 277, 285, and 309 that affect the spectra of the pigments in cone cells expressing them. Positions 274, 275, 277, 279, 285, 298 and 309 together distinguish L opsin from M opsin.

The proteins recited (d)-(z) are exemplary eye disease-associated genes such as in retinitis pigmentosa (polypeptides "e"-"l", "s"-"y"), incomplete achromatopsia (polypeptide "m"), Stargardt's (polypeptide "d"); Leber congenital amaurosis (polypeptide "z"); cone dystrophy, such as cone dystrophy type 4 (polypeptide "n"); retinal cone dystrophy; for example, retinal cone dystrophy type 3A (polypeptide "o"); Cone-rod dystrophy (polypeptide "p"); achromatopsia (polypeptide "q'); and total color blindness, for example, among Pingelapese Islanders (polypeptide "r").

In one embodiment of the invention, the transgene coding sequence is modified, or "codon optimized" to enhance expression by replacing infrequently represented codons with more frequently represented codons. The coding sequence is the portion of the mRNA sequence that encodes the amino acids for translation. During translation, each of 61 trinucleotide codons are translated to one of 20 amino acids, leading to a degeneracy, or redundancy, in the genetic code. However, different cell types, and different animal species, utilize tRNAs (each bearing an anticodon) coding for the same amino acids at different frequencies. When a gene sequence contains codons that are infrequently represented by the corresponding tRNA, the ribosome translation machinery may slow, impeding efficient translation. Expression can be improved via "codon optimization" for a particular species, where the coding sequence is altered to encode the same protein sequence, but utilizing codons that are highly represented, and/or utilized by highly expressed human proteins (Cid-Arregui et al., 2003; J. Virol. 77: 4928).

In one aspect of the present invention, the coding sequence of the transgene is modified to replace codons infrequently expressed in mammal or in primates with codons frequently expressed in primates. For example, in some embodiments, the coding sequence encoded by the transgene encodes a polypeptide having at least 85% sequence identity to a polypeptide encoded by a sequence disclosed above or herein, for example at least 90% sequence identity, e.g. at least 95% sequence identity, at least 98% identity, at least 99% identity, wherein at least one codon of the coding sequence has a higher tRNA frequency in humans than the corresponding codon in the sequence disclosed above or herein.

Figure 3A:
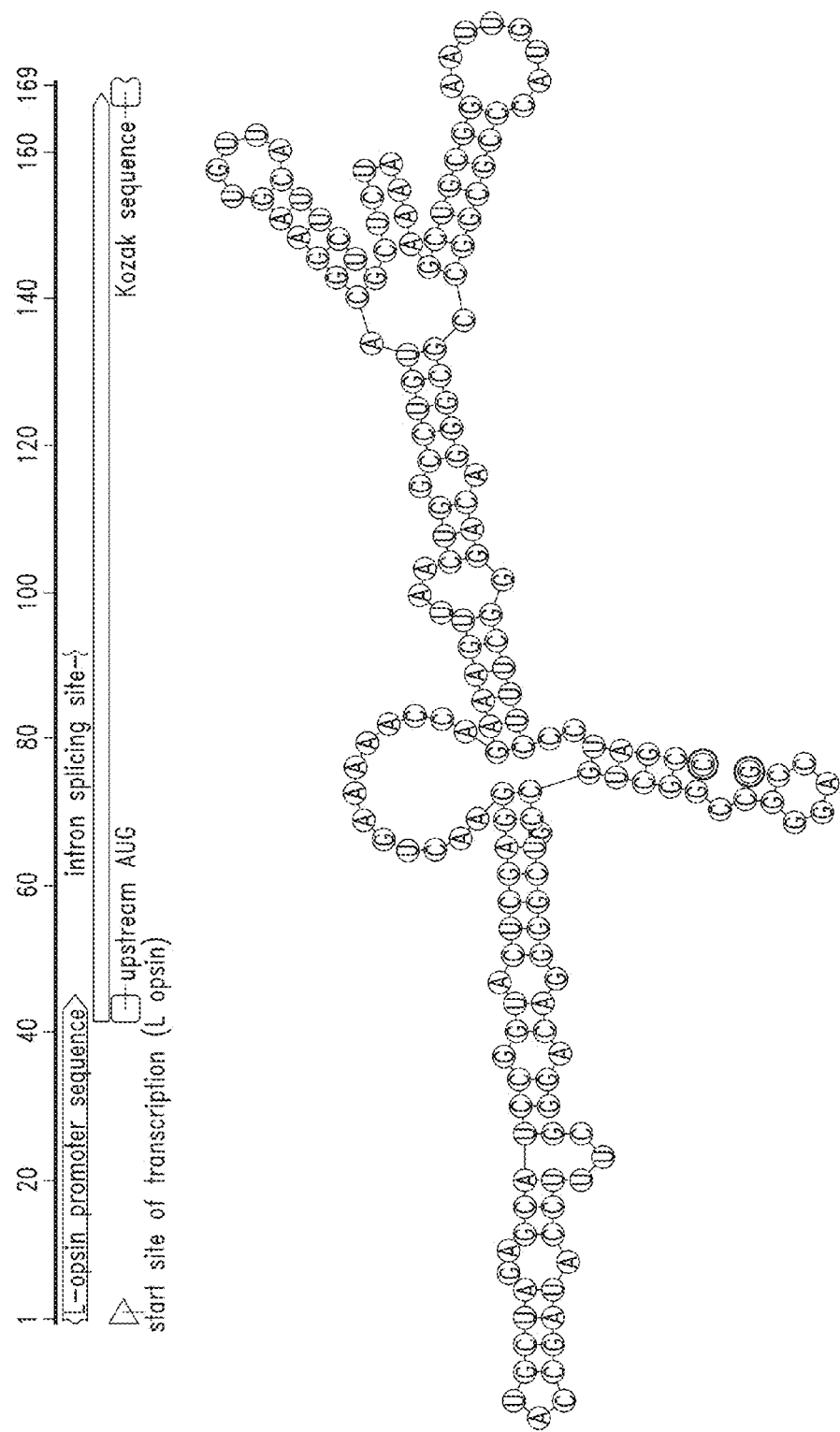
FIG. 3A depicts an example 5'UTR mRNA structure (SEQ ID NO:56), the 5'UTR mRNA structure from pR2.1 (Mancuso et al.). This 5' UTR has two upstream AUGs and open reading frames (ORF), a high level of base pairing and hairpin structure, and a shorter Kozak sequence.
Figure 3B:
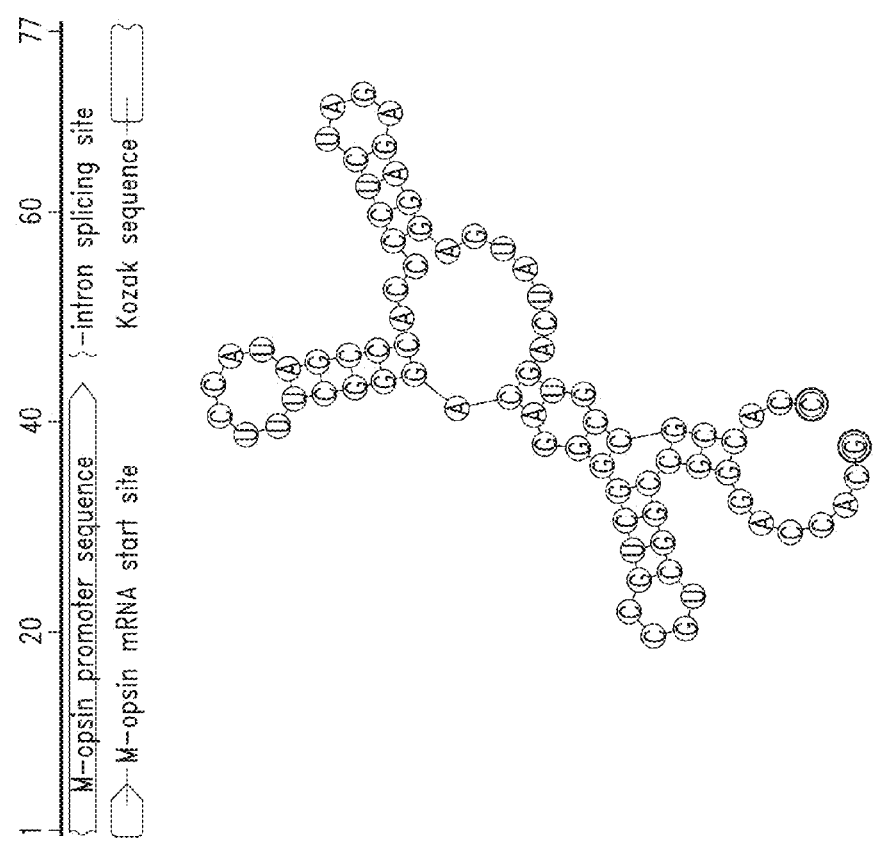
FIG. 3B depicts an example 5'UTR mRNA and structure (SEQ ID NO:57) from an optimized cassette of the present disclosure. The 5' UTR comprises no upstream AUG and no ORFs. In addition, as compared to the 5' UTR of FIG. 3A, the 5' UTR of FIG. 3B is shorter, with less base pairing; and the Kozak sequence is longer.
Figure 4A:
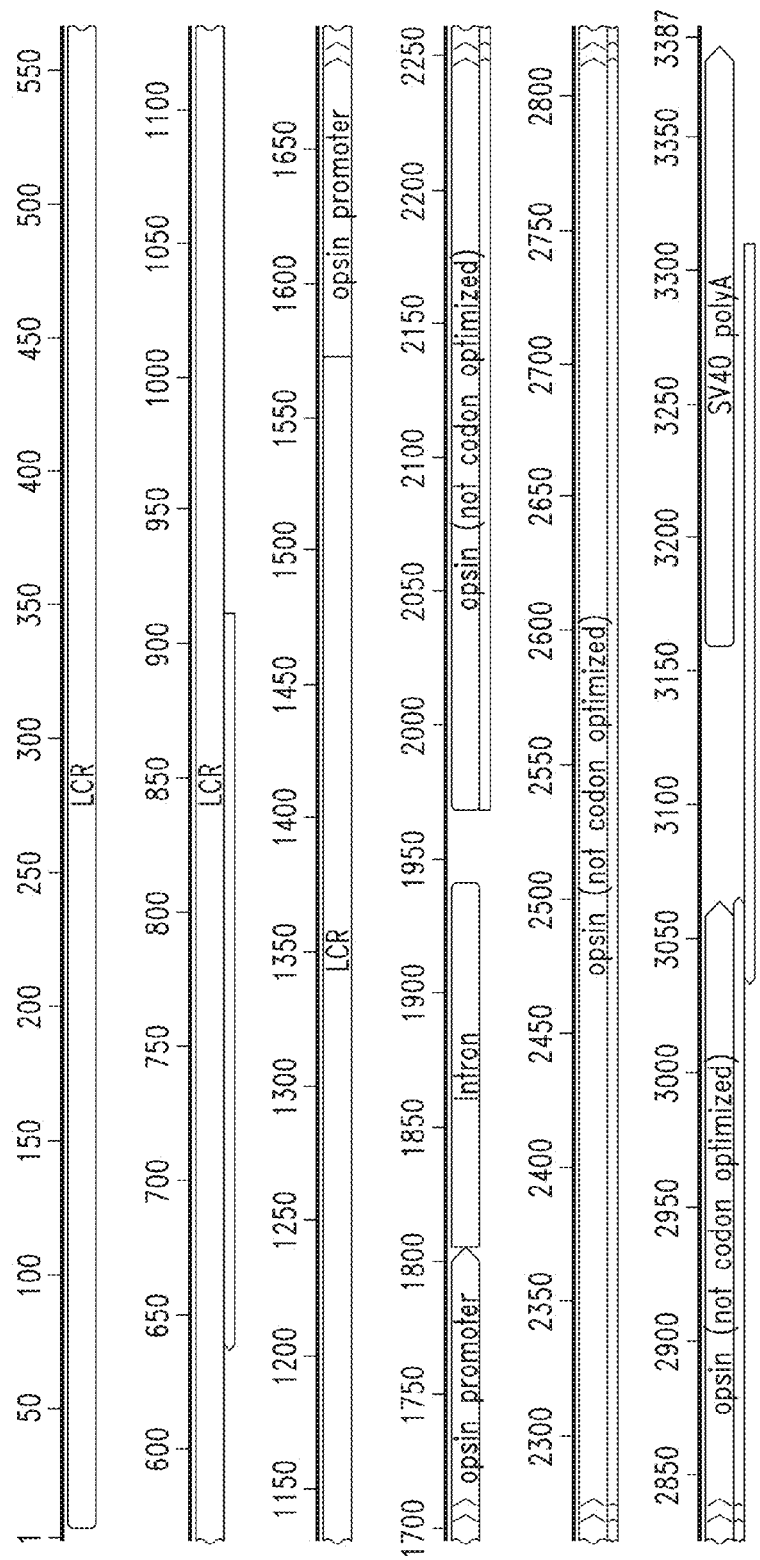
FIG. 4A depicts a polynucleotide cassette before codon optimization. Open reading frames (ORFs) greater than 250 nucleotides in length are shown in gray below the sequence.
Figure 4B:
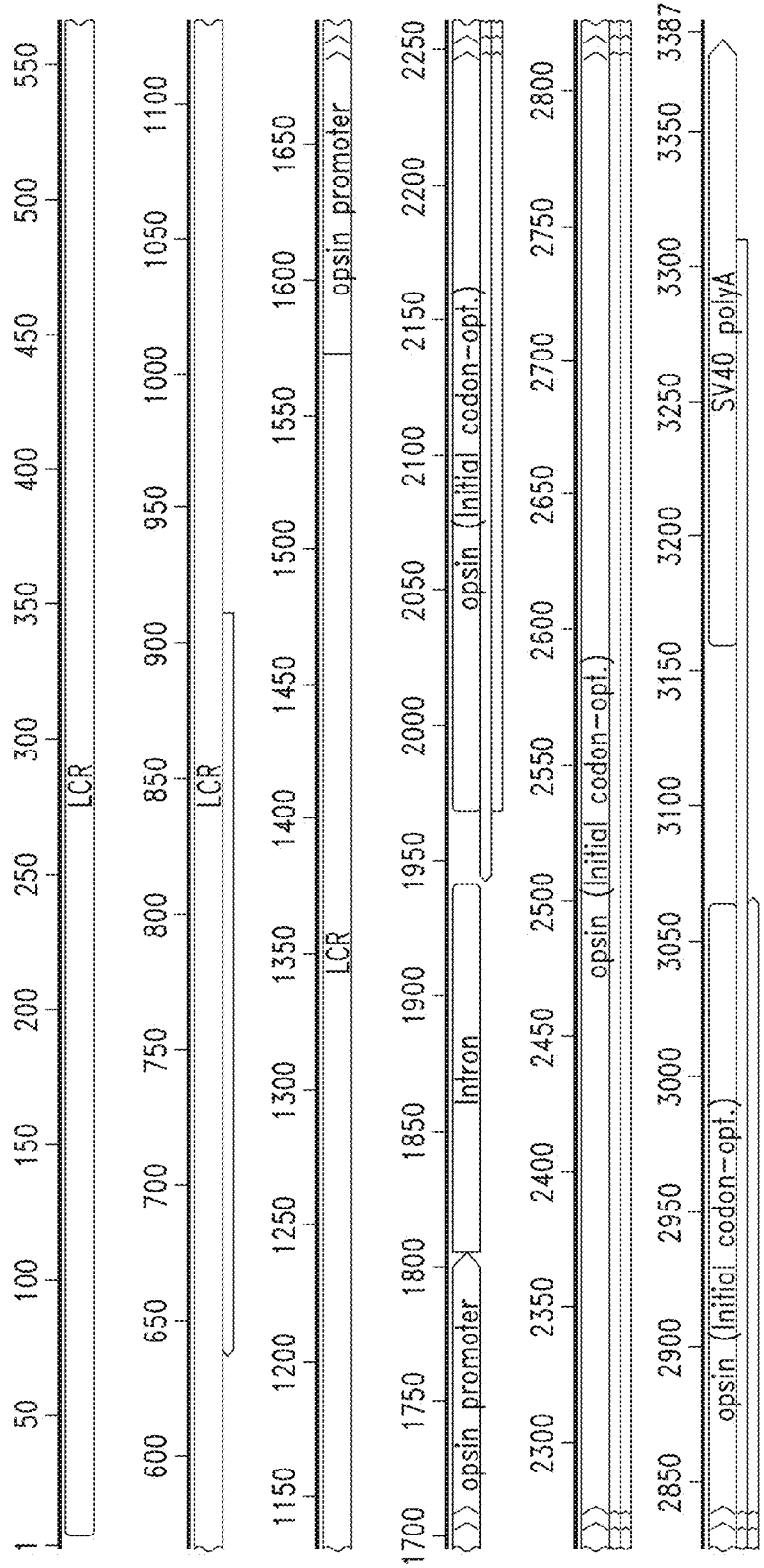
FIG. 4B depicts a polynucleotide cassette after codon optimization, but before removal of non-transgene ORFs. ORFs greater than 250 nucleotides are shown in gray below sequence diagram. Note the introduction of a new ORF in reverse orientation beginning from SV40 polyA and extending 1,365 bases.
Figure 4C:
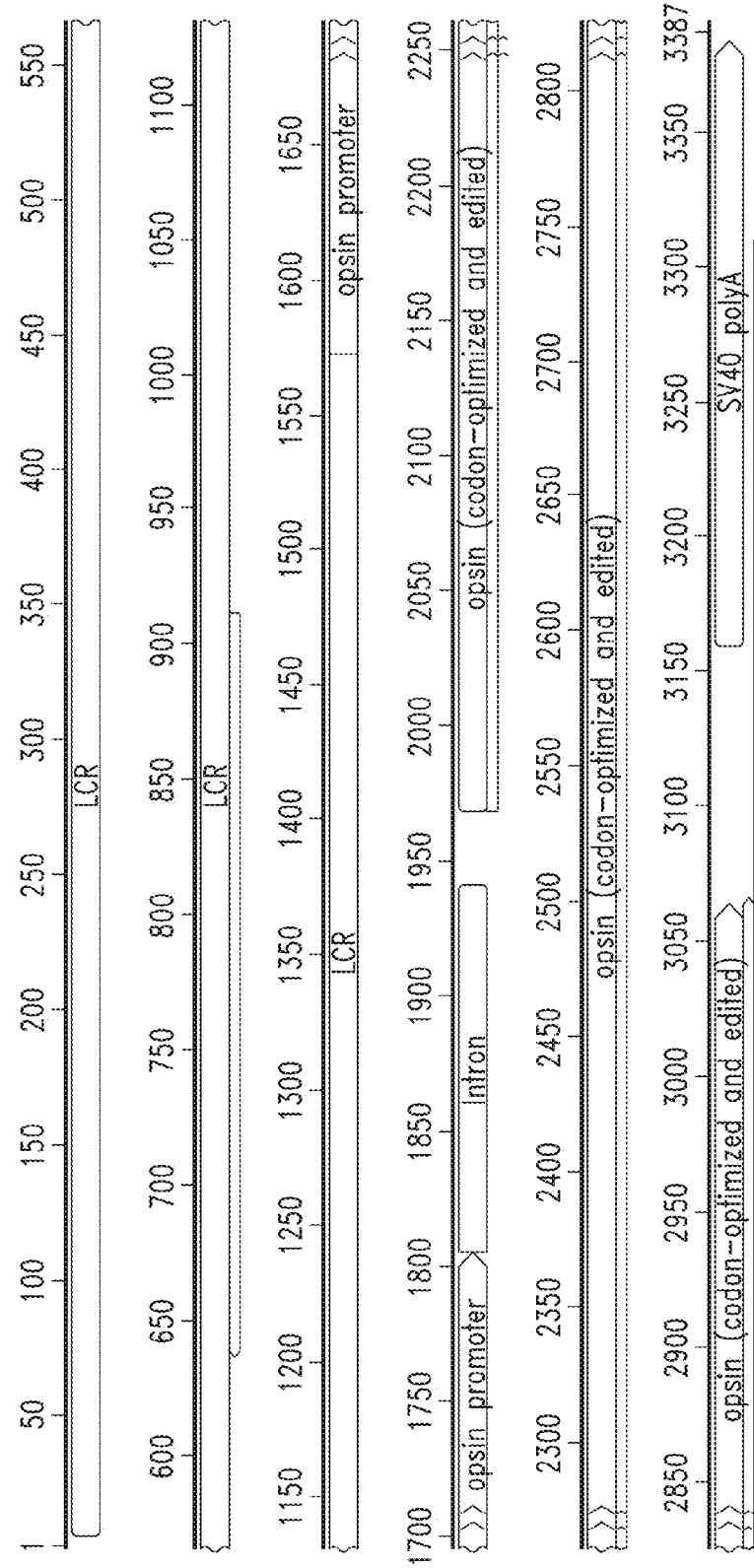
FIG. 4C depicts a polynucleotide cassette after codon optimization and removal of ORFs. ORFs greater than 250 nucleotides are shown in gray below the sequence diagram. Note that the sequence has been optimized so that newly introduced ORFs are shortened or removed.

In an additional embodiment of the invention, the transgene coding sequence is modified to enhance expression by termination or removal of open reading frames (ORFs) that do not encode the desired transgene. An open reading frame (ORF) is the nucleic acid sequence that follows a start codon and does not contains a stop codons. ORFs may be in the forward or reverse orientation, and may be "in frame" or "out of frame" compared with the gene of interest. Such open reading frames have the potential to be expressed in an expression cassette alongside the gene of interest, and could lead to undesired adverse effects. In one aspect of the present invention, the coding sequence of the transgene has been modified to remove open reading frames by further altering codon usage. This was done by eliminating start codons (ATG) and introducing stop codons (TAG, TAA, or TGA) in reverse orientation or out-of-frame ORFs, while preserving the amino acid sequence and maintaining highly utilized codons in the gene of interest (i.e., avoiding codons with frequency<20%). In the present invention, the transgene coding sequence may be optimized by either of codon optimization and removal of non-transgene ORFs or using both techniques. As will be apparent to one of ordinary skill in the art, it is preferable to remove or minimize non-transgene ORFs after codon optimization in order to remove ORFs introduced during codon optimization. Examples of codon optimization and removal of ORFs are shown in FIGS. 3A-3C.

In some embodiments, the polynucleotide cassette of the present invention further comprises a polyadenylation region. As is understood in the art, RNA polymerase II transcripts are terminated by cleavage and additional of a polyadenylation region, also known as a poly A signal, poly A region or poly A tail. The poly A region contains multiple consecutive adenosine monophosphates, often with repeats of the motif AAUAAA. Several efficient polyadenylation sites have been identified, including those from SV40, bovine growth hormone, human growth hormone and rabbit beta globin (Xu et al, 2001; Gene 272: 149; Xu et al., 2002; J Control Rel. 81:155). The most efficient polyA signal for expression of a transgene in cone cells may depend on the cell type and species of interest and the particular vector used. In some embodiments of the invention, the polynucleotide cassette comprises, consists essentially of, or consists of the polyA region selected from the group consisting of SEQ ID NO:74, SEQ ID NO:75, SEQ ID NO:76, SEQ ID NO:77, SEQ ID NO:78, SEQ ID NO:90 or SEQ ID NO:91 or functional fragment or variant thereof of any of the preceding sequences. In certain embodiments, the polyA region comprises SEQ ID NO:90 or a variant thereof. In some such embodiments, the polyA region consists essentially of SEQ ID NO:90 or a variant thereof.

As will be appreciated by the ordinarily skilled artisan, two or more of the aforementioned polynucleotide elements may be combined to create the polynucleotide cassettes of the present disclosure. Thus, for example, the subject polynucleotide cassette may comprise a promoter region comprising an improved promoter sequence in operable linkage with an improved 5'UTR sequence, for example SEQ ID NO:80 in operable combination with SEQ ID NO:84 or SEQ ID NO:85, see, e.g. SEQ ID NO:2, SEQ ID NO:54, SEQ ID NO:55, SEQ ID NO:93, SEQ ID NO:94, or SEQ ID NO:95. As another example, the subject polynucleotide cassette may comprise an improved enhancer sequence or region in operable linkage with an improved promoter sequence or region, for example SEQ ID NO:51 or SEQ ID NO:52 in operable combination with SEQ ID NO:80, SEQ ID NO:2, SEQ ID NO:54, SEQ ID NO:55, or SEQ ID NO:93; see, e.g. SEQ ID NO:92 or SEQ ID NO:95. As another example, the subject polynucleotide cassette may comprise an improved 5'UTR sequence in operable linkage with an improved intron sequence, for example SEQ ID NO:84 or SEQ ID NO:86 in operable combination with SEQ ID NO:60; see, e.g. SEQ ID NO:94 or SEQ ID NO:95. As another example, the subject polynucleotide cassette may comprise an improved 5'UTR sequence in operable linkage with an improved intron sequence and an improved Kozak sequence, for example, SEQ ID NO:84 or SEQ ID NO:86 in operable combination with SEQ ID NO:60 and with SEQ ID NO:73; see, e.g. SEQ ID NO:95. As another example, the subject polynucleotide cassette may comprise an improved enhancer, improved promoter, improved 5'UTR, improved intron, improved kozak and improved polyA region in operable linkage; see, e.g. SEQ ID NO:95. Other combinations of elements both as disclosed herein or as known in the art will be readily appreciated by the ordinarily skilled artisan.

Additionally, as will be recognized by one of ordinary skill in the art, the polynucleotide cassettes may optionally contain other elements including, but not limited to restriction sites to facilitate cloning and regulatory elements for a particular gene expression vector. Examples of regulatory sequence include ITRs for AAV vectors, bacterial sequences for plasmid vectors, attP or attB sites for phage integrase vectors, and transposable elements for transposons.

Gene Therapy Vectors

As alluded to above, in some aspects of the present invention, the subject polynucleotide cassettes are used to deliver a gene to cone cells of an animal, e.g. to determine the effect that the gene has on cell viability and/or function, to treat a cone cell disorder, etc. Accordingly, in some aspects of the invention, the composition that provides for the expression of a transgene in cone cells is a gene delivery vector, wherein the gene delivery vector comprises the polynucleotide cassettes of the present disclosure.

Any convenient gene therapy vector that finds use delivering polynucleotide sequences to cone cells is encompassed by the gene delivery vectors of the present disclosure. For example, the vector may comprise single or double stranded nucleic acid, e.g. single stranded or double stranded DNA. For example, the gene delivery vector may be a naked DNA, e.g. a plasmid, a minicircle, etc. As another example, the gene delivery vector may be a virus, e.g. an adenovirus, an adeno-associated virus, or a retrovirus, e.g. Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) or lentivirus. While embodiments encompassing the use of adeno-associated virus are described in greater detail below, it is expected that the ordinarily skilled artisan will appreciate that similar knowledge and skill in the art can be brought to bear on non-AAV gene therapy vectors as well. See, for example, the discussion of retroviral vectors in, e.g., U.S. Pat. No. 7,585,676 and U.S. Pat. No. 8,900,858, and the discussion of adenoviral vectors in, e.g. U.S. Pat. No. 7,858,367, the full disclosures of which are incorporated herein by reference.

In some embodiments, the gene delivery vector is a recombinant adeno-associated virus (rAAV). In such embodiments, the subject polynucleotide cassette is flanked on the 5' and 3' ends by functional AAV inverted terminal repeat (ITR) sequences. By "functional AAV ITR sequences" is meant that the ITR sequences function as intended for the rescue, replication and packaging of the AAV virion. Hence, AAV ITRs for use in the gene delivery vectors of the invention need not have a wild-type nucleotide sequence, and may be altered by the insertion, deletion or substitution of nucleotides or the AAV ITRs may be derived from any of several AAV serotypes, e.g. AAV1, AAV2, AAV3, AAV4, AAV5, AAV6, AAV7, AAV8, AAV9, AAV10. Preferred AAV vectors have the wild type REP and CAP genes deleted in whole or part, but retain functional flanking ITR sequences.

In such embodiments, the subject polynucleotide cassette is encapsidated within an AAV capsid, which may be derived from any adeno-associated virus serotype, including without limitation, AAV1, AAV2, AAV3, AAV4, AAV5, AAV6, AAV7, AAV8, AAV9, AAV10, etc. For example, the AAV capsid may be a wild type, or native, capsid. Wild type AAV capsids of particular interest include AAV2, AAV5, and AAV9. However, as with the ITRs, the capsid need not have a wild-type nucleotide sequence, but rather may be altered by the insertion, deletion or substitution of nucleotides in the VP1, VP2 or VP3 sequence, so long as the capsid is able to transduce cone cells. Put another way, the AAV capsid may be a variant AAV capsid. Variant AAV capsids of particular interest include those comprising a peptide insertion within residues 580-600 of AAV2 or the corresponding residues in another AAV, e.g. LGETTRP, NETITRP, KAGQANN, KDPKTTN, KDTDTTR, RAGGSVG, AVDTTKF, orSTG-KVPN, as disclosed in US Application No. US 2014/0294771, the full disclosure of which is incorporated by reference herein. In some embodiments, the AAV vector is a "pseudotyped" AAV created by using the capsid (cap) gene of one AAV and the rep gene and ITRs from a different AAV, e.g. a pseudotyped AAV2 created by using rep from AAV2 and cap from AAV1, AAV3, AAV4, AAV5, AAV6, AAV7, AAV8, or AAV9 together with a plasmid containing a vector based on AAV2. For example, the AAV vector may be rAAV2/1, rAAV2/3, rAAV2/4, rAAV2/5, rAAV2/6, rAAV2/7, rAAV2/8, rAAV2/9, etc. Preferably, the rAAV is replication defective, in that the AAV vector cannot independently further replicate and package its genome. For example, when cone cells are transduced with rAAV virions, the gene is expressed in the transduced cone cells, however, due to the fact that the transduced cone cells lack AAV rep and cap genes and accessory function genes, the rAAV is not able to replicate.

Gene therapy vectors, e.g. rAAV) virions encapsulating the polynucleotide cassettes of the present disclosure, may be produced using standard methodology. For example, in the case of rAAV virions, an AAV expression vector according to the invention may be introduced into a producer cell, followed by introduction of an AAV helper construct, where the helper construct includes AAV coding regions capable of being expressed in the producer cell and which complement AAV helper functions absent in the AAV vector. This is followed by introduction of helper virus and/or additional vectors into the producer cell, wherein the helper virus and/or additional vectors provide accessory functions capable of supporting efficient rAAV virus production. The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286, expressly incorporated by reference herein in their entirety. Further compositions and methods for packaging are described in Wang et al. (US 2002/0168342), also incorporated by reference herein in its entirety.

Any suitable method for producing viral particles for delivery of the subject polynucleotide cassettes can be used, including but not limited to those described in the examples that follow. Any concentration of viral particles suitable to effectively transducer cone cells can be prepared for contacting cone cells in vitro or in vivo. For example, the viral particles may be formulated at a concentration of $10^8$ vector genomes per ml or more, for example, $5 \times 10^8$ vector genomes per mL; $10^9$ vector genomes per mL; $5 \times 10^9$ vector genomes per mL, $10^{10}$ vector genomes per mL, $5 \times 10^{10}$ vector genomes per mL; $10^{11}$ vector genomes per mL; $5 \times 10^{11}$ vector genomes per mL; $10^{12}$ vector genomes per mL; $5 \times 10^{12}$ vector genomes per mL; $10^{13}$ vector genomes per mL; $1.5 \times 10^{13}$ vector genomes per mL; $3 \times 10^{13}$ vector genomes per mL; $5 \times 10^{13}$ vector genomes per mL; $7.5 \times 10^{13}$ vector genomes per mL; $9 \times 10^{13}$ vector genomes per mL; $1 \times 10^{14}$ vector genomes per mL, $5 \times 10^{14}$ vector genomes per mL or more, but typically not more than $1 \times 10^{15}$ vector genomes per mL. Similarly, any total number of viral particles suitable to provide appropriate transduction of retinal cone cells to confer the desired effect or treat the disease can be administered to the mammal or to the primate's eye. In various preferred embodiments, at least $10^8$; $5 \times 10^8$; $10^9$; $5 \times 10^9$, $10^{10}$, $5 \times 10^{10}$; $10^{11}$; $5 \times 10^{11}$; $10^{12}$; $5 \times 10^{12}$; $10^{13}$; $1.5 \times 10^{13}$; $3 \times 10^{13}$; $5 \times 10^{13}$; $7.5 \times 10^{13}$; $9 \times 10^{13}$, $1 \times 10^{14}$ viral particles, or $5 \times 10^{14}$ viral particles or more, but typically not more than $1 \times 10^{15}$ viral particles are injected per eye. Any suitable number of administrations of the vector to the mammal or the primate eye can be made. In one embodiment, the methods comprise a single administration; in other embodiments, multiple administrations are made over time as deemed appropriate by an attending clinician.

The subject viral vector may be formulated into any suitable unit dosage, including, without limitation, $1 \times 10^8$ vector genomes or more, for example, $1 \times 10^9$, $1 \times 10^{10}$, $1 \times 10^{11}$, $1 \times 10^{12}$, or $1 \times 10^{13}$ vector genomes or more, in certain instances, $1 \times 10^{14}$ vector genomes, but usually no more than $4 \times 10^{15}$ vector genomes. In some cases, the unit dosage is at most about $5 \times 10^{15}$ vector genomes, e.g. $1 \times 10^{14}$ vector genomes or less, for example $1 \times 10^{13}$, $1 \times 10^{12}$, $1 \times 10^{11}$, $1 \times 10^{10}$, or $1 \times 10^9$ vector genomes or less, in certain instances $1 \times 10^8$ vector genomes or less, and typically no less than $1 \times 10^8$ vector genomes. In some cases, the unit dosage is $1 \times 10^{10}$ to $1 \times 10^{11}$ vector genomes. In some cases, the unit dosage is $1 \times 10^{10}$ to $3 \times 10^{12}$ vector genomes. In some cases, the unit dosage is $1 \times 10^9$ to $3 \times 10^{13}$ vector genomes. In some cases, the unit dosage is $1 \times 10^8$ to $3 \times 10^{14}$ vector genomes.

In some cases, the unit dosage of pharmaceutical composition may be measured using multiplicity of infection (MOI). By MOI it is meant the ratio, or multiple, of vector or viral genomes to the cells to which the nucleic acid may be delivered. In some cases, the MOI may be $1 \times 10^6$. In some cases, the MOI may be $1 \times 10^5$-$1 \times 10^7$. In some cases, the MOI may be $1 \times 10^4$-$1 \times 10^8$. In some cases, recombinant viruses of the disclosure are at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI. In some cases, recombinant viruses of this disclosure are $1 \times 10^8$ to $3 \times 10^{14}$ MOI. In some cases, recombinant viruses of the disclosure are at most about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$ and $1 \times 10^{18}$ MOI.

In some aspects, the amount of pharmaceutical composition comprises about $1\times10^8$ to about $1\times10^{15}$ recombinant viruses, about $1\times10^9$ to about $1\times10^{14}$ recombinant viruses, about $1\times10^{10}$ to about $1\times10^{13}$ recombinant viruses, or about $1\times10^{11}$ to about $3\times10^{12}$ recombinant viruses.

In preparing the subject rAAV compositions, any host cells for producing rAAV virions may be employed, including, for example, mammalian cells (e.g. 293 cells), insect cells (e.g. SF9 cells), microorganisms and yeast. Host cells can also be packaging cells in which the AAV rep and cap genes are stably maintained in the host cell or producer cells in which the AAV vector genome is stably maintained and packaged. Exemplary packaging and producer cells are derived from SF-9, 293, A549 or HeLa cells. AAV vectors are purified and formulated using standard techniques known in the art.

For instances in which cone cells are to be contacted in vivo, the subject polynucleotide cassettes or gene delivery vectors comprising the subject polynucleotide cassette can be treated as appropriate for delivery to the eye. In particular, the present invention include pharmaceutical compositions comprising a polynucleotide cassetee or gene delivery vector described herein and a pharmaceutically-acceptable carrier, diluent or excipient. The subject polynucleotide cassettes or gene delivery vector can be combined with pharmaceutically-acceptable carriers, diluents and reagents useful in preparing a formulation that is generally safe, non-toxic, and desirable, and includes excipients that are acceptable for primate use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfate; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide.

Pharmaceutical compositions suitable for internal use in the present invention further include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In somecases, the composition is sterile and should be fluid to the extent that easy syringability exists. In certain embodiments, it is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser, e.g. syringe, e.g. a prefilled syringe, together with instructions for administration.

The pharmaceutical compositions of the invention encompass any pharmaceutically acceptable salts, esters, or salts of such esters, or any other compound which, upon administration to an animal comprising a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bio-equivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salt" refers to physiologically and pharmaceutically acceptable salts of the compounds of the invention: i.e., salts that retain the desired biological activity of the parent compound and do not impart undesired toxicological effects thereto. A variety of pharmaceutically acceptable salts are known in the art and described, e.g., in in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see Handbook of Pharmaceutical Salts: Properties, Selection, and Use by Stahl and Wermuth (Wiley-VCH, 2002).

Pharmaceutically acceptable base addition salts are formed with metals or amines, such as alkali and alkaline earth metals or organic amines. Metals used as cations comprise sodium, potassium, magnesium, calcium, and the like Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

The subject polynucleotide cassette or gene delivery vector, e.g.recombinant virus (virions), can be incorporated into pharmaceutical compositions for administration to mammalian patients, particularly primates and more particularly humans. The subject polynucleotide cassette or gene delivery vector, e.g. virions can be formulated in nontoxic, inert, pharmaceutically acceptable aqueous carriers, preferably at a pH ranging from 3 to 8, more preferably ranging from 6 to 8. Such sterile compositions will comprise the vector or virion containing the nucleic acid encoding the therapeutic molecule dissolved in an aqueous buffer having an acceptable pH upon reconstitution.

In some embodiments, the pharmaceutical composition provided herein comprise a therapeutically effective amount of a vector or virion in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer in which the pharmaceutical composition comprising the tumor suppressor gene contained in the adenoviral vector delivery system, may be in the range of 6.5 to 7.75, preferably 7 to 7.5, and most preferably 7.2 to 7.4.

Methods

As alluded to above, the subject polynucleotide cassettes and gene delivery vectors, referred to collectively herein as the "subject compositions", find use in expressing a transgene in cone cells of an animal. For example, the subject compositions may be used in research, e.g. to determine the effect that the gene has on cone cell viability and/or function. As another example, the subject compositions may be used in medicine, e.g. to treat a cone cell disorder. Thus, in some aspects of the invention, methods are provided for the expression of a gene in cone cells, the method comprising contacting cone cells with a composition of the present disclosure. In some embodiments, contacting occurs in vitro. In some embodiments, contacting occurs in vivo, i.e., the subject composition is administered to a subject.

For instances in which cone cells are to be contacted in vitro with a subject polynucleotide cassette or gene delivery vector comprising a subject polynucleotide cassette, the cells may be from any mammalian species, e.g. rodent (e.g. mice, rats, gerbils, squirrels), rabbit, feline, canine, goat, ovine, pig, equine, bovine, primate, human. Cells may be from established cell lines, e.g. WERI cells, 661W cells, or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvested from a mammal by any convenient method, e.g. whole explant, biopsy, etc. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

To promote expression of the transgene, the subject polynucleotide cassette or gene delivery vector comprising a subject polynucleotide cassette will be contacted with the cells for about 30 minutes to 24 hours or more, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, 24 hours, etc. The subject polynucleotide cassette or gene delivery vector comprising a subject polynucleotide cassette may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further. Contacting the cells may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Typically, an effective amount of subject polynucleotide cassette or gene delivery vector comprising a subject polynucleotide cassette is provided to produce the expression of the transgene in cells. As discussed elsewhere herein, the effective amount may be readily determined empirically, e.g. by detecting the presence or levels of transgene gene product, by detecting an effect on the viability or function of the cone cells, etc. Typically, an effect amount of subject polynucleotide cassette or gene delivery vector comprising a subject polynucleotide cassette will promote greater expression of the transgene in cone cells than the same amount of a polynucleotide cassette as known in the art, e.g. a pR2.1 (nucleotides 1-2274 of SEQ ID NO:50), pR1.7, pR1.5, pR1.1, or IRBP/GNAT2 cassette. Typically, expression will be enhanced 2-fold or more relative to the expression from a reference, or control, polynucleotide cassette e.g. as known in the art, for example 3-fold, 4-fold, or 5-fold or more, in some instances 10-fold, 20-fold or 50-fold or more, e.g. 100-fold.

In some embodiments, as when the transgene is a selectable marker, the population of cells may be enriched for those comprising the subject polynucleotide cassette by separating the modified cells from the remaining population. Separation may be by any convenient separation technique appropriate for the selectable marker used. For example, if the transgene is a fluorescent marker, cells may be separated by fluorescence activated cell sorting, whereas if the transgene is a cell surface marker, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the cells. Cell compositions that are highly enriched for cells comprising the subject polynucleoties are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of genetically modified cells.

For instances in which cone cells are to be contacted in vivo with a subject polynucleotide cassette or gene delivery vector comprising a subject polynucleotide cassette, the subject may be any mammal, e.g. rodent (e.g. mice, rats, gerbils), rabbit, feline, canine, goat, ovine, pig, equine, bovine, or primate. In certain embodiments, the subject is a primate of the Parvorder Catarrhini. As is known in the art, Catarrhini is one of the two subdivisions of the higher primates (the other being the New World monkeys), and includes Old World monkeys and the apes, which in turn are further divided into the lesser apes or gibbons and the great apes, consisting of the orangutans, gorillas, chimpanzees, bonobos, and humans. In a further preferred embodiment, the primate is a human.

The subject composition may be administered to the retina of the subject by any suitable method. For example, the subject composition may be administered intraocularly via intravitreal injection or subretinal injection. The general methods for delivering a vector via intravitreal injection or via subretinal injection may be illustrated by the following brief outlines. These examples are merely meant to illustrate certain features of the methods, and are in no way meant to be limiting.

For subretinal administration, the vector can be delivered in the form of a suspension injected subretinally under direct observation using an operating microscope. Typically, a volume of 1 to 200 uL, e.g. 50 uL, 100 uL, 150 ul, or 200 uL, but usually no more than 200 uL, of the subject composition will be administered by such methods. This procedure may involve vitrectomy followed by injection of vector suspension using a fine cannula through one or more small retinotomies into the subretinal space. Briefly, an infusion cannula can be sutured in place to maintain a normal globe volume by infusion (of e.g. saline) throughout the operation. A vitrectomy is performed using a cannula of appropriate bore size (for example 20 to 27 gauge), wherein the volume of vitreous gel that is removed is replaced by infusion of saline or other isotonic solution from the infusion cannula. The vitrectomy is advantageously performed because (1) the removal of its cortex (the posterior hyaloid membrane) facilitates penetration of the retina by the cannula; (2) its removal and replacement with fluid (e.g. saline) creates space to accommodate the intraocular injection of vector, and (3) its controlled removal reduces the possibility of retinal tears and unplanned retinal detachment.

For intravitreal administration, the vector can be delivered in the form of a suspension. Initially, topical anesthetic is applied to the surface of the eye followed by a topical antiseptic solution. The eye is held open, with or without instrumentation, and the vector is injected through the sclera with a short, narrow, for example a 30 gauge needle, into the vitreous cavity of the eye of a subject under direct observation. Typically, a volume of 1 to 100 uL, e.g. 25 uL, 50 uL, or 100 uL, and usually no more than 100 uL, of the subject composition may be delivered to the eye by intravitreal injection without removing the vitreous. Alternatively, a vitrectomy may be performed, and the entire volume of vitreous gel is replaced by an infusion of the subject composition. In such cases, up to about 4 mL of the subject composition may be delivered, e.g. to a human eye. Intravitreal administration is generally well tolerated. At the conclusion of the procedure, there is sometimes mild redness at the injection site. There is occasional tenderness, but most patients do not report any pain. No eye patch or eye shield is necessary after this procedure, and activities are not restricted. Sometimes, an antibiotic eye drop is prescribed for several days to help prevent infection.

The methods and compositions of the present disclosure find use in the treatment of any condition that can be addressed, at least in part, by gene therapy of cone photoreceptor cells. Thus, the compositions and methods of the present disclosure find use in the treatment of individuals in need of a cone cell therapy. By a person in need of a cone cell therapy, it is meant an individual having or at risk of developing a cone cell disorder. By a "cone cell disorder" it is meant any disorder impacting retinal cone cells, including but not limited to vision disorders of the eye that are associated with a defect within cone cells, i.e. a cone-instrinsic defect, e.g. macular dystrophies such as Stargardt's macular dystrophy, cone dystrophy, cone-rod dystrophy, Spinocerebellar ataxia type 7, and Bardet-Biedl syndrome-1; as well as color vision disorders, including achromatopsia, incomplete achromatopsia, blue cone monochromacy, and protan, deutan, and tritan defects; as well as vision disorders of the central macula (within primates) that may be treated by targeting cone cells, e.g. age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, rod-cone dystrophy, Leber's congenital amaurosis, and X-linked retinoschisis.

Stargardt's macular dystrophy. Stargardt's macular dystrophy, also known as Stargardt Disease and fundus flavimaculatus, is an inherited form of juvenile macular degeneration that causes progressive vision loss usually to the point of legal blindness. The onset of symptoms usually appears between the ages of six and thirty years old (average of about 16-18 years). Mutations in several genes, including ABCA4, CNGB3, ELOVL4, PROM1, are associated with the disorder. Symptoms typically develop by twenty years of age, and include wavy vision, blind spots, blurriness, impaired color vision, and difficulty adapting to dim lighting. The main symptom of Stargardt disease is loss of visual acuity, which ranges from 20/50 to 20/200. In addition, those with Stargardt disease are sensitive to glare; overcast days offer some relief. Vision is most noticeably impaired when the macula is damaged, which can be observed by fundus exam.

Cone dystrophy. Cone dystrophy (COD) is an inherited ocular disorder characterized by the loss of cone cells. The most common symptoms of cone dystrophy are vision loss (age of onset ranging from the late teens to the sixties), sensitivity to bright lights, and poor color vision. Visual acuity usually deteriorates gradually, but it can deteriorate rapidly to 20/200; later, in more severe cases, it drops to "counting fingers" vision. Color vision testing using color test plates (HRR series) reveals many errors on both red-green and blue-yellow plates. It is believed that the dystrophy is primary, since subjective and objective abnormalities of cone function are found before ophthalmoscopic changes can be seen. However, the retinal pigment epithelium (RPE) rapidly becomes involved, leading to a retinal dystrophy primarily involving the macula. The fundus exam via ophthalmoscope is essentially normal early on in cone dystrophy, and definite macular changes usually occur well after visual loss. The most common type of macular lesion seen during ophthalmoscopic examination has a bull's-eye appearance and consists of a doughnut-like zone of atrophic pigment epithelium surrounding a central darker area. In another, less frequent form of cone dystrophy there is rather diffuse atrophy of the posterior pole with spotty pigment clumping in the macular area. Rarely, atrophy of the choriocapillaris and larger choroidal vessels is seen in patients at an early stage. Fluorescein angiography (FA) is a useful adjunct in the workup of someone suspected to have cone dystrophy, as it may detect early changes in the retina that are too subtle to be seen by ophthalmoscope. Because of the wide spectrum of fundus changes and the difficulty in making the diagnosis in the early stages, electroretinography (ERG) remains the best test for making the diagnosis. Abnormal cone function on the ERG is indicated by a reduced single-flash and flicker response when the test is carried out in a well-lit room (photopic ERG). Mutations in several genes, including GUCA1A, PDE6C, PDE6H, and RPGR, are associated with the disorder.

Cone-rod dystrophy. Cone-rod dystrophy (CRD, or CORD) is an inherited retinal dystrophy that belongs to the group of pigmentary retinopathies. CRD is characterized by retinal pigment deposits visible on fundus examination, predominantly localized to the macular region and the loss of both cone and rod cells. In contrast to rod-cone dystrophy (RCD) resulting from the primary loss in rod photoreceptors and later followed by the secondary loss in cone photoreceptors, CRD reflects the opposite sequence of events: primary cone involvement, or, sometimes, by concomitant loss of both cones and rods. Symptoms include decreased visual acuity, color vision defects, photoaversion and decreased sensitivity in the central visual field, later followed by progressive loss in peripheral vision and night blindness. Mutations in several genes, including ADAM9, PCDH21, CRX, GUCY2D, PITPNM3, PROM1, PRPH2, RAX2, RIMS1, RPGR, and RPGRIP1, are associated with the disorder.

Spinocerebellar ataxia type 7. Spinocerebellar ataxia is a progressive, degenerative, inherited disease characterized by slowly progressive incoordination of gait and is often associated with poor coordination of hands, speech, and eye movements. There are multiple types of SCA, with Spinocerebellar ataxia type 7 (SCA-7) differing from most other SCAs in that visual problems can occur in addition to poor coordination. SCA-7 is associated with automosmal dominant mutations in the ATXN7/SCA7 gene. When the disease manifests itself before age 40, visual problems rather than poor coordination are typically the earliest signs of disease. Early symptoms include difficulty distinguishing colors and decreased central vison. In addition, symptoms of ataxia (incoordination, slow eye movements, and mild changes in sensation or reflexes) may be detectable. Loss of motor control, unclear speech, and difficulty swallowing become prominent as the disease progresses.

Bardet-Biedl syndrome-1. Bardet-Biedl syndrome-1 (BBS-1) is a pleiotropic disorder with variable expressivity and a wide range of clinical variability observed both within and between families. The main clinical features are rod-cone dystrophy, with childhood-onset visual loss preceded by night blindness; postaxial polydactyly; truncal obesity that manifests during infancy and remains problematic throughout adulthood; specific learning difficulties in some but not all individuals; male hypogenitalism and complex female genitourinary malformations; and renal dysfunction, a major cause of morbidity and mortality. Vision loss is one of the major features of Bardet-Biedl syndrome. Problems with night vision become apparent by mid-childhood, followed by blind spots that develop in the peripheral vision. Over time, these blind spots enlarge and merge to produce tunnel vision. Most people with Bardet-Biedl syndrome also develop blurred central vision (poor visual acuity) and become legally blind by adolescence or early adulthood. Bardet-Biedl syndrome can result from mutations in at least 14 different genes (often called BBS genes) known or suspected to play critical roles in cilia function, with mutations in BBS1 and BBS10 being the most common.

Achromatopsia. Achromatopsia, or Rod monochromatism, is a disorder in which subjects experience a complete lack of the perception of color, such that the subject sees only in black, white, and shades of grey. Other symptoms include reduced visual acuity, photophobia, nystagmus, small central scotoma, and eccentric fixation. The disorder is frequently noticed first in children around six months of age by their photophobic activity and/or their nystagmus. Visual acuity and stability of the eye motions generally improve during the first 6-7 years of life (but remain near 20/200). Mutations in CNGB3, CNGA3, GNAT2, PDE6C, and PDE6HI have been associated with the disorder.

Incomplete achromatopsia. Incomplete achromatopsia is similar to Achromatopsia but with less penetrance. In incomplete achromatopsia, the symptoms are similar to those of complete achromatopsia except in a diminished form. Individuals with incomplete achromatopsia have reduced visual acuity with or without nystagmus or photophobia. Furthermore, these individuals show only partial impairment of cone cell function but again have retained rod cell function.

Blue cone monochromacy. Blue cone (S cone) monochromatism (BCM) is a rare X-linked congenital stationary cone dysfunction syndrome, affecting approximately 1 in 100,000 individuals. Affected males with BCM have no functional long wavelength sensitive (L) or medium wavelength sensitive (M) cones in the retina, due to mutations at the genetic locus for the L and M-opsin genes. Color discrimination is severely impaired from birth, and vision is derived from the remaining preserved S cones and rod photoreceptors. BCM typically presents with reduced visual acuity (6/24 to 6/60), pendular nystagmus, photophobia, and patients often have myopia. The rod-specific and maximal electroretinogram (ERG) usually show no definite abnormality, whereas the 30 Hz cone ERG cannot be detected. Single flash photopic ERG is often recordable, albeit small and late, and the S cone ERG is well preserved.

Color vision deficiency. Color vision deficiency (CVD), or color blindness, is the inability or decreased ability to see color, or perceive color differences, under normal lighting conditions. Individuals suffering from color blindness may be identified as such using any of a number of color vision tests, e.g., color ERG (cERG), pseudoisochromatic plates (Ishihara plates, Hardy-Rand-Ritter polychromatic plates), the Farnsworth-Munsell 100 hue test, the Farnsworth's panel D-15, the City University test, Kollner's rule, etc. Examples of color vision deficiencies include protan defects, deutan defects, and tritan defects. Protan defects include protanopia (an insensitivity to red light) and protanomaly (a reduced sensitivity to red light), and are associated with mutations in the L-Opsin gene (OPN1LW). Deutan defects include deuteranopia (an insensitivity to green light) and deutanomaly (a reduced sensitivity to green light), and are associated with mutations in the M-Opsin gene (OPN1MW). Tritan defects include tritanopia (an insensitivity to blue light) and tritanomaly (a reduced sensitivity to blue light), and are associated with mutations in the S-Opsin gene (OPN1SW).

Age-related macular degeneration. Age-related macular degeneration (AMD) is one of the leading causes of vision loss in people over the age of 50 years. AMD mainly affects central vision, which is needed for detailed tasks such as reading, driving, and recognizing faces. The vision loss in this condition results from a gradual deterioration of photoreceptors in the macula. Side (peripheral) vision and night vision are generally not affected.

Researchers have described two major types of age-related macular degeneration, known as the dry, or "non-exudative" form, and the wet, or "exudative" or "neovascular", form, both of which may be treated by delivering transgenes in the context of the subject polynucleotide cassettes.

Dry AMD is characterized by a buildup of yellow deposits called drusen between the retinal pigment epithelium and the underlying choroid of the macula, which may be observed by Fundus photography. This results in a slowly progressive loss of vision. The condition typically affects vision in both eyes, although vision loss often occurs in one eye before the other. Other changes may include pigment changes and RPE atrophy. For example, in certain cases called central geographic atrophy, or "GA", atrophy of the retinal pigment epithelial and subsequent loss of photoreceptors in the central part of the eye is observed. Dry AMD has been associated with mutations in CD59 and genes in the complement cascade.

Wet AMD is a progressed state of dry AMD, and occurs in abut 10% of dry AMD patients. Pathological changes include retinal pigment epithelial cells (RPE) dysfunction, fluid collecting under the RPE, and choroidal neovascularization (CNV) in the macular area. Fluid leakage, RPE or neural retinal detachment and bleeding from ruptured blood vessels can occur in severe cases. Symptoms of wet AMD may include visual distortions, such as straight lines appearing wavy or crooked, a doorway or street sign looking lopsided, or objects appearing smaller or farther away than they really are; decreased central vision; decreased intensity or brightness of colors; and well-defined blurry spot or blind spot in the field of vision. Onset may be abrupt and worsen rapidly. Diagnosis may include the use of an Amsler grid to test for defects in the subject's central vision (macular degeneration may cause the straight lines in the grid to appear faded, broken or distorted), fluorescein angiogram to observe blood vessel or retinal abnormalities, and optical coherence tomography to detect retina swelling or leaking blood vessels. A number of cellular factors have been implicated in the generation of CNV, among which are vascular endothelial growth factor (VEGF), platelet-derived growth factor (PDGF), pigment epithelium-derived factor (PEDF), hypoxia inducible factor (HIF), angiopoietin (Ang), and other cytokines, mitogen-activated protein kinases (MAPK) and others.

Macular telangiectasia. Macular telangiectasia (MacTel) is a form of pathologically dilated blood vessels (telangiectasia) in the parafoveal region of the macula. The tissue deteriorates and the retinal structure becomes scarred due to the development of liquid-filled cysts, which impairs nutrition of the photoreceptor cells and destroys vision permanently. There are two types of MacTel, type 1 and type 2. Macular telangiectasia type 2 is a bilateral disease, whose prevalence has recently been shown to be as high as 0.1% in persons 40 years and older. Biomicroscopy may show reduced retinal transparency, crystalline deposits, mildly ectatic capillaries, blunted venules, retinal pigment plaques, foveal atrophy, and neovascular complexes. Fluorescein angiography shows telangiectatic capillaries predominantly temporal to the foveola in the early phase and a diffuse hyperfluorescence in the late phase. High-resolution optical coherence tomography (OCT) may reveal disruption of the photoreceptor inner segment-outer segment border, hyporeflective cavities at the level of the inner or outer retina, and atrophy of the retina in later stages. In Type 1 macular telangiectasia, the disease almost always occurs in one eye, which differentiates it from Type 2. While MacTel does not usually cause total blindness, it commonly causes loss of the central vision, which is required for reading and driving vision, over a period of 10-20 years.

Retinitis pigmentosa. Retinitis Pigmentosa (RP) is a group of inherited disorders characterized by progressive peripheral vision loss and night vision difficulties (nyctalopia) that can lead to central vision loss. Presenting signs and symptoms of RP vary, but the classic ones include nyctalopia (night blindness, most commonly the earliest symptom in RP); visual loss (usually peripheral, but in advanced cases, central visual loss); and photopsia (seeing flashes of light). Because RP is a collection of many inherited diseases, significant variability exists in the physical findings. Ocular examination involves assessment of visual acuity and pupillary reaction, as well as anterior segment, retinal, and funduscopic evaluation. In some instances, the RP is one aspect of a syndrome, e.g. syndromes that are also associated with hearing loss (Usher syndrome, Waardenburg syndrome, Alport syndrome, Refsum disease); Kearns-Sayre syndrome (external ophthalmoplegia, lid ptosis, heart block, and pigmentary retinopathy); Abetalipoproteinemia (Fat malabsorption, fat-soluble vitamin deficiencies, spinocerebellar degeneration, and pigmentary retinal degeneration); mucopolysaccharidoses (eg, Hurler syndrome, Scheie syndrome, Sanfilippo syndrome); Bardet-Biedl syndrome (Polydactyly, truncal obesity, kidney dysfunction, short stature, and pigmentary retinopathy); and neuronal ceroid lipofuscinosis (Dementia, seizures, and pigmentary retinopathy; infantile form is known as Jansky-Bielschowsky disease, juvenile form is Vogt-Spielmeyer-Batten disease, and adult form is Kufs syndrome). Retinitis pigmentosa is most commonly associated with mutations in the RHO, RP2, RPGR, RPGRIP1, PDE6A, PDE6B, MERTK, PRPH2, CNGB1, USH2A, ABCA4, BBS genes.

Diabetic retinopathy. Diabetic retinopathy (DR) is damage to the retina caused by complications of diabetes, which can eventually lead to blindness. Without wishing to be bound by theory, it is believed that hyperglycemia-induced intramural pericyte death and thickening of the basement membrane lead to incompetence of the vascular walls. These damages change the formation of the blood-retinal barrier and also make the retinal blood vessels become more permeable.

There are two stages of diabetic retinopathy: non-proliferative diabetic retinopathy (NPDR), and proliferative diabetic retinopathy (PDR). Nonproliferative diabetic retinopathy is the first stage of diabetic retinopathy, and is diagnosed by funduscopic exam and coexistent diabetes. In cases of reduced vision, fluorescein angiography may be done to visualize the vessles in the back of the eye to and any retinal ischemia that may be present. All people with diabetes are at risk for developing NPDR, and as such, would be candidates for prophylactic treatment with the subject vectors. Proliferative diabetic retinopathy is the second stage of diabetic retinopathy, characterized by neovascularization of the retina, vitreous hemorrhage, and blurred vision. In some instances, fibrovascular proliferation causes tractional retinal detachment. In some instances, the vessels can also grow into the angle of the anterior chamber of the eye and cause neovascular glaucoma. Individuals with NPDR are at increased risk for developing PDR, and as such, would be candidates for prophylactic treatment with the subject vectors.

Diabetic macular edema. Diabetic macular edema (DME) is an advanced, vision-limiting complication of diabetic retinopathy that affects nearly 30% of patients who have had diabetes for at least 20 years, and is responsible for much of the vision loss due to DR. It results from retinal microvascular changes that compromise the blood-retinal barrier, causing leakage of plasma constituents into the surrounding retina and, consequently, retinal edema. Without wishing to be bound by theory, it is believed that hyperglycemia, sustained alterations in cell signaling pathways, and chronic microvascular inflammation with leukocyte-mediated injury leads to chronic retinal microvascular damage, which triggers an increase in intraocular levels of VEGF, which in turn increases the permeability of the vasculature.

Patients at risk for developing DME include those who have had diabetes for an extended amount of time and who experience one or more of severe hypertension (high blood pressure), fluid retention, hypoalbuminemia, or hyperlipidemia. Common symptoms of DME are blurry vision, floaters, double vision, and eventually blindness if the condition is allowed to progress untreated. DME is diagnosed by funduscopic examination as retinal thickening within 2 disc diameters of the center of the macula. Other methods that may be employed include Optical coherence tomography (OCT) to detect retinal swelling, cystoid edema, and serous retinal detachment; fluorescein angiography, which distinguishes and localizes areas of focal versus diffuse leakage, thereby guiding the placement of laser photocoagulation if laser photocoagulation is to be used to treat the edema; and color stereo fundus photographs, which can be used to evaluate long-term changes in the retina. Visual acuity may also be measured, especially to follow the progression of macular edema and observe its treatment following administration of the subject pharmaceutical compositions.

Retinal vein occlusions. A retinal vein occlusion (RVO) is a blockage of the portion of the circulation that drains the retina of blood. The blockage can cause back-up pressure in the capillaries, which can lead to hemorrhages and also to leakage of fluid and other constituents of blood.

Glaucoma. Glaucoma is a term describing a group of ocular (eye) disorders that result in optic nerve damage, often associated with increased fluid pressure in the eye (intraocular pressure)(IOP). The disorders can be roughly divided into two main categories, "open-angle" and "closed-angle" (or "angle closure") glaucoma. Open-angle glaucoma accounts for 90% of glaucoma cases in the United States. It is painless and does not have acute attacks. The only signs are gradually progressive visual field loss, and optic nerve changes (increased cup-to-disc ratio on fundoscopic examination). Closed-angle glaucoma accounts for less than 10% of glaucoma cases in the United States, but as many as half of glaucoma cases in other nations (particularly Asian countries). About 10% of patients with closed angles present with acute angle closure crises characterized by sudden ocular pain, seeing halos around lights, red eye, very high intraocular pressure (>30 mmHg), nausea and vomiting, suddenly decreased vision, and a fixed, mid-dilated pupil. It is also associated with an oval pupil in some cases. Modulating the activity of proteins encoded by DLK, NMDA, INOS, CASP-3, Bcl-2, or Bcl-xl may treat the condition.

Sorsby's fundus dystrophy. Sorsby's fundus dystrophy is an autosomal dominant, retinal disease associated with mutations in the TIMP3 gene. Clinically, early, mid-peripheral, drusen and colour vision deficits are found. Some patients complain of night blindness. Most commonly, the presenting symptom is sudden acuity loss, manifest in the third to fourth decades of life, due to untreatable submacular neovascularisation. Histologically, there is accumulation of a confluent lipid containing material 30 µm thick at the level of Bruch's membrane.

Vitelliform macular dystrophy. Vitelliform macular dystrophy is a genetic eye disorder that can cause progressive vision loss. Vitelliform macular dystrophy is associated with the buildup of fatty yellow pigment (lipofuscin) in cells underlying the macula. Over time, the abnormal accumulation of this substance can damage cells that are critical for clear central vision. As a result, people with this disorder often lose their central vision, and their eyesight may become blurry or distorted. Vitelliform macular dystrophy typically does not affect side (peripheral) vision or the ability to see at night.

Researchers have described two forms of vitelliform macular dystrophy with similar features. The early-onset form (known as Best disease) usually appears in childhood; the onset of symptoms and the severity of vision loss vary widely. It is associated with mutations in the VMD2/BEST1 gene. The adult-onset form (Adult vitelliform macular dystrophy) begins later, usually in mid-adulthood, and tends to cause vision loss that worsens slowly over time. It has been associated with mutations in the PRPH2 gene. The two forms of vitelliform macular dystrophy each have characteristic changes in the macula that can be detected during an eye examination.

Rod-cone dystrophy. Rod-cone dystrophies are a family of progressive diseases in which rod dysfunction, which leads to night blindness and loss of peripheral visual field expanses, is either the prevailing problem or occurring at least as severely as cone dysfunction. A scallop-bordered lacunar atrophy may be seen in the midperiphery of the retina. The macula is only mildly involved by clinical examination although central retinal thinning is seen in all cases. Dyschromatopsia is mild early and usually becomes more severe. The visual fields are moderately to severely constricted although in younger individuals a typical ring scotoma is present. The peripheral retina contains 'white dots' and often resembles the retinal changes seen in retinitis punctate albescens. Retinitis pigmentosa is the main group of diseases included under this definition and, as a whole, is estimated to affect approximately one in every 3,500 people. Depending on the classification criteria used, about 60-80% of all retinitis pigmentosa patients have a clear-cut rod-cone dystrophy pattern of retinal disease and once other syndromic forms are taken into account, about 50-60% of all retinitis pigmentosas fall in the rod-cone dystrophy nonsyndromic category.

Leber's congenital amaurosis. Leber's congenital amaurosis (LCA) is a severe dystrophy of the retina that typically becomes evident in the first year of life. Visual function is usually poor and often accompanied by nystagmus, sluggish or near-absent pupillary responses, photophobia, high hyperopia, and keratoconus. Visual acuity is rarely better than 20/400. A characteristic finding is Franceschetti's oculo-digital sign, comprising eye poking, pressing, and rubbing. The appearance of the fundus is extremely variable. While the retina may initially appear normal, a pigmentary retinopathy reminiscent of retinitis pigmentosa is frequently observed later in childhood. The electroretinogram (ERG) is characteristically "nondetectable" or severely subnormal. Mutations in 17 genes are known to cause LCA: GUCY2D (locus name: LCA1), RPE65 (LCA2), SPATA7 (LCA3), AIPL1 (LCA4), LCA5 (LCA5), RPGRIP1 (LCA6), CRX (LCAT), CRB1 (LCA5), NMNAT1 (LCA5), CEP290 (LCA10), IMPDH1 (LCA11), RD3 (LCA12), RDH12 (LCA13), LRAT (LCA14), TULP1 (LCA15), KCNJ13 (LCA16), and IQCB1. Together, mutations in these genes are estimated to account for over half of all LCA diagnoses. At least one other disease locus for LCA has been reported, but the gene is not known.

X-linked retinoschisis. X-linked retinoschisis (XLRS) is characterized by symmetric bilateral macular involvement with onset in the first decade of life, in some cases as early as age three months. Fundus examination shows areas of schisis (splitting of the nerve fiber layer of the retina) in the macula, sometimes giving the impression of a spoke wheel pattern. Schisis of the peripheral retina, predominantly inferotemporally, occurs in approximately 50% of individuals. Affected males typically have vision of 20/60 to 20/120. Visual acuity often deteriorates during the first and second decades of life but then remains relatively stable until the fifth or sixth decade. The diagnosis of X-linked juvenile retinoschisis is based on fundus findings, results of electrophysiologic testing, and molecular genetic testing. RS1 is the only gene known to be associated with X-linked juvenile retinoschisis.

An individual affected by a cone cell disorder or at risk for developing a cone cell disorder can be readily identified using techniques to detect the symptoms of the disorder as known in the art, including, without limitation, fundus photography; Optical coherence tomography (OCT); adaptive optics (AO); electroretinography, e.g. ERG, color ERG (cERG); color vision tests such as pseudoisochromatic plates (Ishihara plates, Hardy-Rand-Ritter polychromatic plates), the Farnsworth-Munsell 100 hue test, the Farnsworth's panel D-15, the City university test, Kollner's rule, and the like; and visual acuity tests such as the ETDRS letters test, Snellen visual acuity test, visual field test, contrast sensitivity test, and the like; as will be known by the ordinarily skilled artisan. Additionally or alternatively, the individual affected by a cone cell disorder or at risk for developing a cone cell disorder can be readily identified using techniques to detect gene mutations that are associated with the cone cell disorder as known in the art, including, without limitation, PCR, DNA sequence analysis, restriction digestion, Southern blot hybridization, mass spectrometry, etc. In some embodiments, the method comprises the step of identifying the individual in need of a cone cell therapy. In such instances, any convenient method for determining if the individual has the symptom(s) of a cone cell disorder or is at risk for developing a cone cell disorder, for example by detecting the symptoms described herein or known in the art, by detecting a mutation in a gene as herein or as known in the art, etc. may be utilized to identify the individual in need of a cone cell therapy.

In practicing the subject methods, the subject composition is typically delivered to the retina of the subject in an amount that is effective to result in the expression of the transgene in the cone cells. In some embodiments, the method comprises the step of detecting the expression of the transgene in the cone cells.

There are a number of ways to detect the expression of a transgene, any of which may be used in the subject embodiments. For example, expression may be detected directly, i.e. by measuring the amount of gene product, for example, at the RNA level, e.g. by RT-PCR, Northern blot, RNAse protection; or at the protein level, e.g. by Western blot, ELISA, immunohistochemistry, and the like. As another example, expression may be detected indirectly, i.e. by detecting the impact of the gene product on the viability or function of the cone photoreceptor in the subject. For example, if the gene product encoded by the transgene improves the viability of the cone cell, the expression of the transgene may be detected by detecting an improvement in viability of the cone cell, e.g. by fundus photography, Optical coherence tomography (OCT), Adaptive Optics (AO), and the like. If the gene product encoded by the transgene alters the activity of the cone cell, the expression of the transgene may be detected by detecting a change in the activity of the cone cell, e.g. by electroretinogram (ERG) and color ERG (cERG); functional adaptive optics; color vision tests such as pseudoisochromatic plates (Ishihara plates, Hardy-Rand-Ritter polychromatic plates), the Farnsworth-Munsell 100 hue test, the Farnsworth's panel D-15, the City university test, Kollner's rule, and the like; and visual acuity tests such as the ETDRS letters test, Snellen visual acuity test, visual field test, contrast sensitivity test, and the like, as a way of detecting the presence of the delivered polynucleotide. In some instances, both an improvement in viability and a modification in cone cell function may be detected.

In some embodiments, the subject method results in a therapeutic benefit, e.g. preventing the development of a disorder, halting the progression of a disorder, reversing the progression of a disorder, etc. In some embodiments, the subject method comprises the step of detecting that a therapeutic benefit has been achieved. The ordinarily skilled artisan will appreciate that such measures of therapeutic efficacy will be applicable to the particular disease being modified, and will recognize the appropriate detection methods to use to measure therapeutic efficacy. For example, therapeutic efficacy in treating macular degeneration may be observed as a reduction in the rate of macular degeneration or a cessation of the progression of macular degeneration, effects which may be observed by, e.g., fundus photography, OCT, or AO, by comparing test results after administration of the subject composition to test results before administration of the subject composition. As another example, therapeutic efficacy in treating a progressive cone dysfunction may be observed as a reduction in the rate of progression of cone dysfunction, as a cessation in the progression of cone dysfunction, or as an improvement in cone function, effects which may be observed by, e.g., ERG and/or cERG; color vision tests; functional adaptive optics; and/or visual acuity tests, for example, by comparing test results after administration of the subject composition to test results before administration of the subject composition and detecting a change in cone viability and/or function. As a third example, therapeutic efficacy in treating a color vision deficiency may be observed as an alteration in the individual's perception of color, e.g. in the perception of red wavelengths, in the perception of green wavelengths, in the perception of blue wavelengths, effects which may be observed by, e.g., cERG and color vision tests, for example, by comparing test results after administration of the subject composition to test results before administration of the subject composition and detecting a change in cone viability and/or function.

Expression of the transgene using the subject transgene is expected to be robust. Accordingly, in some instances, the expression of the transgene, e.g. as detected by measuring levels of gene product, by measuring therapeutic efficacy, et.c, may be observed two months or less after administration, e.g. 4, 3 or 2 weeks or less after administration, for example, 1 week after administration of the subject composition. Expression of the transgene is also expected to persist over time. Accordingly, in some instances, the expression of the transgene, e.g. as detected by measuring levels of gene product, by measuring therapeutic efficacy, etc., may be observed 2 months or more after administration of the subject composition, e.g., 4, 6, 8, or 10 months or more, in some instances 1 year or more, for example 2, 3, 4, or 5 years, in certain instances, more than 5 years.

In certain embodiments, the method comprises the step of detecting expression of the transgene in the cone cells, wherein expression is enhanced relative to expression from a polynucleotide cassette not comprising the one or more improved elements of the present disclosure, i.e. a reference control, e.g. the pR2.1 promoter or variants thereof (e.g. pR1.7, pR1.5, pR1.1, etc.) as disclosed in, e.g., US Application No. 2013/0317091, or the synthetic IRBP/GNAT2 promoter as disclosed in US Application No. 2014/0275231; the full disclosures of which are incorporated herein by reference. Typically, expression will be enhanced 2-fold or more relative to the expression from a reference, i.e. a control polynucleotide cassette, e.g. as known in the art, for example 3-fold, 4-fold, or 5-fold or more, in some instances 10-fold, 20-fold or 50-fold or more, e.g. 100-fold, as evidenced by, e.g. earlier detection, higher levels of gene product, a stronger functional impact on the cells, etc.

Typically, if the subject composition is an rAAV comprising the subject a polynucleotide cassette of the present disclosure, an effective amount to achieve a change in will be about $1 \times 10^8$ vector genomes or more, in some cases $1 \times 10^9$, $1 \times 10^{10}$, $1 \times 10^{11}$, $1 \times 10^{12}$, or $1 \times 10^{13}$ vector genomes or more, in certain instances, $1 \times 10^{14}$ vector genomes or more, and usually no more than $1 \times 10^{15}$ vector genomes. In some cases, the amount of vector genomes that is delivered is at most about $1 \times 10^{15}$ vector genomes, e.g. $1 \times 10^{14}$ vector genomes or less, for example $1 \times 10^{13}$, $1 \times 10^{12}$, $1 \times 10^{11}$, $1 \times 10^{10}$, or $1 \times 10^9$ vector genomes or less, in certain instances $1 \times 10^8$ vector genomes, and typically no less than $1 \times 10^8$ vector genomes. In some cases, the amount of vector genomes that is delivered is $1 \times 10^{10}$ to $1 \times 10^{11}$ vector genomes. In some cases, the amount of vector genomes that is delivered is $1 \times 10^{10}$ to $3 \times 10^{12}$ vector genomes. In some cases, the amount of vector genomes that is delivered is $1 \times 10^9$ to $3 \times 10^{13}$ vector genomes. In some cases, the amount of vector genomes that is delivered is $1 \times 10^8$ to $3 \times 10^{14}$ vector genomes.

In some cases, the amount of pharmaceutical composition to be administered may be measured using multiplicity of infection (MOI). In some cases, MOI may refer to the ratio, or multiple of vector or viral genomes to the cells to which the nucleic may be delivered. In some cases, the MOI may be $1 \times 10^6$. In some cases, the MOI may be $1 \times 10^5$-$1 \times 10^7$. In some cases, the MOI may be $1 \times 10^4$-$1 \times 10^8$. In some cases, recombinant viruses of the disclosure are at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI. In some cases, recombinant viruses of this disclosure are $1 \times 10^8$ to $3 \times 10^{14}$ MOI. In some cases, recombinant viruses of the disclosure are at most about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$ and $1 \times 10^{18}$ MOI.

In some aspects, the amount of pharmaceutical composition comprises about $1 \times 10^8$ to about $1 \times 10^{15}$ particles of recombinant viruses, about $1 \times 10^9$ to about $1 \times 10^{14}$ particles of recombinant viruses, about $1 \times 10^{10}$ to about $1 \times 10^{13}$ particles of recombinant viruses, or about $1 \times 10^{11}$ to about $3 \times 10^{12}$ particles of recombinant viruses.

Individual doses are typically not less than an amount required to produce a measurable effect on the subject, and may be determined based on the pharmacokinetics and pharmacology for absorption, distribution, metabolism, and excretion ("ADME") of the subject composition or its by-products, and thus based on the disposition of the composition within the subject. This includes consideration of the route of administration as well as dosage amount, which can be adjusted for subretinal (applied directly to where action is desired for mainly a local effect), intravitreal (applied to the vitreaous for a pan-retinal effect), or parenteral (applied by systemic routes, e.g. intravenous, intramuscular, etc.) applications. Effective amounts of dose and/or dose regimen can readily be determined empirically from preclinical assays, from safety and escalation and dose range trials, individual clinician-patient relationships, as well as in vitro and in vivo assays such as those described herein and illustrated in the Experimental section, below.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Background

New therapies are needed for the treatment of many cone photoreceptor associated disorders, including macular dystrophies such as cone-rod dystrophy, cone dystrophy, Stargardt macular dystrophy, and achromatopsia; color vision disorders such as protan, deutan, and tritan defects; and vision disorders of the central macula such as age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, and X-linked retinoschisis. As these vision disorders are associated with a loss of function and/or viability of the cone photoreceptors, it is hypothesized that these disorders may be treatable by delivering a therapeutic gene to cone photoreceptors to rescue cone viability and function.

Figure 10A:
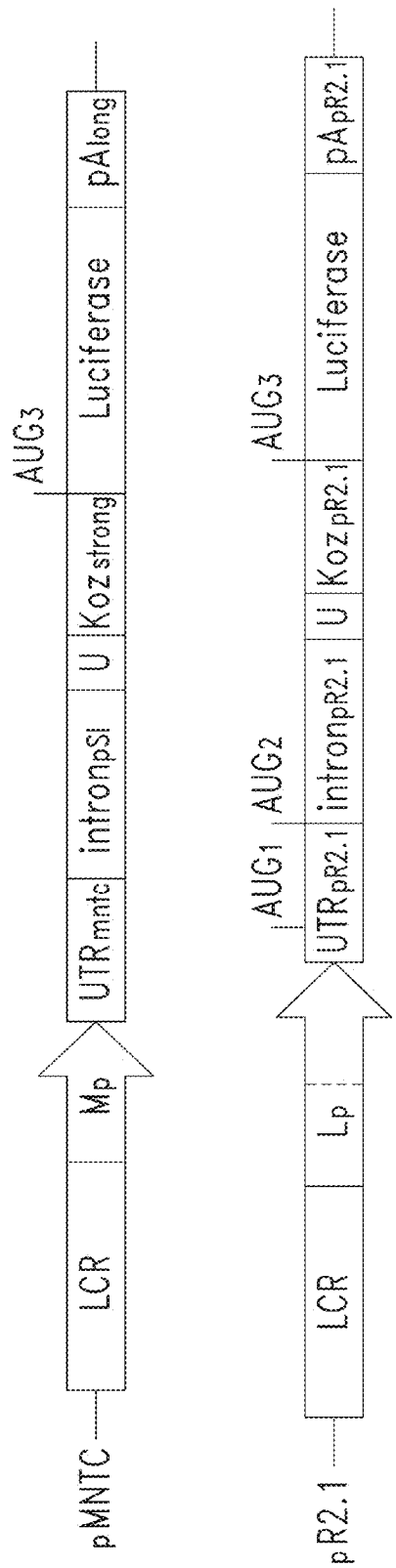
Figure 10B:
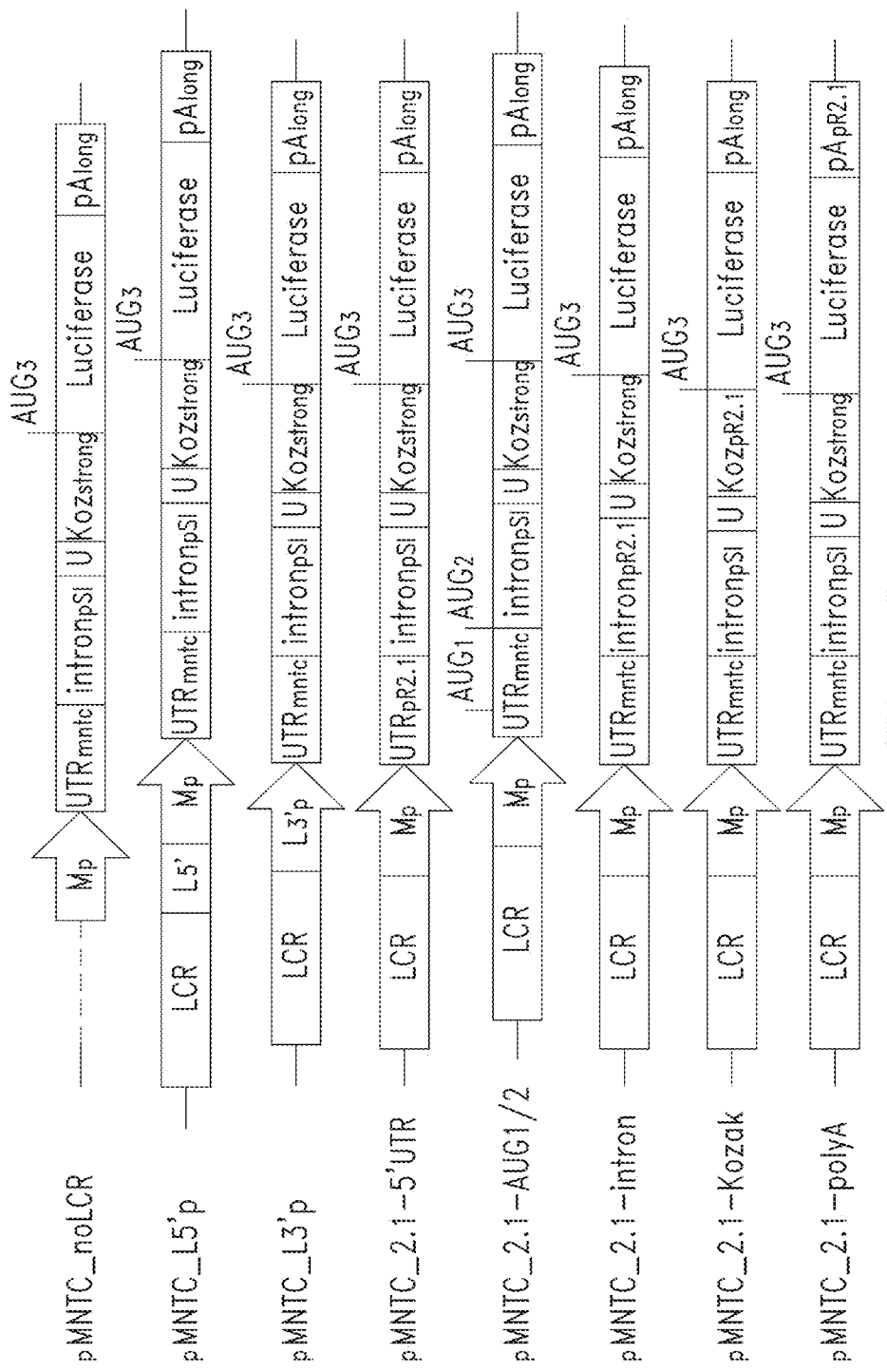
Figure 10C:
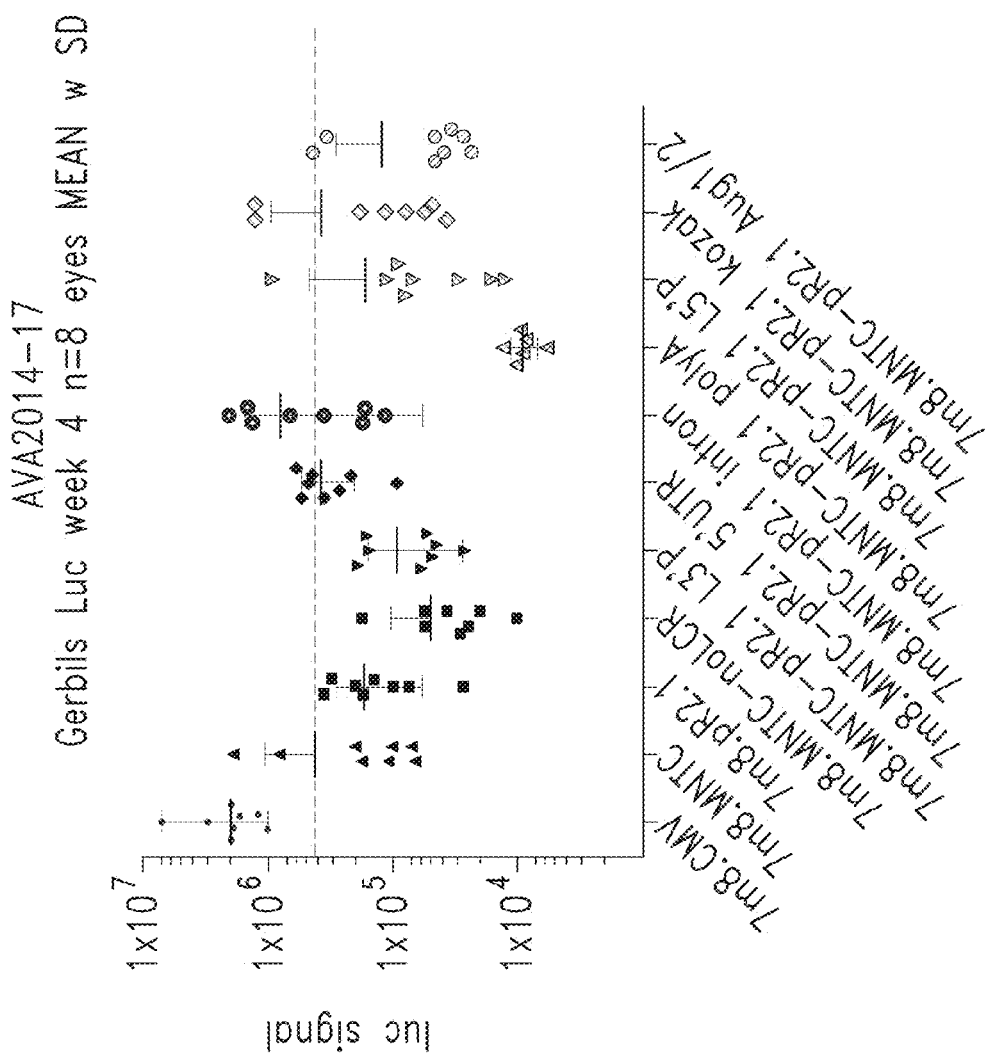
Figure 10D:
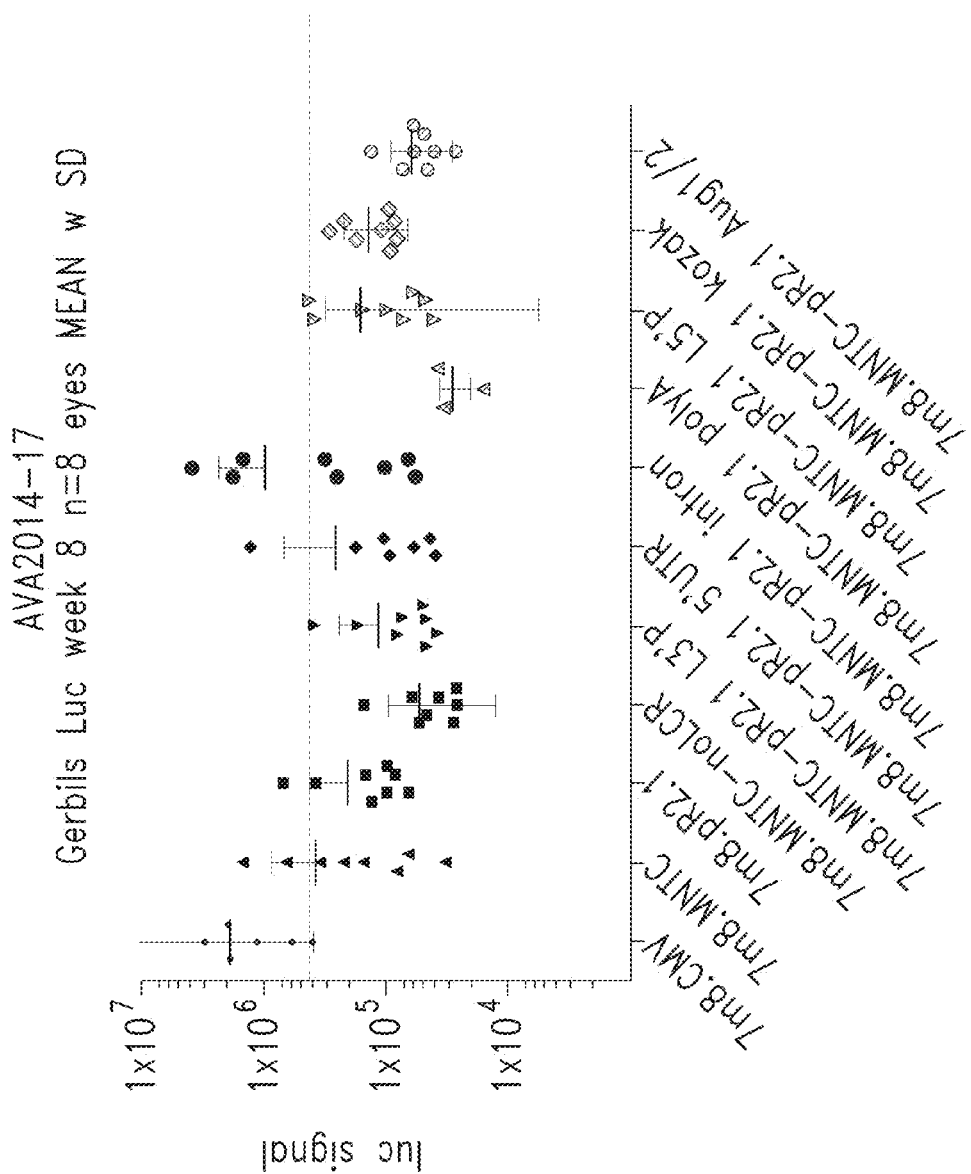

To that end, the polynucleotide cassette "pMNTC" was designed in which enhancer, promoter, 5'UTR, intron, Kozak, and polyadenylation sequences were designed for cone-specific expression (FIG. 10a). The cassette included an LCR enhancer sequence from the L- and M-opsin genomic locus and a truncated promoter sequence from the M-Opsin gene, comprising about 140 nucleotides upstream of the transcriptional start site. In addition, the cassette included a 5' untranslated region (5' UTR) based on the M-opsin 5'UTR but modified to have minimal secondary structure (see FIG. 3) and to include additional sequence at its 3' end into which an intron was inserted. The intronic sequence used was a pSI chimeric intron having the 5'-donor site from the first intron of the human β-globin gene and the branch and 3'-acceptor site from the intron that lies between the leader and the body of an immunoglobulin gene heavy chain variable region (Bothwell, A. L. et al. (1981) Heavy chain variable region contribution to the NPb family of antibodies: Somatic mutation evident in a gamma 2a variable region. Cell 24, 625-37). The sequences of the donor and acceptor sites, along with the branchpoint site, were changed to match the consensus sequences for splicing (Senapathy, P., Shapiro, M. B. and Harris, N. L. (1990) Meth. Enzymol. 183, 252-78). Also included in the pMNTC polynucleotide cassette was a strong Kozak sequence and an SV40 polyadenylation sequence.

Experiments were also performed to identify the best AAV with which to deliver transgenes to cone cells. Successful delivery of polynucleotides to cells of the retina for the purposes of gene therapy has been achieved using viral vectors such as AAV and lentivirus. However, these viruses must be injected subretinally to reach the cells of the non-human primate (NHP) retina, a procedure that carries with it the risk of retinal damage. A less disruptive approach is administration by intravitreal injection. However, efficient transduction of cone photoreceptors following intravitreal delivery of AAV or lentivirus has never been demonstrated: while reports exist of AAVs with the ability to transduce retinal cone cells with high efficiency (Merigan et al. IOVS 2008, 49 E-abstract 4514), later reports have questioned the efficacy of these vectors (Yin et al. IOVS 2011, 52(5):2775-2783).

Results

Figure 5:
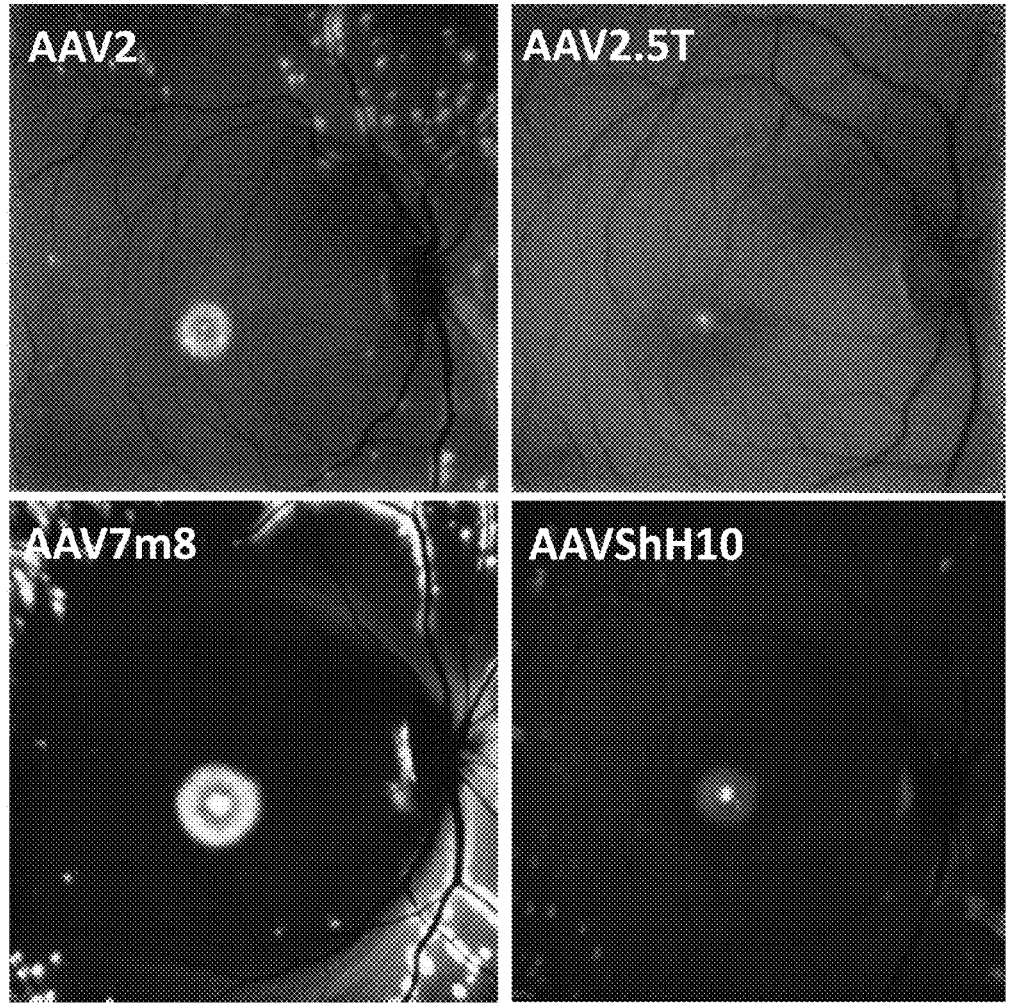
FIG. 5 illustrates how intravitreally-delivered AAV2 variant AAV2-7m8 transduces retinal cells in the fovea centralis and parafovea of primates more efficiently than intravitreally-delivered AAV2. $5 \times 10^{11}$ vector genomes of AAV2.CMV.GFP (upper left); AAV-2.5T.CMV.GFP (upper right) (Excoffon K. J., et al. 2009. Proc. Natl. Acad. Sci. U.S.A. 106:3865-3870); (lower left) AAV2-7.8.CMV.GFP (Dalkara D, et al. Sci Transl Med. 2013 Jun. 12; 5(189): 189ra76); or AAV-ShH10.CMV.GFP (lower right) (Klimczak R R et al. PLoS One. 2009 Oct. 14; 4(10):e7467) was injected into the vitreous of an African green monkey in a volume of 50 uL, and GFP expression was observed 8 weeks later by OCT fluorescence imaging in vivo.
Figure 6A:
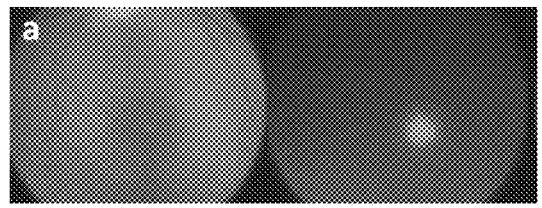
FIG. 6 illustrates how robustly the pMNTC regulatory cassette promotes gene expression in foveal cones of primates. (a-b) AAV2-7m8.MNTC.GFP was injected into the central vitreous of a baboon and expression was observed (a) 5 weeks and (b) 8 weeks later by fundus fluorescence. (c and d) Natural GFP fluorescence within a 15 micron section of the fovea at approximately 6 months after injection with AAV2-7m8.MNTC.GFP at low magnification (c) and high magnification (d).
Figure 6B:
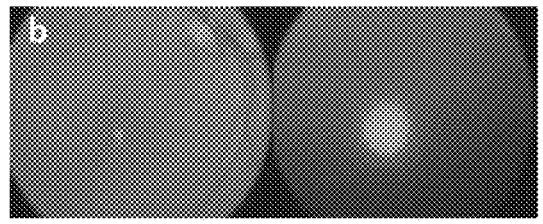
Figure 6C:
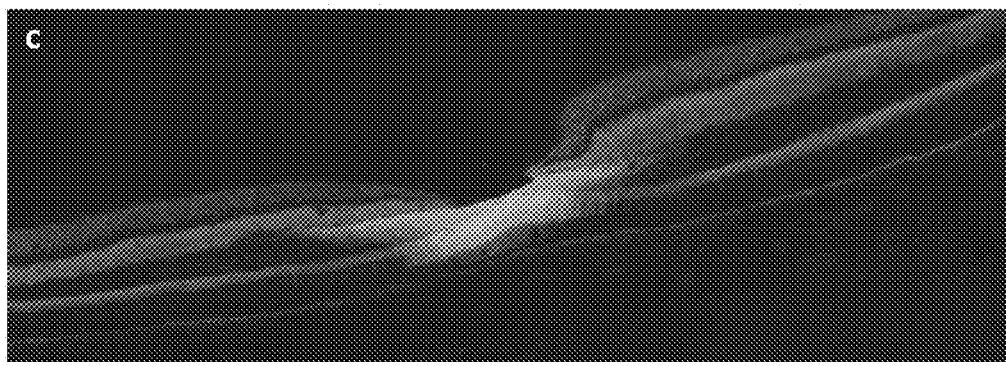
Figure 6D:
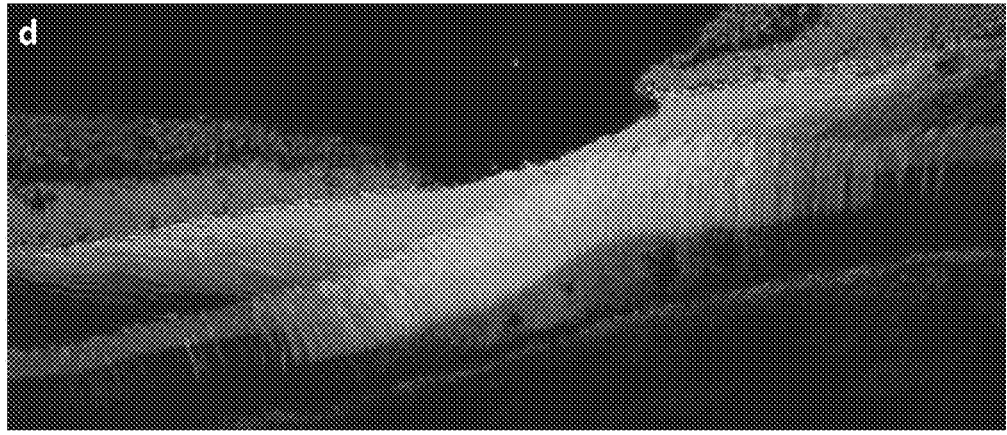

Directed evolution of AAV2 has led to the identification of the viral variant "7m8" that is able to transduce photoreceptors better than wild type AAV2 (Dalkara et al. Sci Transl Med 2013). However, the retina contains two types of photoreceptors—rods and cones—and no reports exist demonstrated whether AAV2-7m8 can transduce cone photoreceptors, per se, and more particularly, cone photoreceptors in the highly cone-enriched area of the fovea. To test this possibility, we delivered AAV2-7m8 carrying an expression cassette of the ubiquitous promoter CMV operably linked to GFP to the retina of African Green monkey by intravitreal injection. Intravitreally delivered AAV2-7m8.CMV.GFP appeared to transduce retinal cells in the fovea centralis (the 0.35 mm diameter rod-free region of retina at the center of the foveal pit) and parafovea (the lip of the depression) of primates more efficiently than intravitreally-delivered AAV2 or other AAV variants previously shown in the art to transduce retinal cells. Neither AAV2-7m8 nor the other AAVs tested tested appeared to be able to transduce the cones of the primate fovea, the 1.5 mm-diameter cone-enriched region of retina that surrounds the foveola and forms the slopes of the pit (FIG. 5).

Figure 8A:
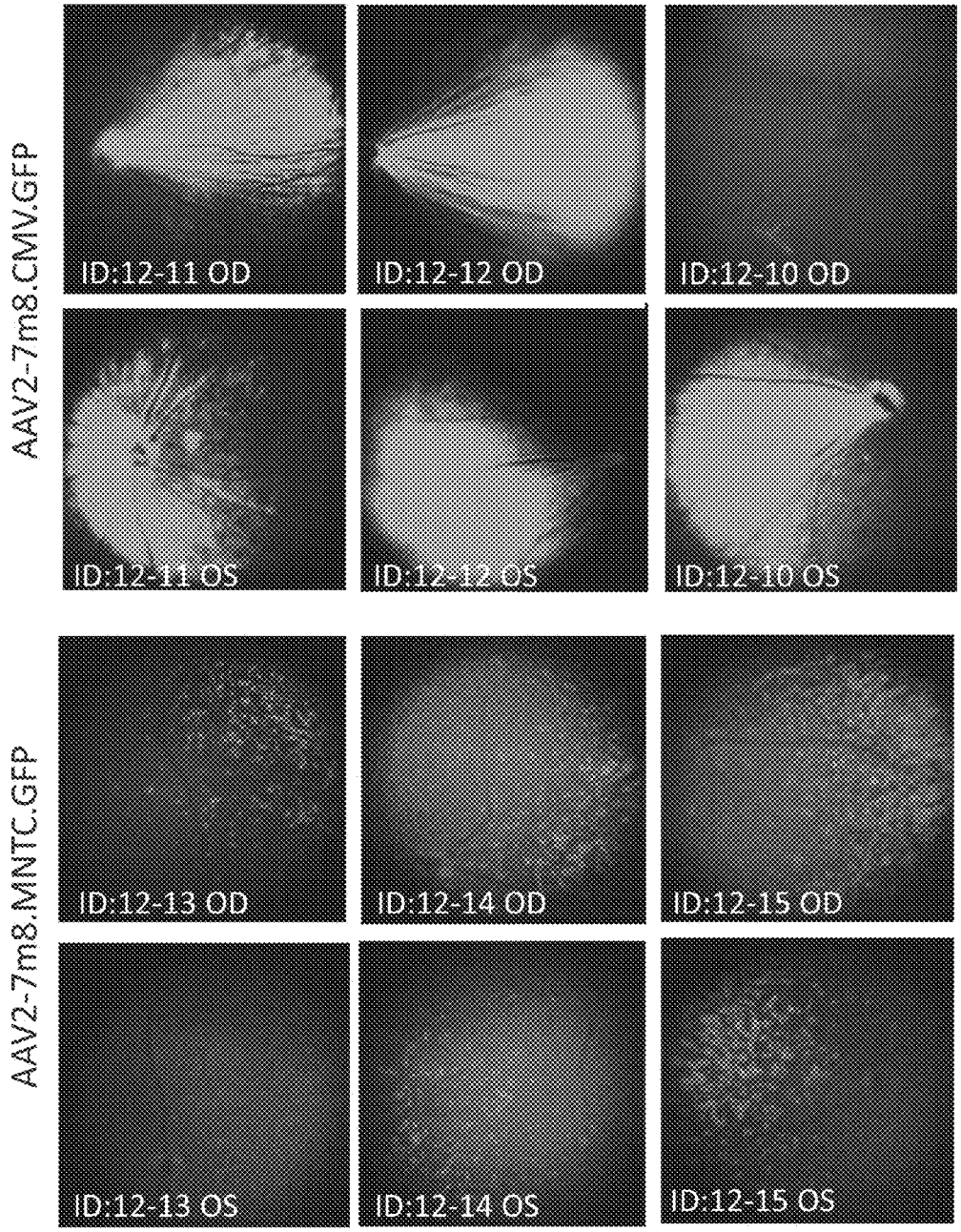
FIG. 8 illustrates gene expression directed by the pMNTC regulatory cassette in the cones of the Mongolian gerbil retina. $1 \times 10^{10} - 2 \times 10^{10}$ vector genomes of virus carrying GFP under the control of the CMV, pR2.1, or MNTC promoter were injected in a volume of 5 uL into the vitreous of a Mongolian gerbil, and GFP expression visualized at the designated time points by fundus fluorescence imaging. (a) Expression of GFP directed by AAV2-7m8.CMV.GFP and AAV2-7m8.MNTC.GFP, visualized 4 weeks after intravitreal administration. Gerbils 12-10, 12-11, and 12-12 were injected with AAV2-7m8.CMV.GFP, while gerbils 12-13, 12-14, and 12-15 were injected with AAV2-7m8.MNTC.GFP. OD, oculus dexter (right eye). OS, oculus sinister (left eye). (b) Expression of GFP directed by AAV2-7m8.pR2.1.GFP and AAV2-7m8.MNTC.GFP, 4 and 8 weeks later as detected by fundus fluorescence imaging.

We next packaged a genome comprising pMNTC operably linked to GFP within the AAV2-7m8 capsid, and assessed the ability of this vector composition to express the GFP transgene in cone cells in vivo when injected intravitreally. Expression was evaluated in a number of species with varying numbers of retinal cones cells among total photoreceptors, including mouse (3% cones), rat (1% cones), gerbil (13% cones), and nonhuman primate (5% cones). Contrary to our results in FIG. 5, strong gene expression could be detected throughout the nonhuman primate fovea (FIG. 6). These data indicate that intravitreally delivered AAV2-7m8 can, in fact, transduce retinal cones, and that pMNTC acts as a robust expression cassette in cone cells. Robust reporter gene expression was also seen in the intravireally injected retina of the rat (data not shown) and gerbil (FIG. 8A), with expression levels and anatomic location correlating with cone abundance and location in all species.

To determine the cell-specificity of pMNTC-directed expression, whole mounts of transduced mouse retina were analyzed by immunohistochemistry using an antibody that is specific for cone L and M opsins. The expression of L/M opsin, which labels the outer segments of cone photoreceptors only, was observed in virtually all of the cones of the mouse retina that expressed GFP from the AAV2-7m8.MNTC.GFP vector (FIG. 7), indicating that MNTC-directed expression of transgenes is highly cone-specific. Moreover 80% or more of the cone outer segments that were labelled by the L/M opsin-specific antibody also expressed the GFP transgene, indicating that AAV2-7m8 transduces cones highly efficiently (FIG. 7).

We next compared the ability of pMNTC to promote expression in cone cells to that of pR2.1. pR2.1 comprises the human L/M opsin enhancer ("LCR") and the promoter region from the human L-Opsin gene. In addition, pR2.1 comprises the L-Opsin 5'UTR fused to additional 5'UTR sequence at its 3' end, into which modified SV40 late 16s intronic sequence has been inserted. This is followed by the L-Opsin Kozak sequence, which is then typically linked in-frame to a transgene. At the end of the cassette is an SV40 polyA tail.

Figure 8B:
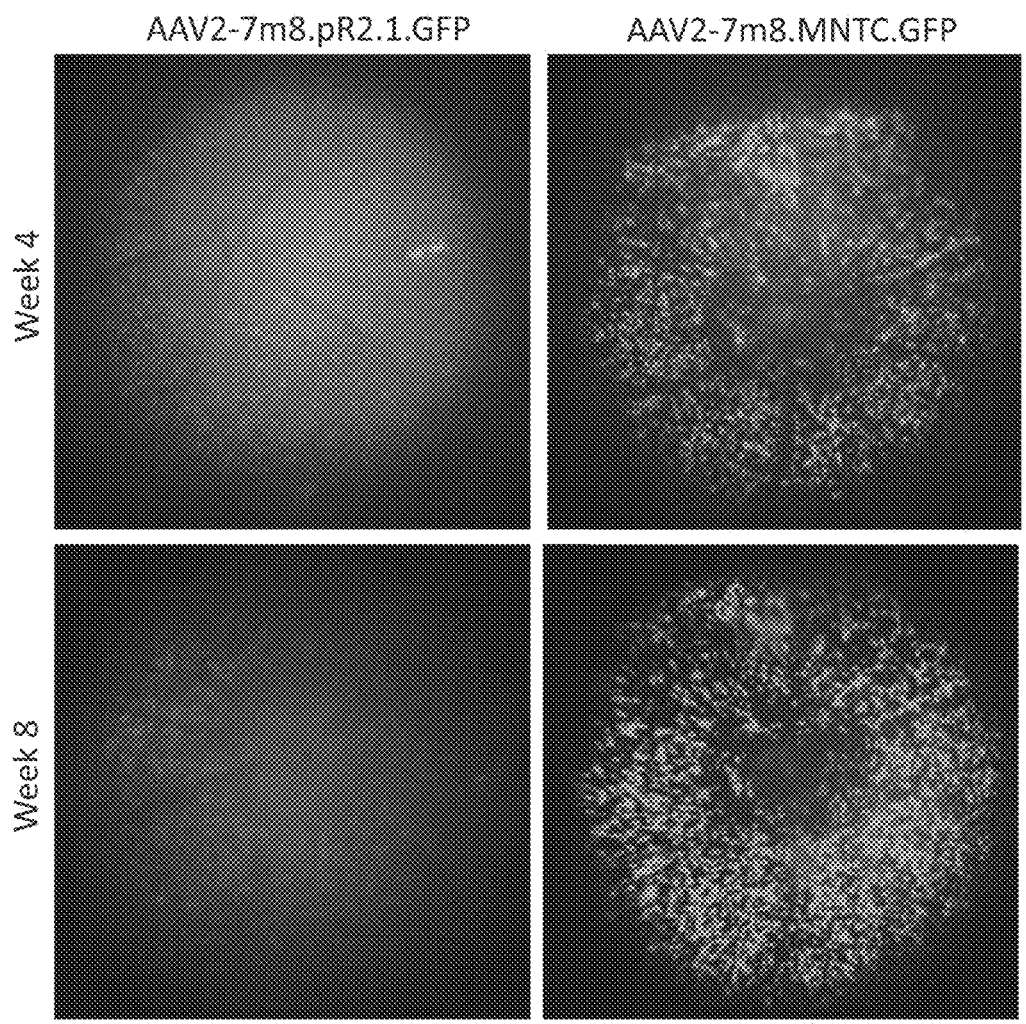
Figure 9A:
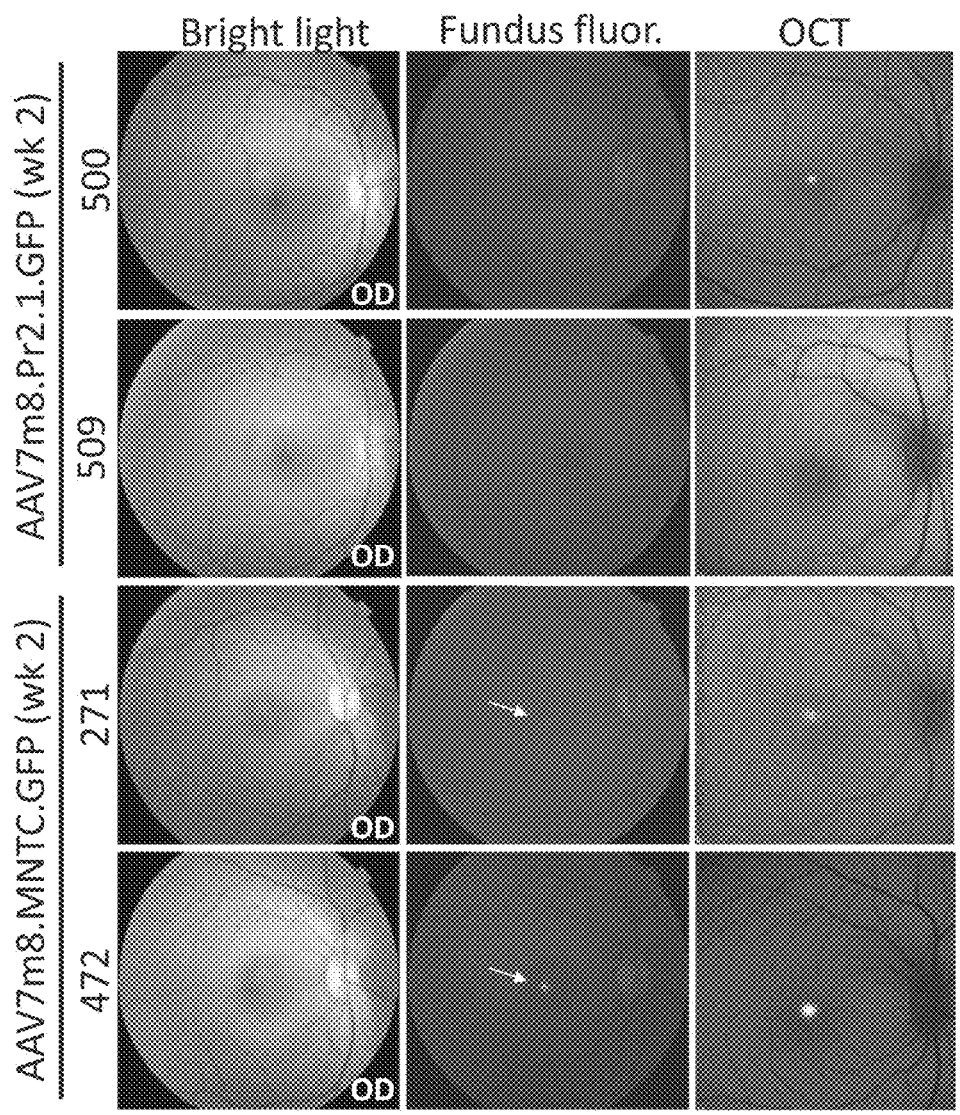
FIGS. 9A-9D demonstrate that the pMNTC regulatory cassette provides for more robust gene expression in foveal cones of primates than the cone promoter pR2.1. $5 \times 10^{11}$ vector genomes of AAV2-7m8.MNTC.GFP or AAV2-7m8.pR2.1.GFP were injected in a volume of 50 uL into the vitreous of African Green Monkeys as indicated (AAV2-
Figure 9B:
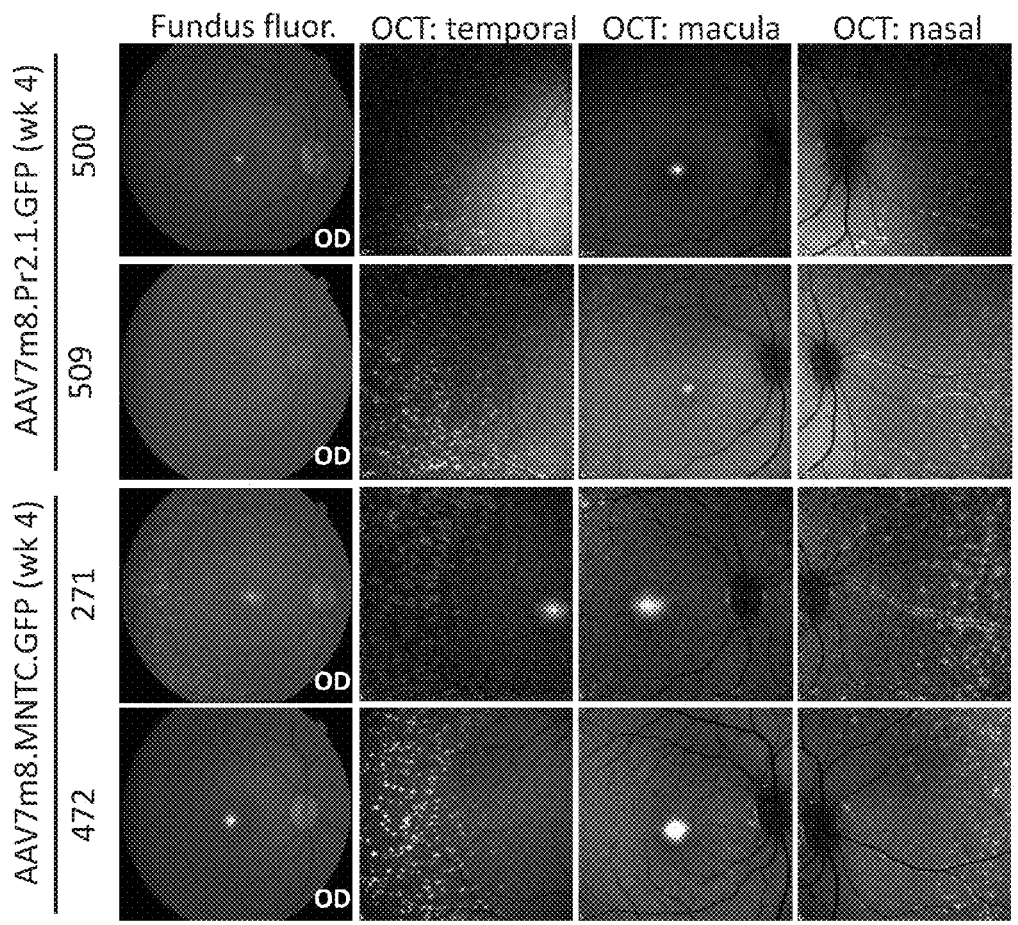
Figure 9C:
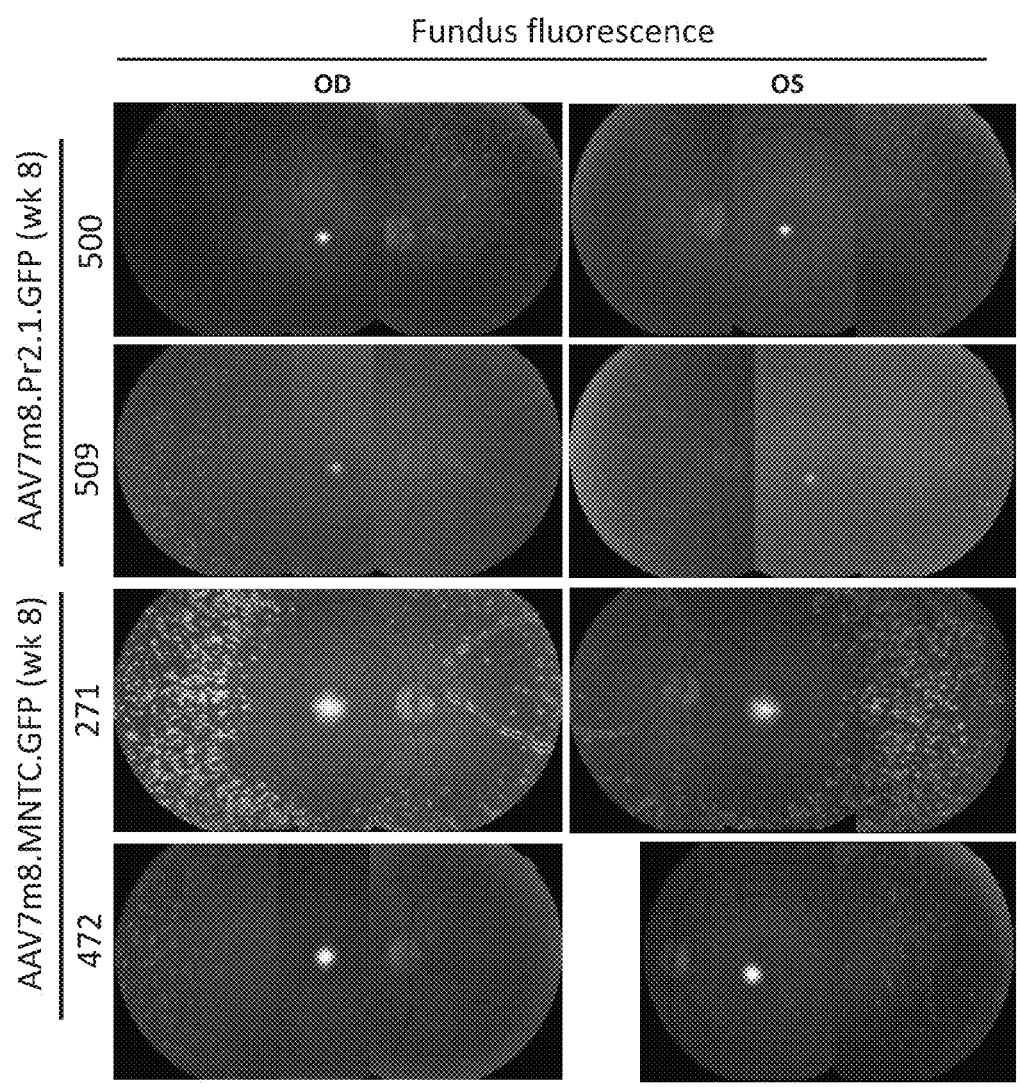
Figure 9D:
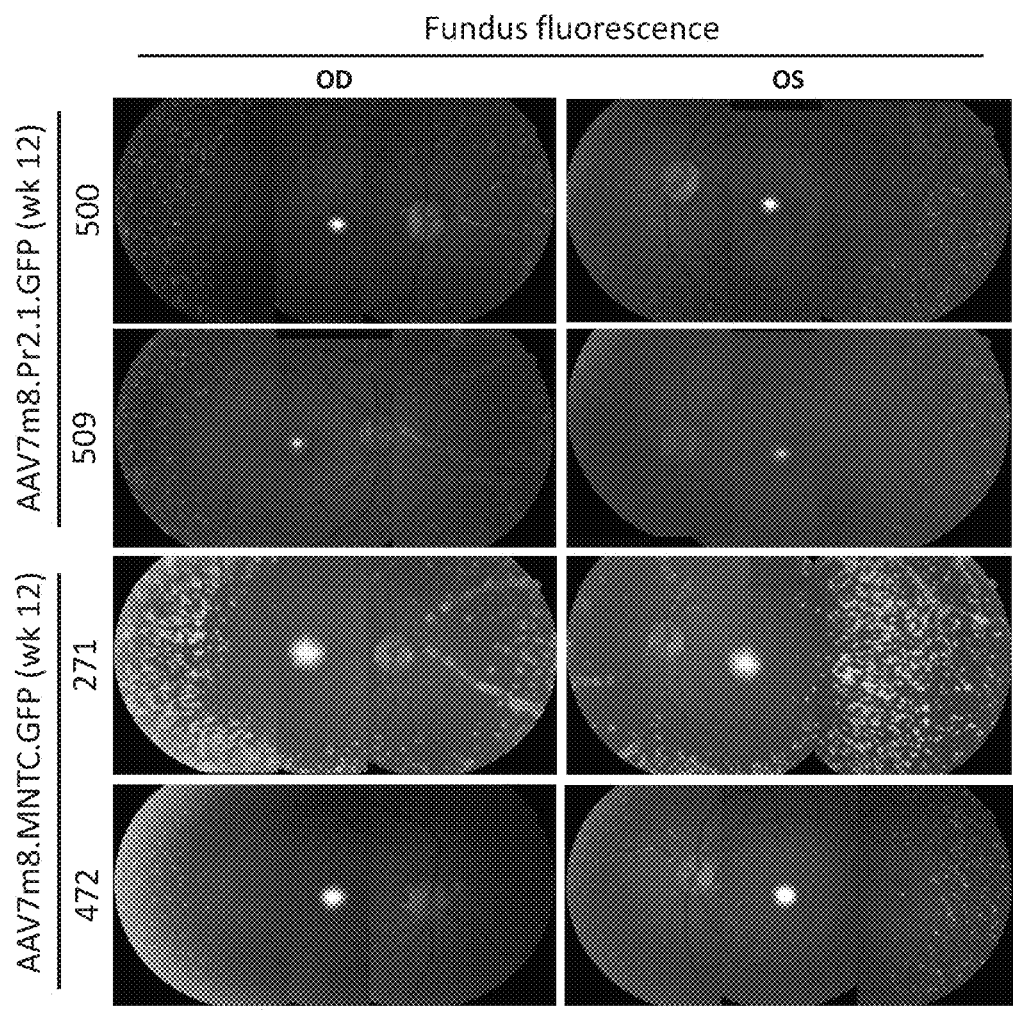

Viral preparations of AAV2-7m8.MNTC.GFP and AAV2-7m8.pR2.1.GFP were delivered intravitreally to the retinas of gerbils and nonhuman primates in vivo, and the retinas imaged in vivo 2 weeks, 4 weeks, 8 weeks, and 12 weeks later by fundus autofluorescence and OCT. GFP reporter expression was detected sooner, more strongly, and in more cones in gerbil retina transduced with rAAV carrying the pMNTC.GFP expression cassette than in gerbil retinas carrying the pR2.1.GFP expression cassette (FIG. 8B). Likewise, GFP reporter expression was detected sooner and in more cones in nonhuman primate retinas transduced with rAAV carrying the pMNTC.GFP expression cassette as compared to NHP retinas transduced with the pR2.1 expression cassette (FIG. 9, n=4 eyes). In both gerbils and NHP, GFP was consistently observed to be stronger from pMNTC than from pR2.1 throughout the duration of the study.

To determine the contribution of each of the elements in the pMNTC expression cassette to the overall improvement in expression, a series of expression constructs were cloned in which each of the elements in pMNTC was substituted one-by-one with the corresponding element from the pR2.1 expression cassette. These constructs were then packaged into AAV2-7m8 and delivered by intravitreal injection to the gerbil retina. Gerbil retinas were assessed 4 and 8 weeks later in vivo by in vivo bioluminescence (IVIS imaging system, PerkinElmer), which provides a quantitative readout of reporter expression across the entire eye.

As expected, expression of the luciferase reporter under the control of pMNTC was higher than expression of the luciferase reporter under the control of pR2.1. Replacement of the pMNTC promoter sequence with the pR2.1 promoter sequence having the most sequence homology to it (SEQ ID NO:83) reduced expression (construct pMNTC_pR2.1 L3'P), as did the inclusion of pR2.1 promoter sequence that lies more distal to the 5'UTR of pR2.1 (SEQ ID NO:82) (construct pMNTCpR2.1-L5'P). Expression was also reduced by the introduction into the pMNTC 5'UTR of two false start sequences ("AUG1" and "AUG2") that were observed in the pR2.1 5'UTR (construct pMNTC_2.1-AUG1/2). Interestingly, expression was not reduced when the pMNTC 5'UTR was replaced with a modified pR2.1 5'UTR sequence in which these false starts had been removed (SEQ ID NO:87, nucleotide 17 changed to C, nt 61 and 62 changed to CA) (pMNTC_pR2.1-5'UTR), suggesting that the pR2.1 5'UTR would promote strong expression in cone cells but for the false AUGs in the pR2.1 5'UTR element. Also interestingly, the pR2.1 intron (SEQ ID NO:59) appeared to provide more robust expression than the pSI chimeric intron of pMNTC, suggesting that inclusion of the pR2.1 intron in the polynucleotide cassettes of the present disclosure may be used to further improve expression in cone cells. Lastly, removal of the L/M enhancer (found in both pR2.1 and pMNTC) reduced expression as well. While the polyA tailed seemed at first to also have a significant impact on expression, re-sequencing of the pMNTC construct comprising this pR2.1 element revealed that the polyA tail was not operably linked to the transgene, thereby explaining why only background levels of expression were observed from this construct. Thus, the L/M opsin LCR, the inclusion of the M opsin core promoter rather than the L opsin promoter, and the exclusion of false starts in the 5'UTR all contribute to the enhancement in gene expression achieved using the pMNTC promoter.

In conclusion, we have identified an AAV variant, the AAV variant comprising a 7m8 peptide in the GH loop, which may be used for the intravitreal delivery of polynucleotides to retinal cones. Likewise, we have identified a number of polynucleotide cassette elements that may be used to promote strong expression in cone photoreceptors. Together, these discoveries represent improvements that may facilitate the development of therapeutic agents for cone-associated disorders.

Materials and Methods

Transgene expression in vitro in WERI-RB-1 cells. WERI-Rb-1 retinoblastoma cells expressing cone photoreceptor pigments cells are transfected with a polynucleotide cassette of the present disclosure according to the method described by Shaaban and Deeb, 1998; IOVS 39(6)885-896. The polynucleotide cassettes are transfected as plasmid DNA using well established techniques of molecular biology, such as cloning (Maniatis et al.) or via de novo DNA synthesis. All regulatory elements are placed in the cassette and used to drive the enhanced GFP protein. Plasmid DNA is then introduced into cells using established techniques for non-viral transfection, for example using a lipid-based transfection reagent (Altogen Biosystems, NV) or Lipofectamine LTX (Life Technologies). Cells are then cultured for 72 hours and eGFP expression is measured using flow cytometry and fluorescence microscopy. Transgene expression in cells transfected with the polynucleotide cassette of the present invention (i.e., constructs designed for cone photoreceptor expression) is compared to the un-optimized counterparts (i.e., those based on pR2.1) and is found to be stronger from cassettes carrying improved elements In vitro expression is also evaluated using other mammalian cell lines that express cone opsins, such as 661W cells (Tan et al., IOVS 2004; 45(3) 764-768).

Similarly, in vitro expression is evaluated using non-photoreceptor cell lines that have been engineered to express cone photoreceptor-specific proteins. Such a system has been described with HEK293 cells that have been genetically engineered to express CRX/Spl (Khani et al., IOVS 2007; 48: 3954). Marker genes are also used (eGFP, dsRed, mCherry, luciferase) as well as physiologic genes (opsin, ACHR genes). Physiologic genes are tested by examining mRNA levels (e.g., by RT-PCR) or protein levels (e.g., by ELISA or Western blot).

Animal care. All experiments conformed to the principles regarding the care and use of animals adopted by the American Physiological Society and the Society for Neuroscience, and were approved by the Institutional Animal Care and Use Committee (IACUC).

Small animal studies. The expression of the gene product encoded by the coding sequence of the expression cassettes are evaluated in vivo in mice, rats, and gerbils. This is accomplished by intravitreal injection in vivo of an rAAV preparation comprising the expression cassette (Li et al., 2008; Mol Vis 48: 332-338). Note that electroporation of plasmid DNA may be performed instead (Matsuda/Cepko).

Mouse studies. Mice used in this study were C57BL/6. Animals were anesthetized with ketamine/xylazine (110 mg/kg intraperitoneal). A beveled 34 gauge disposable needle loaded with test article was inserted into the vitreous of the eye, and $5.04 \times 10^{10}$ vector genomes of rAAV in a volume of 1.5 μl was injected into the vitreous.

Gerbil and rat studies. Mongolian gerbils (Meriones unguiculatus) and brown Norway rats were used in this study. Pupils were dilated with 10% phenylephrine and 0.5% tropicamide. Animals were anesthetized with an intraperitoneal or intramuscular injection of 0.1-0.2 mL of a ketamine/xylazine solution (70 mg/mL ketamine and 10 mg/mL xylazine for rats; 25 mg/mL ketamine and 0.3 mg/mL xylazine for gerbils). A beveled 34 gauge disposable needle loaded with test article in a 100 μL Hamilton syringe was inserted into the vitreous of the eye through the sclera at an optimized superior-temporal point about 1 mm from Limbus. $1 \times 10^{10}$-$2 \times 10^{10}$ vector genomes of test article ($2 \times 10^{10}$ vg of rAAV.GFP, or $1.15 \times 10^{10}$ vg of rAAV.luciferase) in a 5 uL volume was injected slowly with a microinjection pump into the vitreous, after which the needle tip was held in the injected eye at the injected position for 10 seconds so as to ensure adequate test article dispensing. The needle was then withdrawn.

Non-human primate (NHP) studies. The polynucleotide cassettes and expression vectors are also tested in large animals. This is done by using AAV, for example using the techniques of Mancuso et al. Briefly, an AAV cassette is made, the AAV encapsidating the expression cassette is manufactured, and the viral prep is injected intravitreally (up to 170 uL in the vitreous) or subretinally (up to 3, 100 uL injections at different locations; vitrectomy may be performed prior to injection) in nonhuman primates. Expression is evaluated by reporter (GFP), color ERG, and/or behavioral testing using the Cambridge Color Test or on animals trained to make a saccade (eye movement) when a target enters the field of view. The saccades are monitored using an eye tracker. Prior to treatment animals are trained to perform a color vision test or to make a saccade when it sees a colored target. An ERG is performed to estimate the spectral sensitivity of the cones present. Data from the color vision test performance and the ERG provide evidence that the animal is dichromatic (colorblind). For animals that receive a vector carrying the GFP gene, expression is monitored using fundus imaging with RetCam II or similar device under light that produces excitation of the GFP. For animals receiving a photopigment gene that differs in spectral sensitivity compared to the animal's endogenous pigments, expression is monitored using the multifocal color ERG to measure spectral sensitivity at up to 106 different retinal locations, and by behavioral testing.

Baboons were sedated with 10-15 mg/kg ketamine following by sevofluorane. African Green monkeys were sedated with an intramuscular injection of 5:1 ketamine: xylazine mix (0.2 ml/kg of 100 mg/ml ketamine and 20 mg/ml xylazine). Mydriasis was achieved with topical 10% phenylephrine. An eye speculum was placed in the eye to facilitate injections. A drop of proparacaine hydrochloride 0.5% and then 5% betadine solution was applied, followed by a rinse with sterile saline. Baboons (FIG. 6) received 60 μl of a $3.4 \times 10^{13}$ vg preparation of rAAV by intravitreal (ITV) injection to yield a final dose of $2.02 \times 10^{12}$ vg per eye. African Green monkeys received 50 uL of a $1 \times 10^{13}$ preparation of rAAV vector by ITV injection to yield a final dose of $5 \times 10^{11}$ vg per eye. ITV injections to the central vitreous were administered using a 31-gauge 0.375 inch needle (Terumo) inserted inferotemporally at the level of the ora serrata ~2 5 mm poster to the limbus under a surgical magnification to allow full visualization of extraocular and intraocular needle placement. Central vitreous placement was confirmed by direct observation of the needle tip at the time of the injection. Following ITV injections a topical triple antibiotic ointment was administered.

Slit-lamp biomicroscopy. The anterior segment of each monkey eye was examined by slit-lamp biomicroscopy during baseline screening and at week 4 (day 28), week 8 (day 56) and week 12 (day 84) post-injection to monitor inflammation. No abnormalities were observed.

Fundus examination and photography. Eye examination and fundus photography of rat and gerbil retinas was performed using a Phoenix Micron IV fundus microscope. All animals received a baseline screening/photographing to confirm ocular health, and then photographed at the designated timepoints to monitor the expression of the GFP transgene. Any change to the optic nerves and retina or appearance of gross lesions were recorded by a color fundus photography and expression of GFP was visualized using fluorescence fundus imaging with a fluorescein filter.

Retinal examination, fundus color and fluorescence photography, and autofluorescence OCT of NHP were performed by using a Topcon TRC-50EX retinal camera with Canon 6D digital imaging hardware and New Vision Fundus Image Analysis System software and Spectralis OCT Plus. All animals received a baseline imaging. GFP expression was also documented at week 2, 4, 8, and 12 post-intravitreal vector injection.

IVIS Imaging System. Expression of luciferase in the retina following delivery of rAAV.luciferase was quantified in vivo 2, 4 and 8 weeks post-intravitreal injection using an IVIS Imaging System. Gerbils were injected subcutaneously with 150 mg/kg luciferin (PerkinElmer) (15 mg/ml luciferin at a dose of 15 ml/kg). Approximately 22 minutes later, animals were sedated by inhalation of 4% isoflurane for 3-5 minutes. Immediately thereafter, animals were placed on the imaging platform in pairs, and the luminescence of the one eye of each animal quantified followed immediately by imaging of the contralateral eye. A naïve gerbil was used as a negative standard, with background levels of luminescence typically registering a luminescence of $1 \times 10^4$ photons/second. Bioluminescence verification using a phantom mouse (XPM-2 Perkin Elmer phantom mouse for bioluminescence imaging) was performed prior to imaging to ensure calibration of the imaging system.

Immunohistochemistry. Mice were euthanized with a lethal dose of sodium pentobarbital and tissues fixed via cardiac perfusion first with 0.13M phosphate buffered saline (PBS) pH 7.2-7.4 containing 2 units of heparin per mL, followed by 4% paraformaldehyde (PFA) in PBS, followed by 4% paraformaldehyde plus 1% glutaraldehyde in PBS. Glutaraldehyde served to keep the neural retina attached to the RPE so that the cone outer segments would remain intact. Each solution was warmed to ~37° C. just prior to administration and ~35-40 mL of perfusate was delivered at each stage. Once the perfusion was stopped, the mouse was wrapped in a moist paper towel and left to further fix for 2-3 hours before enucleation and dissection.

Permanent ink was used to mark the orientation of the eye, the anterior segment was removed, and the eye-cup was fixed in 4% PFA overnight at 4° C. and then stored in PBS at 4° C. Retinal whole-mounts were made by flattening the dissected retina between tissues soaked in 4% PFA for two hours and then transferring them to a culture plate for 6 more hours of fixation. Afterward, the PFA was replaced with PBS containing 0.03% sodium azide (Sigma).

Antibody labeling was carried out on a rotating table shaker. To block non-specific labeling, whole mounts were incubated overnight at 4° C. with a solution containing 5% donkey serum (Jackson ImmunoResearch, Cat #004-000-120), 1 mg/ml BSA (Jackson ImmunoResearch, Cat #001-000-161), and 0.03% Triton X-100 in PBS (pH 7.4). The primary antibody used in this study was rabbit anti red-green (L/M) opsin diluted 1:200 (Millipore, Cat #AB5405. Specimens were washed in PBS 3 times for 30 minutes each, then incubated at 4° C. overnight with DAPI (4',6-diamidino-2-phenylindole, dihydrochloride 1:10,000; Invitrogen, Cat #D-21490) plus secondary antibodies. The secondary antibody for the L/M-opsin antibody was Alexa Fluor 488 labeled donkey anti-rabbit IgG(H+L) diluted 1:200 in antibody dilution buffer (Invitrogen, Cat # A21206). The incubation with secondary antibody was followed by three 30 minute PBS washes, 30 minutes of post-fixation with 4% paraformaldehyde, and three more 30 minute PBS washes. Finally, the retinal slices were placed on slides with 2% DABCO in glycerol and covered with cover slips.

Microscopy. Widefield images of mouse retina whole mounts were acquired using a Nikon Eclipse E1000 with a 20× (open-air) objective and camera set with a 1.5× optical zoom. For each specimen, 50 optical sections were taken 0.5 μm apart and the M-opsin Z-stack was reconstructed in ImageJ. The Z-stack was oriented so that the lengths of the outer segments were in plane, and the distance between where antibody staining began and ended was measured as an estimate of the length of the outer segments. Further, a 3D projection of the Z-stack was generated and the number of cones with visible M-opsin in the outer segment could be quantified.

Confocal image slices were acquired using an Olympus FluoView™ FV1000. Sections were imaged using a 20× oil immersion lens (40 images taken 0.5 μm apart) and the Z-stacks were reconstructed in ImageJ. Channel exposure levels were balanced within and across images using Adobe Photoshop. For the retinal whole mounts, images were taken using a 10× open-air lens and mosaics were constructed with Adobe Photoshop's native mosaic construction software.

Experiments testing the tissue specificity of the polynucleotide cassettes. In this instance, a construct encoding GFP is injected via one or more routes of administration, such as intravitreal, subretinal, or intravenously. The animal is then sacrificed and tissues are analyzed by qPCR—to detect DNA sequences indicating presence of the construct—and GFP expression—to detect areas where the construct is actively expressed. Whereas absence of DNA sequence indicates lack of biodistribution to a given tissue, the presence of DNA sequence together with the lack of transgene expression (mRNA or protein level) indicates presence of vector but lack of expression in that tissue. In this way, the level of specificity for cone photoreceptors can be established, and used to determine the utility of this invention in terms of restricting expression to target cone photoreceptor cells without expression in non-targeted tissues such as optic nerve, liver, spleen, or brain tissue. Intravitreal AAV is known to biodistribute to the brain (Provost et al) so highly expressed, improved constructs for targeting cone photoreceptors would be useful to limit expression to target cells of the retina and limit potential adverse events associated with off-target transgene expression.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A polynucleotide cassette for enhanced expression of a transgene in cone cells of a mammalian retina, comprising
   (a) a promoter region consisting of a truncated M-Opsin promoter having a sequence identity of 85% or more to SEQ ID NO:80;
   (b) a coding sequence operatively linked to the promoter region; and
   (c) a polyadenylation site operatively linked to the coding sequence.

2. The polynucleotide cassette of claim 1, further comprising a 5' untranslated region (5'UTR) consisting essentially of a sequence having a sequence identity of 85% or more to a sequence selected from the group consisting of SEQ ID NO:56, SEQ ID NO:57, SEQ ID NO:58, SEQ ID NO:84, SEQ ID NO:85, SEQ ID NO:86, SEQ ID NO:87, SEQ ID NO:88, and SEQ ID NO:89.

3. The polynucleotide cassette of claim 2, wherein the 5'UTR does not comprise a polynucleotide ATG.

4. The polynucleotide cassette of claim 2, wherein the 5' UTR consists essentially of a sequence having a sequence identity of 85% or more to the full length of SEQ ID NO:85 or SEQ ID NO:86.

5. The polynucleotide cassette of claim 2, further comprising an intron.

6. The polynucleotide cassette of claim 5, wherein the intron comprises a sequence having a sequence identity of 85% or more to a sequence selected from the group consisting of SEQ ID NO:5, SEQ ID NO:59, and SEQ ID NO:60.

7. The polynucleotide cassette of claim 6, wherein the intron is located within the polynucleotide sequence comprising the 5' UTR.

8. The polynucleotide cassette of claim 1, further comprising a translation initiation sequence.

9. The polynucleotide cassette of claim 8, wherein the translation initiation sequence comprises a polynucleotide sequence consisting essentially of SEQ ID NO:72 or SEQ ID NO:73.

10. The polynucleotide cassette of claim 1, further comprising an enhancer sequence having a sequence identity of 85% or more to SEQ ID NO:52 or a functional fragment thereof.

11. The polynucleotide cassette of claim 10, wherein the enhancer sequence consists essentially of a sequence having a sequence identity of 85% or more to the full length of SEQ ID NO:51.

12. The polynucleotide cassette of claim 1, wherein expression of the coding sequence is greater than expression of the coding sequence when the promoter region is replaced with the promoter region of SEQ ID NO:1 when introduced into a mammalian cone cell.

13. A recombinant adeno-associated virus (rAAV) comprising:
 a) an AAV capsid protein, and
 b) the polynucleotide cassette of claim 1 flanked by AAV ITRs.

14. A pharmaceutical composition comprising the rAAV of claim 13 and a pharmaceutical excipient.

15. A method for expressing a transgene in cone cells, comprising:
 contacting one or more cone cells with an effective amount of the recombinant adeno-associated virus of claim 13, wherein the transgene is expressed at detectable levels in the one or more cone cells.

16. The method according to claim 15, comprising detecting the expression in the cone cells, wherein expression is detected in 60% or more of the cone cells.

17. A method for the treatment or prophylaxis of a cone cell disorder in a mammal in need thereof, comprising administering to the eye of the mammal an effective amount of the pharmaceutical composition of claim 14, wherein the coding sequence encodes a therapeutic gene product, and the rAAV expresses the therapeutic gene product in the cone cells of the mammal.

18. The method of claim 17, wherein the cone cell disorder is a macular dystrophy, a color vision disorder, or a vision disorder of the central macula.

19. The method of claim 18, wherein the color vision disorder is selected from the group consisting of achromotopsia, blue cone monochromacy, a protan defect, a deutan defect, and a tritan defect.

20. The method of claim 18, wherein the method further comprises detecting a change in the disease symptoms, wherein the change comprises an increase in the ability of the mammal to perceive a color.

21. The method of claim 18, wherein the macular dystrophy is selected from the group consisting of Stargardt's macular dystrophy, cone dystrophy, cone-rod dystrophy, Spinocerebellar ataxia type 7, and Bardet-Biedl syndrome-1.

22. The method of claim 18, wherein the vision disorder of the central macula is selected from the group consisting of age-related macular degeneration, macular telangiectasia, retinitis pigmentosa, diabetic retinopathy, retinal vein occlusions, glaucoma, Sorsby's fundus dystrophy, adult vitelliform macular dystrophy, Best's disease, rod-cone dystrophy, Leber's congenital amaurosis, and X-linked retinoschisis.

23. The method of claim 18, wherein the method further comprises detecting a change in the disease symptoms, wherein the change comprises reducing the rate of visual acuity loss of the mammal.

24. The polynucleotide cassette of claim 1, wherein the promoter region consists of SEQ ID NO:80.

25. The polynucleotide cassette of claim 1, wherein the promoter region consists of a truncated M-Opsin promoter having a sequence identity of 95% or more to SEQ ID NO:80.

26. A polynucleotide cassette for enhanced expression of a transgene in cone cells of a mammalian retina, comprising SEQ ID NO:95.

* * * * *